US007566737B2

(12) United States Patent
Delhomel et al.

(10) Patent No.: US 7,566,737 B2
(45) Date of Patent: *Jul. 28, 2009

(54) COMBINATIONS OF SUBSTITUTED 1,3-DIPHENYLPROP-2-EN-1-ONE DERIVATIVES WITH OTHER THERAPEUTICALLY ACTIVE INGREDIENTS

(75) Inventors: Jean-François Delhomel, Acq (FR); Karine Caumont-Bertrand, Frelinghien (FR)

(73) Assignee: Genfit, Loos (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/493,040

(22) Filed: Jul. 26, 2006

(65) Prior Publication Data

US 2007/0032543 A1 Feb. 8, 2007

Related U.S. Application Data

(63) Continuation-in-part of application No. 10/520,079, filed as application No. PCT/FR03/02127 on Jul. 8, 2003.

(30) Foreign Application Priority Data

Jul. 8, 2002 (FR) .................................. 02 08571

(51) Int. Cl.
*A61K 31/382* (2006.01)
(52) U.S. Cl. ........................ 514/432; 514/456; 514/690
(58) Field of Classification Search ........................ None
See application file for complete search history.

(56) References Cited

U.S. PATENT DOCUMENTS

| 3,558,612 | A | 1/1971 | Kuhn et al. |
| 3,994,955 | A | 11/1976 | Sprenger |
| 4,190,671 | A | 2/1980 | Vanstone et al. |
| 4,656,305 | A | 4/1987 | Vanstone et al. |
| 5,276,058 | A | 1/1994 | Satoh et al. |
| 5,326,670 | A | 7/1994 | Kotachi et al. |
| 5,523,302 | A | 6/1996 | Cain et al. |
| 7,385,082 | B2 | 6/2008 | Delhomel et al. |
| 2005/0176808 | A1 | 8/2005 | Najib et al. |

FOREIGN PATENT DOCUMENTS

| DE | 43 27 365 | 2/1995 |
| EP | 0 947 511 | 10/1999 |
| EP | 1 254 658 | 11/2002 |
| EP | 1254658 A1 | 11/2002 |
| FR | 2 248 829 | 5/1975 |
| FR | 2 383 157 | 8/1977 |
| FR | 78 062 79 | 10/1978 |
| FR | 2 841 900 | 1/2004 |
| WO | WO 98/27970 | 7/1998 |
| WO | WO 00/23073 | 4/2000 |
| WO | WO 01/98291 | 12/2001 |
| WO | 2004/005233 | 1/2004 |
| WO | 2004/005243 | 1/2004 |

OTHER PUBLICATIONS

Shibata, "Anti-tumorigenic Chalcones", Stem Cells, vol. 12, 1994, pp. 44-52.
Dimmock et al, "Bioactivities of Chalcones", Current Medicinal Chemistry, Bentham Science Publishers, vol. 6, No. 12, 1999, pp. 1125-1149.
Lebeau et al, "Antioxidant Properties of Di-Tert-Butylhydroylated Flavonoids", Free Radical Biology and Medicine, vol. 29, No. 9, Nov. 1, 2000, pp. 900-912.
Mukherjee et al, "Synthetic and Biological Activity Evaluation Studies on Novel 1,3-Diarylpropenones", Bioorganic & Medicinal Chemistry, vol. 9, No. 2, 2001, pp. 337-345.
Cheng et al, "Broussochalcone A, a potent antioxidant and effective suppressor of inducible nitric oxide synthase in lipopolysaccharide-activated macrophages", Biochemical Pharmacology, vol. 61, No. 8, Apr. 15, 2001, pp. 939-946.
Cheng et al, "Antioxidant properties of butein isolated from *Dalbergia odorifera*", Biochemica et Biophysics Acta, vol. 1392, No. 2/3, Jun. 15, 1998. pp. 291-299.
Rajakumar et al, "Antioxidant Properties of Phenyl Styryl Ketones", Free Radical Research, vol. 22, No. 4, 1995, pp. 309-317.
Arty et al, "Synthesis of benzylideneacetophenones and their inhibition of lipid peroxidation", European Journal of Medicinal Chemistry 2000 France, vol. 35, No. 4, 2000, pp. 449-457.
Database Chemical Abstracts Service, XP002236011, abstract & Zhang et al, "Antioidation of *Peurperia lobata* isoflavones", Tongji Yike Dauxe Xeubao, vol. 26, No. 5, 1997, pp. 340-342.
Stoll et al, Chalcone derivatives antagonize interactions between the human oncoprotein NDM2 and p53, Biochemistry, United States Jan. 16, 2001, vol. 40, No. 2, Jan. 16, 2001, pp. 336-344.
Database Chemical Abstracts Service, XP002262904, abstract & Shi et al, "Synthesis of ethyl Flavone(or chalcone)oxyllsobutyrate and its derivatives as potential antilipidemic agents", Taiwan Yaoxue Zazhi, vol. 27, No. 1-2, 1975, pp. 12-16.
Lebeau et al, "Beneficial effects of different flavonoids, on functional recovery after ischemia and reperfusion in isolated rat heart", Bioorganic & Medicinal Chemistry Letters, vol. 11, No. 1, Jan. 8, 2001, pp. 23-27.
Patent Abstracts of Japan vol. 014, No. 126, Mar. 9, 1990 & JP 02 003670 A Jan. 9, 1990.
Halliwell, "Oxidants and the central nervous system: some fundamental questions. lx oxidant damage relevant to Parkinson's disease, Alzheimer's disease, traumatic injury or stroke?", Acta Neurologica Scandinavica, Supplementum, Denmark 1989, vol. 126, 1989, pp. 23-33,.

(Continued)

*Primary Examiner*—Kamal A Saeed
(74) *Attorney, Agent, or Firm*—Nixon & Vanderhye P.C.

(57) ABSTRACT

The invention concerns novel substituted 1,3-diphenylprop-2-en-1-one derivatives and combinations of said derivatives with other therapeutically active ingredients. The invention also concerns compositions comprising said derivatives or said combinations and uses thereof, for the treatment of cerebrovascular diseases, pathology related to inflammation, neurodegeneration, deregulations of lipid and/or glucose metabolism, cell proliferation and/or differentiation and/or skin or central nervous system ageing.

9 Claims, 28 Drawing Sheets

OTHER PUBLICATIONS

Figure 1:
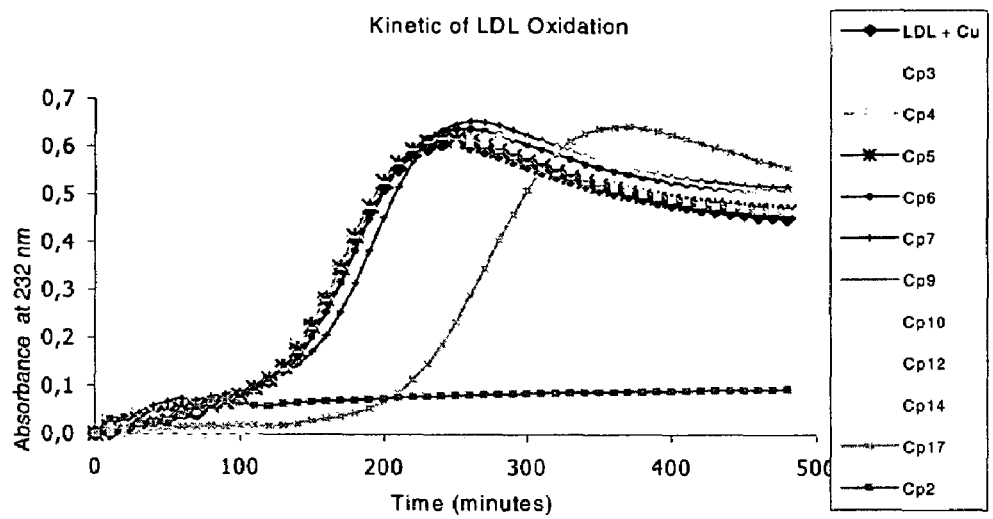

U.S. Appl. No. 10/520,079, filed Apr. 2005, Najib et al.
U.S. Appl. No. 11/493,040, filed Jul. 2006, Delhomel et al.
Sogawa et al, "3,4-Dihydroxychalcones as Potent 5-Lipoxygenase and Cyclooxygenase Inhibitors", Journal of Medicinal Chemistry, American Chemical Society, Washington, US, vol. 36, No. 24, 1993, pp. 3904-3909.
Nakamura et al, "Synthesis and Biological Activities of Fluorinated Chalcone Derivativs", Bioorganic & Medicinal Chemistry, Elsevier Science Ltd, GB, vol. 10, No. 3, Mar. 2002, pp. 699, 706.
Calliste et al, "Chalcones: Structural Requirements for Antioxidant, Estrogenic and Antiproliferative Activities", Anticancer Research, Helenic Anticancer Institute, Athens, GR, vol. 21, No. 6A, 2001, pp. 3949-3956.
Furmn et al, "Di-tert-Butylhydroxylated Flavonoids Protect Endothelial Cells Against Oxidized LDL-Induced Cytotocity", Journal of Biochemical and Molecular Toxicology, Wiley, New York, NY, US, vol. 15, No. 5, 2001, pp. 270-278.
Lim et al, "Synthesis of flavonoids and their effects on aldose reductase and sorbitol accumulation in streptozotocin-induced diabetic rat tissues", Journal of Pharmacy and Pharmacology, London, GB, vol. 53, No. 5, May 2001, pp. 653-668.
Patent Abstracts of Japan, vol. 018, No. 415, Aug. 4, 1994 & JP 06 122623 A, May 6, 1994.
Patent Abstracts of Japan, vol. 012, No. 209, Jun. 15, 1988 & JP 63 010720 A, Jan. 18, 1988.
Haraguchi et al, "Antioxidative and Superoxide Scavenging Activities of Retrochalcones in *Glycyrrhiza Inflata*", Bioorganic & Medicinal Chemistry, Elsevier Science Ltd, GB, vol. 6, No. 3, Mar. 1998, pp. 339-347.
Chemical Abstracts Service XP002236041, abstract & Oganesyan et al, "Study of structure-activity (A) interrelations in the flavonoid series. I. Synthesis of chalcome derivatives and quantitative SA analysis", Khimiko-Farmatseviicheskii Zhurnal, vol. 20, No. 6, 1986, pp. 696-702.
Hsu et al, Structure-Activity Relationships of Substituted Flavonoids. (I), Taiwan-Kexue—Formosanscience, Taipei, TW, vol. 27, No. 1/2, 1973, pp. 23-26.
Szajda et al, "New alkoxycarbonylalkyl oxychalcones and their alpha, beta-dibromo derivatives of potential antimicrobial activity", Die Pharmazie, Germany, East Mar 1989, vol. 44, No. 3, Mar. 1989. pp. 190-191.
Database Chemical Abstracts Service, XP002271330, abstract & Palanowski et al, "Synthesis of potentiao vasoactive compounds. I. phenylacrylophenone derivatives", Acta Poloniae Pharmaceutica (English Translation), vol. 24, No. 6, 1967, pp. 567-574.
Database, Chemical Abstracts Service, XP002271331, abstract & JP 54 019947 A (Taisho Pharmaceutical Co.) Feb. 15, 1979.
Database, Chemical Abstracts Service, XP002271332, abstract & Safak et al, "Chalcones. II. Synthesis of some chalcone derivatives and their antifungal activity against *Candida albicans*", Fabad Farmasotik Bilimler Dergisi, vol. 8, No. 2, 1983, pp. 80-88.
Database, Chemical Abstracts Service, XP002271333, abstract & JP 05 255655 A, (Kanebo Ltd), Oct. 5, 1993.
Database, Chemical Abstracts Service, XP002271334, abstract & Sun et al, "Studies on flavonoids. VIIII. Synthesis of 7-substituted flavones and 2',4-dihydroxy-3-methoxy -4'-substituted chalcones", Gaodeng Xuexiao Huaxue Xuebao, vol. 9, No. 8, 1988, pp. 853.855.
Database, Chemical Abstracts Service, XP002271335, abstract &Szajda et al, Carbon 13 NMR study of o-, m- and p-' (alkoxycarbonyl)alkoxy chalcones and their alpha, beta dibromo derivatives, Magnetic Resonance in Chemistry, vol. 27, No. 4, 1989, pp. 399-402.
Hsieh et al, "Synthesis and Anti-inflammatory Effect of Chalcones and Related Compounds", Pharmaceutical Research, vol. 15, No. 1, 1998, pp. 39-46.
Byrn, et al, "Solid State Chemistry of Drugs", $2^{nd}$ ed., SSCI, Inc., Chapter 10, p. 232-247, 1999.
French et al, "A New Preparation of Substituted 4H-1-Benzothiopyran-4-ones from C(a),N-Benzoylhydrazones or C(a),N-Carboalkoxyhydrazones and Methyl Thiosalicylate," Journal of Heterocyclic Chemistry, 1998, 35, 45-48.
Office Action dated Feb. 26, 2009, issued in connection with U.S. Appl. No. 10/520,078.
King, Frank D. "Bioisosteres, Conformational Restriction, and Prodrugs—Case History: An Example of a Conformational Restriction Approach", Medical Chemistry: Principles and Practice, 1994, Chapter 14, pp. 206-225.

Plasma Insulin at D21

Plasma Glucose at D21

Oxidation reduction vs control in fibroblasts

SEQUENCE LISTING

```
<160> NUMBER OF SEQ ID NOS: 8

<210> SEQ ID NO 1
<211> LENGTH: 22
<212> TYPE: DNA
<213> ORGANISM: artificial
<220> FEATURE:
<223> OTHER INFORMATION: PDK4 forward primer

<400> SEQUENCE: 1
tactccactg ctccaacacc tg                                            22

<210> SEQ ID NO 2
<211> LENGTH: 20
<212> TYPE: DNA
<213> ORGANISM: artificial
<220> FEATURE:
<223> OTHER INFORMATION: PDK4 reverse primer

<400> SEQUENCE: 2
gttcttcggt tccctgcttg                                               20

<210> SEQ ID NO 3
<211> LENGTH: 24
<212> TYPE: DNA
<213> ORGANISM: artificial
<220> FEATURE:
<223> OTHER INFORMATION: UCP2 forward primer

<400> SEQUENCE: 3
gtcggagata ccagagcact gtcg                                          24

<210> SEQ ID NO 4
<211> LENGTH: 20
<212> TYPE: DNA
<213> ORGANISM: artificial
<220> FEATURE:
<223> OTHER INFORMATION: UCP2 reverse primer

<400> SEQUENCE: 4
```

```
cacatcaaca ggggaggcga                                                20

<210> SEQ ID NO 5
<211> LENGTH: 20
<212> TYPE: DNA
<213> ORGANISM: artificial
<220> FEATURE:
<223> OTHER INFORMATION: UCP3 forward primer

<400> SEQUENCE: 5
gcaccgccag atgagttttg                                                20

<210> SEQ ID NO 6
<211> LENGTH: 20
<212> TYPE: DNA
<213> ORGANISM: artificial
<220> FEATURE:
<223> OTHER INFORMATION: UCP3 reverse primer

<400> SEQUENCE: 6
gacgctggag tggtccgctc                                                20

<210> SEQ ID NO 7
<211> LENGTH: 22
<212> TYPE: DNA
<213> ORGANISM: artificial
<220> FEATURE:
<223> OTHER INFORMATION: 18S forward primer

<400> SEQUENCE: 7
cggacacgga caggattgac ag                                             22

<210> SEQ ID NO 8
<211> LENGTH: 20
<212> TYPE: DNA
<213> ORGANISM: artificial
<220> FEATURE:
<223> OTHER INFORMATION: 18S reverse primer

<400> SEQUENCE: 8
aatctcgggt ggctgaacgc                                                20
```

COMBINATIONS OF SUBSTITUTED 1,3-DIPHENYLPROP-2-EN-1-ONE DERIVATIVES WITH OTHER THERAPEUTICALLY ACTIVE INGREDIENTS

The present application is a continuation-in-part of application Ser. No. 10/520,079, filed Apr. 22, 2005, which is a 371 U.S. National Phase of PCT/FR03/02127 filed Jul. 8, 2003, which claims benefit of France 02/08571, filed Jul. 8, 2002, the entire contents of each of which is hereby incorporated by reference.

The invention concerns novel substituted 1,3-diphenylprop-2-en-1-one derivatives and combinations of said derivatives with other therapeutically active ingredients. The invention also concerns compositions comprising said derivatives or said combinations and uses thereof, for the treatment of cerebrovascular diseases, pathology related to inflammation, neurodegeneration, deregulations of lipid and/or glucose metabolism, cell proliferation and/or differentiation and/or skin or central nervous system ageing.

The compounds according to the invention have pharmacological antioxidant properties and PPAR activator properties, which are advantageous. More specifically, compounds according to the invention have antioxydant properties and PPARα and PPARγ activator properties. So the derivatives, combinations and compositions of the invention can be used to treat diseases in which these properties can be useful. The compounds according to the invention are useful in particular for preventing or treating cerebrovascular diseases, cardiovascular diseases, conditions associated with syndrome X, restenosis, dyslipidemias, diabetes, obesity, hypertension, inflammatory diseases, cancers (benign or malignant tumors), neurodegenerative diseases, dermatological diseases and disorders related to oxidative stress, for preventing or treating the effects of ageing in general and for example skin ageing, in particular in the field of cosmetics (development of wrinkles and the like). More particularly, compounds, combinations and compositions according to the invention advantageously allow to treat dyslipidemias and diabetes.

The compounds of the invention have PPAR activator properties. The PPARs (α, γ, β/δ) belong to the hormone-activated nuclear receptor family. The PPARs, or "Peroxisome Proliferator Activated Receptors", are nuclear receptors from the superfamily of transcription factors activated by the following ligands: steroids/thyroid hormones/retinoids. To date, three PPAR isotypes have been identified in mice and humans: PPARα, PPARβ/δ and PPARγ. While PPARβ/δ expression in humans appears to be ubiquitous, PPARα and γ exhibit a differential tissue distribution (Braissant O and Wahli W, 1998). PPARα is expressed in cells with high fatty acid catabolic activity and in cells with high peroxisomal activity (hepatocytes, cardiomyocytes, renal proximal tubules, intestinal mucosa). PPARβ/δ is expressed ubiquitously and abundantly in most tissues. As far as PPARγ expression is concerned, it is limited mainly to adipose tissue, certain immune system cells and retina and is present in only trace amounts in other organs (Braissant O and Wahli W, 1998).

The PPARs contain several domains having different properties. A DNA Binding Domain (DBD) recognizes specific sequences, also called response elements, located in regulatory regions of their target genes. Like other nuclear receptors, the PPARs also contain a Ligand Binding Domain (LBD): the activation of PPARs by their ligand induces the modulation of the expression of genes which contain specific PPAR Response Elements (PPRE) in the promoter region. To activate transcription of their target genes, the activated PPARs must heterodimerize with another nuclear receptor, RXR (Retinoid-X-Receptor). Taking the example of PPARα, its action is mediated by a class of compounds such as the fibrates which have a lipid-lowering effect. Natural ligands have also been identified such as for example fatty acids, eicosanoids (leukotriene $B_4$) and 8(S)-hydroxyeicosatetraenoic acid (Kliewer S A et al., 1997). The PPARs have been associated primarily with lipid and glucose metabolism. PPAR activators, such as fibrates, enable a regulation of plasma cholesterol and triglyceride concentrations via activation of PPARα (Hourton D et al., 2001). Fibrate therapy leads to an increase in fatty acid oxidation in liver. Fibrates also decrease the synthesis of triglycerides (Staels B and Auwerx J, 1998). PPARα activators are also capable of correcting hyperglycemia and insulin level. Fibrates also reduce adipose tissue mass through a mechanism which is independent of food intake and leptin gene expression (Guerre-Millo M et al., 2000). The therapeutic interest of PPARγ agonists has been widely investigated in the treatment of type 2 diabetes (Spiegelman B M, 1998). It has been shown that PPARγ agonists restore insulin sensitivity in target tissues and reduce plasma glucose, lipid and insulin levels both in animal models of type 2 diabetes and in humans (Ram V J, 2003). PPAR activation by ligands also plays a role in regulating the expression of genes that participate in processes such as inflammation, angiogenesis, cell proliferation and differentiation, apoptosis and the activities of iNOS, MMPase and TIMPs. Activation of PPARα in keratinocytes results in a cessation of their proliferation and expression of genes involved in differentiation (Komuves L G et al., 2000). The PPARs have anti-inflammatory properties because they negatively interfere with transcription mechanisms involving other transcription factors like NF-κB or transcriptional activators like STAT and AP-1 (Desvergne B and Wahli W, 1999). Said anti-inflammatory and anti-proliferative properties make the PPARs (and particularly PPARα) interesting therapeutic targets for the treatment of diseases such as vascular occlusive diseases (atherosclerosis, etc.), hypertension, diseases related to neovascularization (diabetic retinopathy, etc.), inflammatory diseases (inflammatory bowel disease, psoriasis, etc.) and neoplastic diseases (carcinogenesis, etc.).

The compounds of the invention have also antioxydant properties. Free radicals play a role in a very wide range of pathologies including allergy, tumor initiation and promotion, cardiovascular diseases (atherosclerosis, ischemia), genetic and metabolic disorders (diabetes), infectious and degenerative diseases (Alzheimer's disease, Parkinson's disease, Prion, etc.) and in ophthalmic disorders (Mates J M et al., 1999). Reactive Oxygen Species (ROS) are produced during normal cell functioning. ROS comprise the hydroxyl radical (OH), superoxide anion ($O_2^-$), hydrogen peroxide ($H_2O_2$) and nitric oxide (NO). Said species are very labile and, due to their high chemical reactivity, constitute a danger to the biological functions of cells. They induce lipid peroxidation, oxidation of certain enzymes and very extensive oxidation of proteins leading to degradation thereof. Protection against lipid peroxidation is a vital process in aerobic organisms, because peroxidation products can cause DNA damage. Thus a deregulation or modification of the equilibrium between the production, processing and elimination of radical species by natural antioxidant defenses leads to the establishment of processes that are deleterious to the cell or organism. ROS are processed via an antioxidant system that comprises an enzymatic component and a non-enzymatic component. The enzymatic system is composed of several enzymes which have the following characteristics:

Superoxide dismutase (SOD) destroys the superoxide radical by converting it to peroxide. The peroxide in turn is acted upon by another enzyme system. Low levels of SOD are continuously produced by aerobic respiration. Three classes of SOD have been identified in humans, each containing Cu, Zn, Fe, Mn or Ni as cofactor. The three forms of human SOD are distributed as follows: a cytosolic Cu—Zn SOD, a mitochondrial Mn—SOD and an extracellular SOD.

Catalase is very efficient at converting hydrogen peroxide ($H_2O_2$) to water and $O_2$. Hydrogen peroxide is enzymatically catabolized in aerobic organisms. Catalase also catalyzes the reduction of a variety of hydroperoxides (ROOH).

Glutathione peroxidase uses selenium as cofactor and catalyzes the reduction of hydroperoxides (ROOH and $H_2O_2$) by using glutathione, and thereby protects cells against oxidative damage.

Non-enzymatic antioxidant defenses comprise molecules which are synthesized or supplied in the diet. Antioxidant molecules are present in different cell compartments. Detoxification enzymes for example eliminate free radicals and are essential to cell life. The three most important types of antioxidant compounds are the carotenoids, vitamin C and vitamin E (Gilgun-Sherki Y et al., 2001).

The PPAR agonist activity and antioxidant properties of the compounds according to the invention can be useful in combinations with other therapeutically active ingredients, to treat pathologies related to inflammation (atherosclerosis, allergy, asthma, eczema, pruritus, etc.), neurodegeneration (Alzheimer's disease, Parkinson's disease, etc.), deregulations of lipid and/or glucose metabolism (diabetes, dyslipidemias, atherosclerosis, obesity, etc.), cell proliferation/differentiation (carcinogenesis, etc.) and disorders related to ageing (skin or central nervous system, etc.).

The present invention concerns novel compositions comprising novel substituted 1,3-diphenylprop-2-en-1-one derivatives in combination with other therapeutically active ingredients.

These novel substituted 1,3-diphenylprop-2-en-1-one derivatives are represented by formula (I) below:

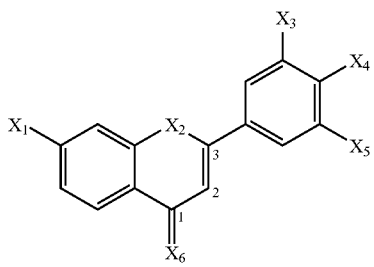

(I)

in which:

X1 represents a halogen or a —R1 group or a group corresponding to the following formula: -G1-R1, X2 represents an hydrogen or a thionitroso group or a hydroxy group or an unsubstituted alkyloxy group or an alkylcarbonyloxy group or a thiol group or an alkylthio group or an alkylcarbonylthio group, X2 can also represent an oxygen or sulfur atom bound to carbon 3 of the propene chain, so as to form a derivative of the type 2-phenyl4H-1-benzopyran-4-one or of the type 2-phenyl-4H-1-benzothiopyran-4-one (this option is depicted in formula (I) by the dotted line), X3 represents a —R3 group or a group corresponding to the following formula: -G3-R3, X4 represents a halogen or a thionitroso group or a —R4 group or a group corresponding to the following formula: -G4-R4, X5 represents a —R5 group or a group corresponding to the following formula: -G5-R5, X6 is an oxygen atom or a nitrogen atom, in the case where X6 is a nitrogen atom, it carries a hydrogen atom or a hydroxy group or an alkyloxy group, R1, R3, R4, R5, which are the same or different, represent a hydrogen atom or an alkyl group substituted or not by at least one substituent selected from group 1 or group 2 defined hereinbelow, G1, G3, G4, G5, which are the same or different, represent an oxygen or sulfur atom, with at least one of the groups X1, X3, X4 or X5 corresponding to the formula -G-R (i.e., -G1-R1, -G3-R3, -G4-R4 or -G5-R5, respectively) and with at least one of the groups R1, R3, R4 or R5 present in the form of an alkyl group having at least one substituent of group 1 or 2, said alkyl group being bound directly to the ring or being associated with a group G (i.e., G1, G3, G4 or G5, respectively) according to the formula -G-R (i.e., -G1-R1, -G3-R3, -G4-R4 or -G5-R5, respectively), the substituents of group 1 are selected in the group consisting of carboxy groups having the formula: —$COOR_6$ and carbamoyl groups having the formula: —$CONR_6R_7$, the substituents of group 2 are selected in the group consisting of sulfonic acid (—$SO_3H$) and sulfonamide groups having the formula: —$SO_2NR_6R_7$, with $R_6$ and $R_7$, which are the same or different, representing a hydrogen atom or an alkyl group possibly substituted by at least one group of type 1 or 2, the optical and geometrical isomers, racemates, tautomers, salts, hydrates and mixtures thereof, with the exception of compounds represented by formula (I) in which:

$X_1$, $X_2$, $X_3$ and $X_5$ each represent a hydrogen atom, $X_6$ represents an oxygen atom and $X_4$ represents a group corresponding to the formula —O—$CR_8R_9$—$COOR_{10}$, where $R_8$ and $R_9$, which are the same or different, represent a C1 to C2 alkyl group (comprising one or two carbon atoms), and $R_{10}$ represents a hydrogen atom or a C1 to C7 alkyl group (comprising one to seven carbon atoms), $X_2$, $X_3$ and $X_5$ each represent a hydrogen atom, $X_1$ represents a halogen atom or a R1 or -G1-R1 group, where R1 represents an unsubstituted C1 to C2 alkyl group and G1 represents an oxygen atom, $X_6$ represents an oxygen atom and $X_4$ represents a group corresponding to the formula —O—$CR_{11}R_{12}$—$COOR_{10}$, where $R_{11}$, and $R_{12}$, which are the same or different, represent a hydrogen atom or a C1 to C2 alkyl group, and $R_{10}$ represents a hydrogen atom or a C1 to C7 alkyl group, and $X_2$ represents a hydrogen atom and $X_1$ represents -G1-R1 where G1 represents an oxygen atom and R1 represents —$CH_2COOH$.

In the scope of the invention, the derivatives represented by formula (I) such as defined hereinabove can adopt a cis or trans conformation.

Advantageously, none of the groups X3, X4 and X5 represents a hydrogen atom. Compounds of formula (I), which meet this definition, constitute compounds of general family (II).

Advantageously, one or two of the groups X3, X4 and X5 represent a hydrogen atom and X1 is an unsubstituted alkyl group. Compounds of formula (I), which meet this definition, constitute compounds of general family (III).

Advantageously, one or two of the groups X3, X4 and X5 represent a hydrogen atom and X2 is a thionitroso group or an alkylcarbonyloxy group or a thiol group or an alkylthio group or an alkylcarbonylthio group, X2 can also represent an oxygen or sulfur atom bound to carbon 3 of the propene chain, so as to form a derivative of the type 2-phenyl-4H-1-benzopyran4-one or of the type 2-phenyl-4H-1-benzothiopyran-4-one (this option is depicted in formula (I) by dotted lines). Compounds of formula (I), which meet this definition, constitute compounds of general family (IV).

Advantageously, one or two of the groups X3, X4 and X5 represent a hydrogen atom and at least one of the groups X1, X3, X4 or X5 is the -G-R form in which G is a sulfur atom. Compounds of formula (I), which meet this definition, constitute compounds of general family (V).

Advantageously, one or two of the groups X3, X4 and X5 represent a hydrogen atom and at least one of the groups X1, X3, X4 or X5 is the -G-R form in which G is an oxygen atom and R is an alkyl group substituted by a substituent from group I in which R6 is not a hydrogen atom. Compounds of formula (I), which meet this definition, constitute compounds of general family (VI).

Advantageously, one or two of the groups X3, X4 and X5 represent a hydrogen atom and at least one of the groups X1, X3, X4 or X5 is the -G-R form in which G is an oxygen atom and R is an alkyl group substituted by a sulfonamide such as defined hereinabove. Compounds with formula (I), which meet this definition, constitute compounds of general family (VII).

Advantageously, X4 is a thionitroso group or a —R4 group or a group corresponding to the formula -G4-R4. Derivatives with formula (I) in which X4 meets this definition constitute derivatives represented by general formula (VIII) in which G4 and R4 are such as defined hereinabove.

Advantageously, X2 is a thionitroso group or a hydroxy group or an alkyloxy group or a thiol group or an alkylthio group. Derivatives with formula (I) in which X2 meets this definition constitute derivatives represented by general formula (IX).

Other advantageous derivatives represented by formula (I) of the invention have a general formula (X) such that X4 is a thionitroso group or a —R4 group or a group corresponding to the formula -G4-R4 and X2 is a thionitroso group or a hydroxy group or an alkyloxy group or a thiol group or an alkylthio group, G4 and R4 being such as defined hereinabove.

Other advantageous derivatives represented by formula (I) of the invention have a general formula (XI) such that X1 represents a —R1 group or a group corresponding to the formula -G1-R1, with R1 being an alkyl group substituted by a substituent which is part of group 1 and G1 and the substituent of group 1 being such as defined hereinabove.

More preferably, another object of the invention concerns derivatives represented by formula (I) to (XI) such as described hereinabove, characterized in that X1 is a -G1-R1 group.

Even more preferably, another object of the invention concerns derivatives represented by formula (I) to (XI) such as described hereinabove, characterized in that X1 is a -G1-R1 group in which G1 is an oxygen atom.

Other advantageous derivatives represented by formula (I) of the invention have a general formula (XII) such that X1 represents a —R1 group or a group corresponding to the formula -G1-R1, with R1 being an alkyl group substituted by a substituent which is part of group 2 and G1 and the substituent of group 2 being such as defined hereinabove.

Other advantageous derivatives represented by formula (I) of the invention have a general formula (XIII) such that X3 represents a —R3 group or a group corresponding to the formula -G3-R3, with R3 being an alkyl group substituted by a substituent which is part of group 1 and G3 and the substituent of group 1 being such as defined hereinabove.

Other advantageous derivatives represented by formula (I) of the invention have a general formula (XIV) such that X3 represents a —R3 group or a group corresponding to the formula -G3-R3, with R3 being an alkyl group substituted by a substituent which is part of group 2 and G3 and the substituent of group 2 being such as defined hereinabove.

Other advantageous derivatives represented by formula (I) of the invention have a general formula (XV) such that X4 represents a —R4 group or a group corresponding to the formula -G4-R4, with R4 being an alkyl group substituted by a substituent which is part of group 1 and G4 and the substituent of group 1 being such as defined hereinabove.

More preferably, another object of the invention concerns derivatives represented by formula (I) to (XV) such as described hereinabove, characterized in that X4 is a -G4-R4 group.

Even more preferably, another object of the invention concerns derivatives represented by formula (I) to (XV) such as described hereinabove, characterized in that X4 is a -G4-R4 group in which G4 is an oxygen atom.

Even more preferably, another object of the invention concerns derivatives represented by formula (I) to (XV) such as described hereinabove, characterized in that X4 is a -G4-R4 group in which G4 is an oxygen atom, and X3 or X5 respectively represent —R3 or -G3-R3, on the one hand, and —R5 or -G5-R5, on the other hand, with R3 or R5 being alkyl groups carrying a substituent of group 1, said substituent of group 1 being such as defined hereinabove.

Another object of the invention concerns derivatives represented by formula (I) such as defined hereinabove, characterized in that X4 is a -G4-R4 group, R4 is such as defined hereinabove and X3 or X5 respectively represent —R3 or -G3-R3, on the one hand, and —R5 or -G5-R5, on the other hand, with R3 or R5 being an alkyl group carrying a substituent of group 1, said substituent of group 1 being such as defined hereinabove.

Other advantageous derivatives represented by formula (I) of the invention have a general formula (XVI) such that X4 represents a —R4 group or a group corresponding to the formula -G4-R4 with R4 being an alkyl group substituted by a substituent which is part of group 2 and G4 the substituent of group 2 being such as defined hereinabove.

Other advantageous derivatives represented by formula (I) of the invention have a general formula (XVII) such that X1 represents a halogen.

Other advantageous derivatives represented by formula (I) of the invention have a general formula (XVIII) such that X1 represents a —R1 group with R1 being a C1 to C4 alkyl group substituted or not by at least one substituent which is part of group 1 or group 2 defined hereinabove.

Other advantageous derivatives represented by formula (I) of the invention have a general formula (XIX) such that X1 represents a -G1R1 group with R1 being a C1 to C3 alkyl group substituted or not by at least one substituent which is part of group 1 or group 2 defined hereinabove.

Other advantageous derivatives represented by formula (I) of the invention have a general formula (XX) such that X1 represents a —R1 group with R1 being a C5 to C24 alkyl group substituted or not by at least one substituent which is part of group 1 or group 2 defined hereinabove.

Other advantageous derivatives represented by formula (I) of the invention have a general formula (XXI) such that X1 represents a -G1R1 group with R1 being a C4 to C24 alkyl group substituted or not by at least one substituent which is part of group 1 or group 2 defined hereinabove.

Other advantageous derivatives represented by formula (I) of the invention have a general formula (XXII) such that X6 represents an oxygen atom.

Another object of the invention concerns derivatives represented by formula (I) in which X1, X3, X4 or X5 represent —OC(CH$_3$)$_2$COOR$_6$ with R$_6$ being such as defined hereinabove.

Another object of the invention concerns derivatives represented by formula (I) in which X1, X3, X4 or X5 represent —SC(CH$_3$)$_2$COOR$_6$ with R$_6$ being such as defined hereinabove.

Advantageously, the invention concerns derivatives represented by formula (I) in which at least one of the groups X1, X3, X4 or X5 corresponds to the formula -G-R in which G is a sulfur atom.

Other advantageous derivatives are represented by formula (I) in which X2 represents a hydrogen atom or a thionitroso group or a hydroxy group or an alkylcarbonyloxy or an unsubstituted alkyloxy group or a thiol group or an alkylthio group or an alkylcarbonylthio group, X2 can also represent a sulfur atom bound to carbon 3 of the propene chain, so as to form a derivative of the type 2-phenyl-4H-1-benzothiopyran-4-one and with none of the groups X3, X4 and X5 representing a hydrogen atom.

Other advantageous derivatives are represented by formula (I) in which X1 represents a group -G1-R1, wherein G1 represents an oxygen atom and R1 is —C(CH$_3$)$_2$COOR$_6$, X2 represents a hydrogen atom or a thionitroso group or a hydroxy group or an alkylcarbonyloxy or an unsubstituted alkyloxy group or a thiol group or an alkylthio group or an alkylcarbonylthio group, X2 can also represent a sulfur atom bound to carbon 3 of the propene chain, so as to form a derivative of the type 2-phenyl-4H-1-benzothiopyran-4-one and with none of the groups X3, X4 and X5 representing a hydrogen atom.

Other advantageous derivatives are represented by formula (I) in which X1 represents a —R1 group, X2 represents a hydrogen atom or a thionitroso group or a hydroxy group or an alkylcarbonyloxy or an unsubstituted alkyloxy group or a thiol group or an alkylthio group or an alkylcarbonylthio group, X2 can also represent a sulfur atom bound to carbon 3 of the propene chain, so as to form a derivative of the type 2-phenyl4H-1-benzothiopyran4-one, R1 represents a hydrogen atom or an alkyl group substituted or not by at least one substituent which is part of group 1 defined hereinbelow and with none of the groups X3, X4 and X5 representing a hydrogen atom.

Other advantageous derivatives are represented by formula (I) in which X1 represents a -G1R1 group, X2 represents a hydrogen atom or a thionitroso group or a hydroxy group or an alkylcarbonyloxy or an unsubstituted alkyloxy group or a thiol group or an alkylthio group or an alkylcarbonylthio group, X2 can also represent a sulfur atom bound to carbon 3 of the propene chain, so as to form a derivative of the type 2-phenyl-4H-1-benzothiopyran-4-one, R1 represents a hydrogen atom or a C4 to C24 alkyl group substituted or not by at least one substituent which is part of group 1 or group 2 defined hereinabove and with none of the groups X3, X4 and X5 representing a hydrogen atom.

According to the invention, the term "alkyl" designates a saturated hydrocarbon function, linear, branched or cyclic, halogenated or not, having more particularly from 1 to 24, preferably 1 to 10, carbon atoms such as methyl, ethyl, propyl, isopropyl, butyl, isobutyl, tert-butyl, pentyl, neopentyl, n-hexyl. Groups containing one or two carbon atoms or containing from two to seven carbon atoms are particularly preferred. Methyl and ethyl groups are quite particularly preferred.

The term "thionitroso" refers to a nitroso group bound to the aromatic ring through a sulfur atom.

The term "alkyloxy" designates an alkyl chain bound to the ring by an oxygen atom.

The term "alkylthio" refers to an alkyl chain bound to the aromatic ring by a sulfur atom (thioether bond).

According to a particular embodiment of the invention, preferred compounds are indicated below with their corresponding formulas:

1-[2-hydroxy-4-chlorophenyl]-3-[4-carboxydimethylmethyloxyphenyl]prop-2-en-1-one and 1-[2-hydroxy-4-chlorophenyl]-3-[4-isopropyloxycarbonyl dimethylmethyloxyphenyl]prop-2-en-1-one

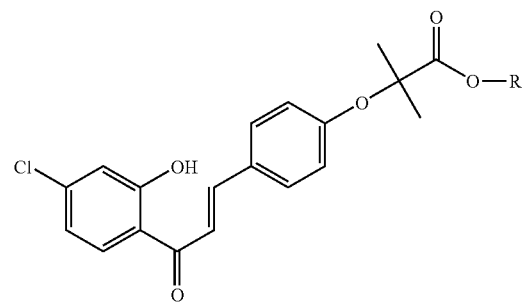

R=—H, —CH(CH$_3$)$_2$

1-[2-hydroxyphenyl]-3-[4-carboxydimethylmethyloxyphenyl]prop-2-en-1-one and 1-[2-hydroxyphenyl]-3-[4-isopropyloxycarbonyldimethylmethyloxyphenyl]prop-2-en-1-one

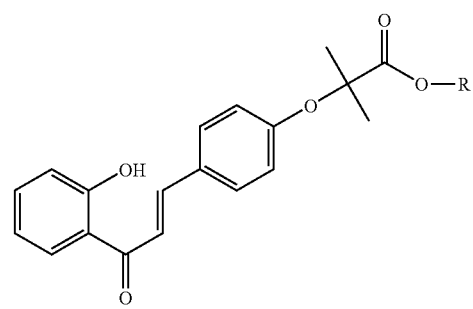

R=—H, —CH(CH$_3$)$_2$

1-[2-methylcarbonyloxyphenyl]-3-[4-carboxydimethylm-
ethyloxyphenyl]prop-2-en-1-one and 1-[2-methylcarbo-
nyloxyphenyl]-3-[4-isopropyloxycarbonyldimethyl
methyloxyphenyl]prop-2-en-1-one 1-[2-hydroxyphenyl]-3-[3-carboxydimethylmethyloxy-4-
hydroxy-5-tertbutylphenyl]prop-2-en-1-one and 1-[2-hy-
droxyphenyl]-3-[3-isopropyloxycarbonyldimethyl-
methyloxy-4-hydroxy-5-tertbutylphenyl]prop-2-en-1-one

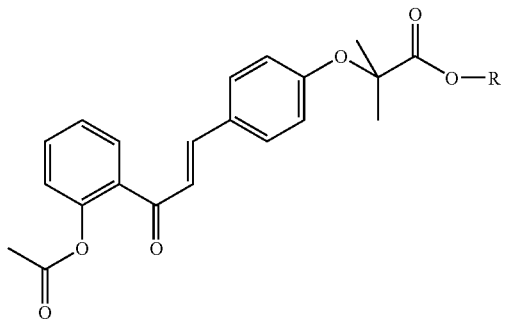

R=—H, —CH(CH$_3$)$_2$

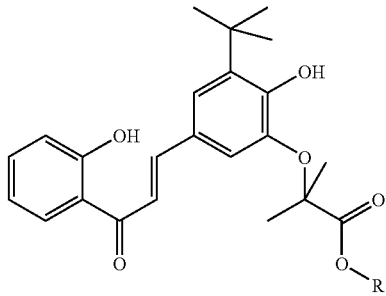

R=—H, —CH(CH$_3$)$_2$

1-[2-hydroxyphenyl]-3-[4-carboxydimethylmethyloxyphe-
nyl]-1-hydroxyiminoprop-2-ene and 1-[2-hydroxyphe-
nyl]-3-[4-isopropyloxycarbonyldimethyl-
methyloxyphenyl]-1-hydroxyiminoprop-2-ene 1-[2-hydroxy-4-chlorophenyl]-3-[3-carboxydimethylm-
ethyloxy-4-hydroxy-5-tertbutylphenyl]prop-2-en-1-one
and 1-[2-hydroxy-4-chlorophenyl]-3-[3-isopropyloxycar-
bonyldimethylmethyloxy-4-hydroxy-5-tertbutylphenyl]
prop-2-en-1-one

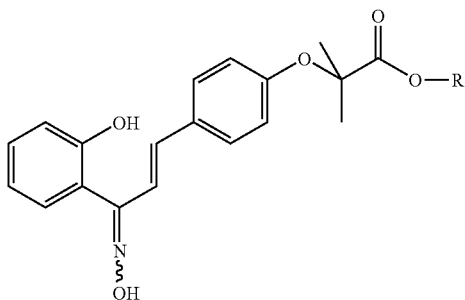

R=—H, —CH(CH$_3$)$_2$

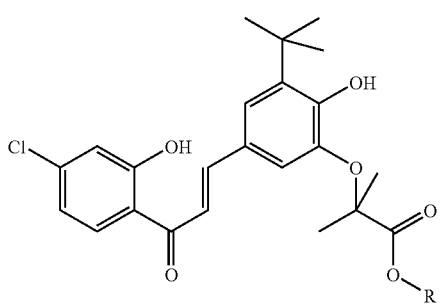

R=—H, —CH(CH$_3$)$_2$

1-[2-hydroxy-4-carboxydimethylmethyloxyphenyl]-3-[3,5-
ditertbutyl-4-hydroxyphenyl]prop-2-en-1-one, 1-[2-hy-
droxy-4-isopropyloxycarbonyldimethyl-
methyloxyphenyl]-3-[3,5-ditertbutyl-4-hydroxyphenyl]
prop-2-en-1-one and 1-[2-hydroxy-4-
ethoxycarbonyldimethylmethyloxyphenyl]-3-[3,5-
ditertbutyl-4-hydroxyphenyl]prop-2-en-1-one 1-[2-hydroxyphenyl]-3-[3-carboxydimethylmethyl-4-hy-
droxy-5-tertbutylphenyl]prop-2-en-1-one and 1-[2-hy-
droxyphenyl]-3-[3-isopropyloxycarbonyldimethyl-
methyl-4-hydroxy-5-tertbutylphenyl]prop-2-en-1-one

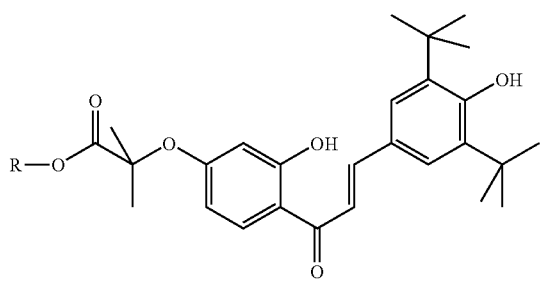

R=—H, —CH(CH$_3$)$_2$, —C$_2$H$_5$

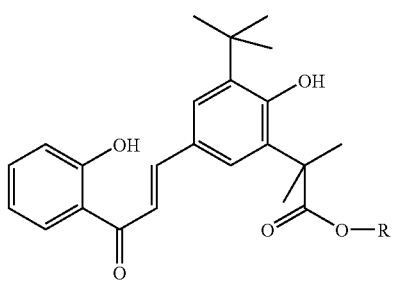

R=—H, —CH(CH3)$_2$

1-[2-hydroxy-4-chlorophenyl]-3-[3-carboxydimethylm-
ethyl-4-hydroxy-5-tertbutylphenyl]prop-2-en-1-one and
1-[2-hydroxy-4-chlorophenyl]-3-[3-isopropyloxycarbon-
yldimethylmethyl-4-hydroxy-5-tertbutylphenyl]prop-2-
en-1-one

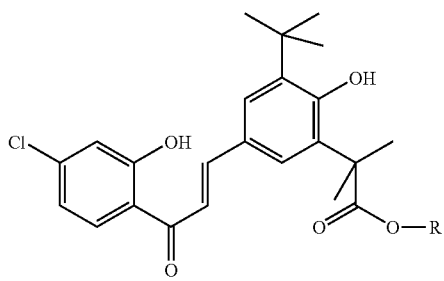

R=—H, —CH(CH$_3$)$_2$

1-[2-hydroxy-4-chlorophenyl]-3-[3,5-dimethoxy-4-car-
boxydimethylmethyl oxyphenyl]prop-2-en-1-one and
1-[2-hydroxy-4-chlorophenyl]-3-[3,5-dimethoxy-4-iso-
propyloxycarbonyldimethylmethyloxyphenyl]prop-2-en-
1-one

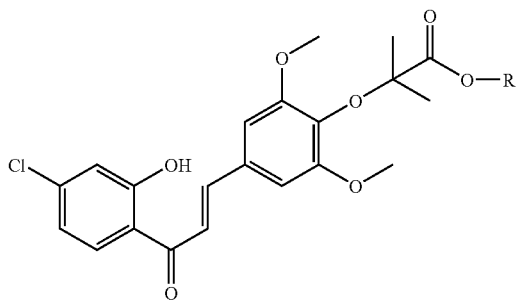

R=—H, —CH(CH$_3$)$_2$

1-[2-hydroxyphenyl]-3-[3,5-dimethoxy-4-carboxydimethyl-
methyloxyphenyl]prop-2-en-1-one and 1-[2-hydroxyphe-
nyl]-3-[3,5-dimethoxy-4-isopropyloxycarbonyldimethyl-
methyloxyphenyl]prop-2-en-1-one

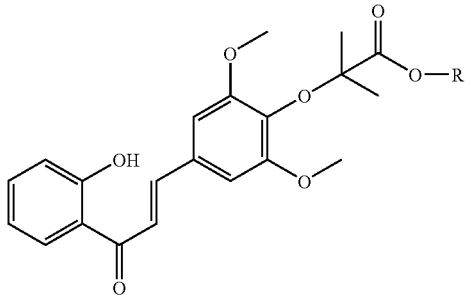

R=—H, —CH(CH$_3$)$_2$

1-[2-hydroxy-4-carboxydimethylmethyloxyphenyl]-3-[3,5-
dimethoxy-4-hydroxyphenyl]prop-2-en-1-one and 1-[2-
hydroxy-4-isopropyloxycarbonyldimethyl-
methyloxyphenyl]-3-[3,5-dimethoxy4-hydroxyphenyl]
prop-2-en-1-one

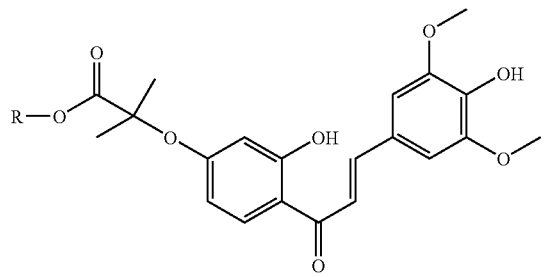

R=—H, —CH(CH$_3$)$_2$

1-[2-hydroxy-4-chlorophenyl]-3-[3,4-dihydroxy-5-carboxy-
dimethylmethyloxyphenyl]prop-2-en-1-one and 1-[2-hy-
droxy-4-chlorophenyl]-3-[3,4-dihydroxy-5-isopropy-
loxycarbonyldimethylmethyloxyphenyl]-2-propen-1-one

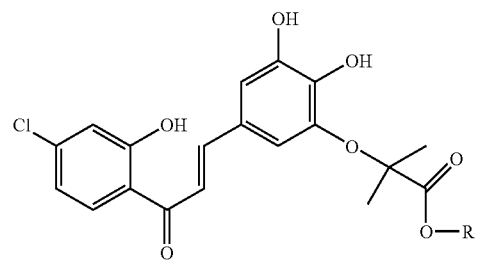

R=—H, —CH(CH$_3$)$_2$

1-[2-hydroxy-4-carboxydimethylmethyloxyphenyl]-3-[3,5-
dimethyl-4-hydroxyphenyl]prop-2-en-1-one and 1-[2-hy-
droxy-4-isopropyloxycarbonyl dimethylmethyloxyphe-
nyl]-3-[3,5-dimethyl-4-hydroxyphenyl]prop-2-en-1-one

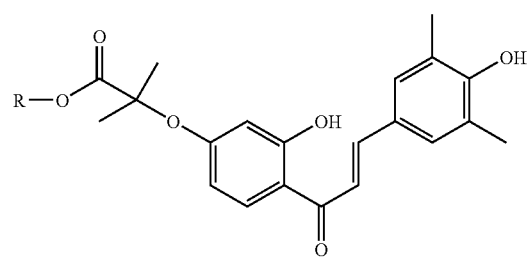

R=—H, —CH(CH$_3$)$_2$

1-[2-hydroxy-4-chlorophenyl]-3-[3,5-dimethyl-4-carboxydimethylmethyl oxyphenyl]prop-2-en-1-one and 1-[2-hydroxy-4-chlorophenyl]-3-[3,5-dimethyl-4-isopropyloxycarbonyldimethylmethyloxyphenyl]prop-2-en-1-one 1-[2-hydroxyphenyl]-3-[4-carboxydimethylmethylthiophenyl]prop-2-en-1-one and 1-[2-hydroxyphenyl]-3-[4-isopropyloxycarbonyldimethylmethylthiophenyl]prop-2-en-1-one

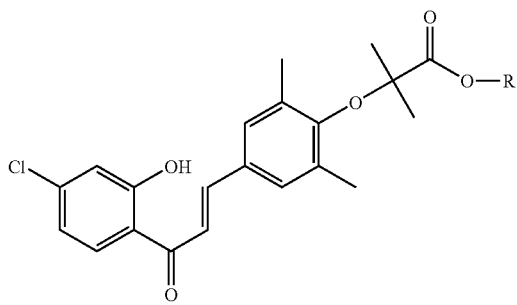

R=—H, —CH(CH₃)₂

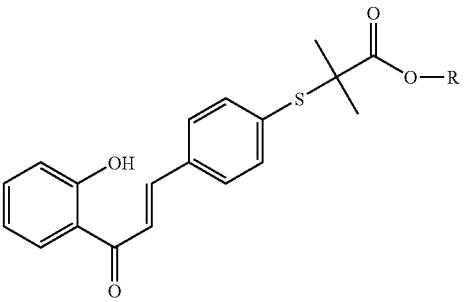

R=—H, —CH(CH₃)₂

1-[2-hydroxyphenyl]-3-[3,5-dimethyl-4-carboxydimethylmethyloxyphenyl]prop-2-en-1-one and 1-[2-hydroxyphenyl]-3-[3,5-dimethyl-4-isopropyloxycarbonyl dimethylmethyloxyphenyl]prop-2-en-1-one 1-[2-mercapto-4-methyloxyphenyl]-3-[4-carboxydimethylmethyloxyphenyl]prop-2-en-1-one and 1-[2-mercapto-4-methyloxyphenyl]-3-[4-isopropyloxycarbonyldimethylmethyloxyphenyl]prop-2-en-1-one

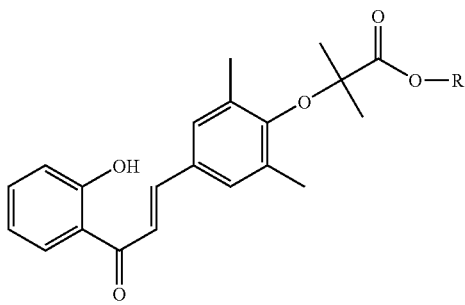

R=—H, —CH(CH₃)₂

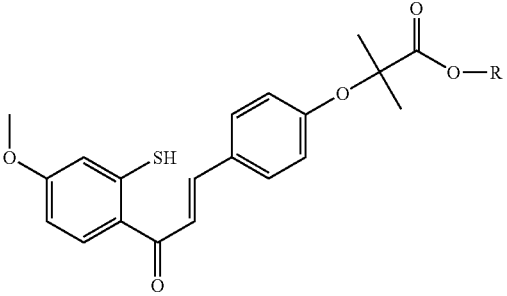

R=—H, —CH(CH₃)₂

1-[2-hydroxyphenyl]-3-[3-carboxydimethylmethyloxyphenyl]prop-2-en-1-one and 1-[2-hydroxyphenyl]-3-[3-isopropyloxycarbonyldimethylmethyloxyphenyl]prop-2-en-1-one 1-[4-heptylphenyl]-3-[3-methyl-4-carboxydimethylmethyloxyphenyl]prop-2-en-1-one and 1-[4-heptylphenyl]-3-[3-methyl-4-isopropyloxycarbonyldimethylmethyloxyphenyl]prop-2-en-1-one

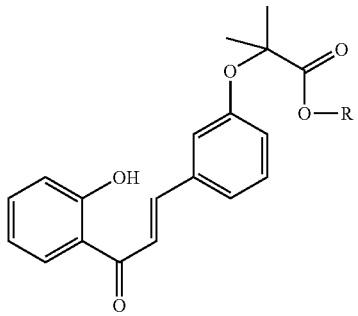

R=—H, —CH(CH₃)₂

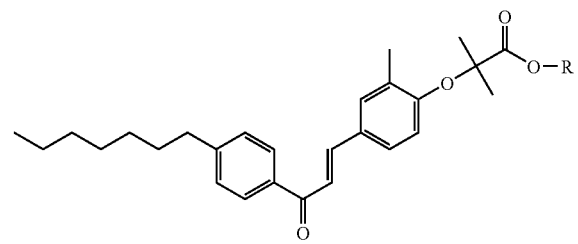

R=—H, —CH(CH₃)₂

15

1-[2-hydroxy-4-carboxydimethylmethyloxyphenyl]-3-[3,5-dibromo-4-hydroxyphenyl]prop-2-en-1-one

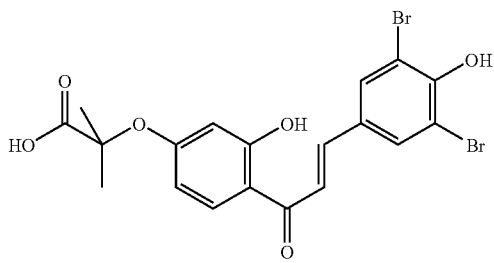

1-[2-hydroxy-4-carboxydimethylmethyloxyphenyl]-3-[3-hydroxyphenyl]prop-2-en-1-one

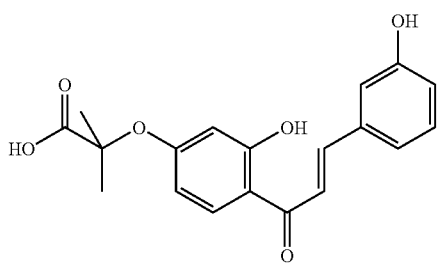

1-[2-hydroxy-4-carboxydimethylmethyloxyphenyl]-3-[4-methylthiophenyl]prop-2-en-1-one

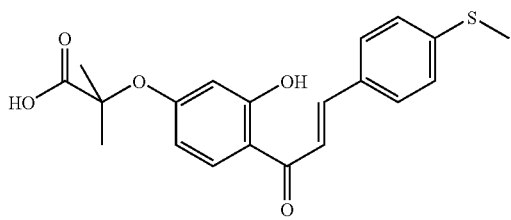

1-[2,4-dihydroxyphenyl]-3-[4-carboxydimethylmethyloxyphenyl]prop-2-en-1-one

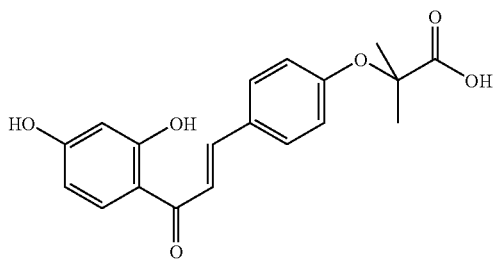

16

1-[4-hydroxyphenyl]-3-[4-carboxydimethylmethyloxyphenyl]prop-2-en-1-one

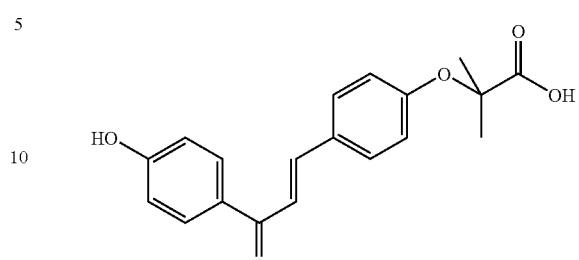

1-[4-chlorophenyl]-3-[3,5-dimethyl-4-tertbutyloxycarbonyldimethylmethyloxyphenyl]prop-2-en-1-one

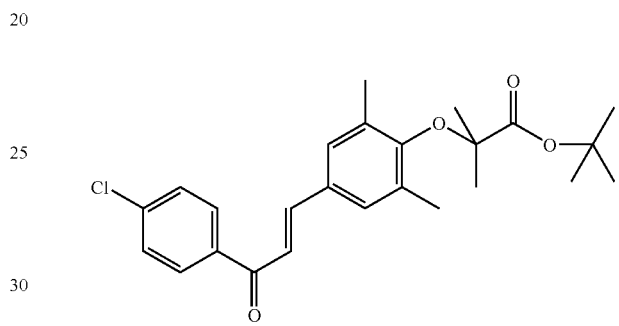

1-[4-chlorophenyl]-3-[3,5-dimethyl-4-isopropyloxycarbonyldimethylmethyloxyphenyl]prop-2-en-1-one

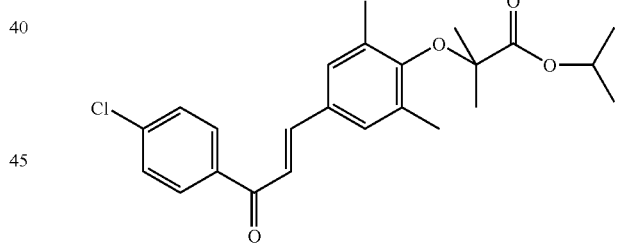

1-[4-chlorophenyl]-3-[3,5-dimethyl-4-carboxydimethylmethyloxyphenyl]prop-2-en-1-one

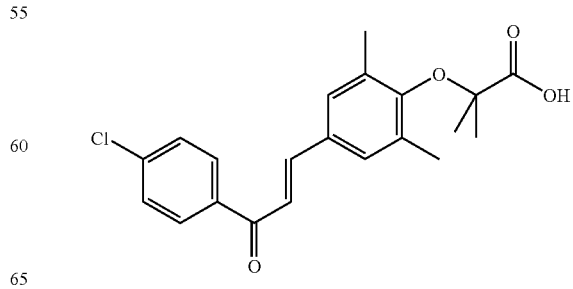

17
1-[2-hydroxy-4-carboxydimethylmethyloxyphenyl]-3-[4-chlorophenyl]prop-2-en-1-one

18
1-[4-carboxydimethylmethyloxyphenyl]-3-[4-chlorophenyl]prop-2-en-1-one

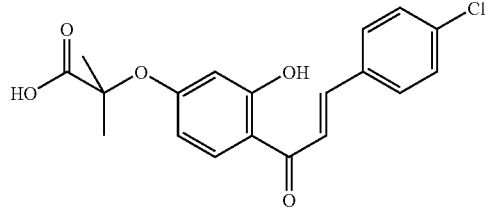

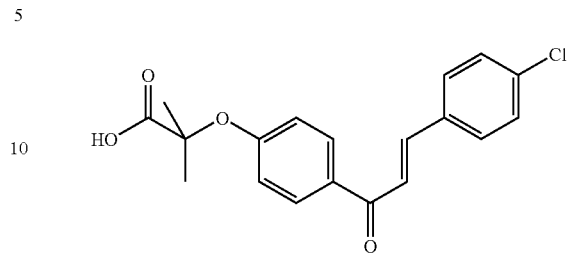

1-[4-chloro-2-hydroxyphenyl]-3-[4-carboxydimethylmethylthiophenyl]prop-2-en-1-one 1-[4-carboxydimethylmethylthiophenyl]-3-[4-methylthiophenyl]prop-2-en-1-one

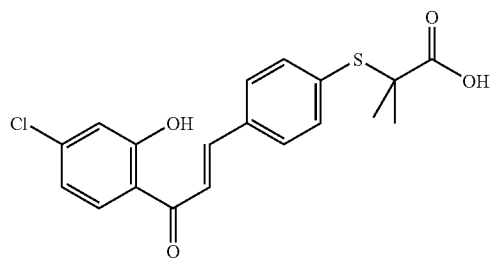

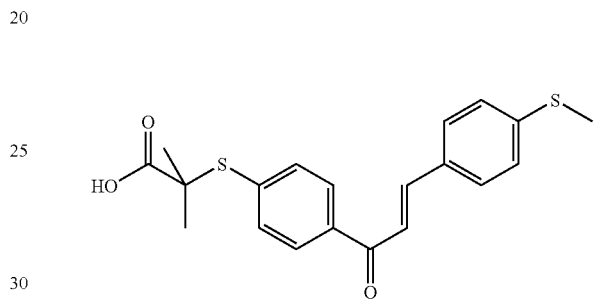

1-[4-carboxydimethylmethyloxyphenyl]-3-[3,5-dimethyl-4-hydroxyphenyl]prop-2-en-1-one 1-[2-hydroxy-4-bromophenyl]-3-[3,5-dimethyl-4-carboxydimethylmethyloxyphenyl]prop-2-en-1-one

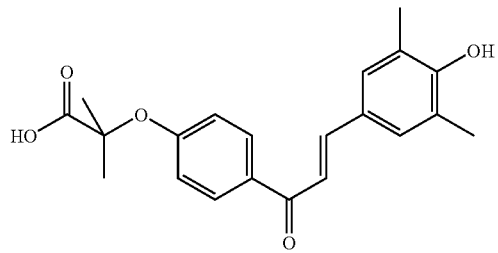

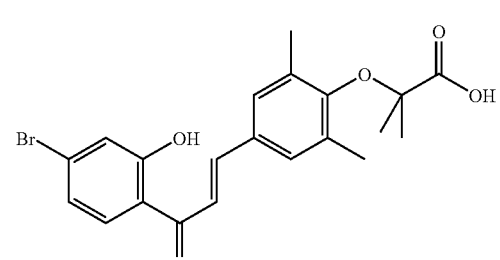

1-[4-methylthiophenyl]-3-[4-carboxydimethylmethyloxyphenyl]prop-2-en-1-one

1-[4-carboxydimethylmethyloxyphenyl]-3-[4-methylthiophenyl]prop-2-en-1-one

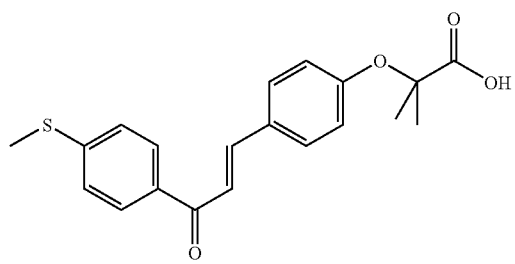

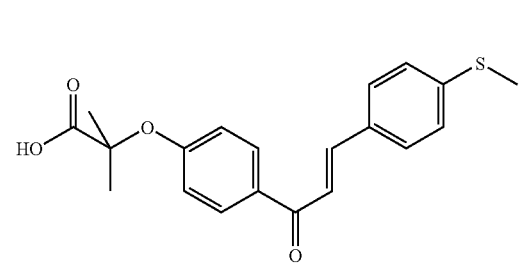

1-[4-methylthiophenyl]-3-[3,5-dimethyl-4-tertbutyloxycar-
bonyldimethylmethyloxyphenyl]prop-2-en-1-one

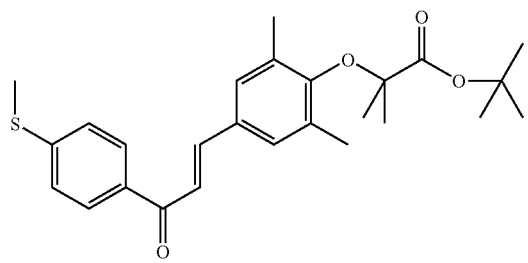

1-[4-methylthiophenyl]-3-[3,5-dimethyl-4-isopropyloxycar-
bonyldimethylmethyloxyphenyl]prop-2-en-1-one

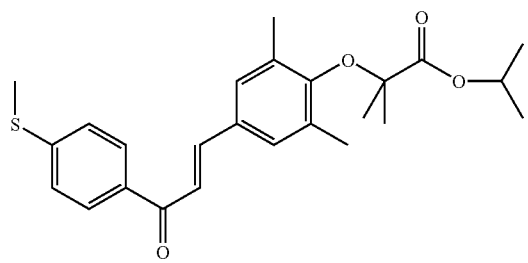

1-[4-methylthiophenyl]-3-[3,5-dimethyl-4-carboxydimeth-
ylmethyloxyphenyl]prop-2-en-1-one

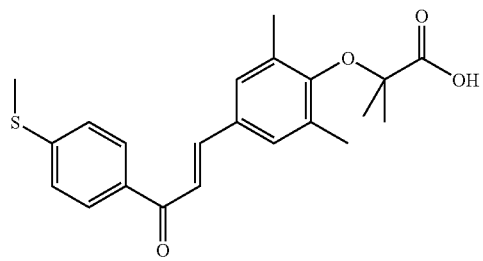

1-[2-methoxyphenyl]-3-[3,5-dimethyl-4-tertbutyloxycarbo-
nyldimethylmethyloxyphenyl]prop-2-en-1-one

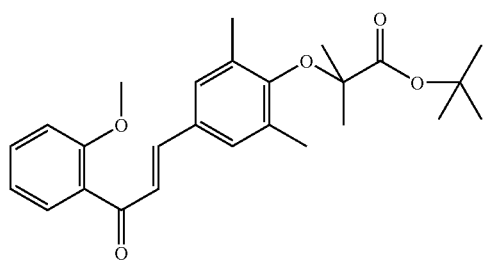

1-[2-methoxyphenyl]-3-[3,5-dimethyl-4-carboxydimethyl-
methyloxyphenyl]prop-2-en-1-one

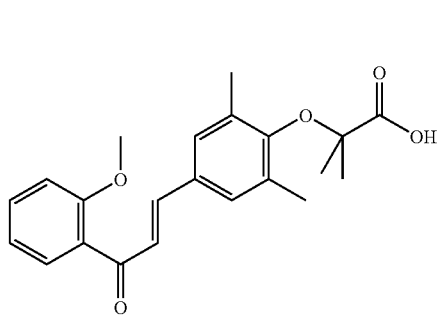

1-[4-hexyloxyphenyl]-3-[3,5-dimethyl-4-tertbutyloxycarbo-
nyldimethylmethyloxyphenyl]prop-2-en-1-one

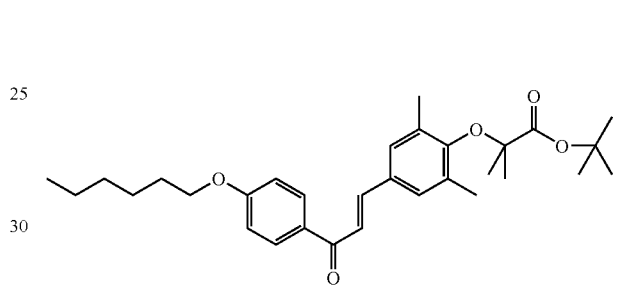

1-[4-hexyloxyphenyl]-3-[3,5-dimethyl-4-carboxydimethyl-
methyloxyphenyl]prop-2-en-1-one

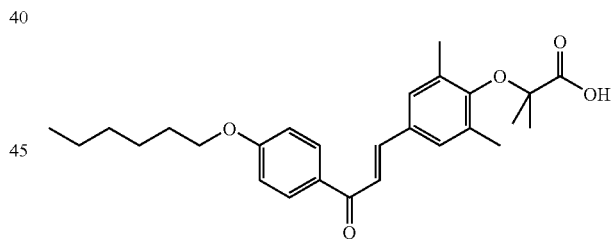

2-(3,5-dimethyl-4-tertbutyloxycarbonyldimethyl-
methyloxyphenyl)-7-chloro-4H-1-benzopyran-4-one

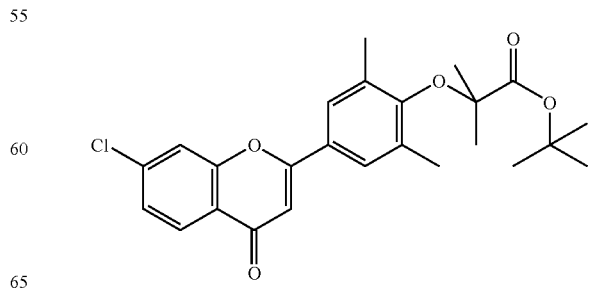

21

2-(3,5-dimethyl-4-carboxydimethylmethyloxyphenyl)-7-chloro-4H-1-benzopyran-4-one

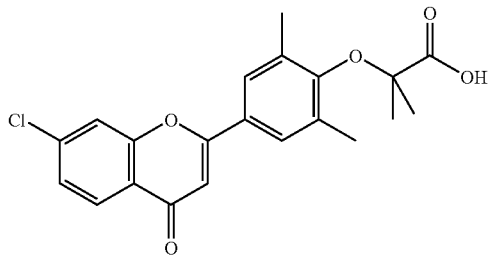

1-[2-methyloxy-4-chlorophenyl]-3-[3,5-dimethyl-4-tertbutyloxycarbonyldimethylmethyloxyphenyl]prop-2-en-1-one

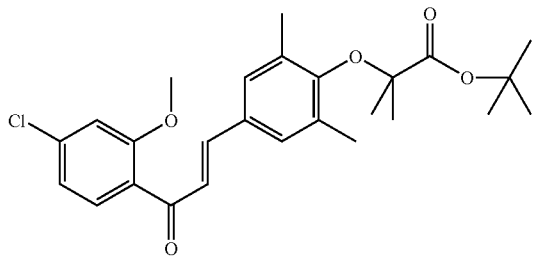

1-[2-methyloxy-4-chlorophenyl]-3-[3,5-dimethyl-4-carboxydimethylmethyloxyphenyl]prop-2-en-1-one

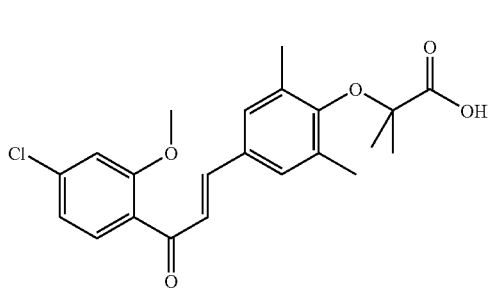

1-[4-heptylphenyl]-3-[3,5-dimethyl-4-tertbutyloxycarbonyldimethylmethyloxyphenyl]prop-2-en-1-one

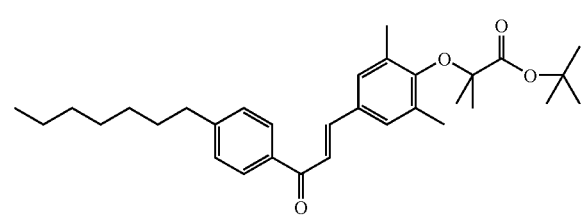

22

1-[4-heptylphenyl]-3-[3,5-dimethyl-4-carboxydimethylmethyloxyphenyl]prop-2-en-1-one

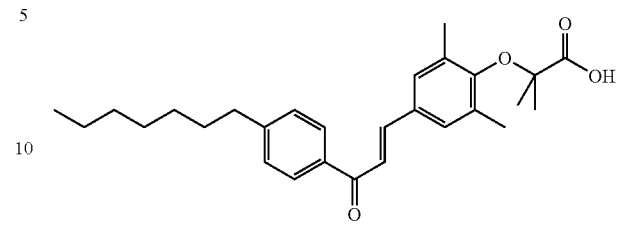

1-[4-bromophenyl]-3-[3,5-dimethyl-4-tertbutyloxycarbonyldimethylmethyloxyphenyl]prop-2-en-1-one

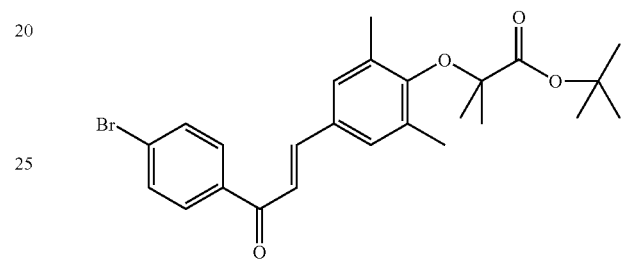

1-[4-bromophenyl]-3-[3,5-dimethyl-4-carboxy dimethylmethyloxyphenyl]prop-2-en-1-one

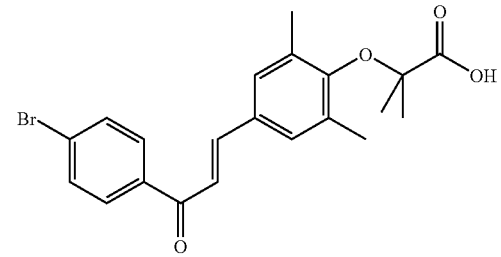

1-[4-trifluoromethylphenyl]-3-[3-methyl-4-tertiobutyloxycarbonylmethyloxyphenyl]prop-2-en-1-one

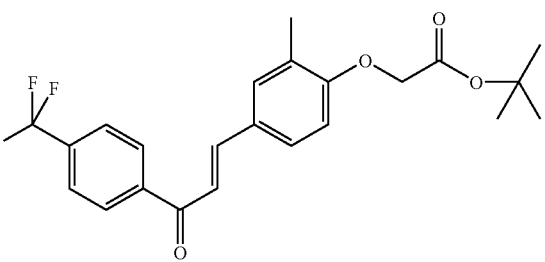

23

1-[4-trifluoromethylphenyl]-3-[3-methyl-4-carboxymethyloxyphenyl]prop-2-en-1-one

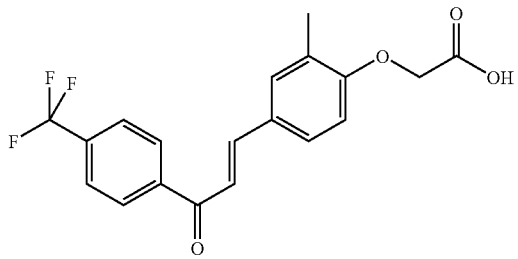

1-[4-bromophenyl]-3-[3-tertiobutyl-4-tertiobutyloxycarbonyldimethylmethyloxyphenyl]prop-2-en-1-one

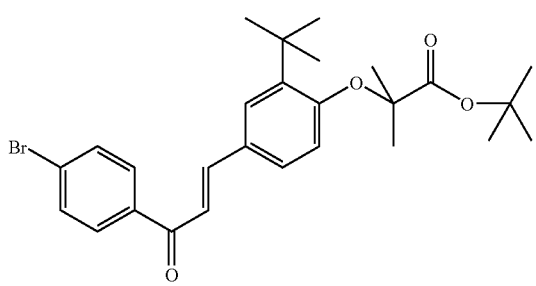

1-[4-bromophenyl]-3-[3-tertiobutyl-4-carboxydimethylmethyloxyphenyl]prop-2-en-1-one

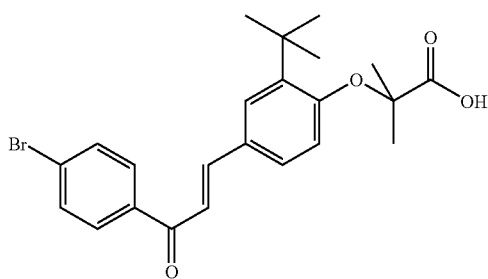

1-[4-bromophenyl]-3-[3-trifluoromethyl-4-carboxydimethylmethyloxyphenyl]prop-2-en-1-one

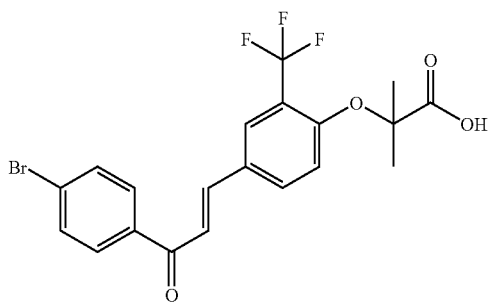

24

1-[2-trifluoromethyloxyphenyl]-3-[3,5-dimethyl-4-tertiobutyloxycarbonyldimethylmethyloxyphenyl]prop-2-en-1-one

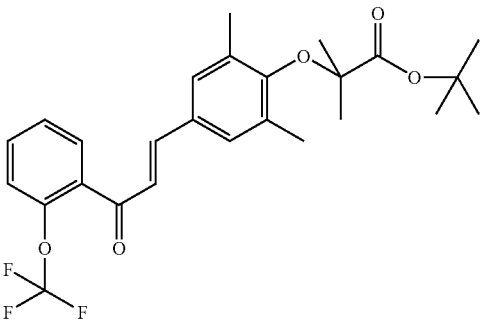

1-[2-trifluoromethyloxyphenyl]-3-[3,5-dimethyl-4-carboxydimethylmethyloxyphenyl]prop-2-en-1-one

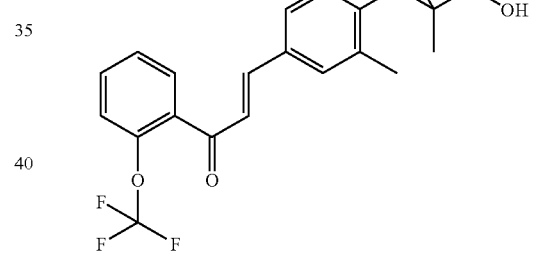

1-[4-bromophenyl]-3-[3-cyclohexyl-4-tertiobutyloxycarbonyldimethylmethyloxyphenyl]prop-2-en-1-one

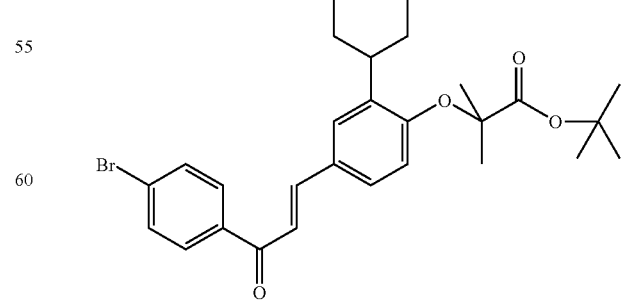

25

1-[4-bromophenyl]-3-[3-cyclohexyl-4-carboxydimethylm-
ethyloxyphenyl]prop-2-en-1-one

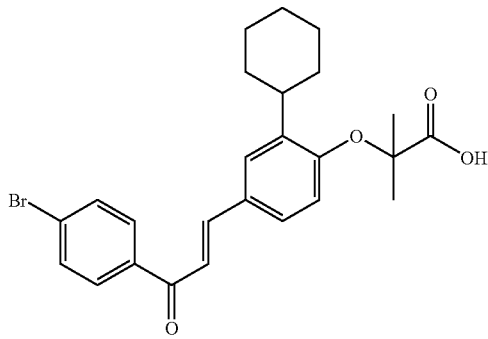

1-[4-methylthiophenyl]-3-[3-trifluoromethyl-4-tertiobuty-
loxycarbonyldimethylmethyloxyphenyl]prop-2-en-1-one

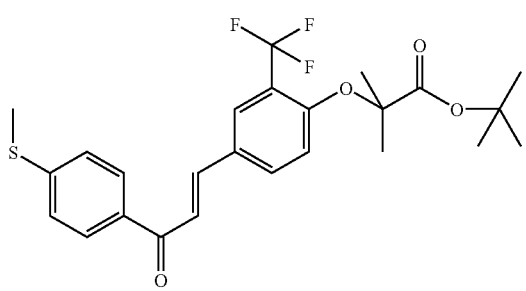

1-[4-methylthiophenyl]-3-[3-trifluoromethyl-4-carboxy-
dimethylmethyloxyphenyl]prop-2-en-1-one

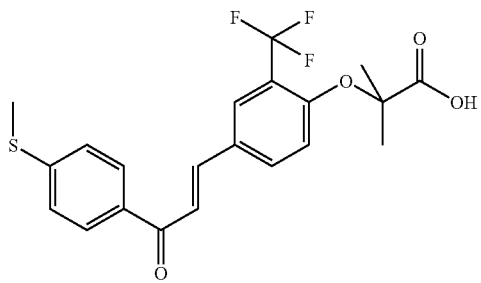

1-[4-methylsulfonylphenyl]-3-[3,5-dimethyl-4-tertiobuty-
loxycarbonyldimethylmethyloxyphenyl]prop-2-en-1-one

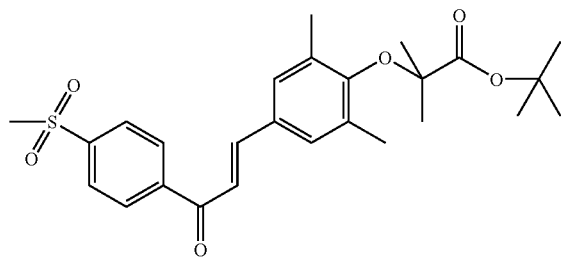

26

1-[4-methylsulfonylphenyl]-3-[3,5-dimethyl-4-carboxydim-
ethylmethyloxyphenyl]prop-2-en-1-one

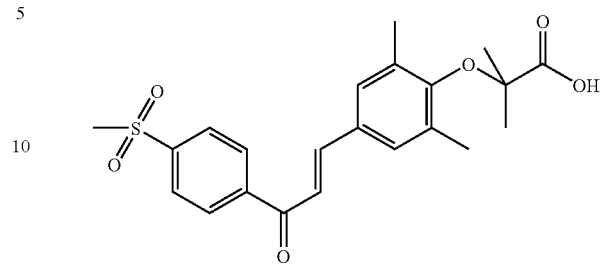

1-[4-trifluoromethylthiophenyl]-3-[3,5-dimethyl-4-tertiobu-
tyloxycarbonyldimethylmethyloxyphenyl]prop-2-en-1-
one

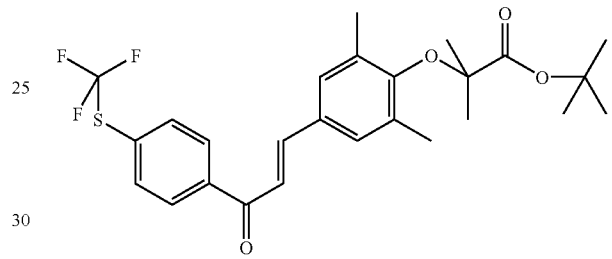

1-[4-trifluoromethylthiophenyl]-3-[3,5-dimethyl-4-car-
boxydimethylmethyloxyphenyl]prop-2-en-1-one

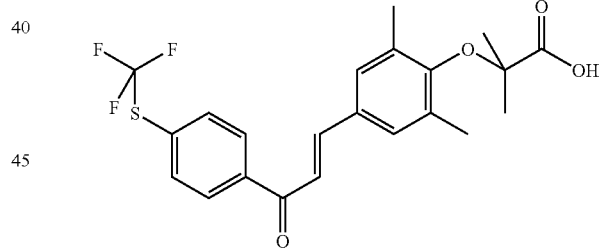

1-[4-isopropylphenyl]-3-[3,5-dimethyl-4-tertiobutyloxycar-
bonyldimethylmethyloxyphenyl]prop-2-en-1-one

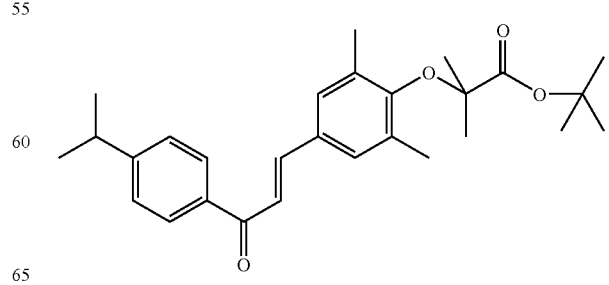

27

1-[4-isopropylphenyl]-3-[3,5-dimethyl-4-carboxydimethyl-
methyloxyphenyl]prop-2-en-1-one

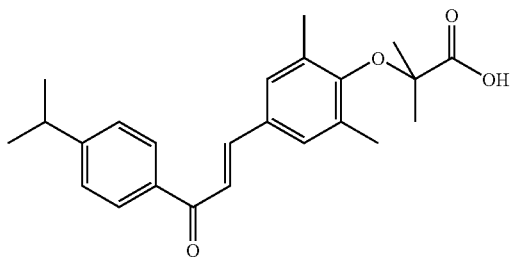

1-[4-trifluoromethylphenyl]-3-[3,5-dimethyl-4-tertiobuty-
loxycarbonyldimethylmethyloxyphenyl]prop-2-en-1-one

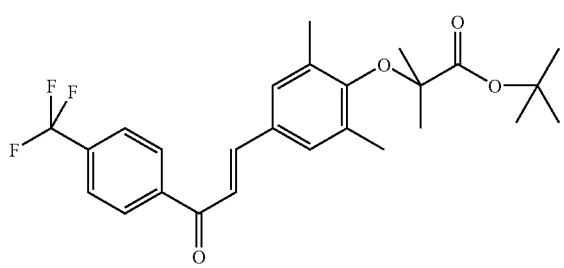

1-[4-trifluoromethylphenyl]-3-[3,5-dimethyl-4-carboxy-
dimethylmethyloxyphenyl]prop-2-en-1-one

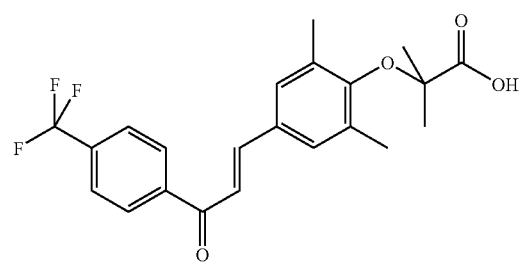

1-[4-hydroxyphenyl]-3-[3,5-dimethyl-4-carboxydimethyl-
methyloxyphenyl]prop-2-en-1-one

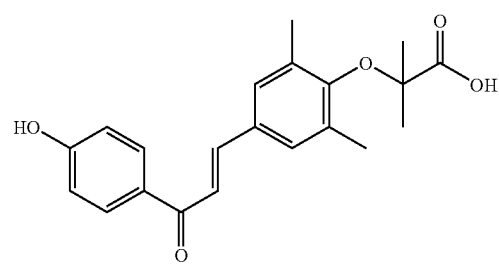

28

1-[2-methylthiophenyl]-3-[3,5-dimethyl-4-tertiobutyloxy-
carbonyldimethylmethyloxyphenyl]prop-2-en-1-one

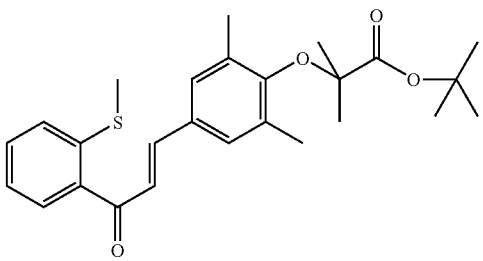

1-[2-methylthiophenyl]-3-[3,5-dimethyl-4-carboxydimeth-
ylmethyloxyphenyl]prop-2-en-1-one

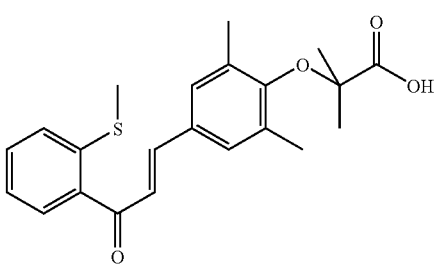

1-[4-trifluoromethyloxyphenyl]-3-[3,5-dimethyl-4-tertiobu-
tyloxycarbonyldimethylmethyloxyphenyl]prop-2-en-1-
one

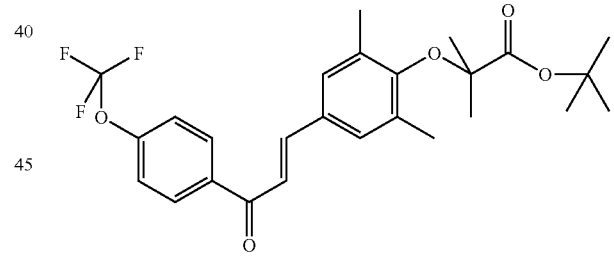

1-[4-trifluoromethyloxyphenyl]-3-[3,5-dimethyl-4-carboxy-
dimethylmethyloxyphenyl]prop-2-en-1-one

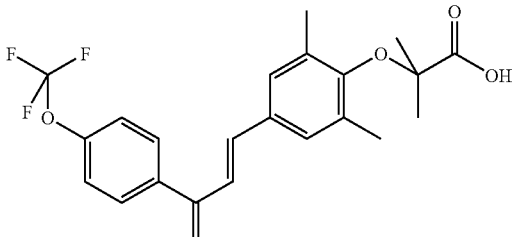

29

1-[4-iodophenyl]-3-[3,5-dimethyl-4-tertiobutyloxycarbon-
yldimethylmethyloxyphenyl]prop-2-en-1-one

30

1-[4-fluorophenyl]-3-[3,5-dimethyl-4-tertiobutyloxycarbon-
yldimethylmethyloxyphenyl]prop-2-en-1-one

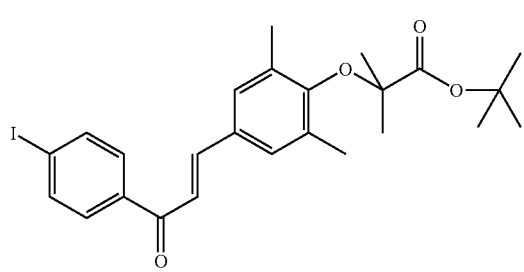

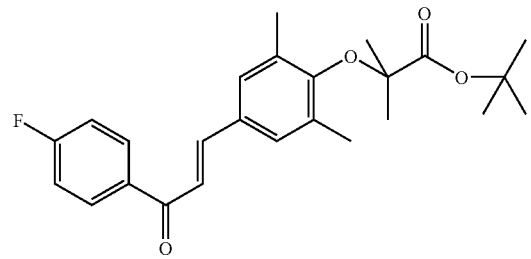

1-[4-fluorophenyl]-3-[3,5-dimethyl-4-carboxydimethylm-
ethyloxyphenyl]prop-2-en-1-one 1-[4-iodophenyl]-3-[3,5-dimethyl-4-carboxydimethylm-
ethyloxyphenyl]prop-2-en-1-one

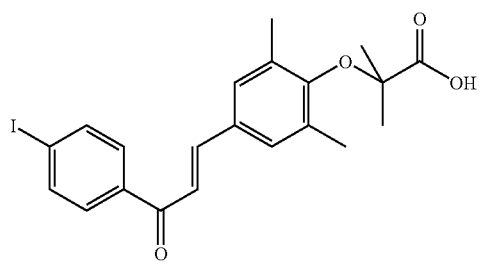

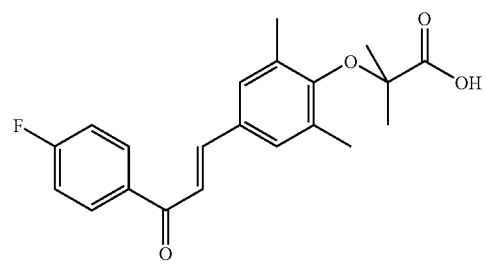

1-[4-nonyloxyphenyl]-3-[3,5-dimethyl-4-tertiobutyloxycar-
bonyldimethylmethyloxyphenyl]prop-2-en-1-one

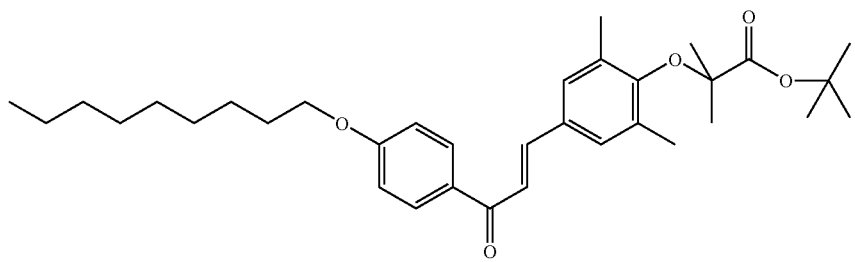

1-[4-nonyloxyphenyl]-3-[3,5-dimethyl-4-carboxydimethyl-
methyloxyphenyl]prop-2-en-1-one

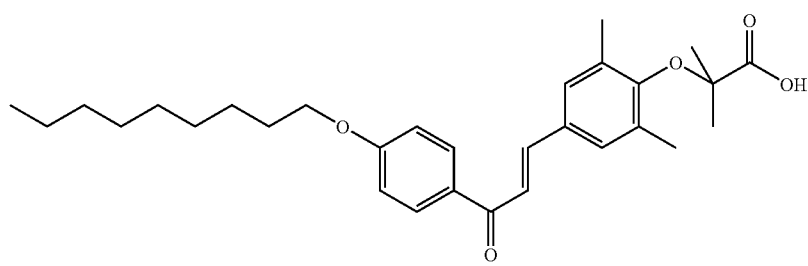

31

1-[4-propyloxyphenyl]-3-[3,5-dimethyl-4-tertiobutyloxy-
carbonyldimethylmethyloxyphenyl]prop-2-en-1-one

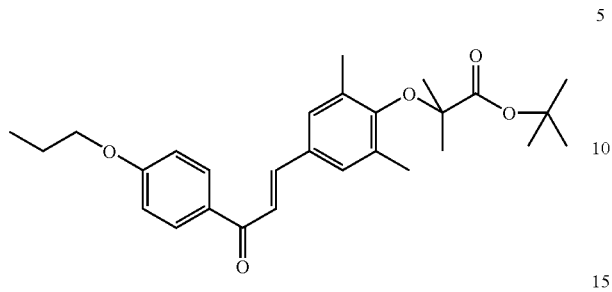

1-[4-propyloxyphenyl]-3-[3,5-dimethyl-4-carboxydimeth-
ylmethyloxyphenyl]prop-2-en-1-one

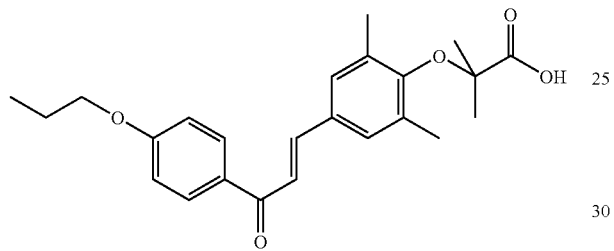

1-[4-methylthiophenyl]-3-[3,5-dimethyl-4-tertiobutyloxy-
carbonylmethyloxyphenyl]prop-2-en-1-one

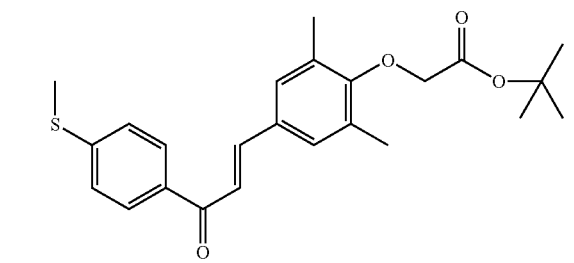

1-[4-methylthiophenyl]-3-[3,5-dimethyl-4-carboxymethy-
loxyphenyl]prop-2-en-1-one

32

1-[4-methylthiophenyl]-3-[3,5-diisopropyl-4-tertiobuty-
loxycarbonylmethyloxyphenyl]prop-2-en-1-one

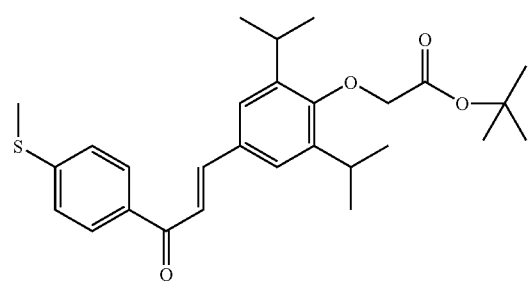

1-[4-methylthiophenyl]-3-[3,5-diisopropyl-4-carboxym-
ethyloxyphenyl]prop-2-en-1-one

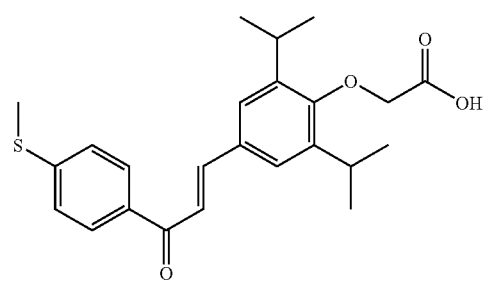

1-[4-(2-bromoethyloxy)phenyl]-3-[3,5-dimethyl-4-carboxy-
dimethylmethyloxyphenyl]prop-2-en-1-one

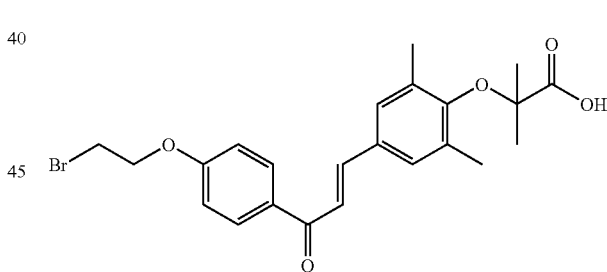

1-[4-octadecyloxyphenyl]-3-[3,5-dimethyl-4-tertiobuty-
loxycarbonyldimethylmethyloxyphenyl]prop-2-en-1-one

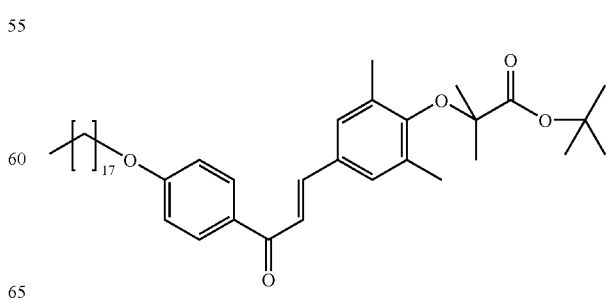

33

1-[4-octadecyloxyphenyl]-3-[3,5-dimethyl-4-carboxydimethylmethyloxyphenyl]prop-2-en-1-one

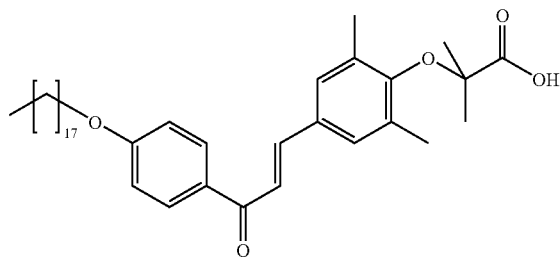

1-[4-dodecyloxyphenyl]-3-[3,5-dimethyl-4-tertiobutyloxycarbonyldimethylmethyloxyphenyl]prop-2-en-1-one

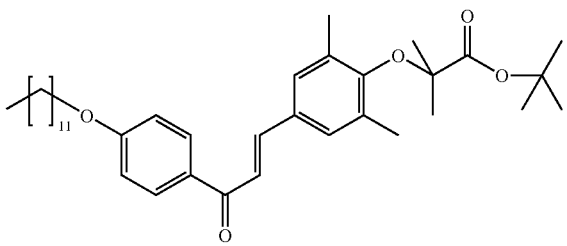

1-[4-dodecyloxyphenyl]-3-[3,5-dimethyl-4-carboxydimethylmethyloxyphenyl]prop-2-en-1-one

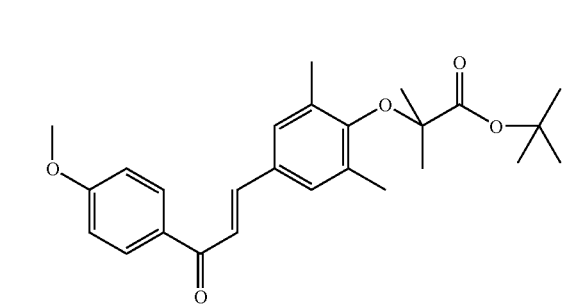

1-[4-methyloxyphenyl]-3-[3,5-dimethyl-4-tertiobutyloxycarbonyldimethylmethyloxyphenyl]prop-2-en-1-one

34

1-[4-methyloxyphenyl]-3-[3,5-dimethyl-4-carboxydimethylmethyloxyphenyl]prop-2-en-1-one

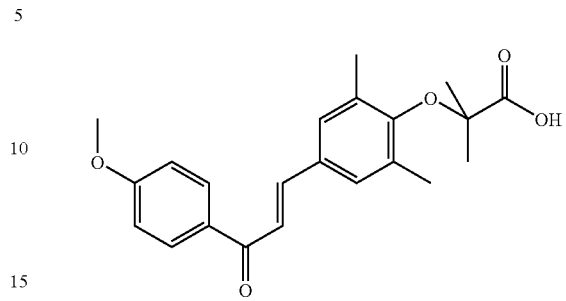

1-[2-hexyloxyphenyl]-3-[3,5-dimethyl-4-tertiobutyloxycarbonyldimethylmethyloxyphenyl]prop-2-en-1-one

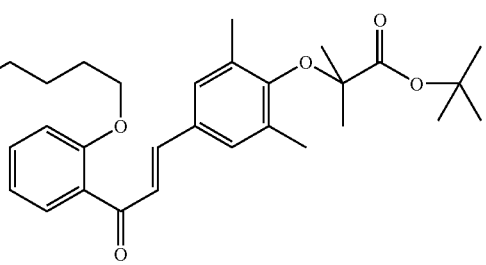

1-[2-hexyloxyphenyl]-3-[3,5-dimethyl-4-carboxydimethylmethyloxyphenyl]prop-2-en-1-one

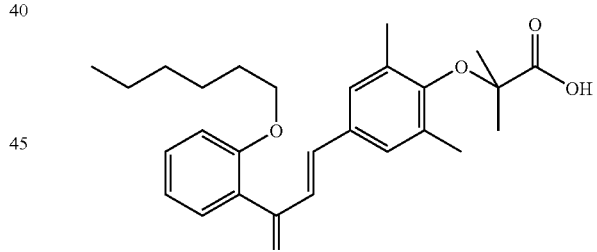

1-[4-hexylthiophenyl]-3-[3,5-dimethyl-4-tertiobutyloxycarbonyldimethylmethyloxyphenyl]prop-2-en-1-one

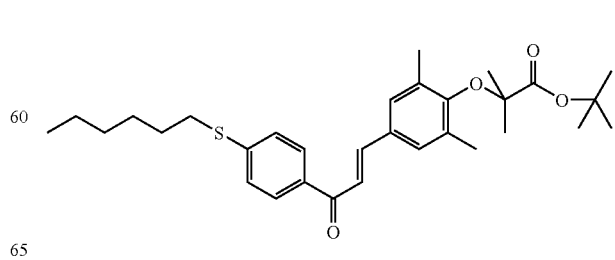

1-[4-hexylthiophenyl]-3-[3,5-dimethyl-4-carboxydimethyl-methyloxyphenyl]prop-2-en-1-one

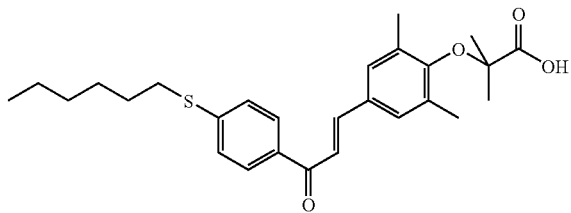

1-[4-tertiobutyloxycarbonyldimethylmethyloxyphenyl]-3-[3,5-ditertiobutyl-4-hydroxyphenyl]prop-2-en-1-one

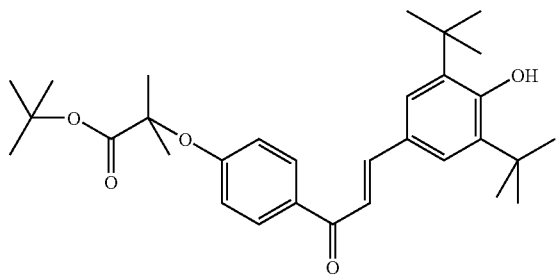

1-[4-carboxydimethylmethyloxyphenyl]-3-[3,5-ditertiobutyl-4-hydroxyphenyl]prop-2-en-1-one

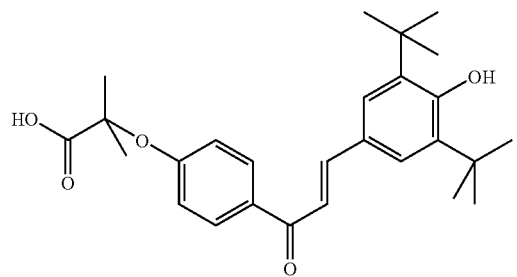

The inventive compounds also include their optical and geometric isomers, salts, solvates and prodrugs, which after administration to a subject, are converted to compounds represented by formula (I) and/or metabolites of compounds represented by formula (I) which display similar therapeutic activity to compounds represented by formula (I).

According to the invention, the most preferred compounds are indicated below:
1-[4-methylthiophenyl]-3-[3,5-dimethyl-4-carboxydimethylmethyloxyphenyl]prop-2-en-1-one,
1-[4-bromophenyl]-3-[3,5-dimethyl-4-carboxydimethylmethyloxyphenyl]prop-2-en-1-one,
1-[4-trifluoromethyloxyphenyl]-3-[3,5-dimethyl-4-carboxydimethylmethyloxyphenyl]prop-2-en-1-one,
1-[4-trifluoromethylphenyl]-3-[3,5-dimethyl-4-carboxydimethylmethyloxyphenyl]prop-2-en-1-one,
1-[4-hexyloxyphenyl]-3-[3,5-dimethyl-4-carboxydimethylmethyloxyphenyl]prop-2-en-1-one,
1-[4-trifluoromethylthiophenyl]-3-[3,5-dimethyl-4-carboxydimethylmethyloxyphenyl]prop-2-en-1-one,
1-[4-propyloxyphenyl]-3-[3,5-dimethyl-4-carboxydimethylmethyloxyphenyl]prop-2-en-1-one.

The invention concerns also a pharmaceutical composition comprising, in a pharmaceutically acceptable support, at least one compound represented by formula (I) such as defined hereinabove, possibly in association with another active therapeutic agent.

The invention also concerns the use of at least one compound represented by formula (I) for preparing a pharmaceutical composition for practicing a method of treatment of the human or animal body.

The pharmaceutical compositions or compounds represented by formula (I) according to the invention are advantageously used for the treatment of cerebrovascular pathology, such as cerebral ischemia or cerebral hemorrhagic stroke, a pathology related to inflammation, neurodegeneration, deregulations of lipid and/or glucose metabolism, cell proliferation and/or differentiation and/or skin or central nervous system ageing, such as allergy, asthma, eczema, psoriasis, pruritus, Alzheimer's disease, Parkinson's disease, diabetes, atherosclerosis, obesity, carcinogenesis, etc. In fact, it was found surprisingly that compounds represented by formula (I) have advantageous pharmacological properties as antioxidants and activators of PPAR, specifically PPARα and PPARγ.

The compositions comprising at least one compound represented by formula (I) such as described hereinabove may or may not include at least one compound represented by formula (I), wherein:
X1, X2, X3 and X5 each represent a hydrogen atom, X6 represents an oxygen atom and X4 represents a group corresponding to the formula —O—CR$_8$R$_9$—COOR$_{10}$, where R$_8$ and R$_9$, which are the same or different, represent a C1 to C2 alkyl group, and R$_{10}$ represents a hydrogen atom or a C1 to C7 alkyl group, and
X2, X3 and X5 each represent a hydrogen atom, X1 represents a halogen atom or a R1 or -G1-R1 group, where R1 represents an unsubstituted C1-C2 alkyl group and G1 represents an oxygen atom, X6 represents an oxygen atom and X$_4$ represents a group corresponding to the formula —O—CR$_{11}$R$_{12}$—COOR$_{10}$, where R$_{11}$ and R$_{12}$, which are the same or different, represent a hydrogen atom or a C1 to C2 alkyl group, and R$_{10}$ represents a hydrogen atom or a C1 to C7 alkyl group, and
X2 represents a hydrogen atom and X1 represents -G1-R1 where G1 represents an oxygen atom and R1 represents —CH$_2$COOH.

The invention also concerns a method for treating pathologies related to cerebrovascular pathology, such as cerebral ischemia or cerebral hemorrhagic stroke, a pathology related to inflammation, neurodegeneration, deregulations of lipid and/or glucose metabolism, cell proliferation and/or differentiation and/or skin or central nervous system ageing, such as allergy, asthma, eczema, psoriasis, pruritus, Alzheimer's disease, Parkinson's disease, diabetes, atherosclerosis, obesity, carcinogenesis, etc. comprising administering to a subject, particularly human, an effective dose of a compound represented by general formula (I) or of a pharmaceutical composition such as defined hereinabove.

The invention also provides a method for preparing compounds represented by formula (I).

The method according to the invention comprises contacting in basic medium or in acidic medium at least one compound represented by formula (A) with at least one compound represented by formula (B), formulas (A) and (B) being:

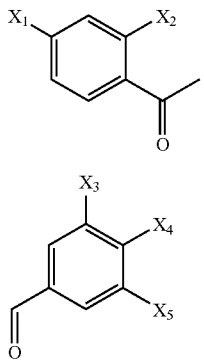

formulas in which X1, X2, X3, X4 and X5 are such as defined hereinabove.

The conditions for carrying out said reaction in acidic or basic medium are within reach of those skilled in the art and wide variations are possible.

Said two compounds are advantageously contacted in stoechiometric proportions. Contact is preferably done at room temperature (between approximately 18° C. and 25° C.) and at atmospheric pressure.

In basic medium, the reaction is preferably carried out in the presence of a strong base, such as an alkaline earth metal hydroxide, like sodium hydroxide or an alkaline metal alcoholate like sodium ethylate.

In acidic medium, the reaction is preferably carried out in the presence of a strong acid, such as hydrochloric acid.

The reaction pathway may be depicted as follows:

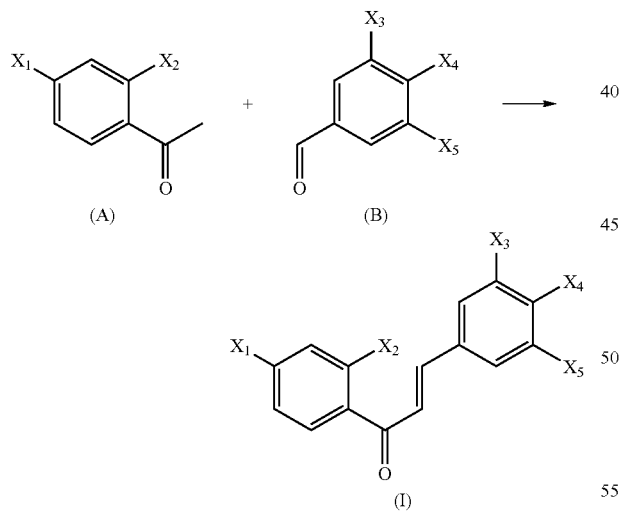

The synthesis in basic medium may be carried out in the following manner:

One molar equivalent of ketone (compound (A)) and one molar equivalent of aldehyde (compound (B)) are solubilized in a hydroalcoholic solution of 20 molar equivalents of sodium hydroxide. The mixture is stirred for approximately 18 hours at room temperature (between 18° C. and 25° C.). The medium is then acidified (in particular to a pH of approximately 2) in particular with hydrochloric acid. The expected substituted 1,3-diphenylprop-2-en-1-one can be obtained by precipitation or solid/liquid extraction after evaporation of the reaction medium. It can then be purified by silica gel chromatography or by crystallization.

The synthesis in acidic medium may be carried out in the following manner:

One molar equivalent of ketone (compound (A)) and one molar equivalent of aldehyde (compound (B)) are solubilized in an ethanol solution saturated with gaseous hydrochloric acid. The mixture is stirred at room temperature for approximately 6 hours and the solvent is eliminated, in particular by vacuum evaporation. The substituted 1,3-diphenylprop-2-en-1-one is purified, in particular by chromatography on silica gel.

The method for preparing compounds represented by formula (I) allows the preparation of compounds referred to hereinbelow as starting materials and intermediate compounds. The invention also has as its object certain starting materials and intermediate compounds obtained as provided for in the invention.

Said compounds (starting materials and intermediates) are more particularly selected in the group consisting of:
1-[4-chlorophenyl]-3-[3,5-dimethyl-4-hydroxyphenyl]prop-2-en-1-one, 1-[4-methylthiophenyl]-3-[3,5-dimethyl-4-hydroxyphenyl]prop-2-en-1-one, 1-[2-methoxyphenyl]-3-[3,5-dimethyl-4-hydroxyphenyl]prop-2-en-1-one, 1-[4-hexyloxyphenyl]-3-[3,5-dimethyl-4-hydroxyphenyl]prop-2-en-1-one, 1-[2-hydroxy-4-chlorophenyl]-3-[3,5-dimethyl-4-hydroxyphenyl]prop-2-en-1-one, 2-(3,5-dimethyl-4-hydroxyphenyl)-7-chloro-4H-1-benzopyran-4-one, 1-[2-methyloxy-4-chlorophenyl]-3-[3,5-dimethyl-4-hydroxyphenyl]prop-2-en-1-one, 1-[4-bromophenyl]-3-[3,5-dimethyl-4-hydroxyphenyl]prop-2-en-1-one, 1-[4-heptylphenyl]-3-[3,5-dimethyl-4-hydroxyphenyl]prop-2-en-1-one, 1-[4-trifluoromethylphenyl]-3-[3-methyl-4-hydroxyphenyl]prop-2-en-1-one, 1-[4-bromophenyl]-3-[3-tertiobutyl-4-hydroxyphenyl]prop-2-en-1-one, 1-[2-trifluoromethyloxyphenyl]-3-[3,5-dimethyl-4-hydroxyphenyl]prop-2-en-1-one, 1-[4-methylthiophenyl]-3-[3-trifluoromethyl-4-hydroxyphenyl]prop-2-en-1-one, 1-[4-methylsulfonylphenyl]-3-[3,5-dimethyl-4-hydroxyphenyl]prop-2-en-1-one, 1-[4-trifluoromethylthiophenyl]-3-[3,5-dimethyl-4-hydroxyphenyl]prop-2-en-1-one, 1-[4-isopropylphenyl]-3-[3,5-dimethyl-4-hydroxyphenyl]prop-2-en-1-one, 1-[4-trifluoromethylphenyl]-3-[3,5-dimethyl-4-hydroxyphenyl]prop-2-en-1-one, 1-[2-methylthiophenyl]-3-[3,5-dimethyl-4-hydroxyphenyl]prop-2-en-1-one, 1-[4-trifluoromethyloxyphenyl]-3-[3,5-dimethyl-4-hydroxyphenyl]prop-2-en-1-one, 1-[4-iodophenyl]-3-[3,5-dimethyl-4-hydroxyphenyl]prop-2-en-1-one, 1-[4-nonyloxyphenyl]-3-[3,5-dimethyl-4-hydroxyphenyl]prop-2-en-1-one, 1-[4-propyloxyphenyl]-3-[3,5-dimethyl-4-hydroxyphenyl]prop-2-en-1-one, 1-[4-methylthiophenyl]-3-[3,5-diisopropyl-4-hydroxyphenyl]prop-2-en-1-one, 1-[4-octadecyloxyphenyl]-3-[3,5-dimethyl-4-hydroxyphenyl]prop-2-en-1-one, 1-[4-dodecyloxyphenyl]-3-[3,5-dimethyl-4-hydroxyphenyl]prop-2-en-1-one, 1-[4-methoxyphenyl]-3-[3,5-dimethyl-4-hydroxyphenyl]prop-2-en-1-one, 1-[2-hexyloxyphenyl]-3-[3,5-dimethyl-4-hydroxyphenyl]prop-2-en-1-one, 1-[4-hexylthiophenyl]-3-[3,5-dimethyl-4-hydroxyphenyl]prop-2-en-1-one.

More specifically, the invention concerns combinations of said novel substituted 1,3-diphenylprop-2-en-1-one derivatives with other therapeutically active ingredients and compositions comprising said combinations.

An object of this invention is a pharmaceutical composition comprising, in a pharmaceutically acceptable support, at least one compound as described above, in association with one or more other therapeutic and/or cosmetic active ingredients. This is beneficially a pharmaceutical composition for the treatment or prophylaxis of the human or animal body.

This pharmaceutical composition comprises, in a pharmaceutically acceptable support, at least one compound represented by formula (I) in association with another therapeutically active ingredient, said compound being a substituted 1,3-diphenylprop-2-en-1-one derivative represented by formula (I) below:

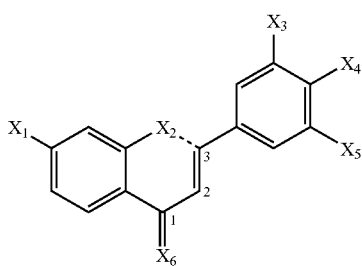

in which

X1 represents a halogen or a —R1 group or a group corresponding to the following formula: -G1-R1, X2 represents a hydrogen atom or a thionitroso group or a hydroxy group or an alkylcarbonyloxy or an unsubstituted alkyloxy group or a thiol group or an alkylthio group or an alkylcarbonylthio group, X2 can also represent an oxygen or sulfur atom bound to carbon 3 of the propene chain, so as to form a derivative of the type 2-phenyl-4H-1-benzopyran-4-one or of the type 2-phenyl-4H-1-benzothiopyran-4-one, X3 represents a —R3 group or a group corresponding to the following formula: -G3-R3, X4 represents a halogen or a thionitroso group or a —R4 group or a group corresponding to the following formula: -G4-R4, X5 represents a —R5 group or a group corresponding to the following formula: -G5-R5, X6 is an oxygen atom or a nitrogen atom, in the case where X6 is a nitrogen atom, it carries a hydrogen atom or a hydroxy group or an alkyloxy group.

R1, R3, R4, R5, which are the same or different, represent a hydrogen atom or an alkyl group substituted or not by a substituent which is part of group 1 or group 2 defined hereinbelow, G1, G3, G4, G5, which are the same or different, represent an oxygen or sulfur atom, with at least one of the groups X1, X3, X4 or X5 corresponding to the formula -G-R, and with at least one of the groups R1, R3, R4 or R5 present in the form of an alkyl group containing at least one substituent of group 1 or 2, said alkyl group being bound directly to the ring or being associated with a group G according to the formula -GR, substituents from group 1 are selected in the group consisting of carboxy groups corresponding to the formula: —COOR$_6$ and carbamoyl groups corresponding to the formula: —CONR$_6$R$_7$, substituents from group 2 are selected in the group consisting of sulfonic acid (—SO$_3$H) and sulfonamide groups corresponding to the formula: —SO$_2$NR$_6$R$_7$, with R$_6$ and R$_7$, which are the same or different, representing a hydrogen atom or an alkyl group possibly substituted by at least one group of the type 1 or 2, the optical and geometric isomers, racemates, tautomers, salts, hydrates and mixtures thereof.

The combination or composition comprising at least one compound represented by formula (I) such as described hereinabove, in association with another therapeutically active substance, may or may not include at least one compound represented by formula (I), wherein:

X1, X2, X3 and X5 each represent a hydrogen atom, X6 represents an oxygen atom and X4 represents a group corresponding to the formula —O—CR$_8$R$_9$—COOR$_{10}$, where R$_8$ and R$_9$, which are the same or different, represent a C1 to C2 alkyl group, and R$_{10}$ represents a hydrogen atom or a C1 to C7 alkyl group, and X2, X3 and X5 each represent a hydrogen atom, X1 represents a halogen atom or a —R1 or -G1-R1 group, where R1 represents an unsubstituted C1-C2 alkyl group and G1 represents an oxygen atom, X6 represents an oxygen atom and X4 represents a group corresponding to the formula —O—CR$_{11}$R$_{12}$—COOR$_{10}$, where R$_{11}$ and R$_{12}$, which are the same or different, represent a hydrogen atom or a C1 to C2 alkyl group, and R$_{10}$ represents a hydrogen atom or a C1 to C7 alkyl group, and X2 represents a hydrogen atom and X1 represents -G1-R1 where G1 represents an oxygen atom and R1 represents —CH$_2$COOH.

The compositions containing at least one compound of the invention and another active ingredient can be as a combined preparation for simultaneous, separate or sequential use in the same therapy. It will be appreciated that the compounds of the combination may be administered simultaneously, either in the same or different pharmaceutical formulation or sequentially. If there is sequential administration, the delay in administering the second active ingredient should not be such as to lose the benefit of the efficacious effect of the combination of the active ingredients. The administration of a compound of formula (I) in combination with another therapeutic agent could enhance the therapeutic effect of the other agent, and vice-versa. It is a feature of this invention that the use of such drug combinations will enhance the effect of each agent and therefore may allow to reduce quantities of each agent to be used and furthermore, therefore allow better management of drug related toxicity and side effects.

Thus according to one aspect, the present invention provides a combination comprising a compound represented by formula (I) and another therapeutic agent as hereinbelow described. The present invention deals with said therapeutic combinations and with pharmaceutical compositions containing said combinations.

The invention also concerns the use of a compound or a composition such as defined hereinabove for preparing a pharmaceutical composition for practicing a method of treatment of the human or animal body.

As an example (and not limitatively), compounds represented by formula (I) such as described hereinabove can advantageously be administered in combination with other therapeutic and/or cosmetic agents, marketed or in development, such as:

Antidiabetics: secretagogues (sulfonylureas (glibenclamide, glimepiride, gliclazide, etc.), glinides (repaglinide, nateglinide, etc.)), alpha-glucosidase inhibitors (miglitol, etc.), PPARγ agonists (thiazolidinediones such as rosiglitazone or pioglitazone), mixed PPARα/PPARγ agonists (tesaglitazar, muraglitazar), pan-PPARs (activate PPARα, PPARγ and PPARβ), biguanides (metformin), DPP-IV (Dipeptidyl Peptidase IV) inhibitors (MK-431, vildagliptin, etc), GLP-1 (Glucagon-Like Peptide 1) analogues (exenatide), etc.

insulin lipid-lowering and/or cholesterol-lowering molecules: Fibrates (fenofibrate, gemfibrozil), HmGCoA (Hydroxymethylglutaryl Coenzyme A reductase) inhibitors (statins such as atorvastatin, simvastatin, fluvastatin), cholesterol absorption inhibitors (ezetimibe, phytosterols), CETP (Cholesteryl Ester Transfer Protein) inhibitors (torcetrapib), ACAT (AcylCoA-Cholesterol Acyl Transferase) inhibitors, MTP (Microsomal Triglyceride Transfer Protein) inhibitors, sequestering agents of biliary acids (cholestyramine), vitamin E, polyunsaturated fatty acids, omega 3 fatty acids, nicotinic acid derivatives (niacin), etc.

anti-hypertension agents and hypotension agents: ACE (Angiotensin-Converting Enzyme) inhibitors (captopril, enalapril, ramipril or quinapril), the angiotensin II receptor antagonists (losartan, valsartan, telmisartan, eposartan, irbesartan, etc.), beta blockers (atenolol, metoprolol, labetalol, propranolol), thiazidic and non-thiazidic diuretics (furosemide, indapamide, hydrochlorthiazide, anti-aldosterone), vasodilatators like alpha receptor blokers (prazosin or urapidil) or minoxidil, calcium channel blockers (nifedipine, felodipine or amlodipine, diltizem or verapamil), etc.

anti-platelet agents: Aspirin, Ticlopidine, Dipyridamol, Clopidogrel, flurbiprofen, etc.

anti-obesity agents: Sibutramine, lipase inhibitors (orlistat), PPAR$_\delta$ agonists and antagonists, cannabinoid CB1 receptor antagonists (rimonabant), etc.

anti-inflammatories: for example, corticoids (prednisone, betamethazone, dexamethazone, prednisolone, methylprednisolone, hydrocortisone, etc.), NSAID or Non-Steroidian Anti-Inflammatories Drugs derived from indole (indomethacin, sulindac), NSAID of the arylcarboxylic group (thiaprofenic acid, diclofenac, etodolac, flurbiprofen, ibuprofen, ketoprofen, naproxen, nabumetone, alminoprofen), NSAID derived from oxicam (meloxicam, piroxicam, tenoxicam), NSAID from the fenamate group, selective COX2 inhibitors (celecoxib, rofecoxib), etc.

anti-oxidant agents: for example probucol, etc.

agents used in the treatment of cardiac insufficiency: thiazidic or non-thiazidic diuretics (furosemide, indapamide, hydrochlorthiazide, anti-aldosterone), ACE inhibitors (captopril, enalapril, ramipril or quinapril), digitalics (digoxin, digitoxin), beta blockers (atenolol, metoprolol, labetalol, propranolol), Phosphodiesterase inhibitors (enoximone, milrinone), etc.

agents used for the treatment of coronary insufficiency: beta blockers (atenolol, metoprolol, labetalol, propranolol), calcium channel blockers (nifedipine, felodipine or amlodipine, bepridil, diltiazem or verapamil), NO releasing agents (trinitrin, isosorbide dinitrate, molsidomine), Amiodarone, etc.

antineoplastics: cytotoxic agents (agents interacting with DNA, alkylating agents, cisplatin and derivatives), cytostatic agents (GnRH analogues, somatostatin analogues, progestins, anti-oestrogens, aromatase inhibitors, etc.), immune reaction modulators (interferons, IL2, etc.), etc.

anti-asthmatics such as bronchodilatators (beta 2 receptor agonists), corticoids, cromoglycate, leucotriene receptor antagonists (montelukast), etc.

corticoids used in the treatment of pathologies of the skin such as psoriasis and dermatitis vasodilatators and/or anti-ischemic agents (buflomedil, extract of Ginkgo Biloba, naftidrofuryl, pentoxifylline, piribedil, etc.).

Preferentially, the other therapeutic and/or cosmetic agents, marketed or in development, is selected in the group consisting of:

The PPARγ agonist rosiglitazone

The angiotensin II receptor antagonist irbesartan

The cholesterol absorption inhibitor ezetimibe

The HmGCoA inhibitor "simvastatin"

Fenofibrate.

The pharmaceutical composition comprising at least one compound represented by formula (I) such as described hereinabove, in association with another therapeutically active substance, is advantageously used for the treatment of cerebrovascular diseases, cardiovascular diseases, conditions associated with syndrome X, restenosis, dyslipidemias, diabetes, obesity, hypertension, inflammatory diseases, cancers (benign or malignant tumors), neurodegenerative diseases, dermatological diseases and disorders related to oxidative stress, for preventing or treating the effects of ageing in general and for example skin ageing, in particular in the field of cosmetics (development of wrinkles and the like).

It is preferably a pharmaceutical composition for the treatment of diabetes and dyslipidemias.

The invention also concerns a method for the treatment of cerebrovascular diseases, cardiovascular diseases, conditions associated with syndrome X, restenosis, dyslipidemias, diabetes, obesity, hypertension, inflammatory diseases, cancers (benign or malignant tumors), neurodegenerative diseases, dermatological diseases and disorders related to oxidative stress, for preventing or treating the effects of ageing in general and for example skin ageing, comprising administering to a subject, particularly human, in need of such treatment an effective dose of a compound, combination or pharmaceutical composition such as defined hereinabove, including compounds represented by general formula (I) in which:

X1, X2, X3 and X5 each represent a hydrogen atom, X6 represents an oxygen atom and X4 represents a group corresponding to the formula —O—$CR_8R_9$—$COOR_{10}$, where $R_8$ and $R_9$, which are the same or different, represent a C1 to C2 alkyl group and $R_6$ represents a hydrogen atom or a C1 to C7 alkyl group, X2, X3 and X5 each represent a hydrogen atom, X1 represents a halogen atom or a —R1 or -G1-R1 group, where R1 represents an unsubstituted C1 to C2 alkyl group and G1 represents an oxygen atom, X6 represents an oxygen atom and X4 represents a group corresponding to the formula —O—$CR_{11}R_{12}$—$COOR_{10}$, where $R_{11}$ and $R_{12}$, which are the same or different, represent a hydrogen atom or a C1 to C2 alkyl group, and $R_{10}$ represents a hydrogen atom or a C1 to C7 alkyl group, and X2 represents a hydrogen atom and X2 represents -G1-R1 where G1 represents an oxygen atom and R1 represents —$CH_2COOH$.

Another object of the invention concerns a method for the treatment of cerebrovascular diseases, cardiovascular diseases, conditions associated with syndrome X, restenosis, dyslipidemias, diabetes, obesity, hypertension, inflammatory diseases, cancers (benign or malignant tumors), neurodegenerative diseases, dermatological diseases and disorders related to oxidative stress, for preventing or treating the effects of ageing in general and for example skin ageing, comprising administering to a subject, particularly human, in need of such treatment an effective dose of a compound, combination or pharmaceutical composition such as defined hereinabove, with the exception of compounds having general formula (I) in which:

X1, X2, X3 and X5 each represent a hydrogen atom, X6 represents an oxygen atom and X4 represents a group corresponding to the formula —O—$CR_8R_9$—$COOR_{10}$, where $R_8$ and $R_9$, which are the same or different, represent a C1 to C2 alkyl group, and $R_6$ represents a hydrogen atom or a C1 to C7 alkyl group, X2, X3 and X5 each represent a hydrogen atom, X1 represents a halogen atom or a —R1 or -G1-R1 group, where R1 represents an unsubstituted C1 to C2 alkyl group and G1 represents an oxygen atom, X6 represents an oxygen atom and X4 represents a group corresponding to the formula —O—$CR_{11}R_{12}$—$COOR_{10}$, where $R_{11}$ and $R_{12}$, which are the same or different, represent a hydrogen atom or a C1 to C2 alkyl group, and $R_{10}$ represents a hydrogen atom or a C1 to C7 alkyl group, and X2 represents a hydrogen atom and X1 represents -G1-R1 where G1 represents an oxygen atom and R1 represents —$CH_2COOH$.

According to the invention, the term <<treatment>> designates the curative or preventive treatment.

The pharmaceutical compositions according to the invention advantageously comprise one or more pharmaceutically acceptable excipients or vehicles. Examples include saline, physiological, isotonic, buffered solutions and the like, compatible with pharmaceutical use and known to those skilled in the art. The compositions may contain one or more agents or vehicles selected in the group consisting of dispersants, solubilizers, stabilizers, preservatives, and the like. Agents or vehicles that can be used in the formulations (liquid and/or injectable and/or solid) are in particular methylcellulose, hydroxymethylcellulose, carboxymethylcellulose, polysorbate 80, mannitol, gelatin, lactose, plant oils, acacia, and the like. The compositions may be formulated as suspensions for injection, gels, oils, tablets, suppositories, powders, capsules, gelules, and the like, possibly by means of pharmaceutical forms or devices ensuring prolonged and/or delayed release. For this type of formulation, an agent such as cellulose, carbonates or starches is advantageously used.

The inventive compounds or compositions may be administered in different ways and in different forms. For instance, they may be administered by the oral or systemic route, such as for example by the intravenous, intramuscular, subcutaneous, transdermal, intra-arterial route, etc. For injections, the compounds are generally formulated as liquid suspensions, which can be injected through syringes or by infusion, for example. It is understood that the injection rate and/or the injected dose may be adapted by those skilled in the art according to the patient, the pathology, the method of administration, etc. Typically, the compounds of formula (I) are administered at doses ranging from 1 μg to 2 g per administration, preferably from 0.1 mg to 1 g, in particular from 0.1 to 100 mg, per administration. The administrations may be given daily or repeated several times a day, as the case may be.

LEGENDS OF FIGURES

Figures 1, 2:
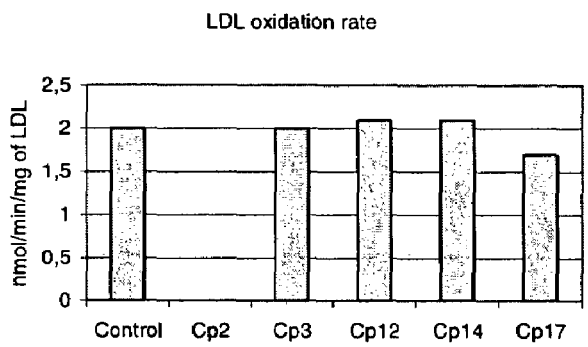
Figures 1, 2, 3:
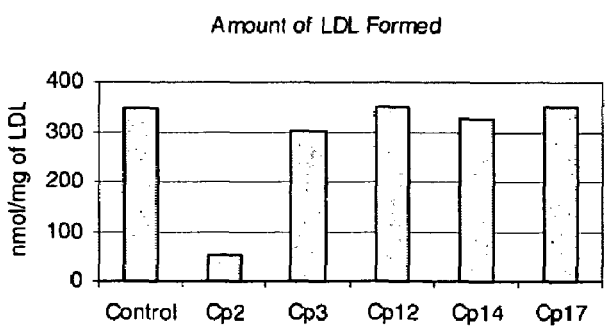

FIGS. 1-1, 1-2, 1-3: Evaluation of the antioxidant properties of compounds 2, 3, 4, 5, 6, 7, 9, 10, 12, 14 and 17 on LDL oxidation by copper (Cu).

FIG. 1-1 shows the results of the experiment measuring formation of conjugated dienes over time. It can be seen that incubation of LDL with the test compounds at a concentration of $10^{-4}$M delayed conjugated diene formation. The lag phase was 111 minutes for copper alone as compared with a lag phase of 132, 145, 134 and 203 minutes, respectively, when LDL were incubated with compound 3, 12, 14, 17. The lag phase was greater than 480 minutes when LDL were incubated with compound 2. This lag in the formation of conjugated dienes is characteristic of antioxidants.

FIG. 1-2 shows the rate of diene formation after different treatments. Incubation of the compounds with LDL in the presence of copper slowed the rate of conjugated diene formation. This rate was 2 nmol/min/mg of LDL with copper alone, 1.7 nmol/min/mg of LDL when LDL were incubated in the presence of $10^{-4}$M compound 17, and not determined for compound 2 at $10^{-4}$M (not measurable because too low).

FIG. 1-3 represents the maximum amount of conjugated dienes formed over time. Incubation of LDL with copper led to formation of 348 nmol of conjugated dienes per mg of LDL; incubation with compound 2 at $10^{-4}$M led to an 84% decrease in conjugated diene formation (54.4 nmol per mg of LDL). In the presence of compounds 3 and 14, conjugated diene formation was respectively 303 and 327 nmol per mg of LDL.

FIGS. 1-4, 1-5, 1-6: Evaluation of the antioxidant properties of compounds 18, 19, 21 and 22 on LDL oxidation by copper (Cu).

FIG. 1-4 shows that incubation of LDL with the test compounds at a concentration of $10^{-4}$M delayed conjugated diene formation. The lag phase was 178 minutes for copper alone as compared with a lag phase of 241, 481 and 241 minutes (from the experimental determination), respectively, when LDL were incubated with compounds 18, 21 or 22. This lag in the formation of conjugated dienes is characteristic of antioxidants.

FIG. 1-5 shows the rate of diene formation after different treatments. The rate of formation of conjugated dienes was 1.6 nmol/min/mg of LDL with copper alone, 1.4 nmol/min/mg of LDL when LDL were incubated in the presence of compound 18 at $10^{-4}$M, 1.3 nmol/min/mg of LDL when LDL were incubated in the presence of compounds 22 and not determined for compound 21 at $10^{-4}$M (not measurable because too low).

FIG. 1-6 represents the maximum amount of conjugated dienes formed over time. Incubation of LDL with copper led to formation of 353 nmol of conjugated dienes per mg of LDL. Incubation with compound 21 at $10^{-4}$M inhibited conjugated diene formation. Conjugated diene formation was respectively 305, 345 and 345 nmol per mg of LDL in the presence of compounds 18, 19 and 22.

FIGS. 1-7, 1-8: Evaluation of the antioxidant properties of compounds 25 and 29 on LDL oxidation by copper (Cu).

FIG. 1-7 shows the results of the experiment measuring formation of conjugated dienes over time. It can be seen that incubation of LDL with the test compounds at a concentration of $10^{-4}$M delayed conjugated diene formation. The lag phase was 82 minutes for copper alone as compared with a lag phase of 120 and 135 minutes (from the experimental determination), respectively, when LDL were incubated with compounds 25 and 29.

FIG. 1-8 represents the maximum amount of conjugated dienes formed over time. Incubation of LDL with copper led to formation of 393 nmol of conjugated dienes per mg of LDL. In the presence of compound 25, this value was 378 nmol per mg of LDL.

FIGS. 1-9, 1-10, 1-11: Evaluation of the antioxidant properties of compounds 31, 33 and 35 on LDL oxidation by copper (Cu).

FIG. 1-9 shows the results of the experiment measuring formation of conjugated dienes over time. It can be seen that incubation of LDL with the test compounds at a concentration of $10^{-4}$M delayed conjugated diene formation. The lag phase was 80 minutes for copper alone as compared with a lag phase of 139, 247 and 149 minutes (from the experimental determination), respectively, when LDL were incubated with compounds 31, 33 and 35. This lag in the formation of conjugated dienes is characteristic of antioxidants.

FIG. 1-10 shows the rate of diene formation after different treatments. Incubation of the compounds with LDL in the presence of copper slowed the rate of conjugated diene formation. This rate was 1.9 nmol/min/mg of LDL with copper alone, 1.6 nmol/min/mg of LDL when LDL were incubated in the presence of compound 31 at $10^{-4}$M, 0.8 nmol/min/mg of LDL when LDL were incubated in the presence of compound 33 and 1.5 nmol/min/mg of LDL when LDL were incubated in the presence of compound 35.

FIG. 1-11 represents the maximum amount of conjugated dienes formed over time. Incubation of LDL with copper led to formation of 298 nmol of conjugated dienes per mg of LDL, as compared with 257 nmol per mg of LDL in the presence of compound 33.

FIGS. 1-12, 1-13, 1-14: Evaluation of the antioxidant properties of compounds 37, 38 and 41 on LDL oxidation by copper (Cu).

FIG. 1-12 shows the results of the experiment measuring formation of conjugated dienes over time. It can be seen that incubation of LDL with the test compounds at a concentration of $10^{-4}$M delayed conjugated diene formation. The lag phase was 120 minutes for copper alone as compared with a lag phase of 196, 284 and 411 minutes (from the experimental determination), respectively, when LDL were incubated with compounds 37, 38 and 41.

FIG. 1-13 shows the rate of diene formation after different treatments. Incubation of the compounds with LDL in the presence of copper slowed the rate of conjugated diene formation. This rate was 1.8 nmol/min/mg of LDL with copper alone, 1.49 nmol/min/mg of LDL when LDL were incubated in the presence of compound 37 at $10^{-4}$M, 0.71 nmol/min/mg of LDL when LDL were incubated in the presence of compound 38 and 0.54 nmol/min/mg of LDL when LDL were incubated in the presence of compound 41.

FIG. 1-14 represents the maximum amount of conjugated dienes formed over time. Incubation of LDL with copper led to formation of 372 nmol of conjugated dienes per mg of LDL, as compared with 338 nmol per mg of LDL, 244 nmol per mg of LDL and 71 nmol per mg of LDL in the presence of compounds 37, 38 and 41, respectively.

The lag phase in the formation of conjugated dienes, the reduction in the rate of diene formation and the decrease in the total amount of dienes formed are characteristics of antioxidants.

FIGS. 2-1, 2-2, 2-3, 2-4, 2-5, 2-6: Evaluation of PPARα agonist properties of the inventive compounds in the PPARα/Gal4 transactivation system.

The results are expressed as the induction factor (luminescent signal relative to untreated cells) after the different treatments. The higher the induction factor the more potent the PPARα agonist activity.

FIG. 2-1: The results show the induction factors for compounds 3, 4, 7, 8 and 9. The results show that compound 3 produced a maximum 30-fold induction at a concentration of 10 μM, compound 4 had a maximum induction factor of 60 at 100 μM, 22 at 30 μM and 4 at 10 μM. Compound 7 had a maximum induction factor of 50 at 30 μM. Compound 8 activated the system with a maximum induction factor of 10 at 100 μM. Compound 9 had a maximal induction factor of 28 at 100 μM, the highest concentration.

FIG. 2-2: The results show the induction factors for compounds 11, 12, 13, 14 and 17.

The results show that compound 11 produced a maximum 10-fold induction at a concentration of 100 μM, compound 12 had a maximum induction factor of 22 at 100 μM, 8 at 10 μM and 1 at 10 μM. Compounds 13 and 14 had induction factors comprised between 1.1 and 1.5 at the different concentrations tested. Compound 17 activated the system with a maximum induction factor of 85 at 10 μM and a minimum induction factor of 13.8 at the 100 μM concentration.

FIG. 2-3: The results show the induction factors for compounds 19, 20, 21 and 22.

The results show that compound 19 produced a maximum 15.6-fold induction at 10 μM, compound 20 had a maximum induction factor of 53 at 10 μM. Compound 21 had induction factors comprised between 0.8 and 22 at the different concentrations tested. Compound 22 activated the system with a maximum induction factor of 50 at the 10 μM concentration.

Figures 1, 2, 3, 4:
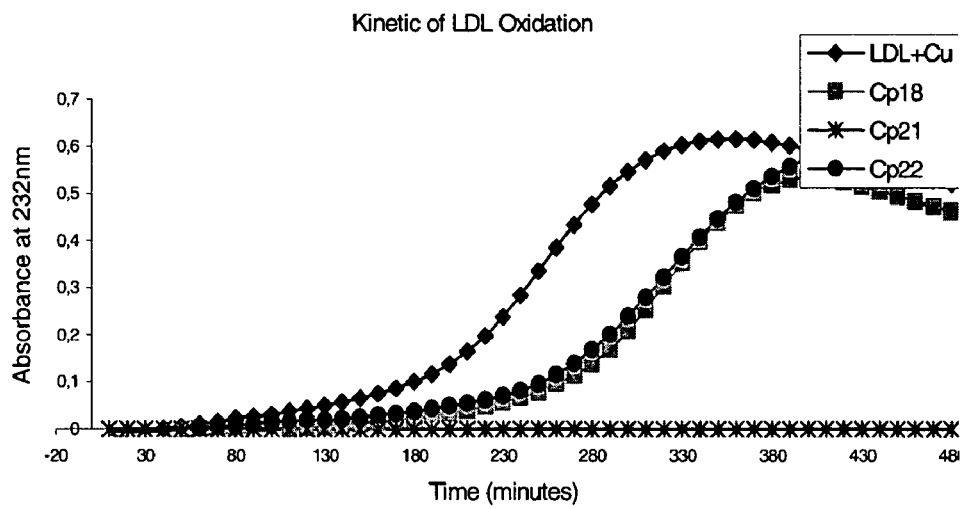

FIG. 2-4: The results show the induction factors for compounds 23, 24, 25, 26 and 29.

Compound 23 had a maximum induction factor of 3.6 at 10 μM, compound 24 had a maximum induction factor of 11 at 10 μM. Compound 25 activated the system with induction factors comprised between 7 and 21 according to the concentrations tested. Compound 26 had a maximum induction factor of 7.8 for the 10 μM concentration. Compound 29 had induction factors of 28 and 25 at 1 and 10 μM, respectively.

FIG. 2-5: The results show the induction factors for compounds 31 and 33.

Compound 31 activated the system with an induction factor of 15.5 at the concentration of 10 μM. The induction factors for compound 33 were 22, 44 and 77 for the 1, 10 and 100 μM concentrations, respectively.

FIG. 2-6: The results show the induction factors for compounds 37, 38 and 41.

The maximum induction factors for compounds 37, 38 and 41 were 27, 22 and 34, respectively, at the 10 or 1 μm concentrations.

These results demonstrate that the inventive compounds tested exhibit PPARα ligand activity and therefore enable the transcriptional activation thereof.

FIG. 2-7: Evaluation of PPARγ agonist properties of the inventive compounds in the PPARγ/Gal4 transactivation system.

The results show the induction factors for compounds 17, 33 and 29.

Compound 17 had a maximum induction factor of 25 at 10 μM. Compound 33 had a maximum induction factor of 45.6 at 100 μM and compound 29 of 33.9 at 10 μM. These results demonstrate that the inventive compounds tested exhibit PPARγ ligand activity and therefore enable the transcriptional activation thereof.

FIGS. 2-8, 2-9 and 2-10: In vitro evaluation of PPARα, γ and δ agonist properties of the inventive compound 54 in the PPAR/Gal4 transactivation system. The maximal activity of compound 54 on PPAR α is observed at the concentration of 0.03 μM. FIGS. 2-9 and 2-10 show that compound 54 can activate PPAR γ and PPAR δ as well.

FIGS. 2-11, 2-12 and 2-13: In vitro evaluation of PPARα, γ and δ agonist properties of the inventive compound 58 in the PPAR/Gal4 transactivation system. The maximal activity of compound 58 on PPARα is observed at the concentration of 0.3 µM and at 1µM on PPARγ FIG. 2-13 shows that compound 58 can activate PPAR δ as well.

FIGS. 2-14, 2-15 and 2-16: In vitro evaluation of PPARα, β and γ agonist properties of the inventive compound 62 in the PPAR/Gal4 transactivation system. The maximal activity of compound 62 is observed at the concentration of 0.3 µM on PPARα, 10 µM on PPARγ and 3 µM on PPARδ.

FIGS. 2-17, 2-18 and 2-19: In vitro evaluation of PPARα, β and δ agonist properties of the inventive compound 70 in the PPAR/Gal4 transactivation system. The maximal activity of compound 70 is observed at the concentration of 0.03 µM on PPARα. FIGS. 2-18 and 2-19 show that compound 70 can also activate PPAR γ and PPAR δ.

FIGS. 3-1 and 3-2: Evaluation of the acute and prophylactic neuroprotective properties of the inventive compounds FIG. 3-1: Prophylactic Neuroprotection.

This figure shows infarct volume in $mm^3$ measured after intraluminal occlusion of the middle cerebral artery for 60 minutes followed by reperfusion for 24 hours before sacrifice. FIG. 3-1 shows infarct volume observed with three groups of C57Black/6 mice. Two of these animal groups were treated by gavage with compound 15 at 200 mg/kg/day or with compound 42 at 200 mg/kg/day for 14 days before occlusion. It can be seen that infarct volume in untreated animals was 37 $mm^3$ as compared with 24 $mm^3$ for animals treated with compound 42 and 32 $mm^3$ with compound 15.

FIG. 3-2: Acute Neuroprotection.

FIG. 3-2 shows infarct volume observed with three groups of C57 black/6 mice. Animals were treated with compound 15 at 200 mg/kg/day or with compound 42 at 200 mg/kg/day for 72 hours after occlusion.

It can be seen that total corrected infarct volume in untreated animals was 41 $mm^3$ as compared with 29 $mm^3$ for animals treated with compound 42 and 15.

The results presented in FIGS. 3-1 and 3-2 demonstrate the efficacy of the compounds as neuroprotective compounds. Said compounds are active as prophylactic treatment and as acute treatment.

FIGS. 4-1 to 4-22: Evaluation of the effect of the inventive compounds on metabolism of triglycerides and cholesterol.

FIGS. 4-1, 4-2, 4-3, 4-4: Evaluation of the effect of compounds 7 and 17 on metabolism of triglycerides and cholesterol in hApoE2 Knock-in transgenic mice. Animals were treated by gavage with each compound at a dose of 200 mg/kg for 7 days. FIGS. 4-1 and 4-2 illustrate the decrease in plasma concentrations of triglycerides and cholesterol induced by compounds 7 and 17.

FIGS. 4-3 and 4-4 show triglyceride and cholesterol distribution in lipoparticles evaluated by exclusion chromatography. It can also be seen that treatment with compounds 7 and 17 decreased the triglycerides and cholesterol in this lipoparticle subfraction.

Figures 1, 2, 3, 4, 5:
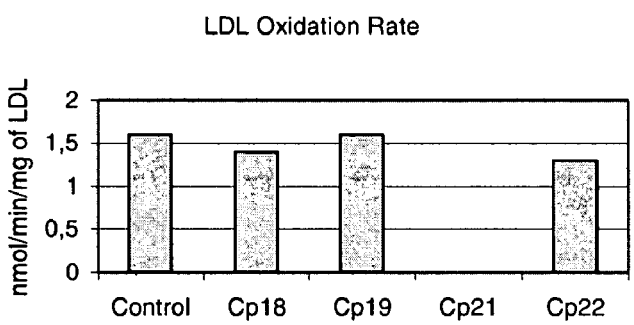
Figures 1, 2, 3, 4, 5, 6:
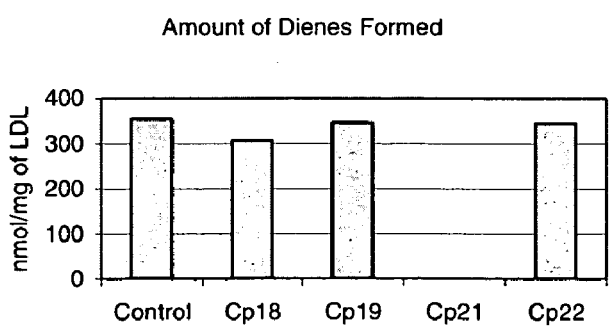

FIGS. 4-5, 4-6, 4-7, 4-8: Evaluation of the effects of compound 29 on triglycerides and cholesterol metabolism in hApoE2 Knock-in transgenic mice. Animals were treated with compound 29 at the following doses: 200, 50, 12.5 and 3.125 mg/kg/day for 8 days. FIGS. 4-5 and 4-6 illustrate the dose-dependent decrease in plasma triglycerides and cholesterol levels with a greater decrease with increasing doses of compound 29. FIGS. 4-7 and 4-8 show triglycerides and cholesterol distribution in lipoparticles evaluated by exclusion chromatography. A decrease in triglycerides and cholesterol in this lipoparticle subfraction can be seen after treatment with various concentrations of compound 29.

FIGS. 4-9, 4-10, 4-11, 4-12: Evaluation of the effects of compounds 33 and 41 on triglycerides and cholesterol metabolism in hApoE2 Knock-in transgenic mice. The animals were treated with the different compounds at a dose of 50 mg/kg/day for 8 days. FIGS. 4-9 and 4-10 show the decrease in plasma triglycerides and cholesterol induced by compounds 33 and 41. FIGS. 4-11 and 4-12 show triglyceride and cholesterol distribution in lipoparticles evaluated by exclusion chromatography. A decrease of triglycerides and cholesterol in this lipoparticle subfraction can be seen after treatment with compounds 33 and 41.

FIGS. 4-13, 4-14, 4-15, 4-16, 4-17, 4-18, 4-19. 4-20 Evaluation of the effects of compounds 82, 70, 62, 58, 54, 50, 29 on triglycerides and cholesterol metabolism in hApoE2 Knock-in transgenic mice. The animals were treated with the different compounds at a dose of 50 mg/kg/day for 7 or 8 days. FIGS. 4-14, 4-16, 4-18, 4-20 show the decrease of plasma triglycerides and FIGS. 4-13, 4-15, 4-17, 4-19 show the decrease of plasma cholesterol induced by compounds.

FIGS. 4-21, 4-22: Evaluation of the effect of compound 62 on triglycerides and cholesterol metabolism in hApoE2 Knock-in transgenic mice. The animals were treated with the compound at doses of 1, 3, 10 and 30 mg/kg/day for 14 days. FIGS. 4-21, 4-22 show the decrease in plasma cholesterol and triglycerides induced by compound 62.

FIGS. 5-1 to 5-4: Evaluation of the antidiabetic effect of compounds 29 and 62 according to the invention on insulin and glucose in C57BLKS-m $Lepr^{db}$ transgenic mice.

FIG. 5-1 and FIG. 5-2. Four groups of animals were treated with Compound 29 at different doses (0.1 to 100 mg/Kg/day) for 28 days. Plasma insulin and glucose levels were measured. The decrease of glucose and insulin levels as a dose/response effect suggests an improvement in insulin sensitivity.

FIG. 5-3 and FIG. 5-4. Four groups of animals were treated with Compound 62 at different doses (0.1 to 30 mg/Kg/day) for 21 days. Plasma insulin and glucose levels were measured. As observed with Compound 29 in FIGS. 5-1 and 5-2, the decrease of glucose and insulin level as a dose/response effect suggests an improvement in insulin sensitivity.

FIGS. 6-1, 6-2 and 6-3: Evaluation of PPARδ agonist properties of the inventive compounds The PPARα knock-out mouse model was used to characterize in vivo PPARδ activation. Animals were treated for 3 days at the dose of 150 mg/kg/day. Total RNA was isolated from heart and skeletal muscle (quadriceps). Messenger RNAs were quantified by quantitative RT-PCR and expression levels were normalized using 18S gene as reference.

Induction, after treatment, of UCP2 expression in the skeletal muscle and UCP3 and PDK4 expression in the heart demonstrates in vivo the activation of PPARδ isoform by compound 41.

Figures 1, 2, 3, 4, 5, 6, 7:
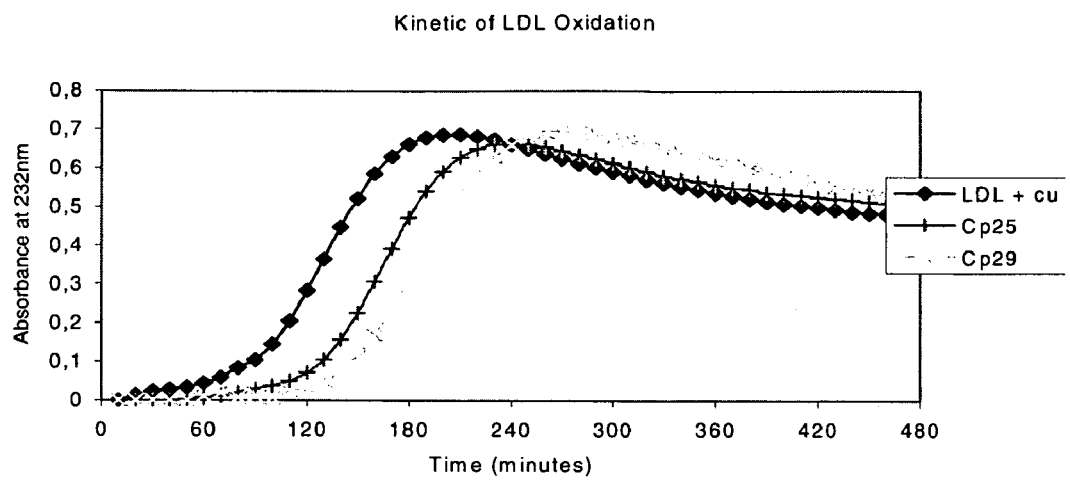

FIGS. 7-1 and 7-2: Evaluation of the antioxidant properties of compounds 29, 33, 41, 70, 62, 58, 54 on cell cultures.

Results are presented in % of oxidative reduction versus control cells. As a positive control Trolox (TLx), a powerful antioxidant has been incorporated in the experiences. Fluorescence intensity was lower in the cells incubated with the inventive compounds than in untreated cells.

Figures 1, 2, 3, 4, 5, 6, 7, 8:
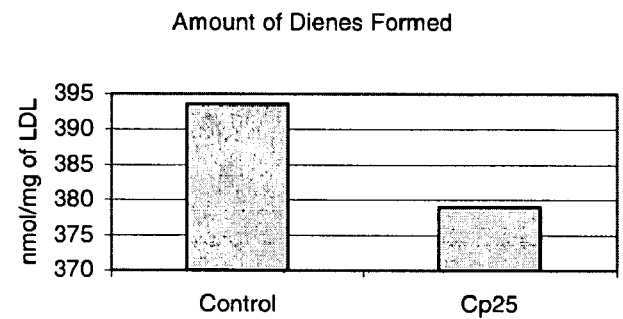
Figures 1, 2, 3, 4, 5, 6, 7, 8, 9:
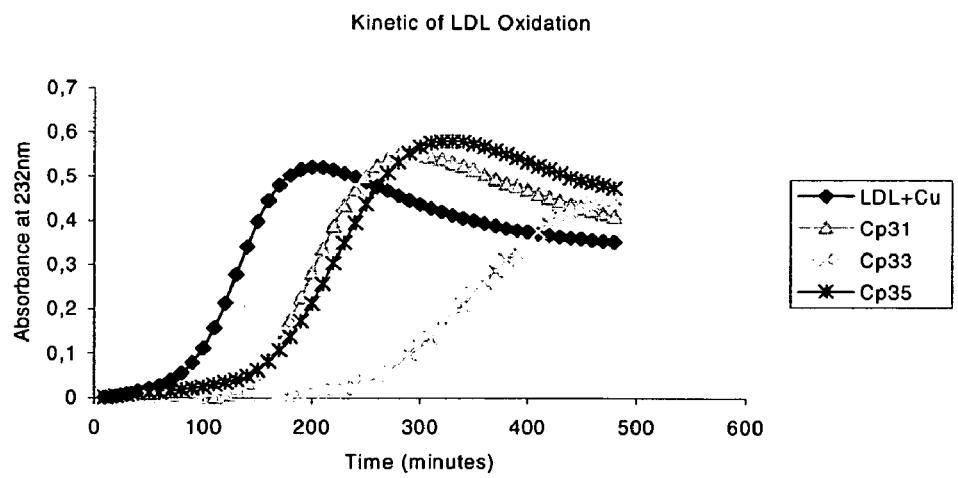
Figures 1, 2, 3, 4, 5, 6, 7, 8, 9, 10:
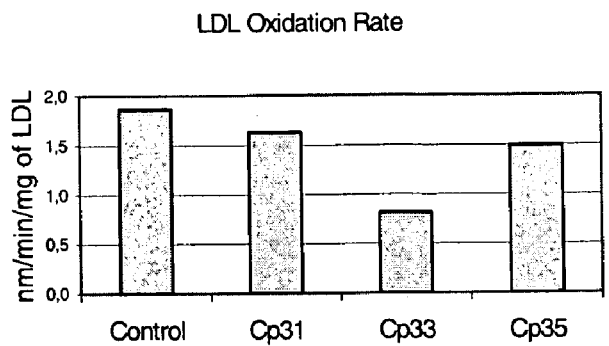
Figures 1, 2, 3, 4, 5, 6, 7, 8, 9, 10, 11:
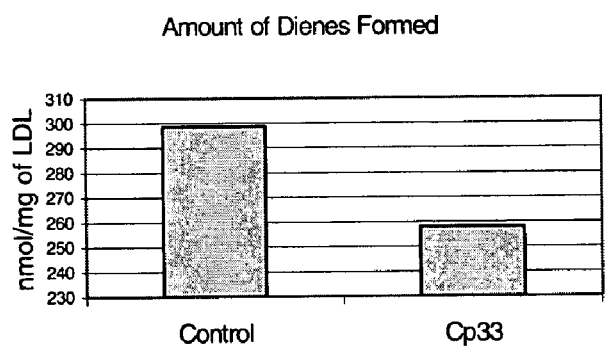
Figures 1, 2, 3, 4, 5, 6, 7, 8, 9, 10, 11, 12:
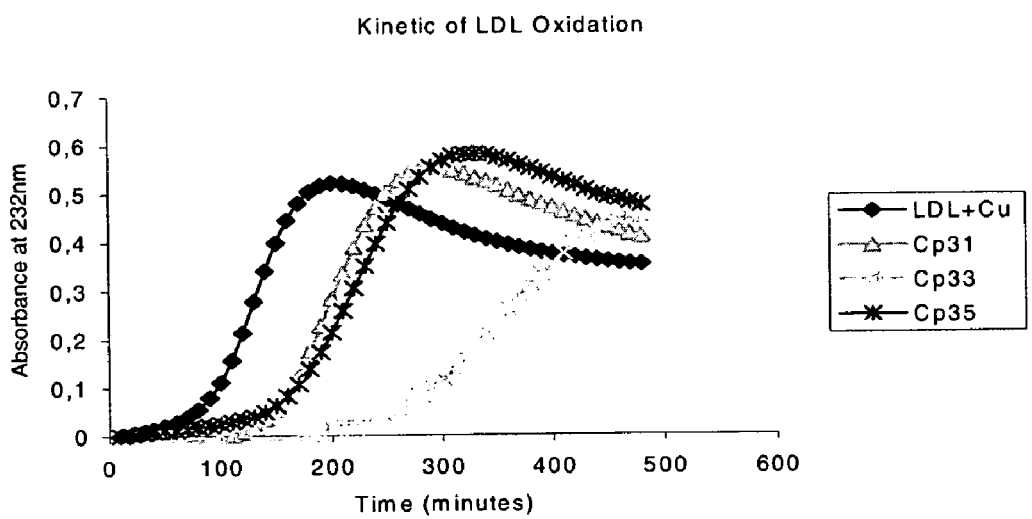
Figures 1, 2, 3, 4, 5, 6, 7, 8, 9, 10, 11, 12, 13:
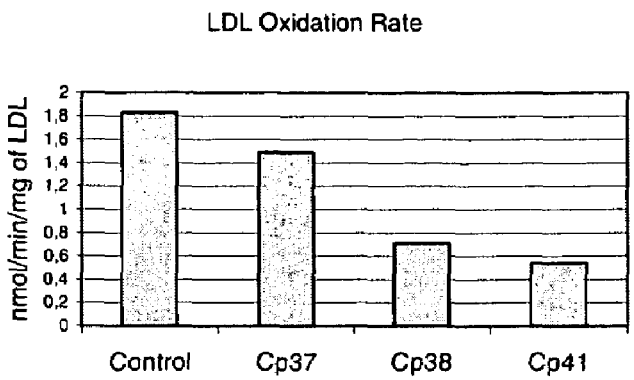
Figures 1, 2, 3, 4, 5, 6, 7, 8, 9, 10, 11, 12, 13, 14:
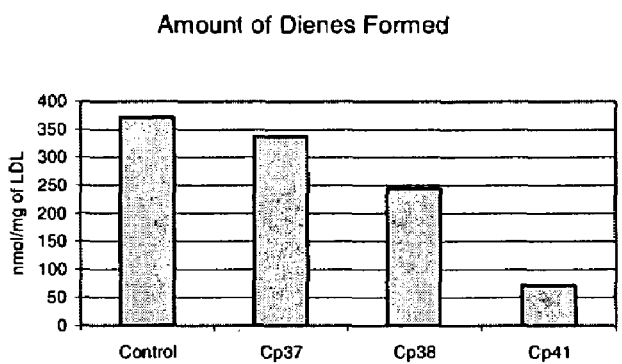
Figures 1, 2:
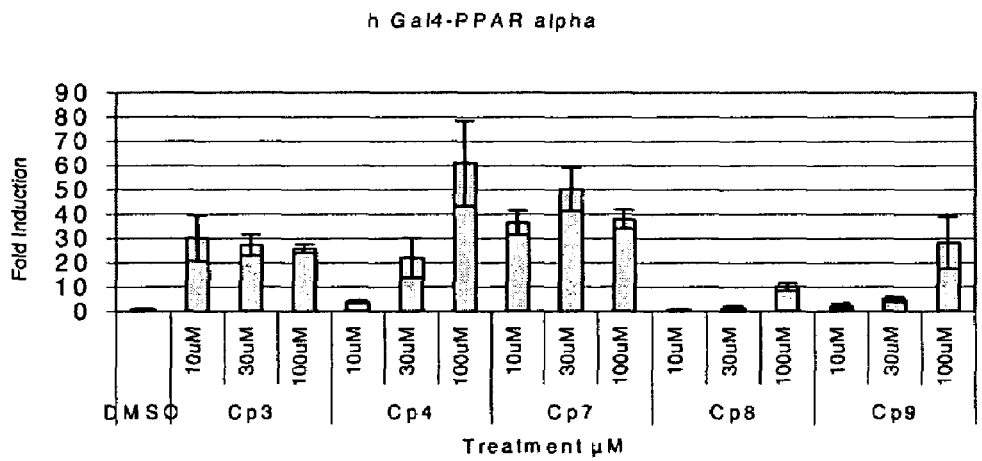
Figure 2:
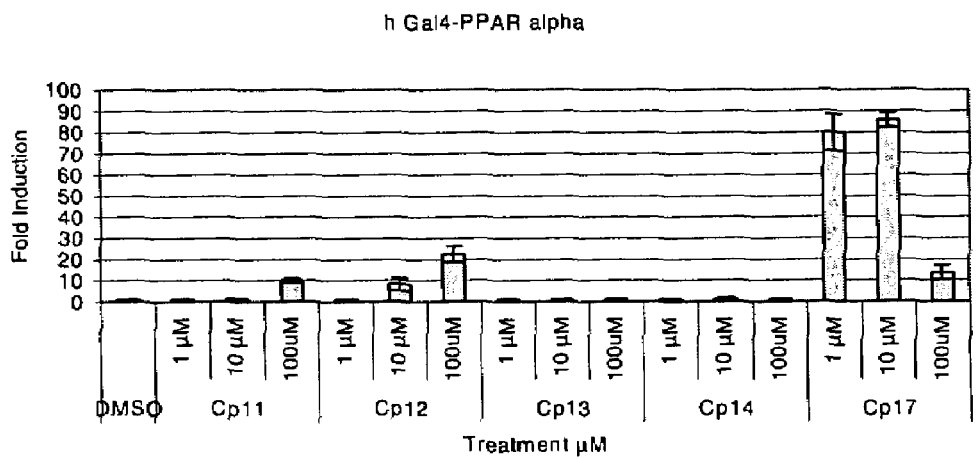
Figures 2, 3:
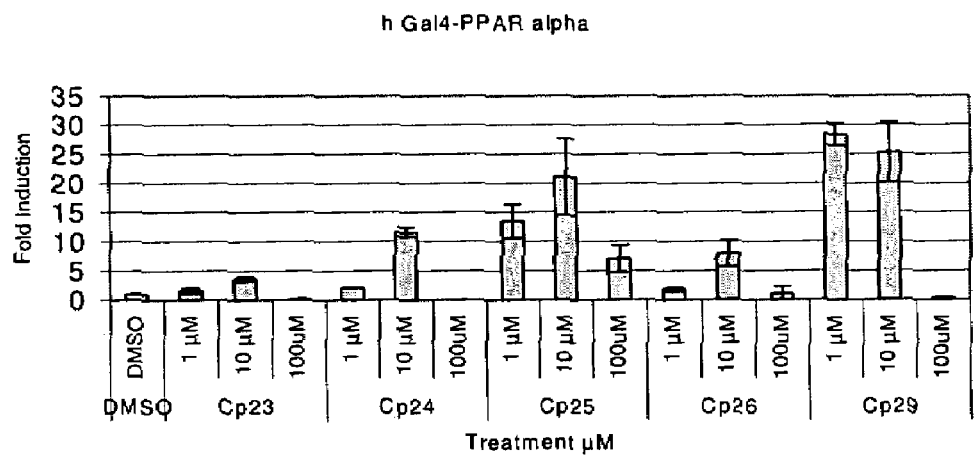
Figures 2, 3, 4:
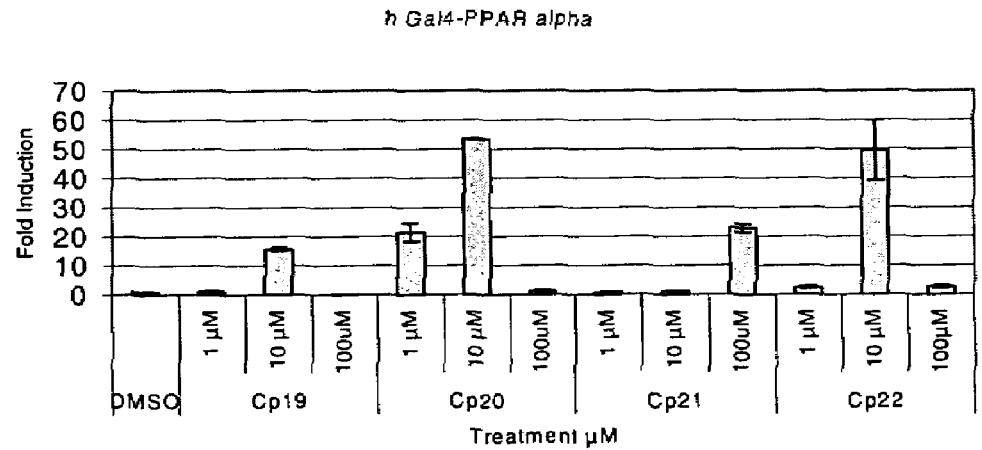
Figures 2, 3, 4, 5:
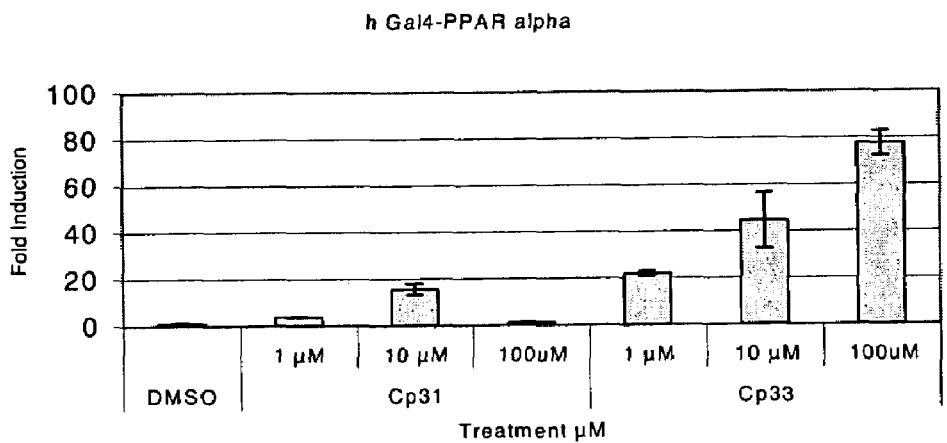
Figures 2, 3, 4, 5, 6:
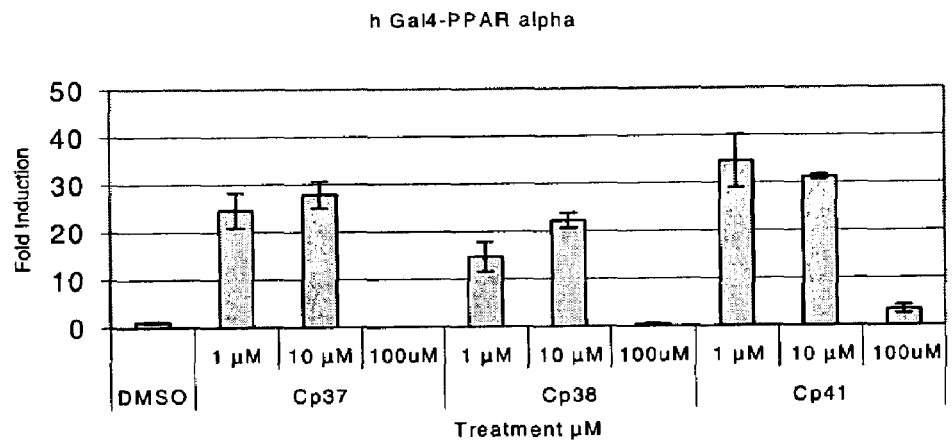
Figures 2, 3, 4, 5, 6, 7:
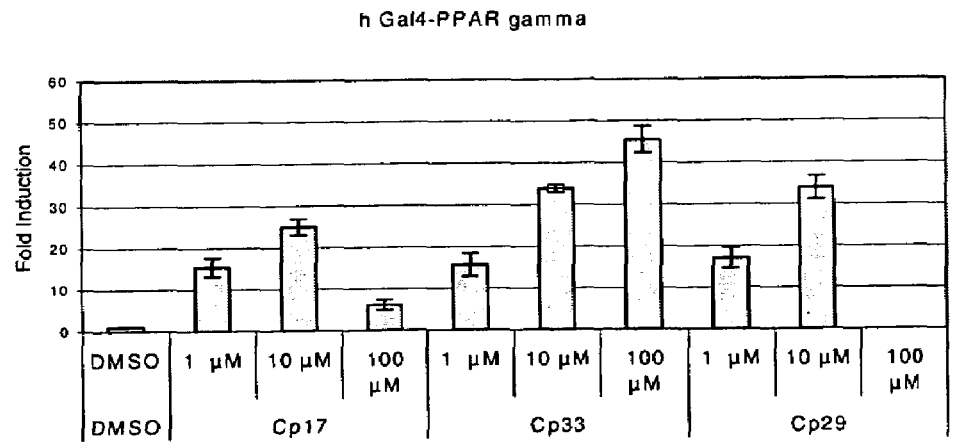
Figures 2, 3, 4, 5, 6, 7, 8:
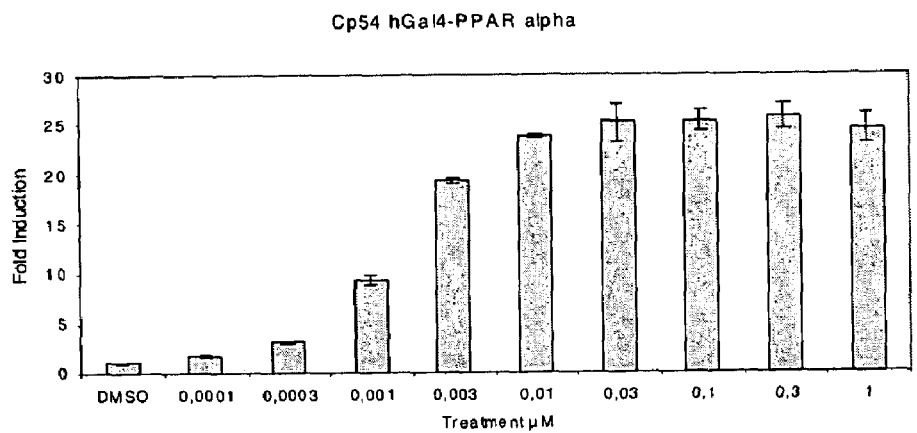
Figures 2, 3, 4, 5, 6, 7, 8, 9:
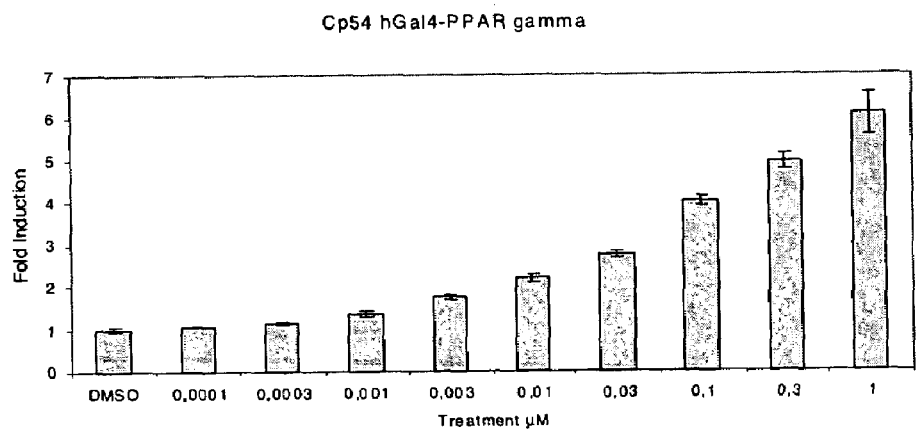
Figures 2, 3, 4, 5, 6, 7, 8, 9, 10:
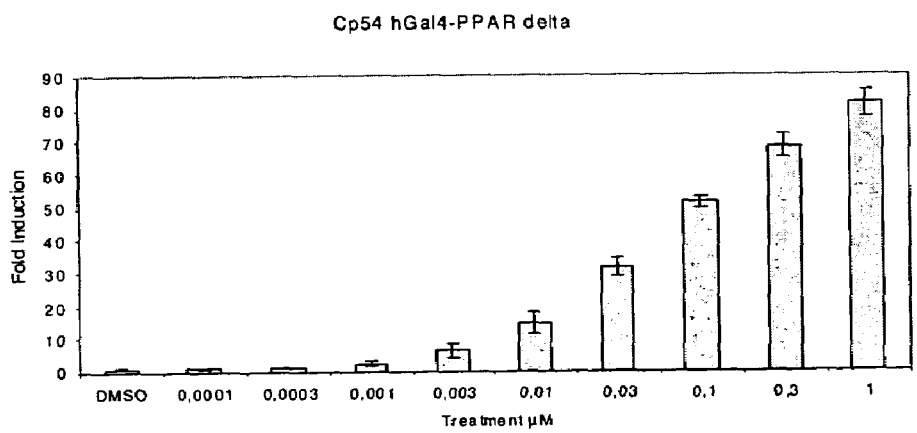
Figures 2, 3, 4, 5, 6, 7, 8, 9, 10, 11:
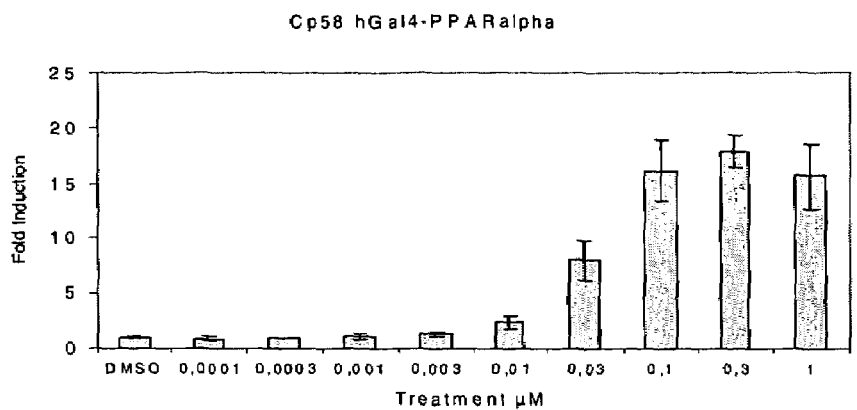
Figures 2, 3, 4, 5, 6, 7, 8, 9, 10, 11, 12:
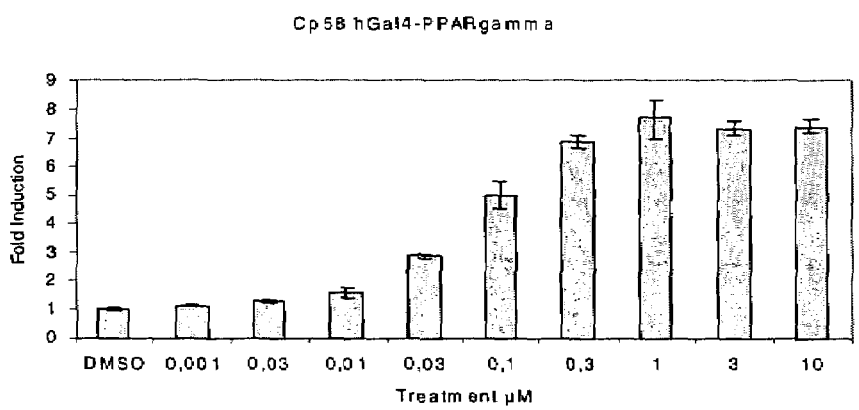
Figures 2, 3, 4, 5, 6, 7, 8, 9, 10, 11, 12, 13:
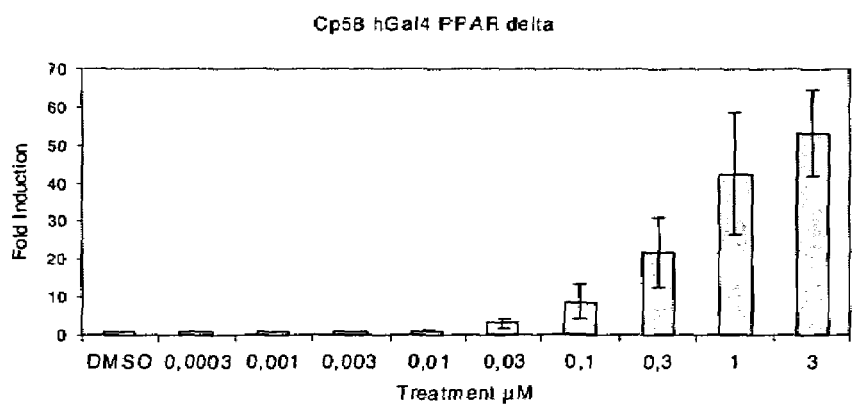
Figures 2, 3, 4, 5, 6, 7, 8, 9, 10, 11, 12, 13, 14:
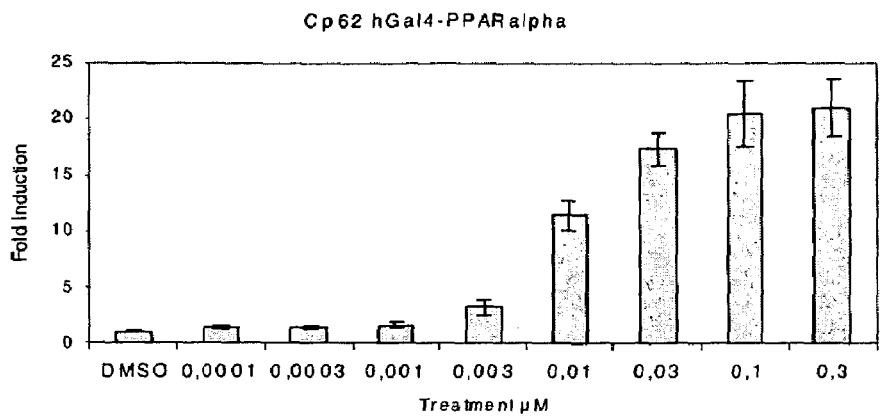
Figures 2, 3, 4, 5, 6, 7, 8, 9, 10, 11, 12, 13, 14, 15:
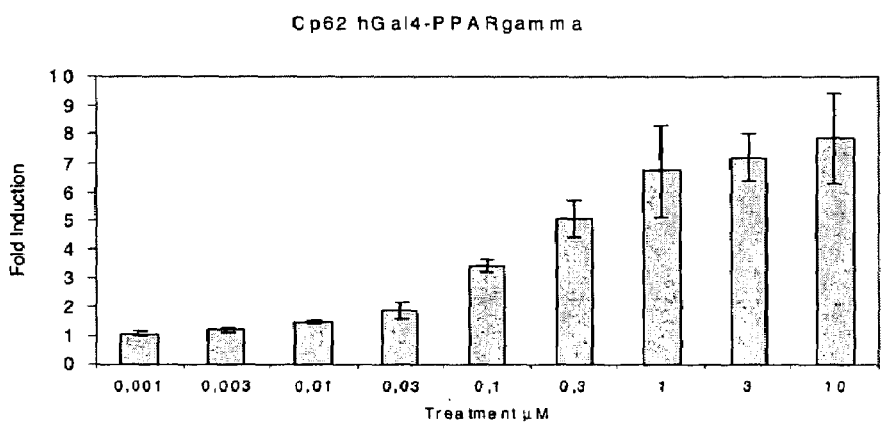
Figures 2, 3, 4, 5, 6, 7, 8, 9, 10, 11, 12, 13, 14, 15, 16:
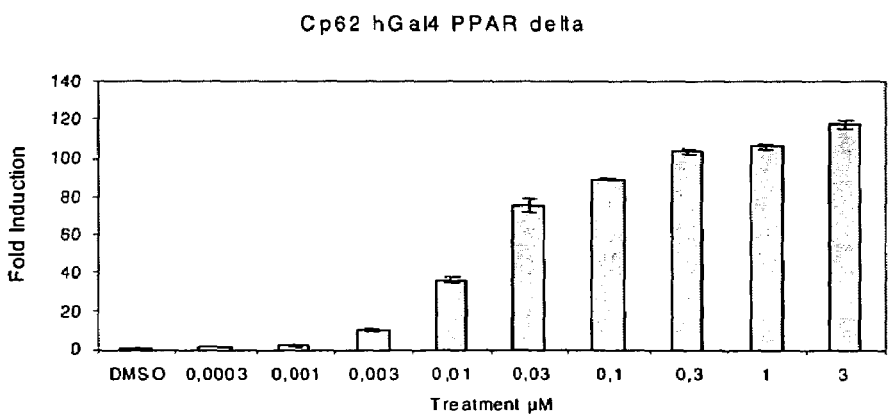
Figures 2, 3, 4, 5, 6, 7, 8, 9, 10, 11, 12, 13, 14, 15, 16, 17:
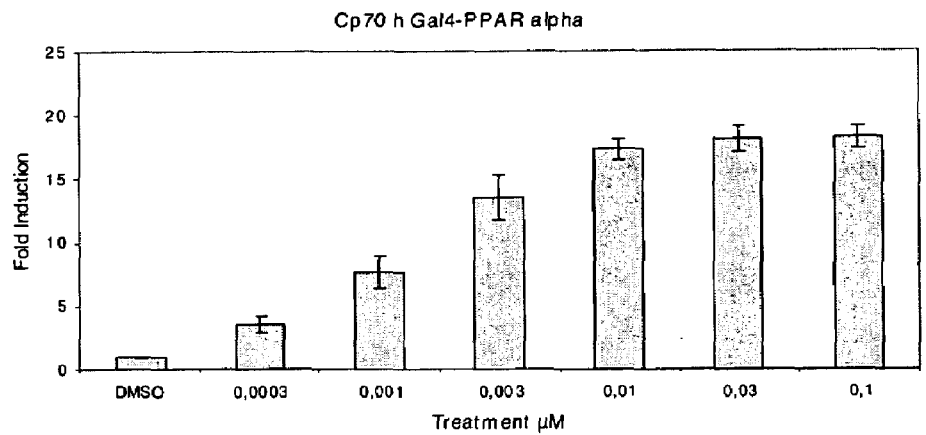
Figures 2, 3, 4, 5, 6, 7, 8, 9, 10, 11, 12, 13, 14, 15, 16, 17, 18:
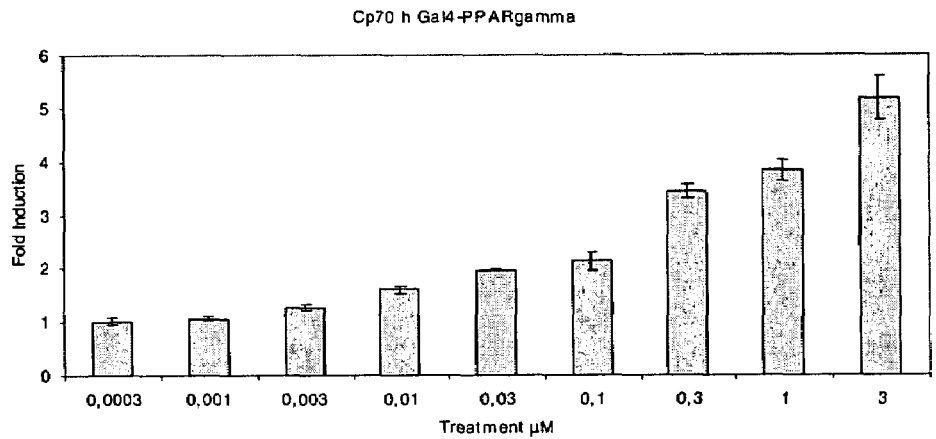
Figures 2, 3, 4, 5, 6, 7, 8, 9, 10, 11, 12, 13, 14, 15, 16, 17, 18, 19:
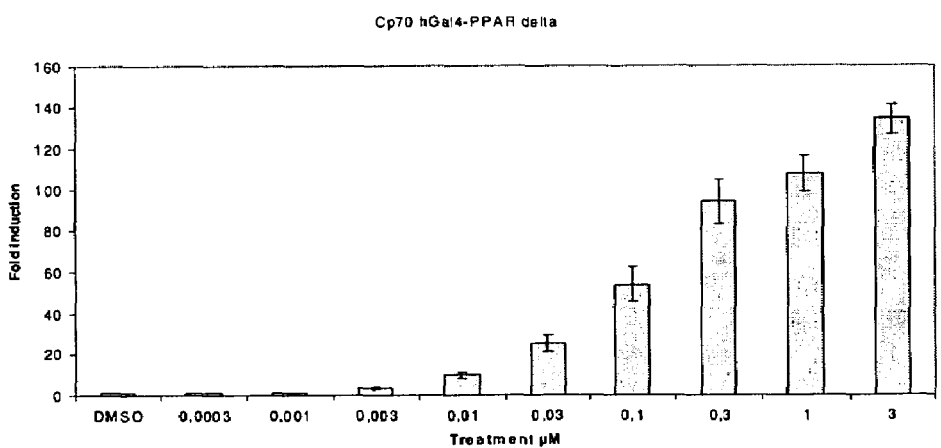
Figures 1, 3:
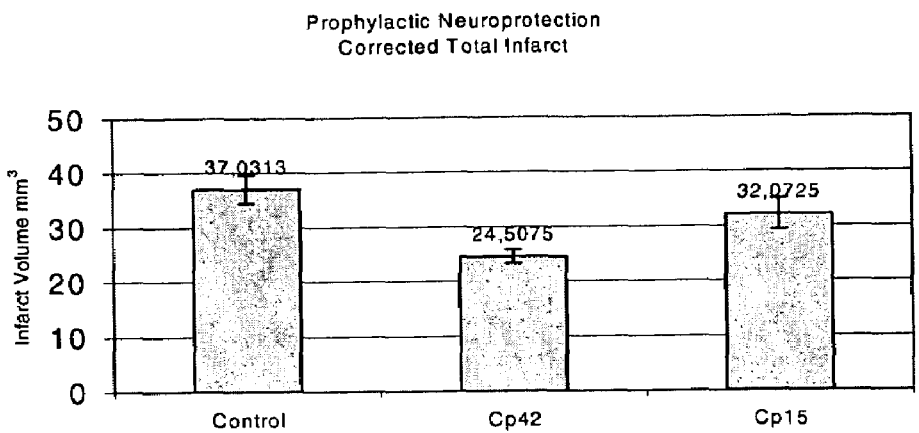
Figures 2, 3:
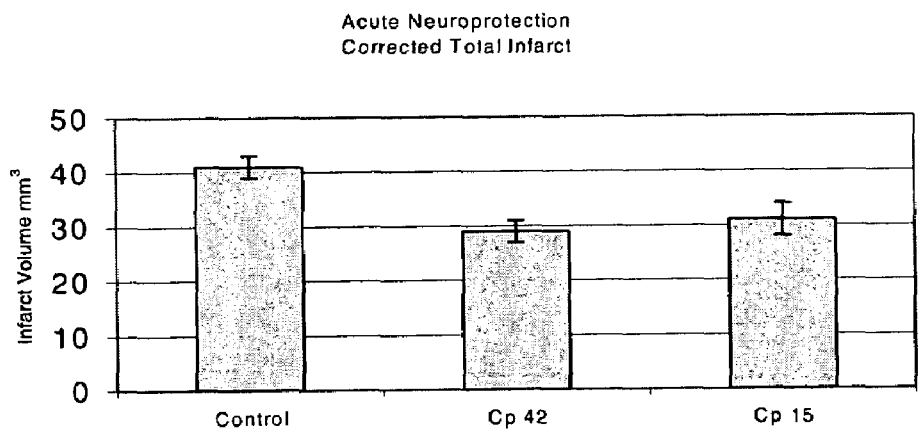
Figures 1, 4:
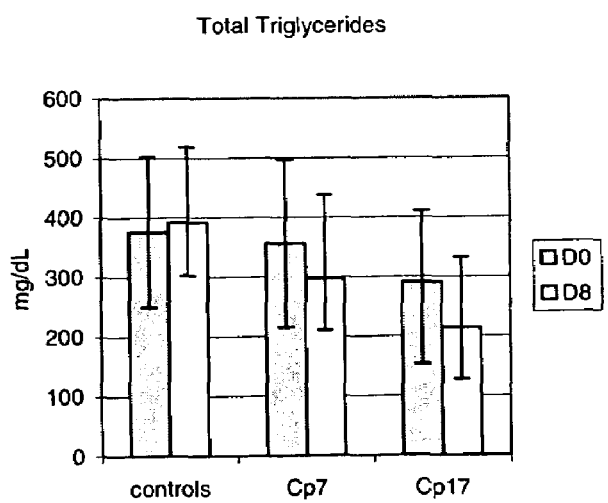
Figures 2, 4:
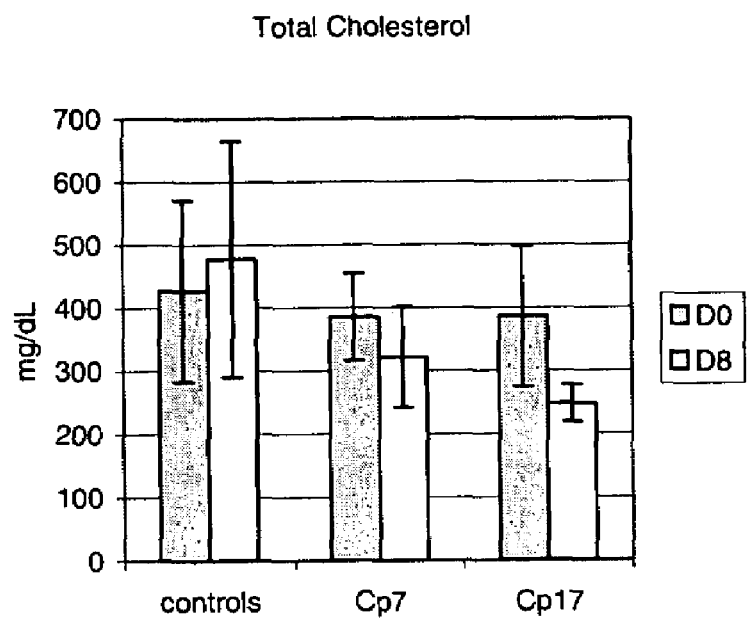
Figures 3, 4:
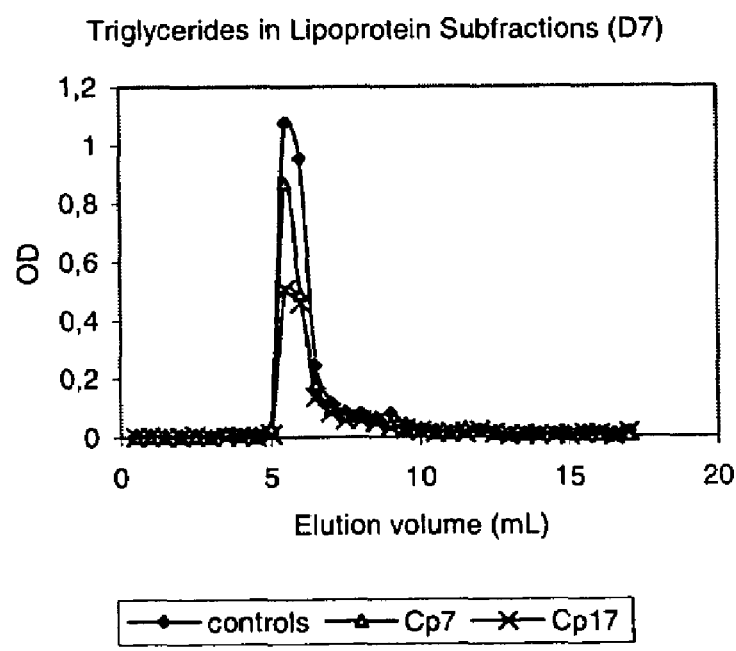
Figure 4:
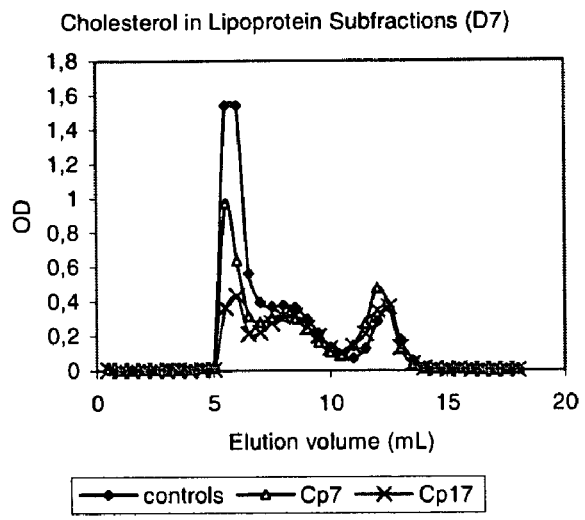
Figures 4, 5:
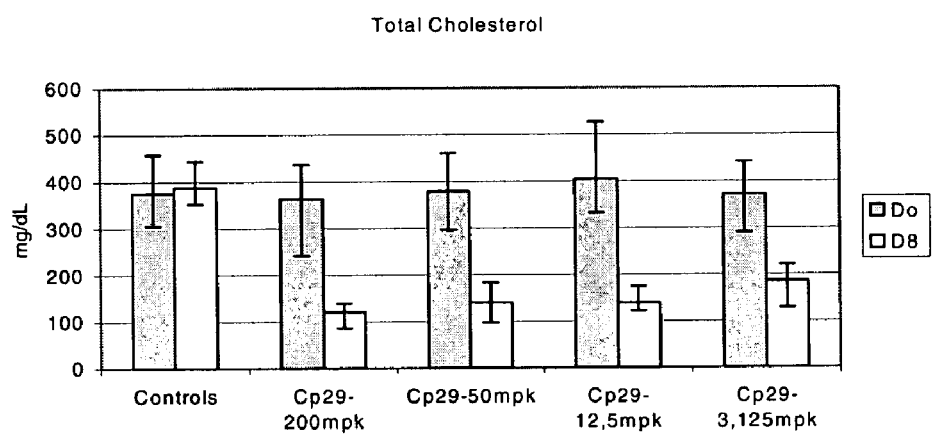
Figures 4, 5, 6:
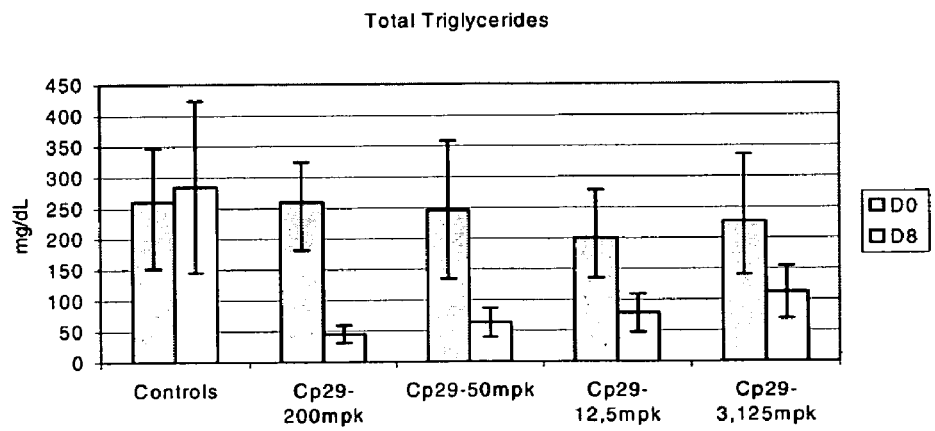
Figures 4, 5, 6, 7:
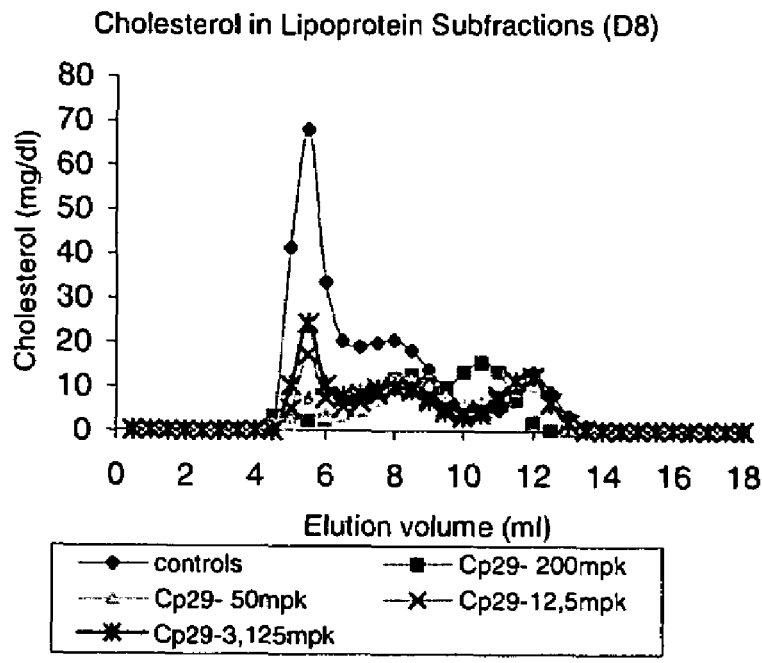
Figures 4, 5, 6, 7, 8:
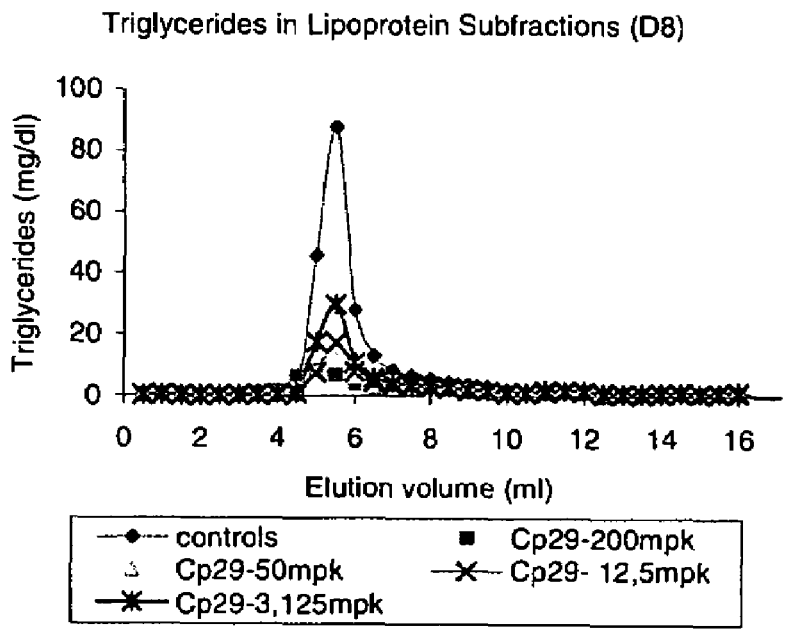
Figures 4, 5, 6, 7, 8, 9:
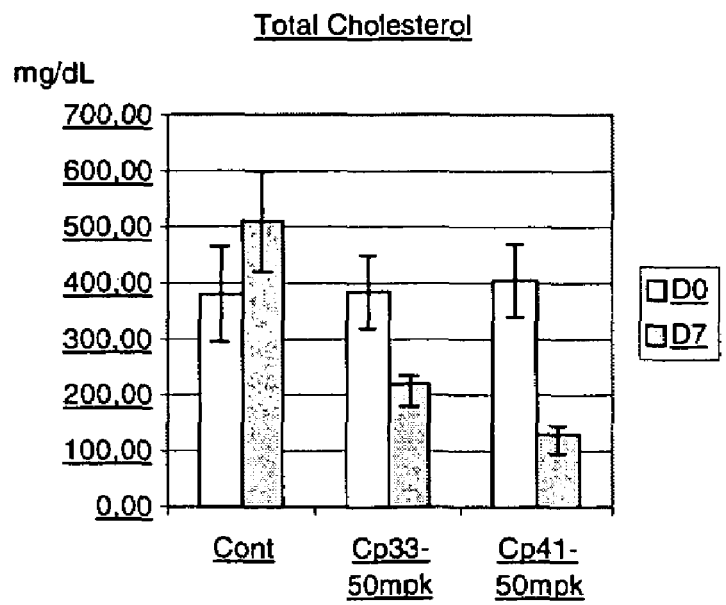
Figures 4, 5, 6, 7, 8, 9, 10:
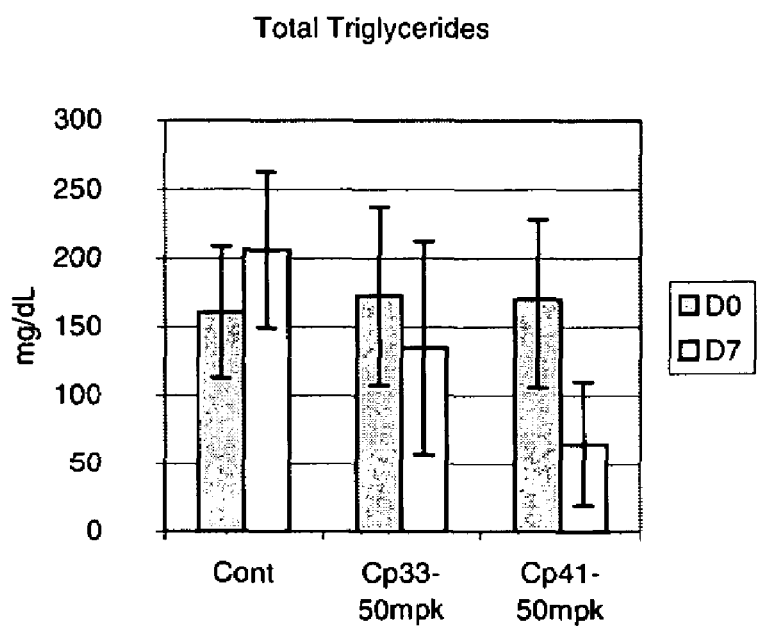
Figures 4, 5, 6, 7, 8, 9, 10, 11:
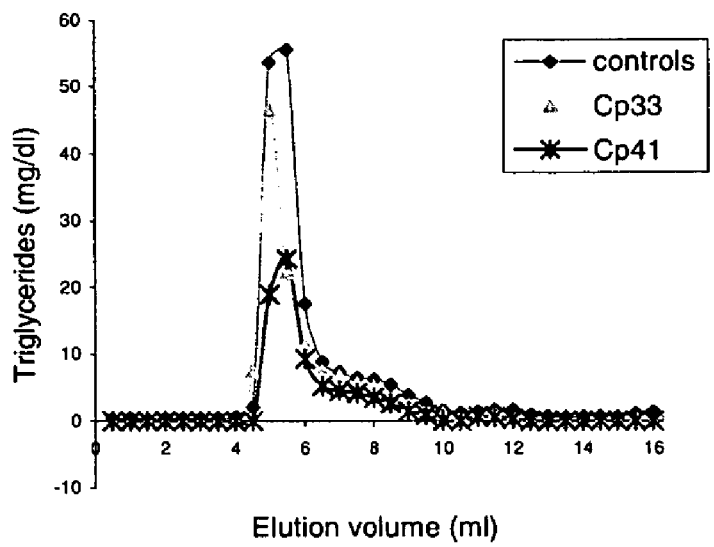
Figures 4, 5, 6, 7, 8, 9, 10, 11, 12:
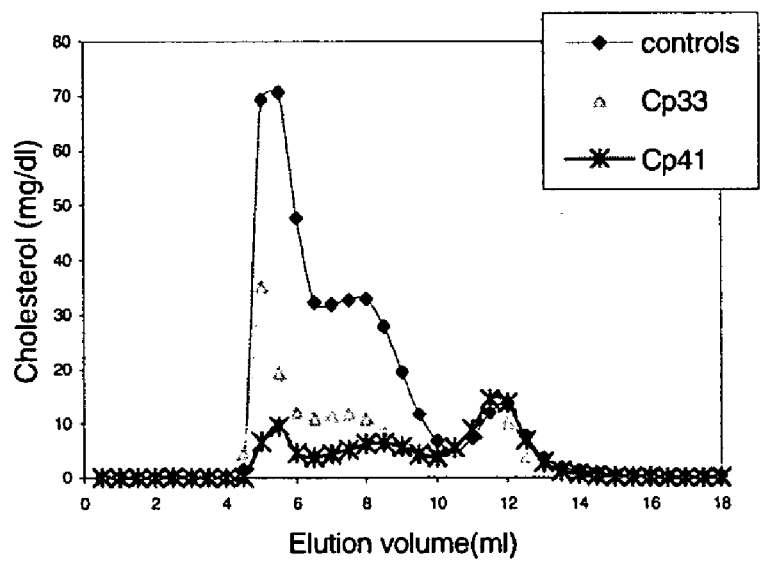
Figures 4, 5, 6, 7, 8, 9, 10, 11, 12, 13:
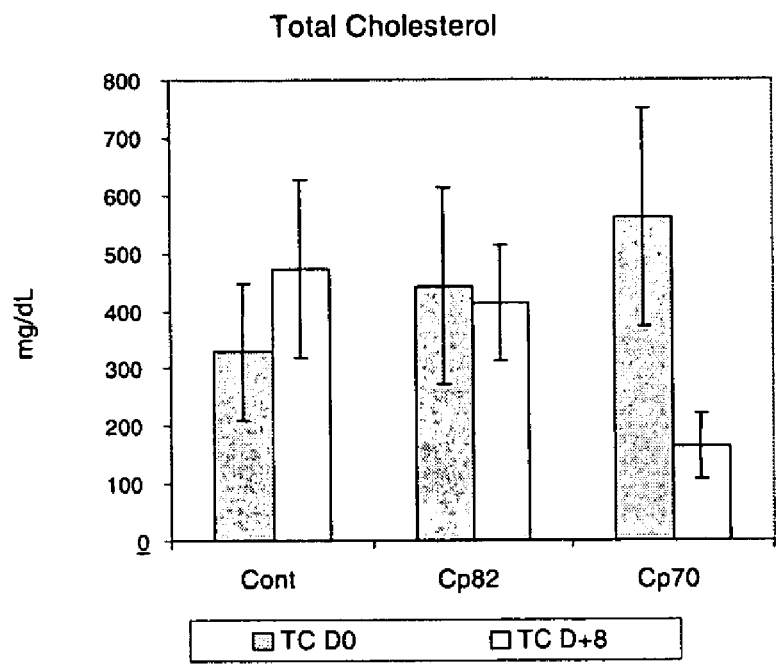
Figures 4, 5, 6, 7, 8, 9, 10, 11, 12, 13, 14:
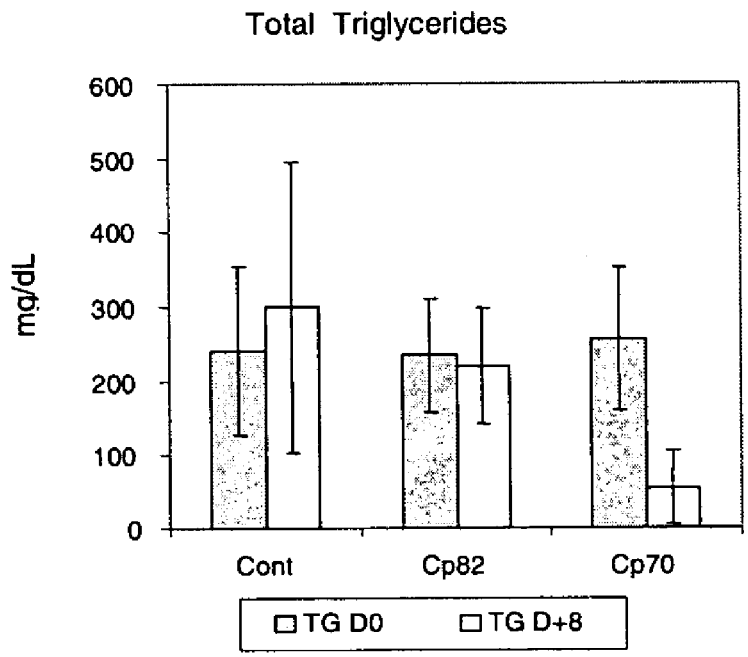
Figures 4, 5, 6, 7, 8, 9, 10, 11, 12, 13, 14, 15:
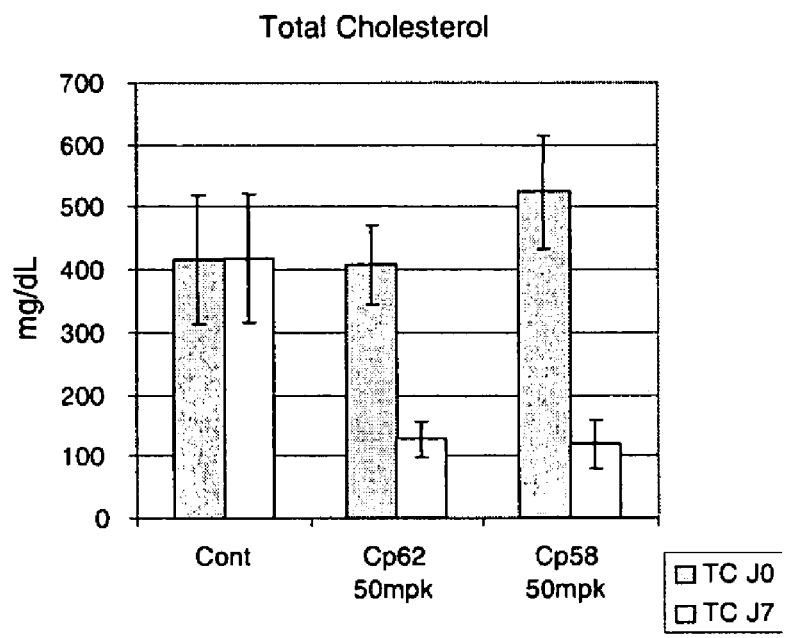
Figures 4, 5, 6, 7, 8, 9, 10, 11, 12, 13, 14, 15, 16:
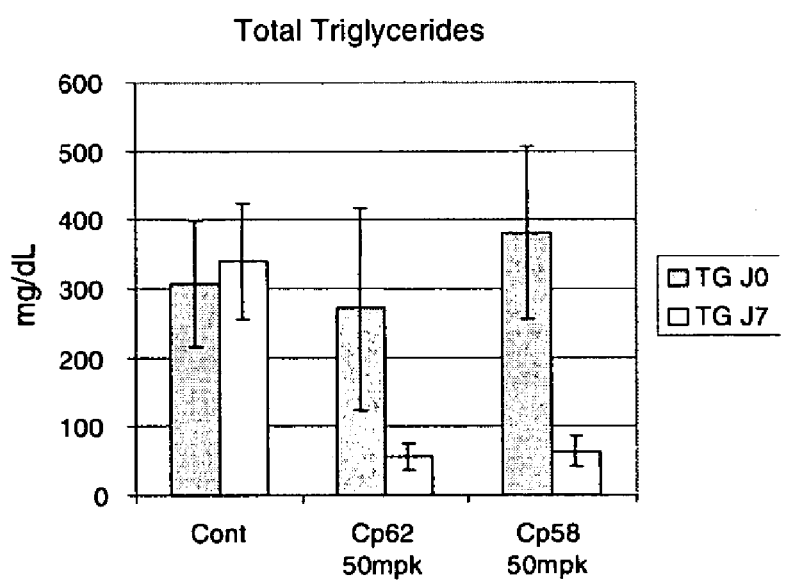
Figures 4, 5, 6, 7, 8, 9, 10, 11, 12, 13, 14, 15, 16, 17:
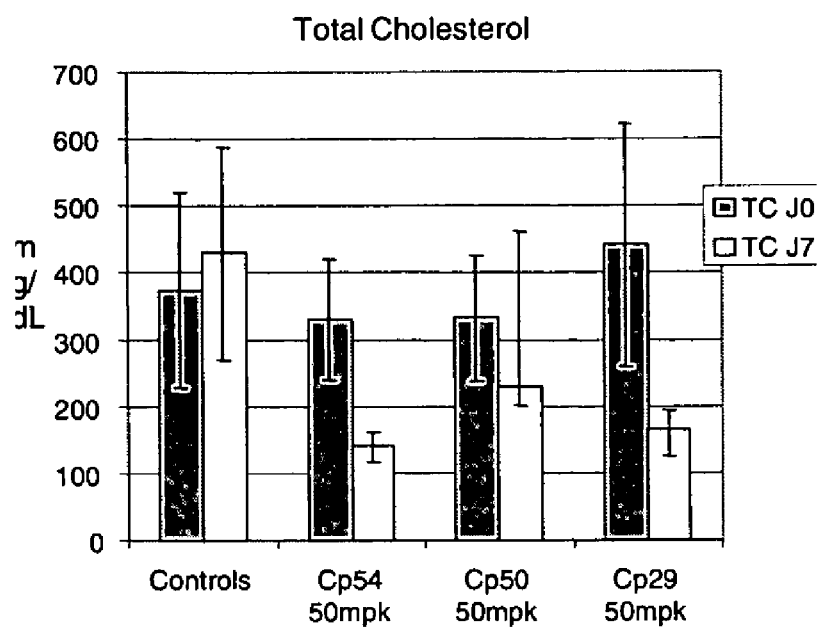
Figures 4, 5, 6, 7, 8, 9, 10, 11, 12, 13, 14, 15, 16, 17, 18:
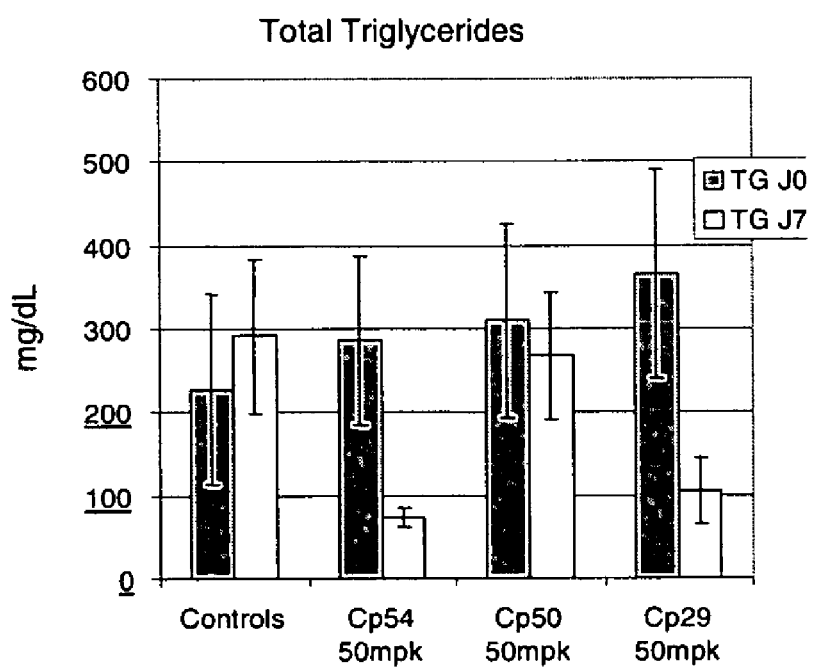
Figures 4, 5, 6, 7, 8, 9, 10, 11, 12, 13, 14, 15, 16, 17, 18, 19:
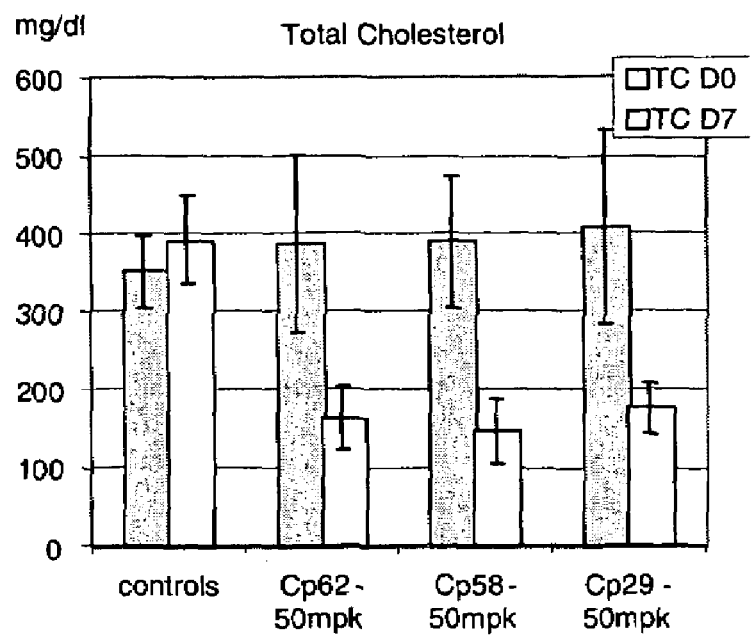
Figures 4, 5, 6, 7, 8, 9, 10, 11, 12, 13, 14, 15, 16, 17, 18, 19, 20:
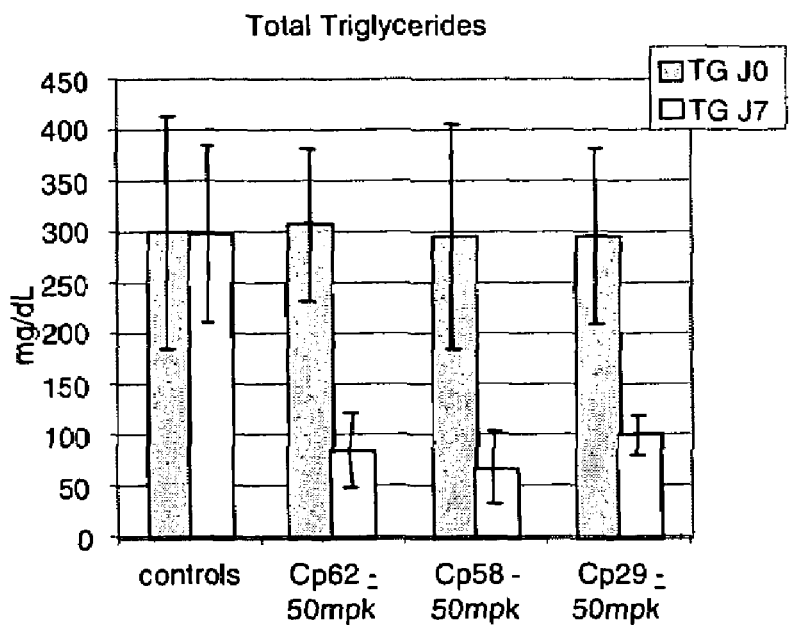
Figures 4, 5, 6, 7, 8, 9, 10, 11, 12, 13, 14, 15, 16, 17, 18, 19, 20, 21:
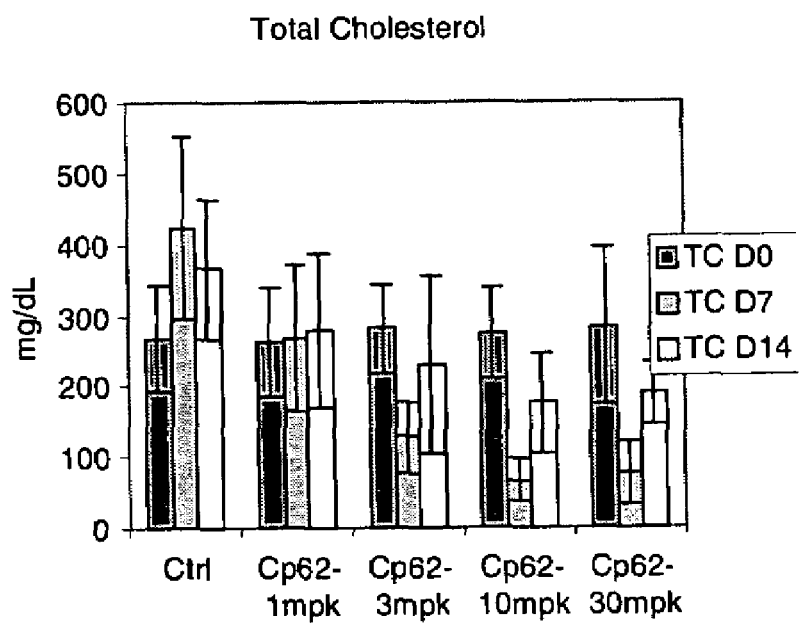
Figures 4, 5, 6, 7, 8, 9, 10, 11, 12, 13, 14, 15, 16, 17, 18, 19, 20, 21, 22:
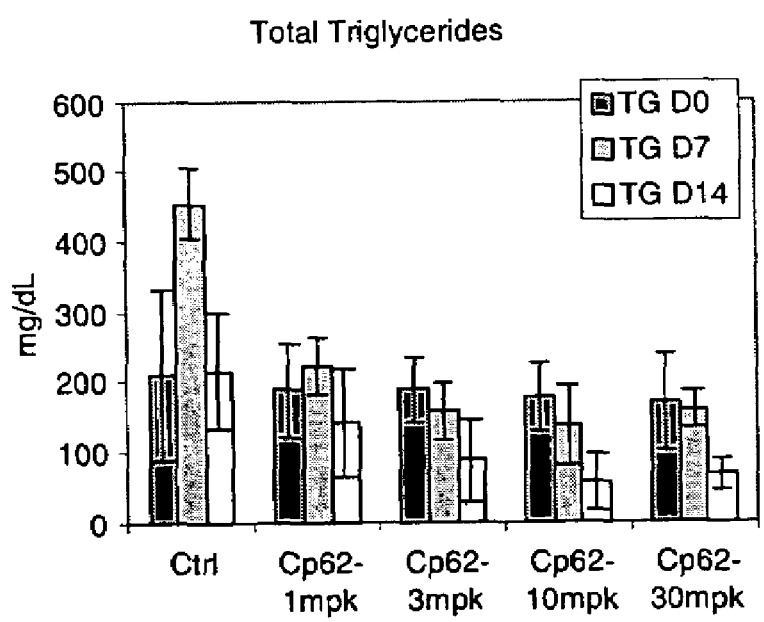
Figures 1, 5:
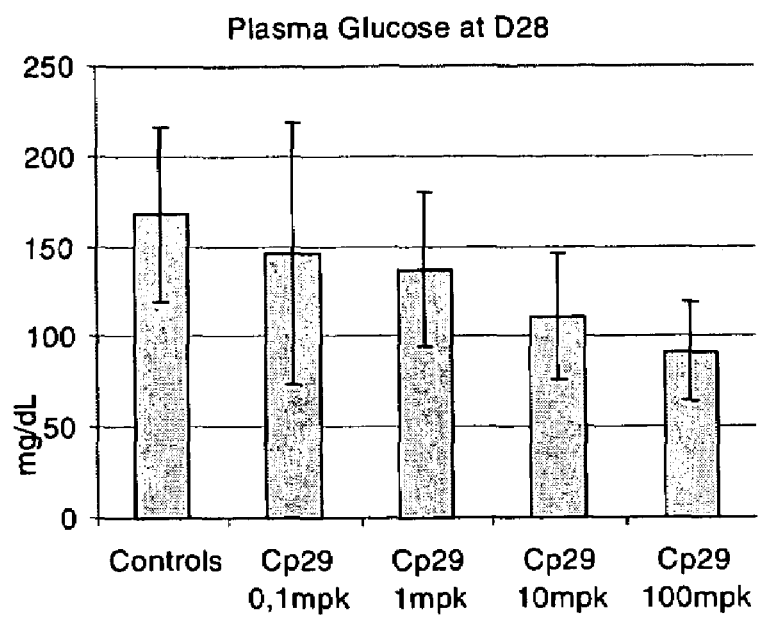
Figures 2, 5:
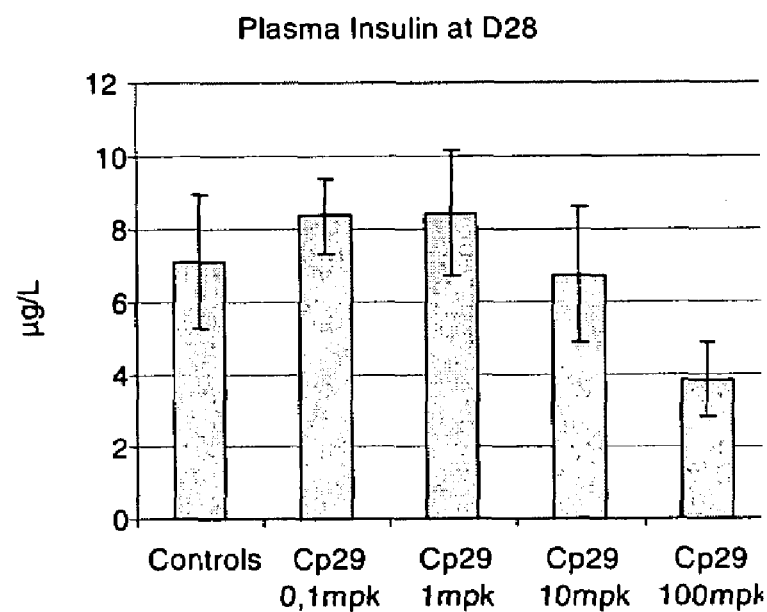
Figures 3, 5:
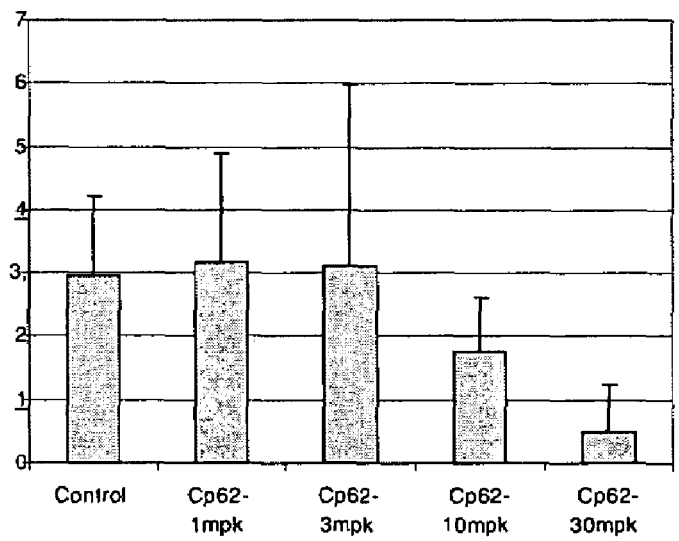
Figures 4, 5:
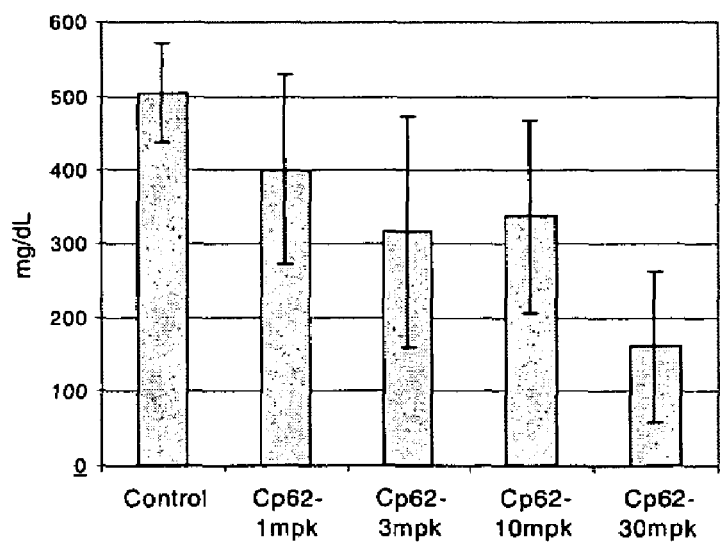
Figures 1, 6:
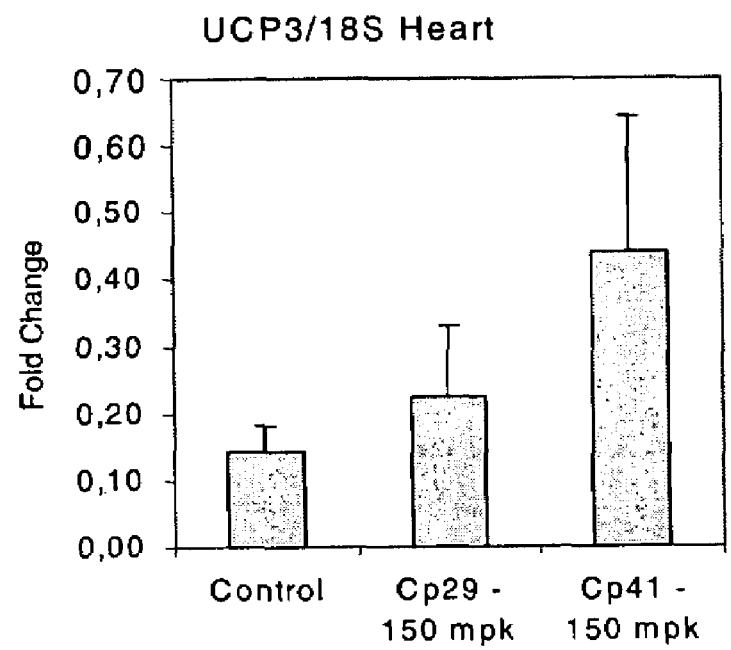
Figures 2, 6:
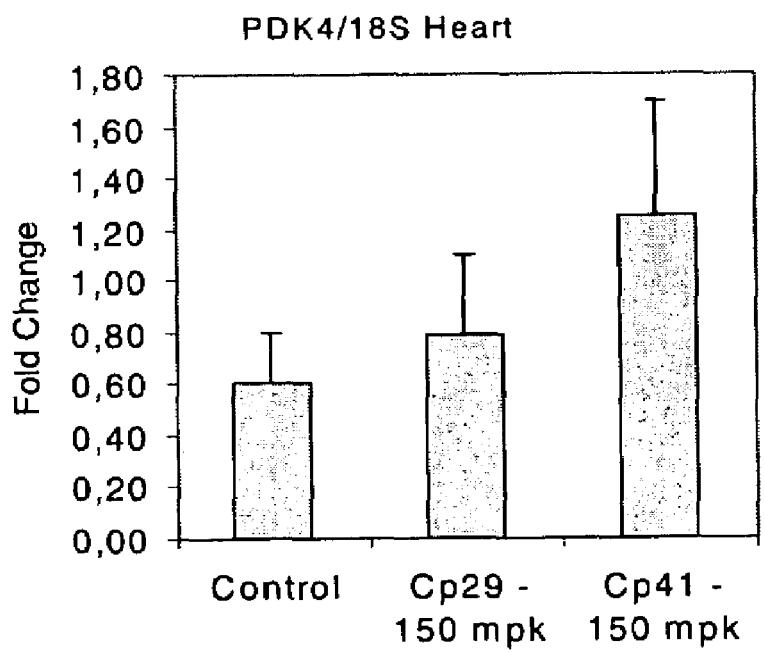
Figures 3, 6:
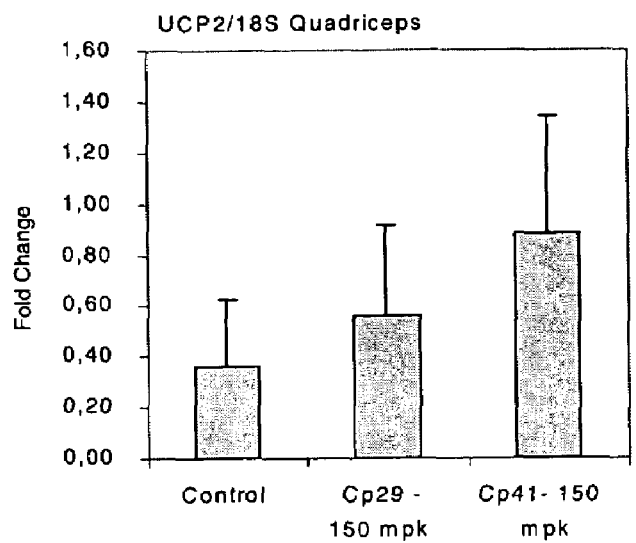
Figures 1, 7:
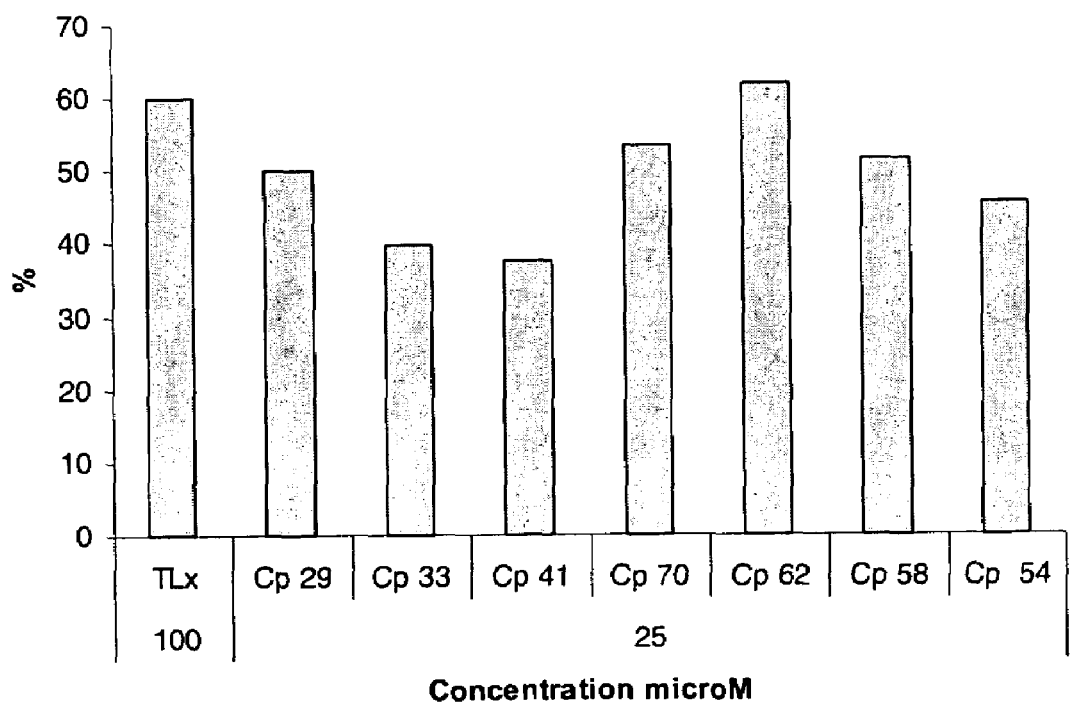
Figures 2, 7:
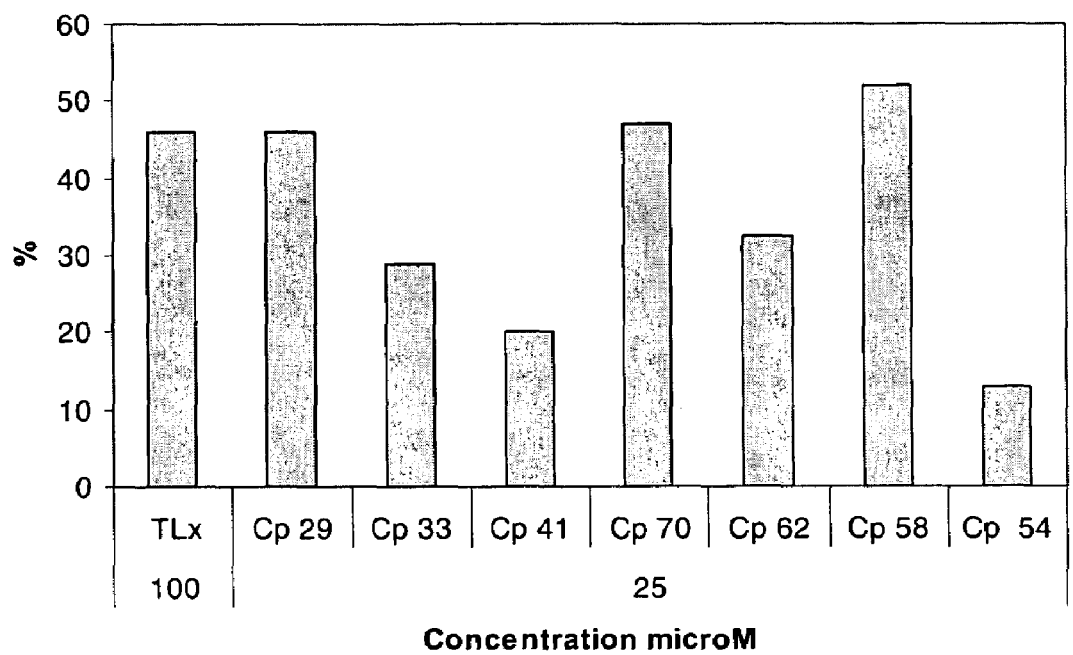
Figures 1, 8:
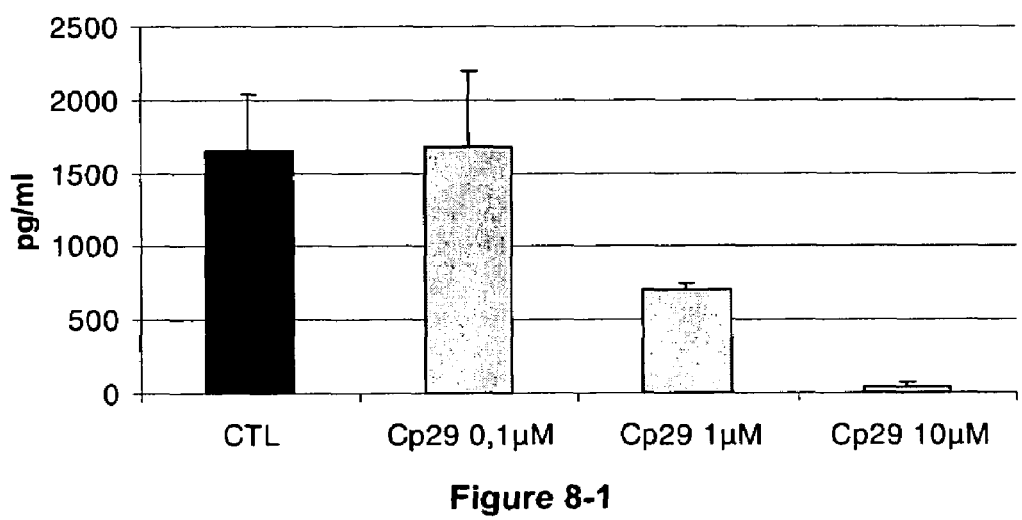
Figures 2, 8:
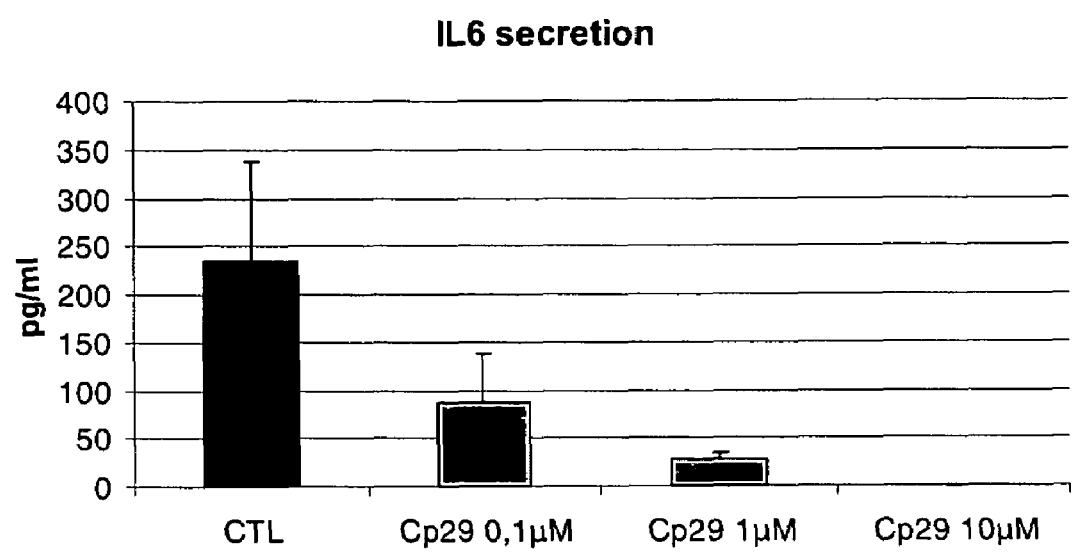

FIGS. 8-1 and 8-2: Evaluation of the anti-inflammatory properties of compound 29.

FIG. 8-1 shows the TNF☐ secretion by human macrophages pre-treated during 24 hours with compound 29 at different concentrations and stimulated with LPS during 6 hours. When compared to the non-treated cells, we observe that the treatment with the inventive compound 29, at doses of 1 and 10 µM, induces a decrease of the TNF☐ secretion. This result indicates that compound 29 has anti-inflammatory properties.

FIG. 8-2 shows the IL-6 secretion by human macrophages pre-treated during 24 hours with compound 29 at different concentrations and stimulated with LPS during 6 hours. When compared to the non-treated cells, we observe that the treatment with the inventive compound 29, at doses of 0.1, 1 and 10 µM, induces a decrease of the TNF☐ secretion. This result indicates that compound 29 has anti-inflammatory properties.

Other aspects and advantages of the invention will become apparent in the following examples, which are given for purposes of illustration and not by way of limitation.

EXAMPLES

The inventive compounds were prepared according to the general methods outlined below.

DESCRIPTION OF GENERAL SYNTHETIC METHODS OF THE INVENTION

Synthesis of 1,3-diphenylprop-2-en-1-ones

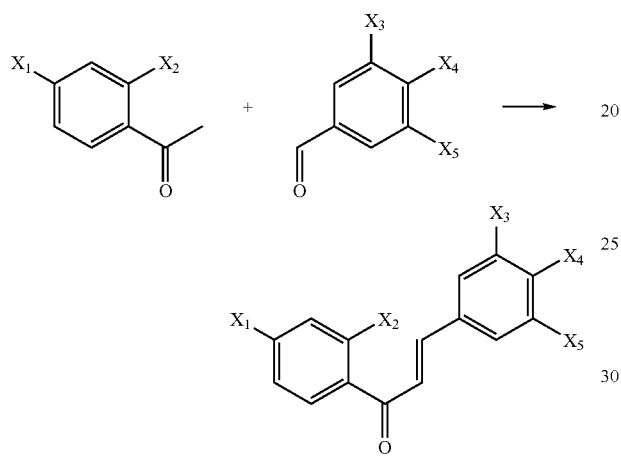

in which X1, X2, X3, X4 and X5 are such as defined hereinabove.

General Method 1: Synthesis of 1,3-diphenylprop-2-en-1-ones in Acidic Medium

The ketone (1 eq) and the aldehyde (1 eq) were dissolved in ethanol solution saturated with gaseous hydrochloric acid. The reaction was stirred at room temperature for 6 hours and the solvent was then eliminated by vacuum evaporation. 1,3-diphenylprop-2-en-1-one was purified by chromatography on silica gel.

General Method 2: Synthesis of 1,3-diphenylprop-2-en-1-ones in Basic Medium

The ketone (1 eq) and the aldehyde (1 eq) were dissolved in a hydroalcoholic solution of sodium hydroxide (20 eq). The mixture was stirred at room temperature for 18 hours. The medium was acidified to pH=2 with hydrochloric acid. 1,3-diphenylprop-2-en-1-one was obtained by precipitation or solid/liquid extraction after evaporation of the reaction medium. It was purified by silica gel chromatography or by recrystallization.

General Method 3: Synthesis of substituted 1,3-diphenyl-prop-2-en-1-ones in the Presence of Sodium Ethylate Sodium (1 eq) was dissolved in absolute ethanol. The ketone (1 eq) and the aldehyde (1 eq) were added. The reaction mixture was stirred at room temperature for 12 hours and 2 N sodium hydroxide (5 eq) was then added. The mixture was kept at 100° C. for 12 hours. The reaction medium was acidified by adding 6 N aqueous hydrochloric acid solution. The solvent was eliminated by vacuum evaporation. The residue was purified by chromatography on silica gel or by recrystallization.

General Method 4: O-Alkylation of phenols and S-alkylation of thiophenols

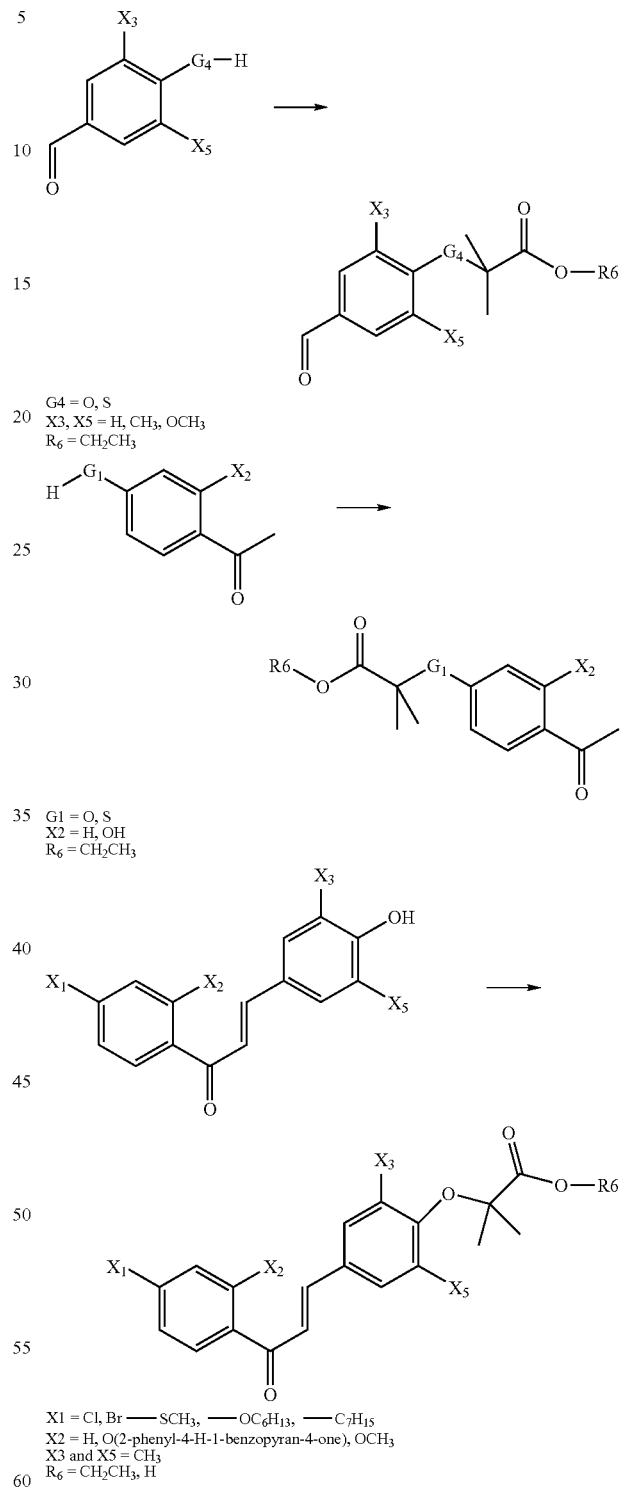

The phenol (1 eq) was dissolved in acetonitrile. The halogenated derivative (1 to 10 eq) and potassium carbonate (5 eq) were then added. The reaction medium was briskly stirred under reflux for approximately 10 hours. The salts were eliminated by filtration, the solvent and excess reagent were eliminated by vacuum evaporation and the expected product was purified by silica gel chromatography.

General Method 5: Acid Hydrolysis of Tertbutylic Esters

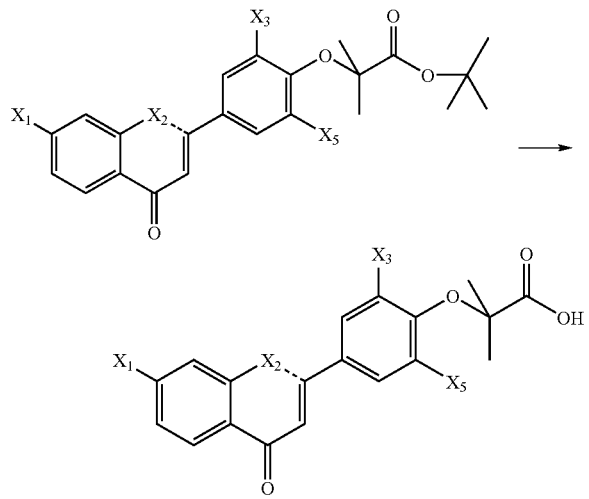

X3 and X5=CH$_3$,

X2=H, O(2-phenyl-4-H-1-benzopyran-4-one), OCH$_3$,

X1=Cl, Br, —SCH$_3$, OC$_6$H$_{13}$, —C$_7$H15$_{15}$

The tert-butylic ester (1 eq) was dissolved in dichloromethane, trifluoroacetic acid (10 eq) was added, and the mixture was stirred at room temperature for 12 hours. The resulting product was purified by chromatography on silica gel or by recrystallization.

Synthesis of Starting Materials used to Synthesize the Inventive Compounds:

Starting Material 1

2'-Hydroxy-4'-(ethoxycarbonyldimethylmethoxy) acetophenone

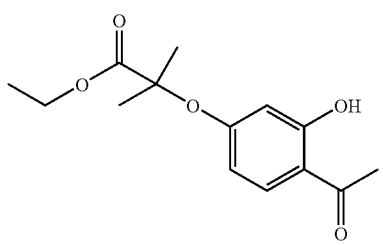

This compound was synthesized from 2',4'-dihydroxyacetophenone and ethyl bromoisobutyrate (1 eq) according to general method 4 described earlier.

It was purified by chromatography on silica gel (elution: cyclohexane/ethyl acetate 9:1).

$^1$H NMR CDCl$_3$ δppm: 1.25 (t, J=7.17 Hz, 3H), 1.67 (s, 6H), 2.56 (s, 3H), 4.24 (q, J=7.17 Hz, 2H), 6.27 (d, J=2.55 Hz, 1H), 6.37 (dd, J=2.55 Hz, J=8.72 Hz, 1H), 7.62 (d, J=8.72 Hz, 1H), 12.6 (signal, 1H).

Reference: U.S. Pat. No. 3,629,290 (1970), Fisons Pharmaceutical

Starting Material 2

3-chlorophenyl acetate

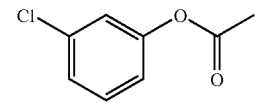

3-chlorophenol was dissolved in dichloromethane. Triethylamine (1 eq) and acetic anhydride (2 eq) were added. The mixture was stirred at room temperature for 5 hours. Solvent was eliminated by vacuum evaporation. The evaporation residue was taken up in dichloromethane, dried on magnesium sulfate and the solvent was eliminated by vacuum evaporation. Purification was made by chromatography on silica gel (elution: cyclohexane/ethyl acetate 95:5).

$^1$H NMR CDCl$_3$ δppm: 2.29 (s, 3 H), 6.99-7.33 (m, 4 H).

Starting Material 3

4'-Chloro-2'-hydroxyacetophenone

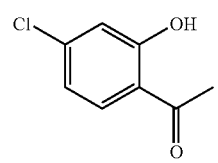

3-chlorophenyl acetate (starting material 2) was mixed with aluminium chloride (3 eq). The mixture was heated at 200° C. for 1 hour. The reaction medium was cooled to room temperature then poured in ice. The aqueous phase was extracted with methylene chloride which was dried on magnesium sulfate then vacuum evaporated.

Purification was made by silica gel chromatography (elution: cyclohexane/ethyl acetate 95:5).

$^1$H NMR CDCl$_3$ δppm: 3.41 (s, 3 H), 6.81 (dd, J=8.82 Hz, J=1.47 Hz, 1H), 6.91 (d, J=1.47 Hz, 1H), 7.60 (d, J=8.82 Hz, 1 H), 12.33 (s, 1H)

Starting Material 4

4-Ethyloxycarbonyldimethylmethyloxybenzaldehyde

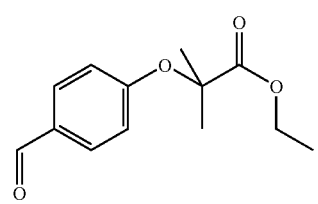

This compound was synthesized from 4-hydroxyabenzaldehyde and ethyl bromoisobutyrate according to general method 4 described earlier.

Purification was made by silica gel chromatography (elution: cyclohexane/ethyl acetate 9:1).

$^1$H NMR CDCl$_3$ δppm: 1.20 (t, J=6.96 Hz, 3H), 1.67 (s, 6H), 4.21 (q, J=6.96 Hz, 2H), 6.89 (d, J=8.91 Hz, 2H), 7.79 (d, J=8.94 Hz, 2H), 9.87 (S, 1H).

Starting Material 5

3,5-dimethyloxy-4-ethyloxycarbonyldimethylmethyloxybenzaldehyde

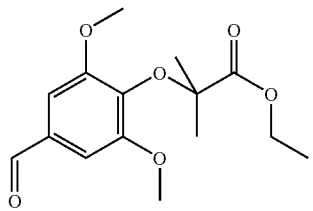

This compound was synthesized from 3,5-dimethyloxy-4-hydroxyabenzaldehyde and ethyl bromoisobutyrate according to general method 4 described earlier.

Purification was made by silica gel chromatography (elution: cyclohexane/ethyl acetate 8:2).

$^1$H NMR CDCl$_3$ δppm: 1.33 (t, J=7.29 Hz, 3H), 1.50 (s, 6H), 3.84 (s, 6H), 4.27 (q, J=7.29 Hz, 2H), 7.08 (s, 2H), 9.86 (s, 1H).

Starting Material 6

3,5-dimethyl-4-ethyloxycarbonyldimethylmethyloxybenzaldehyde

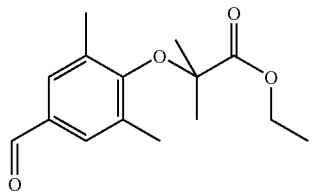

This compound was synthesized from 3,5-dimethyl-4-hydroxyabenzaldehyde and ethyl bromoisobutyrate according to general method 4 described earlier.

Purification was made by silica gel chromatography (elution: cyclohexane/ethyl acetate 95:5).

$^1$H NMR CDCl$_3$ δppm: 1.37 (t, J=7.14 Hz, 3H), 1.50 (s, 6H), 2.29 (s, 6H), 4.30 (q, J=7.14 Hz, 2H), 7.54 (s, 2H), 9.88 (s, 1H).

Starting Material 7

3-Ethyloxycarbonyldimethylmethyloxybenzaldehyde

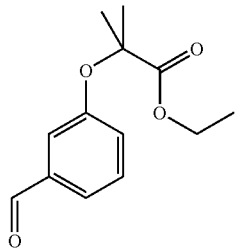

This compound was synthesized from 3-hydroxybenzaldehyde and ethyl bromoisobutyrate according to general method 4 described earlier.

Purification was made by silica gel chromatography (elution:cyclohexane/ethyl acetate 9:1).

$^1$H NMR CDCl$_3$ δppm: 1.24 (t, J=7.27 Hz, 3H), 1.62 (s, 6H), 4.25 (q, J=7.27 Hz, 2H), 7.11 (m, 1H), 7.31 (m, 1H), 7.40 (t, J=8.19 Hz, 1H), 7.49 (m, 1H), 9.93 (s, 1H).

Starting Material 8

4-Ethyloxycarbonyldimethylmethylthiobenzaldehyde

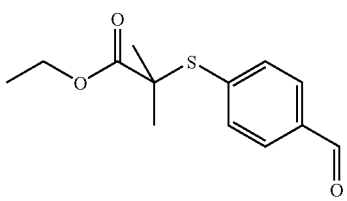

4-Methylthiobenzaldehyde (1 eq) was dissolved in methylene chloride and the solution cooled to 0° C. Metachloroperbenzoic acid (1.5 eq) was added in small fractions. The reaction was followed by thin-layer chromatography. Additional metachloroperbenzoic acid was possibly added so as to obtain total disappearance of the starting product. The precipitate was eliminated by filtration. Calcium hydroxide (1.5 eq) was added and the mixture was stirred for another 15 min. The solid was eliminated by filtration, the filtrate dried on magnesium sulfate and the methylene chloride was then eliminated by vacuum evaporation.

The evaporation residue was taken up in trifluoroacetic anhydride, then heated under reflux for 30 min and evaporated to dryness. The residue was taken up in methanol/triethylamine solution, stirred at room temperature for 15 minutes, then the solvents were eliminated by vacuum evaporation. The oily residue was taken up in a saturated aqueous ammonium chloride solution then extracted with methylene chloride. The organic phase was dried on magnesium sulfate and vacuum evaporated.

The resulting 4-mercaptobenzaldehyde intermediate was used without further purification. It was alkylated according to general method 4 to yield 4-ethyloxycarbonyldimethylmethylthiobenzaldehyde.

Purification was made by silica gel chromatography (elution: cyclohexane/ethyl acetate 9:1).

$^1$H NMR CDCl$_3$ δppm: 1.22 (t, J=7.46 Hz, 3H), 2.60 (s, 6H), 4.15 (q, J=7.46 Hz, 2H), 7.53 (d, J=8.38 Hz, 2H), 7.88 (d, J=8.39 Hz, 2H), 9.99 (s, 1H).

Starting Material 9

4'-Ethyloxycarbonyldimethylmethyloxyacetophenone

This compound was synthesized from 4'-hydroxyacetophenone and ethyl bromoisobutyrate according to general method 4 described earlier.

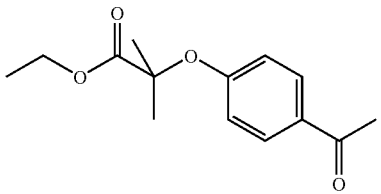

Purification was made by silica gel chromatography (elution: cyclohexane/ethyl acetate 9:1).

$^1$H NMR CDCl$_3$ δppm: 1.17 (t, J=5.64 Hz, 3H), 1.61 (s, 6H), 2.50 (s, 3H), 4.18 (q, J=5.64 Hz, 2H), 6.78 (d, J=8.82 Hz, 2H), 7.83 (d, J=8.81 Hz, 2H).

Starting Material 10

3-bromophenyl acetate

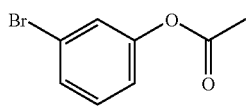

3-bromophenol was dissolved in dichloromethane. Triethylamine (1 eq) and acetic anhydride (2 eq) were added and the mixture was stirred at room temperature for 5 hours. The solvent was eliminated by vacuum evaporation. The evaporation residue was taken up in dichloromethane then dried on magnesium sulfate. The solvent was eliminated by vacuum evaporation.

Purification was made by silica gel chromatography (elution: cyclohexane/ethyl acetate 95:5).

$^1$H NMR CDCl$_3$ δppm: 2.30 (s, 3H), 7.0-7.4 (m, 4H).

Starting Material 11

4'-bromo -2'-hydroxyacetophenone

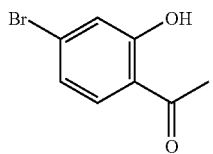

3-bromophenyl acetate (starting material 10) was mixed with aluminium chloride (3 eq), and the mixture was heated at 200° C. for 1 hour. The reaction medium was cooled to room temperature then poured in ice. The aqueous phase was extracted with methylene chloride which was dried on magnesium sulfate.

Purification was made by silica gel chromatography (elution: cyclohexane/ethyl acetate 95:5).

$^1$H NMR CDCl$_3$ δppm: 2.59 (s, 3H), 7.01 (d, J=8.5 Hz, 1H), 7.13 (s, 1H), 7.55 (d, J=8.5 Hz, 1H), 12.33 (s, 1H).

Starting Material 12

4'-Ethyloxycarbonyldimethylmethylthioacetophenone

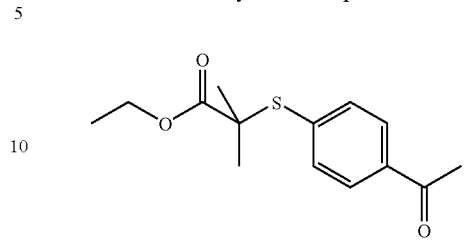

4'-methylthioacetophenone was dissolved in methylene chloride and the solution cooled to 0° C. Metachloroperbenzoic acid (1.5 eq) was added in small fractions. The reaction was followed by thin-layer chromatography. Additional metachloroperbenzoic acid was possibly added so as to obtain total disappearance of the starting product. The precipitate was eliminated by filtration. Calcium hydroxide (1.5 eq) was added and the mixture was stirred for another 15 min. The solid was eliminated by filtration, the filtrate dried on magnesium sulfate and the methylene chloride was then eliminated by vacuum evaporation.

The evaporation residue was taken up in trifluoroacetic anhydride, then heated under reflux for 30 min and evaporated to dryness. The residue was taken up in methanol/triethylamine solution, stirred at room temperature for 15 minutes, then the solvents were eliminated by vacuum evaporation. The oily residue was taken up in a saturated aqueous ammonium chloride solution then extracted with methylene chloride. The organic phase was dried on magnesium sulfate then vacuum evaporated.

The resulting 4-mercaptoacetophenone intermediate was used without further purification. It was alkylated according to general method 4 to yield 4-ethyloxycarbonyldimethylmethylthioacetophenone.

Purification was made by silica gel chromatography (elution: cyclohexane/ethyl acetate 9:1).

$^1$H NMR CDCl$_3$ δppm: 1.21 (t, J=7.32 Hz, 3H), 1.51 (s, 6H), 2.59 (s, 3H), 4.12 (q, J=7.32 Hz, 2H), 7.51 (d, J=8.40 Hz, 2H), 7.79 (d, J=8.40 Hz, 2H).

SYNTHESIS OF INTERMEDIATE COMPOUNDS USED TO SYNTHESIZE THE INVENTIVE COMPOUNDS

Intermediate Compound 1

1-[4-chlorophenyl]-3-[3,5-dimethyl-4-hydroxyphenyl]prop-2-en-1-one

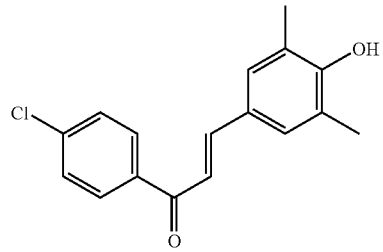

This compound was synthesized from 4-chloroacetophenone and 3,5-dimethyl-4-hydroxybenzaldehyde according to general method 1 described earlier.

Purification was made by chromatography on silica gel (elution: cyclohexane/ethyl acetate 95:5).

¹H NMR CDCl₃ δppm: 2.30 (s, 6H), 7.32 (s, 2H), 7.34 (d, J=15.25 Hz, 1H), 7.47 (d, J=8.86 Hz, 2H), 7.75 (d, J=15.26 Hz, 1H), 7.97 (d, J=8.86 Hz, 2H).

Intermediate Compound 2

1-[4-methylthiophenyl]-3-[3,5-dimethyl-4-hydroxyphenyl]prop-2-en-1-one

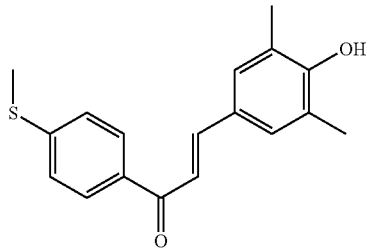

This compound was synthesized from 4'-methylthioacetophenone and 3,5-dimethyl-4-hydroxybenzaldehyde according to general method 1 described earlier.

Purification was made by chromatography on silica gel (elution: cyclohexane/ethyl acetate 8:2).

¹H NMR DMSO-d₆ δppm: 2.22 (s, 6H), 2.54 (s, 3H), 7.36 (d, J=8.20 Hz, 2H), 7.48 (s, 2H), 7.62 (d, J=15.7 Hz, 1H), 7.74 (d, J=15.7 Hz, 1H), 8.10 (d, J=8.20 Hz, 2H), 8.92 (s, 1H).

Intermediate Compound 3

1-[2-methoxyphenyl]-3-[3,5-dimethyl-4-hydroxyphenyl]prop-2-en-1-one

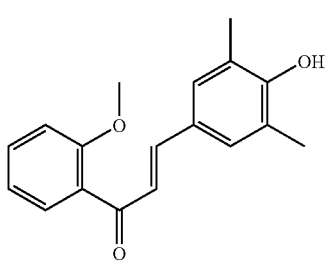

This compound was synthesized from 2'-methoxyacetophenone and 3,5-dimethyl-4-hydroxybenzaldehyde according to general method 1 described earlier.

Purification was made by chromatography on silica gel (elution: cyclohexane/ethyl acetate 8:2).

¹H NMR DMSO-d₆ δppm: 2.39 (s, 6H), 2.22 (s, 3H), 7.58 (s, 2H), 7.67-7.62 (m, 3H), 7.82 (d, J=15.5 Hz, 1H), 8.17 (d, 1H), 12.96 (s, 1H).

Intermediate Compound 4

1-[4-hexyloxyphenyl]-3-[3,5-dimethyl-4-hydroxyphenyl]prop-2-en-1-one

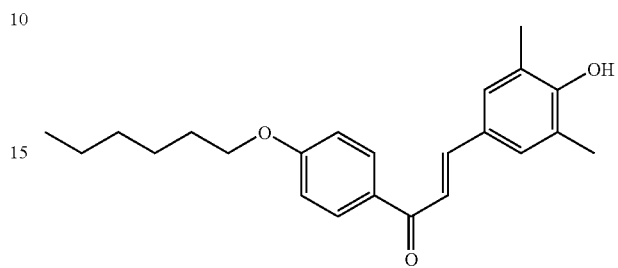

This compound was synthesized from 4-hexyloxyacetophenone and 3,5-dimethyl-4-hydroxybenzaldehyde according to general method 1 described earlier.

The expected compound was precipitated in the reaction medium, dried and used without further purification for the following reaction.

¹H NMR DMSO-d₆ δppm: 0.88 (m, 3H), 1.28-1.43 (m, 6H), 1.72 (m, 2H), 2.21 (s, 6H), 4.05 (t, J=6.42 Hz, 2H), 7.40 (d, J=8.43 Hz, 2H), 7.48 (s, 2H), 7.57 (d, J=15.24 Hz, 1H), 7.72 (d, J=15.24 Hz, 1H), 8.12 (d, J=8.43 Hz, 2H), 8.89 (s, 1H).

Intermediate Compound 5

1-[2-hydroxy-4-chlorophenyl]-3-[3,5-dimethyl-4-hydroxyphenyl]prop-2-en-1-one

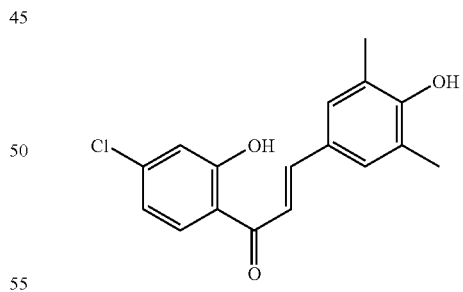

This compound was synthesized from 4'-chloro-2'-hydroxyacetophenone (starting material 3) and 3,5-dimethyl-4-hydroxybenzaldehyde according to general method 1 described earlier.

Purification was made by chromatography on silica gel (toluene: 10).

¹H NMR DMSO-d₆ δppm: 2.21 (s, 6H), 7.1 (m, 2H), 7.55 (s, 2H), 7.72 (d, J=15.4 Hz, 1H), 7.80 (d, J=15.4 Hz, 1H), 8.25 (d, J=9.0 Hz, 1H), 9.09 (s, 1H), 13.04 (s, 1H).

Intermediate Compound 6

2-(3,5-dimethyl-4-hydroxyphenyl)-7-chloro4H-1-benzopyran-4-one

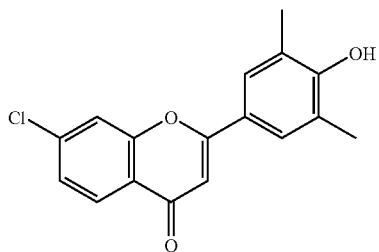

This compound was synthesized from 1-[2-hydroxy-4-chlorophenyl]-3-[3,5-dimethyl-4-hydroxyphenyl]prop-2-en-1-one (intermediate compound 5) according to the following method:

1-[2-hydroxy-4-chlorophenyl]-3-[3,5-dimethyl-4-hydroxyphenyl]prop-2-en-1-one was dissolved in dimethylsulfoxide, an iodine crystal was added, and the mixture was kept under reflux for 10 min.

The reaction medium was brought to room temperature, hydrolyzed. The precipitate was dried, rinsed with sodium thiosulfate solution then with water.

Purification was made by dissolution in methylene chloride and precipitation by addition of heptane.

$^1$H NMR DMSO-d$_6$ δppm: 2.25 (s, 6H), 6.87 (s, 1H), 7.51 (d, J=8.55 Hz, 1H), 7.73 (s, 2H), 7.98 (m, 2H).

Intermediate Compound 7

1-[2-methyloxy-4-chlorophenyl]-3-[3,5-dimethyl-4-hydroxyphenyl]prop-2-en-1-one

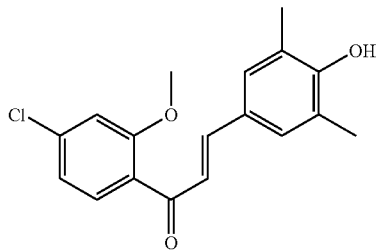

This compound was synthesized from 4'-chloro-2'-methoxyacetophenone and 3,5-dimethyl-4-hydroxybenzaldehyde according to general method 1 described earlier.

Purification was made by chromatography on silica gel (elution: cyclohexane/ethyl acetate 85:15).

$^1$H NMR DMSO-d$_6$ δppm: 2.21 (s, 6H), 3.90 (s, 3H), 7.12 (m, 1H), 7.23 (d, J=15.5 Hz, 1H), 7.29 (s, J=1.80 Hz, 1H), 7.38 (d, J=15.5 Hz, 1H), 7.41 (s, 2H), 7.48 (d, J=7.98 Hz, 1H).

Intermediate Compound 8

1-[4-bromophenyl]-3-[3,5-dimethyl-4-hydroxyphenyl]prop-2-en-1-one

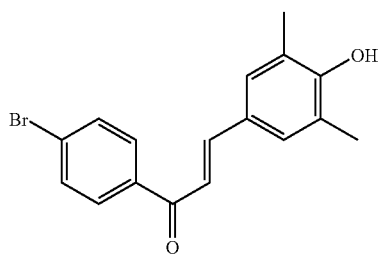

This compound was synthesized from 4'-bromoacetophenone and 3,5-dimethyl-4-hydroxybenzaldehyde according to general method 1 described earlier.

Purification was made by chromatography on silica gel (elution: cyclohexane/ethyl acetate 85:15).

$^1$H NMR DMSO-d$_6$ δppm: 2.30 (s, 6H), 7.32 (s, 2H), 7.56-7.66 (m, 3H), 7.75 (d, J=15.27 Hz, 1H), 7.90 (d, J=8.70 Hz, 2H), 9.82 (s, 1H).

Intermediate Compound 9

1-[4-heptylphenyl]-3-[3,5-dimethyl-4-hydroxyphenyl]prop-2-en-1-one

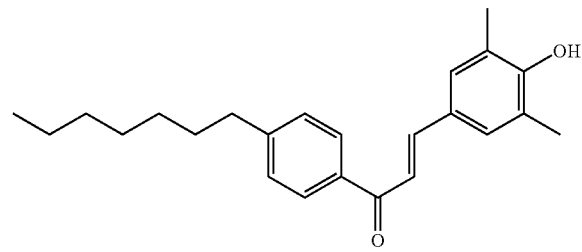

This compound was synthesized from 4'-heptylacetophenone and 3,5-dimethyl-4-hydroxybenzaldehyde according to general method 1 described earlier.

Purification was made by chromatography on silica gel (elution: cyclohexane/ethyl acetate 85:15).

$^1$H NMR DMSO-d$_6$ δppm: 0.84 (m, 3H), 1.25 (m, 8H), 1.60 (m, 2H), 2.21 (s, 6H), 2.65 (t, J=7.50 Hz, 2H), 7.35 (d, J=8.02 Hz, 2H), 7.48 (s, 2H), 7.60 (d, J=15.48 Hz, 1H), 7.71 (d, J=15.48 Hz, 1H), 8.05 (d, J=8.02 Hz, 2H), 8.92 (s, 1H).

Intermediate Compound 10

1-[4-trifluoromethylphenyl]-3-[3-methyl-4-hydroxyphenyl]prop-2-en-1-one

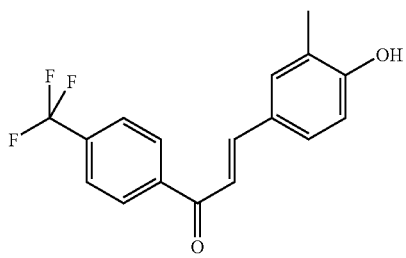

This compound was synthesized from 4'-trifluoromethylacetophenone and 3-methyl-4-hydroxybenzaldehyde according to general method 1 described earlier.

Purification was made by chromatography on silica gel (elution: cyclohexane/ethyl acetate 95:5).

$^1$H NMR CDCl$_3$ δppm: 2.31 (s, 3H), 6.20 (s, 1H), 6.86 (d, 1H, J=8.46 Hz), 7.37 (d, 1H, J=15.50 Hz), 7.40 (dd, 1H, J=8.46 Hz, J=1.74 Hz), 7.47 (s, 1H), 7.77 (d, 2H, J=8.20 Hz), 7.79 (d, 1H, J=15.50 Hz), 8.1 (d, 2H, J=8.19 Hz).

Intermediate Compound 11

1-[4-bromophenyl]-3-[3-tertiobutyl-4-hydroxyphenyl]prop-2-en-1-one

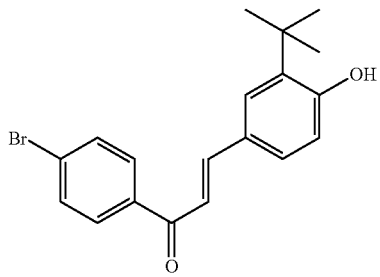

This compound was synthesized from 4'-bromoacetophenone and 3-tertiobutyl-4-hydroxybenzaldeyhde according to general method 1 described earlier.

Purification was made by chromatography on silica gel (elutio: cyclohexane/dichloromethane 8:2).

$^1$H NMR CDCl$_3$ δppm: 1.46 (s, 9H), 5.88 (s, 1H), 6.78 (d, 1H, J=8.20 Hz), 7.34 (d, 1H, J=15.60 Hz), 7.41 (dd, 1H, J=8.20 Hz 1.77 Hz), 7.56 (d, 1H, J=1.77 Hz) 7.65 (d, 2H, J=8.61 Hz), 7.82 (d, 1H, J=15.60 Hz), 7.9 (d, 2H, J=8.61 Hz).

Intermediate Compound 12

1-[2-trifluoromethyloxyphenyl]-3-[3,5-dimethyl-4-hydroxyphenyl]prop-2-en-1-one

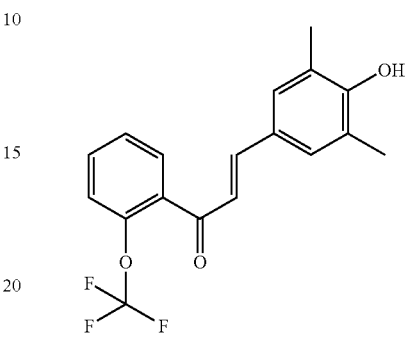

This compound was synthesized from 2'-trifluoromethylacetophenone and 3,5-dimethyl-4-hydroxybenzaldehyde according to general method 1 described earlier.

Purification was made by chromatography on silica gel (elution: cyclohexane/dichloromethane 3:7).

$^1$H NMR CDCl$_3$ δppm: 2.28 (s, 6H), 5.03 (s, 1H), 7.06 (d, 1H, J=15.75 Hz), 7.26 (s, 2H), 7.03-7.60 (m, 4H), 7.65 (d, 1H, J=7.32 Hz).

Intermediate Compound 13

1-[4-methylthiophenyl]-3-[3-trifluoromethyl-4-hydroxyphenyl]prop-2-en-1-one

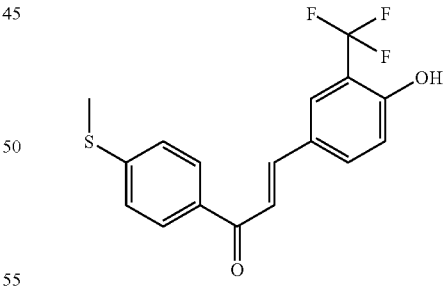

This compound was synthesized from 4'-methylthioacetophenone and 4-hydroxy-3-trifluoromethylbenzaldehyde according to general method 1 described earlier.

Purification was made by chromatography on silica gel (elution: cyclohexane/ethyl acetate 85:15).

$^1$H NMR CDCl$_3$ δppm: 2.57 (s, 3H), 7.09 (d, 1H, J=8.43 Hz), 7.40 (d, 2H, J=8.43 Hz), 7.72 (d, 1H, J=15.78 Hz), 7.88 (d, 1H, J=15.78 Hz), 8.01 (d, 1H, J=8.43 Hz), 8.10 (s, 1H), 8.12 (d, 2H, J=8.43 Hz), 11.23 (s, 1H).

Intermediate Compound 14

1-[4-methylsulfonylphenyl]-3-[3,5-dimethyl-4-hydroxyphenyl]prop-2-en-1-one

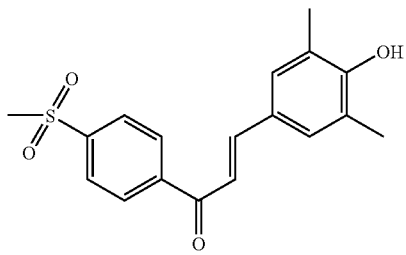

This compound was synthesized from 4'-methylsulfonylacetophenone and 3,5-dimethyl-4-hydroxybenzandehyde according to general method 1 described earlier.

Purification was made by chromatography on silica gel (elution: cyclohexane/ethyl acetate 5:5).

$^1$H NMR CDCl$_3$ δppm: 2.68 (s, 3H), 3.09 (s, 6H), 7.33 (s, 2H), 7.34 (d, 1H, J=15.60 Hz), 7.76 (d, 1H, J=15.60 Hz), 8.06 (d, 2H, J=8.55 Hz), 8.15 (d, 2H, J=8.55 Hz).

Intermediate Compound 15

1-[4-trifluoromethylthiophenyl]-3-[3,5-dimethyl-4-hydroxyphenyl]prop-2-en-1-one

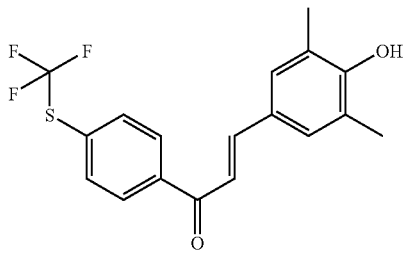

This compound was synthesized from 4'-trifluoromethylthioacetophenone and 3,5-dimethyl-4-hydroxybenzandehyde according to general method 1 described earlier.

The expected compound was crystallized in the reaction medium at 0° C., it was filtered and washed with cyclohexane.

$^1$H NMR CDCl$_3$ δppm: 2.30 (s, 6H), 7.23 (s, 2H), 7.35 (d, 1H, J=15.72 Hz), 7.75 (d, 1H, J=15.72 Hz), 7.78 (d, 2H, J=8.32 Hz), 8.03 (d, 2H, J=8.32 Hz).

Intermediate Compound 16

1-[4-isopropylphenyl]-3-[3,5-dimethyl-4-hydroxyphenyl]prop-2-en-1-one

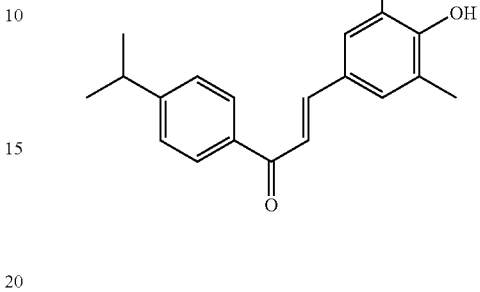

This compound was synthesized from 4'-isopropylacetophenone and 3,5-dimethyl-4-hydroxybenzandehyde according to general method 1 described earlier.

Purification was made by chromatography on silica gel (elution: cyclohexane/acetate d'ethyle 7:3).

$^1$H NMR CDCl$_3$ δppm: 1.25 (d, 6H), 2.30 (s, 6H), 3.00 (m, 1H), 5.13 (s, 1H), 7.31 (s, 2H), 7.35 (d, 2H, J=7.90 Hz), 7.41 (d, 1H, J=16.10 Hz), 7.73 (d, 1H, J=16.10 Hz), 7.98 (d, 2H, J=7.90 Hz).

Intermediate Compound 17

1-[4-trifluoromethylphenyl]-3-[3,5-dimethyl-4-hydroxyphenyl]prop-2-en-1-one

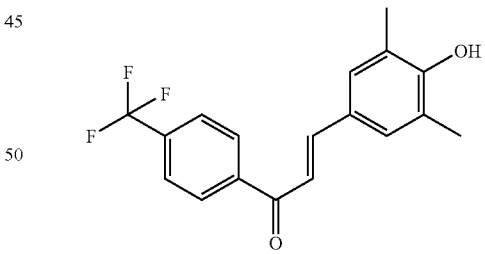

This compound was synthesized from 4'-trifluoromethylacetophenone and 3,5-dimethyl-4-hydroxybenzandehyde according to general method 1 described earlier.

The expected compound was crystallized in the reaction medium, after filtration, it was used without further purification for the following reaction.

$^1$H NMR CDCl$_3$ δppm: 2.31 (s, 6H), 5.14 (s, 1H), 7.32 (s, 2H), 7.37 (d, 1H, J=15.48 Hz), 7.75 (d, 1H, J=15.48 Hz), 7.78 (d, 2H, J=8.03 Hz), 8.09 (d, 2H, J=8.03 Hz).

Intermediate Compound 18

1-[2-methylthiophenyl]-3-[3,5-dimethyl-4-hydroxyphenyl]prop-2-en-1-one

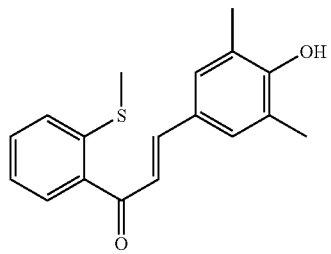

This compound was synthesized from 2'-methylthioacetophenone and 3,5-dimethyl-4-hydroxybenzandehyde according to general method 1 described earlier.

Purification was made by chromatography on silica gel (elution: elution: cyclohexane/ethyl acetate 8:2).

$^1$H NMR CDCl$_3$ δppm: 2.28 (s, 6H), 2.47 (s, 3H), 7.15 (d, 1H, J=15.75 Hz), 7.24 (dd, 1H, J=1.13 Hz, J=7.29 Hz), 7.26 (s, 2H), 7.39 (d, 1H, J=7.32 Hz), 7.47 (dd, 1H, J=1.17 Hz, 7.02 Hz), 7.53 (d, 1H, J=15.75 Hz), 7.67 (dd, 1H, J=1.47 Hz, J=7.62 Hz).

Intermediate Compound 19

1-[4-trifluoromethyloxyphenyl]-3-[3,5-dimethyl-4-hydroxyphenyl]prop-2-en-1-one

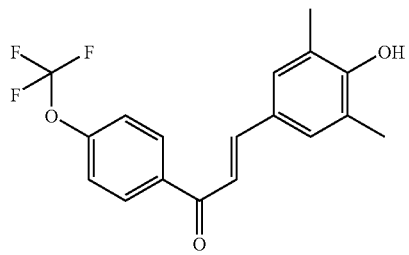

This compound was synthesized from 4'-trifluoromethyloxyacetophenone and 3,5-dimethyl-4-hydroxybenzandehyde according to general method 1 described earlier.

Purification was made by chromatography on silica gel (elution: cyclohexane/ethyl acetate 8:2).

$^1$H NMR CDCl$_3$ δppm: 2.29 (s, 6H), 7.30-7.40 (m, 5H), 7.75 (d, 1H, J=15.69 Hz), 8.06 (d, 2H, J=7.98 Hz).

Intermediate Compound 20

1-[4-iodophenyl]-3-[3,5-dimethyl-4-hydroxyphenyl]prop-2-en-1-one

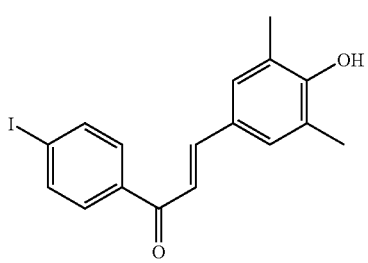

This compound was synthesized from 4'-iodoacetophenone and 3,5-dimethyl-4-hydroxybenzandehyde according to general method 1 described earlier.

Purification was made by chromatography on silica gel (elution: cyclohexane/ethyl acetate 8:2).

$^1$H NMR CDCl$_3$ δppm: 2.30 (s, 6H), 7.30 (m, 3H), 7.74 (m, 3H), 7.85 (d, 2H,=8.25 Hz).

Intermediate Compound 21

1-[4-fluorophenyl]-3-[3,5-dimethyl-4-hydroxyoxyphenyl]prop-2-en-1-one

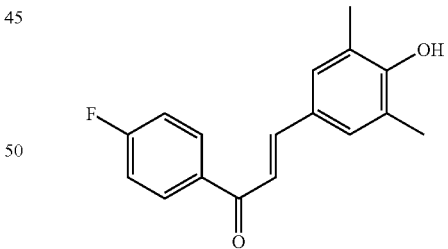

This compound was synthesized from 4'-fluoroacetophenone and 3,5-dimethyl-4-hydroxybenzandehyde according to general method 1 described earlier.

Purification was made by chromatography on silica gel (elution: cyclohexane/ethyl acetate 8:2).

$^1$H NMR CDCl$_3$ δppm: 2.34 (s, 6H), 7.17 (m, 2H), 7.26-7.34 (m, 3H), 7.74 (d, 1H, J=15.45 Hz), 8.06 (m, 2H), 9.81 (s, 1H).

Intermediate Compound 22

1-[4-nonyloxyphenyl]-3-[3,5-dimethyl-4-hydroxyphenyl]prop-2-en-1-one

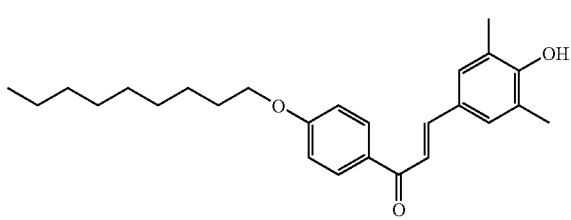

This compound was synthesized from 4'-nonyloxyacetophenone and 3,5-dimethyl-4-hydroxybenzandehyde according to general method 1 described earlier.

The expected compound was crystallized in the reaction medium at 0° C., it was filtered and washed with heptane.

$^1$H NMR CDCl$_3$ δppm: 0,90 (m, 3H), 1.29-1.75 (m, 12H), 1.75-1.84 (m, 2H), 2.29 (s, 6H), 4.04 (t, 2H, J=6.54 Hz), 6.97 (d, 2H, J=8.70 Hz), 7.30 (s, 2H), 7.42 (d, 1H, J=15.51 Hz), 7.73 (d, 1H, J=15.51 Hz), 8.03 (d, 2H, J=8.73 Hz).

Intermediate Compound 23

1-[4-propyloxyphenyl]-3-[3,5-dimethyl-4-hydroxyphenyl]prop-2-en-1-one

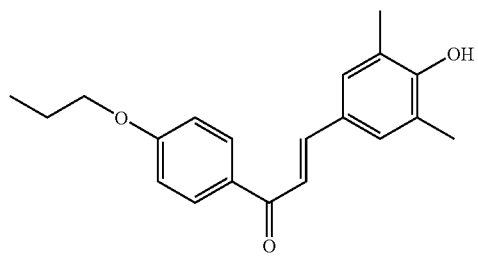

This compound was synthesized from 4'-propyloxyacetophenone and 3,5-dimethyl-4-hydroxybenzandehyde according to general method 1 described earlier.

The expected compound was crystallized in the reaction medium, after filtration, it was purified by crystallization (dichloromethane/heptane).

$^1$H NMR CDCl$_3$ δppm: 1.07 (t, 3H, J=7.35 Hz), 1.88 (m, 2H), 2.30 (s, 6H), 4.01 (t, 2H, J=6.63 Hz), 6.98 (d, 2H, J=8.82 Hz), 7.30 (s, 2H), 7.43 (d, 1H, J=15.50 Hz), 7.74 (d, 1H, J=15.50 Hz), 8.04 (d,2H, J=8.82 Hz).

Intermediate Compound 24

1-[4-methylthiophenyl]-3-[3,5-diisopropyl-4-hydroxyphenyl]prop-2-en-1-one

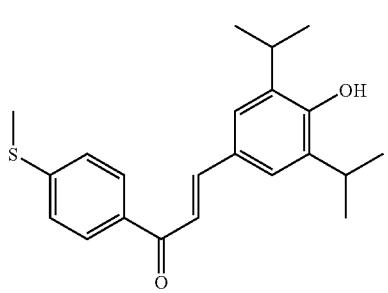

This compound was synthesized from 4'-methylthioacetophenone and 3,5-diisopropyl-4-hydroxybenzandehyde according to general method 1 described earlier.

The expected compound was crystallized in the reaction medium, after filtration, it was used without further purification for the following reaction.

$^1$H NMR CDCl$_3$ δppm: 1.31 (d, 12H, J=7.08 Hz), 2.55 (s, 3H), 3.19 (m, 2H), 7.33 (d, 2H, J=8.19 Hz), 7.37 (s, 2H), 7.39 (d, 1H, J=15.60 Hz), 7.80 (d, 1H, J=15.60 Hz), 7.97 (d, 2H, J=8.19 Hz).

Intermediate Compound 25

1-[4-octadecyloxyphenyl]-3-[3,5-dimethyl-4-hydroxyphenyl]prop-2-en-1-one

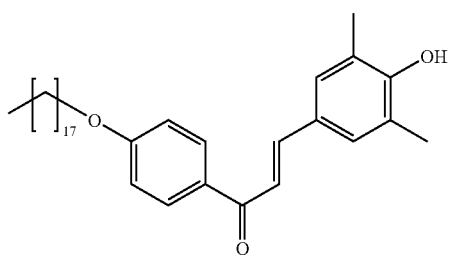

This compound was synthesized from 4'-octadecyloxyacetophenone and 3,5-dimethyl-4-hydroxybenzandehyde according to general method 1 described earlier.

Purification was made by chromatography on silica gel (elution: cyclohexane/ethyl acetate 9:1).

$^1$H NMR CDCl$_3$ δppm: 0.88 (t, 3H, J=7.08 Hz), 1.26-1.46 (m, 30H), 1.73-1.84 (m, 2H), 2.19 (s, 6H), 4.04 (t, 2H, J=6.54 Hz), 6.96 (d, 2H, J=8.73 Hz), 7.30 (s, 2H), 7.43 (d, 1H, J=15.80 Hz), 7.73 (d, 1H, J=15.80 Hz), 8.03 (d, 2H, J=8.73 Hz).

Intermediate Compound 26

1-[4-dodecyloxyphenyl]-3-[3,5-dimethyl-4-hydroxyphenyl]prop-2-en-1-one

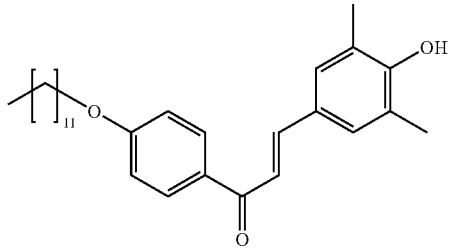

This compound was synthesized from 4'-dodecyloxyacetophenone and 3,5-dimethyl-4-hydroxybenzandehyde according to general method 1 described earlier.

The expected compound was crystallized in the reaction medium, after filtration, it was purified by chromatography on silica gel (elution: cyclohexane/ethyl acetate 8:2).

$^1$H NMR CDCl$_3$ δppm: 0.89 (m, 3H), 1.27 (m, 18H), 4.04 (t, J=4.04 Hz, 2H), 6.96 (d, 2H J=9.05 Hz), 7.31 (s, 2H), 7.42 (d, 1H, J=15.45 Hz), 7.52 (d, 1H, J=15.45 Hz), 8.03 (d, 2H, J=9.05 Hz).

Intermediate Compound 27

1-[4-methoxyphenyl]-3-f3,5-dimethyl-4-hydroxyphenyl]prop-2-en-1-one

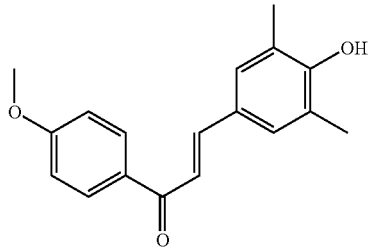

This compound was synthesized from 4'-methoxyacetophenone and 3,5-dimethyl-4-hydroxybenzandehyde according to general method 1 described earlier.

Purification was made by chromatography on silica gel (elution: cyclohexane/ethyl acetate 8:2).

$^1$H NMR CDCl$_3$ δppm: 2.30 (s, 6H), 3.89 (s, 3H), 5.37 (s, 1H), 6.98 (d, 2H, J=8.66 Hz), 7.31 (s, 2H), 7.42 (d, 1H, J=15.75 Hz), 7.73 (d, 1H, J=15.75 Hz), 8.06 (d, 2H, J=8.66 Hz).

Intermediate Compound 28

1-[2-hexyloxyphenyl]-3-[3,5-dimethyl-4-hydroxyphenyl]prop-2-en-1-one

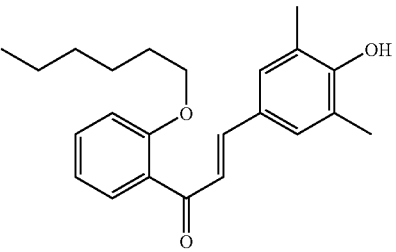

This compound was synthesized from 2'-hexyloxyacetophenone and 3,5-dimethyl-4-hydroxybenzandehyde according to general method 1 described earlier.

The expected compound was crystallized in the reaction medium, after filtration, it was washed with ethanol and used without further purification for le following reaction.

$^1$H NMR CDCl$_3$ δppm: 0.79 (m, 3H), 1.26 (m, 4H), 1.41 (m, 2H), 1.79 (m, 2H), 2.27 (s, 6H), 4.05 (t, 2H, J=6.54 Hz), 6.97 (d, 1H, J=8.16 Hz), 7.02(m, 1H), 7.24 (s, 2H), 7.32 (d, 1H J=15.80 Hz), 7.44 (m, 1H), 7.54 (d, 1H, J=15.80 Hz), 7.63 (dd, 1H, J=1.62 Hz, J=7.08 Hz).

Intermediate Compound 29

1-[4-hexylthiophenyl]-3-[3,5-dimethyl-4-hydroxyphenyl]prop-2-en-1-one

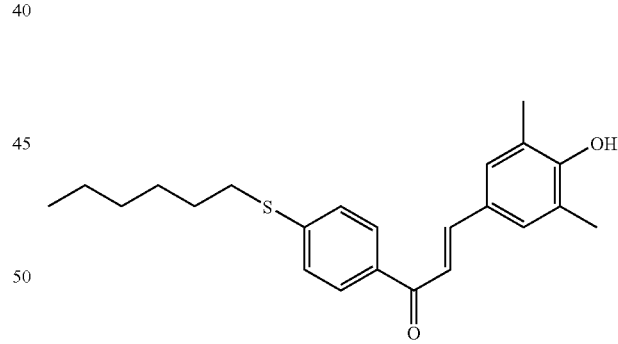

This compound was synthesized from starting material 4'-hexylthioacetophenone and 3,5-dimethyl-4-hydroxybenzandehyde according to general method 1 described earlier.

The expected compound was crystallized in the reaction medium, after filtration, it was washed with ethyl acetate and crystallized (ethanol).

$^1$H NMR CDCl$_3$ δppm: 0.91 (t, 3H, J=7.10 Hz), 1.33 (m, 4H), 1.48 (m, 2H), 1.72 (m, 2H), 2.30 (s, 6H), 3.01 (t, 2H, J=7.08 Hz), 7.31 (s, 2H), 7.34 (d, 2H, J=8.40 Hz), 7.38 (d, 1H, J=15.90 Hz), 7.73 (d, 1H, J=15.90 Hz), 7.95 (d, 2H, J=8.40 Hz).

Intermediate Compound 30

1-[4-hydroxyphenyl]-3-[3,5-ditertiobutyl-4-hydroxyphenyl]prop-2-en-1-one

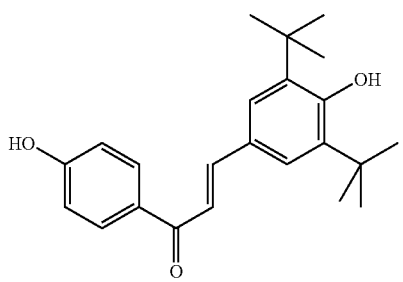

This compound was synthesized from starting material 4'-hydroxyacetophenone and 3,5-dimethyl-4-hydroxybenzandehyde according to general method 1 described earlier.

Purification was made by chromatography on silica gel (elution: cyclohexane/ethyl acetate 7:3).

$^1$H NMR CDCl$_3$ δppm: 1.48 (s, 18H), 7.04 (d, 2H, J=7.85 Hz), 7.43 (d, 1H, J=15.24 Hz), 7.49 (s, 2H), 7.85 (d, 1H, J=15.24 Hz), 8.02 (d, 2H, J=7.85 Hz).

SYNTHESIS OF THE INVENTIVE COMPOUNDS

Compound 1

1-[2-hydroxy-4-ethoxycarbonyldimethylmethyloxyphenyl]-3-[3,5-ditertbutyl-4-hydroxyphenyl]prop-2-en-1-one

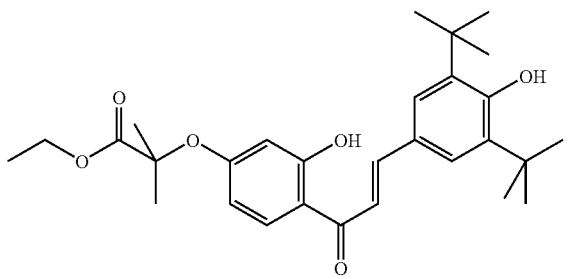

This compound was synthesized from 2'-hydroxy-4'-(ethoxycarbonyldimethylmethoxy)acetophenone (starting material 1) and 3,5-ditertbutyl-4-hydroxybenzaldehyde according to general method 1 described earlier.

Purification was made by chromatography on silica gel (elution: cyclohexane/ethyl acetate 9:1).

$^1$H NMR CDCl$_3$ δppm: 1.25 (t, J=7.11 Hz, 3H), 1.45 (s, 18H), 1.70 (s, 6H), 4.26 (q, J=7.11 Hz, 2H), 5.63 (s, 1H), 6.33 (d, J=2.37 Hz, 1H), 6.42 (dd, J=8.80 Hz, J=2.37 Hz, 1H), 7.41 (d, J=15.39 Hz, 1H), 7.5 (s, 2H), 7.83 (d, J=8.8 Hz, 1H), 7.88 (J=15.39 Hz, 1H), 13.5 (s, 1H).

Compound 2

1-[2-hydroxy-4-carboxydimethylmethyloxyphenyl]-3-[3,5-ditertbutyl-4-hydroxyphenyl]prop-2-en-1-one

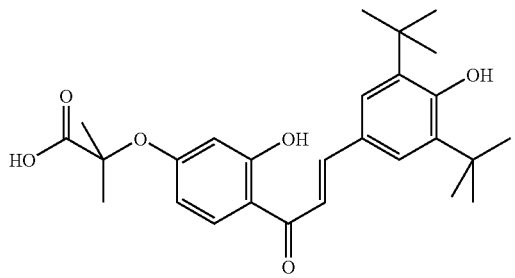

This compound was synthesized from 1-[2-hydroxy-4-ethoxycarbonyldimethylmethyloxyphenyl]-3-[3,5-ditertbutyl-4-hydroxyphenyl]prop-2-en-1-one (compound 1) according to the following method:

The ester was dissolved in ethanol, an aqueous 1N sodium hydroxide solution (5 eq) was added, and the mixture was kept under reflux for 10 hours. The medium was acidified by addition of 12 N hydrochloric acid then extracted with ethyl acetate. The organic phase was dried on magnesium sulfate then vacuum evaporated.

Purification was made by preparative HPLC (reverse phase RP18, Licrospher 12 μm, elution: water-methanol-trifluoroacetic acid: 22:78:0.1).

$^1$H NMR CDCl$_3$ δppm: 1.49 (s, 18H), 1.73 (s, 6H), 5.62 (s, 1H), 6.44 (d, J=15.5 Hz, 1H), 7.01 (m, 2H), 7.57 (t, 1H), 7.81 (d, J=15.5 Hz, 1H), 7.87 (d, 2H), 7.93 (d, 1H), 8.26(d,1H).

MS (ES-MS): 453.2 (M−1).

Compound 3

1-[2-hydroxy-4-chlorophenyl]-3-[4-carboxydimethylmethyloxyphenyl]prop-2-en-1-one

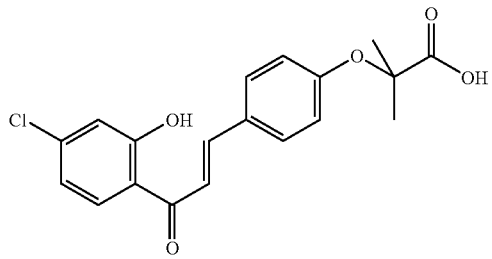

This compound was synthesized from 2'-hydroxy-4'-chloroacetophenone and 4-ethyloxycarbonyldimethylmethyloxybenzaldehyde (starting material 4) according to general method 2 described earlier.

Purification was made by chromatography on silica gel (elution: cyclohexane/ethyl acetate 9:1).

$^1$H NMR DMSO-d$_6$ δppm: 1.58 (s, 6H), 6.87 (d, J=8.54 Hz, 2H), 7.05 (dd, J=8.54 Hz, 1.83 Hz, 1H), 7.09 (d, J=1.2 Hz, 1H), 7.90-7.80 (m, 4H), 8.25 (m, 8.52 Hz, 1H), 12.84 (s, 1H), 13.26 (s, 1H).

MS (ES-MS): 359.0 (M−1).

Compound 4

1-[2-hydroxyphenyl]-3-[4-carboxydimethylmethyloxyphenyl]prop-2-en-1-one

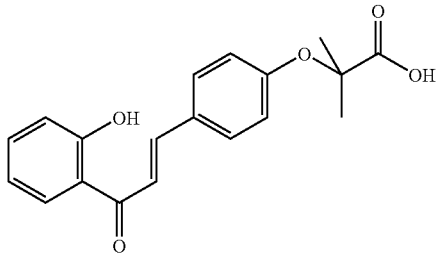

This compound was synthesized from 2'-hydroxyacetophenone and 4-ethyloxycarbonyldimethylmethyloxybenzaldehyde (starting material 4) according to general method 2 described earlier.

Purification was by made chromatography on silica gel (elution: cyclohexane/ethyl acetate 9:1).

$^1$H NMR DMSO-$d_6$ δppm: 1.58 (s, 6H), 6.88 (d, 2H), 7.01 (m, 2H), 7.57 (t, 1H), 7.81 (d, J=15.5 Hz, 1H), 7.87 (d, 2H), 7.93 (d, J=15.5 Hz, 1H), 8.26 (d, 1H), 12.69 (s, 1H).

MS (ES-MS): 325.1 (M−1).

Compound 5

1-[2-hydroxyphenyl]-3-[3,5-dimethoxy-4-carboxydimethylmethyloxyphenyl]prop-2-en-1-one

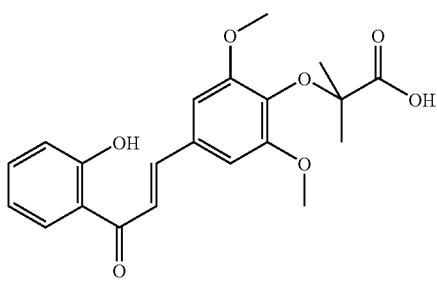

This compound was synthesized from 2'-hydroxyacetophenone and 3,5-dimethyloxy-4-ethyloxycarbonyldimethylmethyloxybenzaldehyde (starting material 5) according to general method 2 described earlier.

Purification was made by chromatography on silica gel (elution: cyclohexane/ethyl acetate 9:1).

$^1$H NMR DMSO-$d_6$ δppm: 1.35 (s, 6H), 3.80 (s, 6H), 7.00-7.03 (m, 2H), 7.25 (s, 2H), 7.59 (t, 1H, J=8.07 Hz, 1H), 7.81 (d, J=15.5 Hz, 1 H), 8.00 (d, J=15.5 Hz, 1H), 8.31 (d, J=8.07 Hz, 1H), 12.36 (s, 1H), 12.69 (s, 1H).

MS (ES-MS): 385.3 (M−1).

Compound 6

1-[2-hydroxy-4-chlorophenyl]-3-[3,5-dimethoxy-4-carboxydimethylmethyloxyphenyl]prop-2-en-1-one

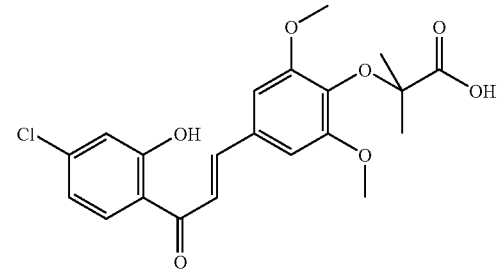

This compound was synthesized from 4'-chloro-2'-hydroxy acetophenone (starting material 3) and 3,5-dimethyloxy-4-ethyloxycarbonyldimethylmethyloxybenzaldehyde (starting material 5) according to general method 2 described earlier.

Purification was made by chromatography on silica gel (elution: cyclohexane/ethyl acetate 9:1).

$^1$H NMR DMSO-$d_6$ δppm: 1.34 (s, 6H), 3.80 (s, 6H), 7.08 (dd, J=1.77 Hz, 1H), 7.12 (d, J=1.77 Hz, 1H), 7.24 (s, 2H), 7.79 (d, J=15.4 Hz, 1H), 7.93 (d, J=15.4 Hz, 1H), 8.27 (d, J=8.3 Hz, 1H), 12.36 (s, 1H), 12.69 (s, 1H).

MS (ES-MS): 419.0 (M−1).

Compound 7

1-[2-hydroxy-4-chlorophenyl]-3-[3,5-dimethyl-4-carboxydimethyl methyloxyphenyl]prop-2-en-1-one

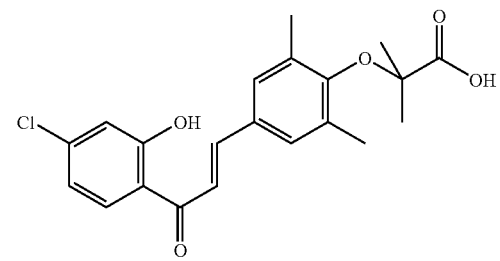

This compound was synthesized from 4'-chloro-2'-hydroxyacetophenone (starting material 3) and 3,5-dimethyl-4-ethyloxycarbonyldimethylmethyloxybenzaldehyde (starting material 6) according to general method 2 described earlier.

Purification was made by chromatography on silica gel (elution: cyclohexane/ethyl acetate 9:1).

$^1$H NMR DMSO-$d_6$ δppm: 1.39 (s, 6H), 2.22 (s, 6H), 7.07 (m, 1H), 7.12 (d, J=2.07 Hz, 1H), 7.61 (s, 2H), 7.74 (d, J=15.5 Hz, 1H), 7.87 (d, J=15.5 Hz, 1H), 8.26 (d, 1H), 12.76 (s, 1H).

MS (ES-MS): 387.1 (M−1).

Compound 8

1-[2-hydroxy-4-carboxydimethylmethyloxyphenyl]-3-[3,5-dibromo-4-hydroxyphenyl]prop-2-en-1-one

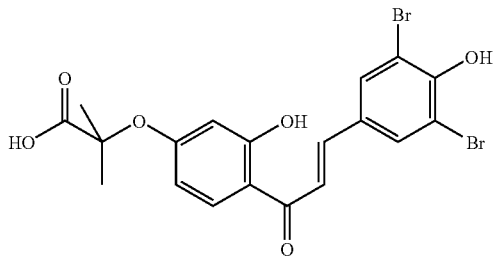

This compound was synthesized from 2'-hydroxy-4'-(ethoxycarbonyldimethylmethyloxy)acetophenone (starting material 1) and 3,5-dibromo-4-hydroxybenzaldehyde according to general method 2 described earlier.

Purification was made by chromatography on silica gel (elution: cyclohexane/ethyl acetate 9:1).

$^1$H NMR CDCl$_3$ δppm: 1.60 (s, 6H), 6.24 (d, J=2.47 Hz, 1H), 6.43 (dd, J=2.47 Hz, J=8.84 Hz, 1H), 7.70 (d, J=15.5 Hz, 1H), 7.96 (d, J=15.5 Hz, 1H), 8.22 (s, 2H), 8.34 (d, J=8.84 Hz, 1H), 13.34 (s, 1H).

MS (ES-MS): 498.6 (M−1).

Compound 9

1-[2-hydroxyphenyl]-3-[3-carboxydimethylmethyloxyphenyl]prop-2-en-1-one

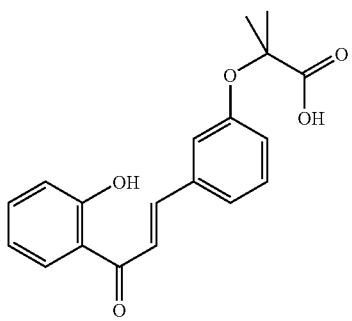

This compound was synthesized from 2'-hydroxyacetophenone and 3-ethyloxycarbonyldimethylmethyloxybenzaldehyde (starting material 7) according to general method 2 described earlier.

Purification was made by chromatography on silica gel (elution: cyclohexane/ethyl acetate 9:1).

$^1$H NMR DMSO-d$_6$ δppm: 1.56 (s, 6H), 6.91 (dd, J=8.01 Hz, J=2.47 Hz, 1H), 7.03-6.99 (m, 2H), 7.41-7.36 (m, 2H), 7.60-7.52 (m, 2H), 7.77 (d, J=15.5, 1H), 8.00 (d, J=15.5 Hz, 1H), 8.31 (dd, J=8.63 Hz, J=1.85 Hz, 1H), 12.47 (s, 1H), 13.17 (s, 1H).

MS (ES-MS): 325.8(M−1).

Compound 10

1-[2-hydroxy-4-carboxydimethylmethyloxyphenyl]-3-[3-hydroxyphenyl]prop-2-en-1-one

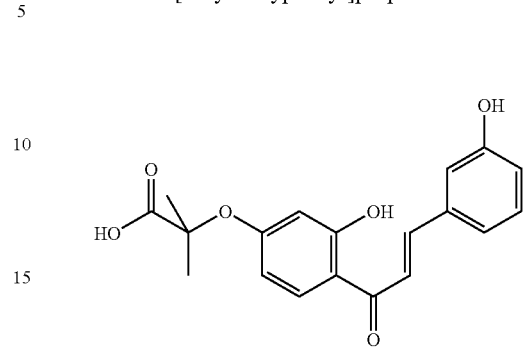

This compound was synthesized from 2'-hydroxy-4'-(ethoxycarbonyl dimethylmethyloxy)acetophenone (starting material 1) and 3-hydroxybenzaldehyde according to general method 2 described earlier.

Purification was made by chromatography on silica gel (elution: cyclohexane/ethyl acetate 9:1).

$^1$H NMR DMSO-d$_6$ δppm: 1.60 (s, 6H), 6.25 (d, J=2.47 Hz, 1H), 6.43 (dd, J=2.47 Hz, 9.09 Hz, 1H), 6.89 (m, 1H), 7.35-7.24 (m, 3H), 7.73 (d, 1H), 7.92 (d, J=15.5 Hz, 1H), 8.27 (d, J=15.5 Hz, 1H), 13.21 (s, 1H), 13.39 (s, 1H).

MS (ES-MS): 341(M−1).

Compound 11

1-[2-hydroxyphenyl]-3-[3,5-dimethyl-4-carboxydimethylmethyloxyphenyl]prop-2-en-1-one

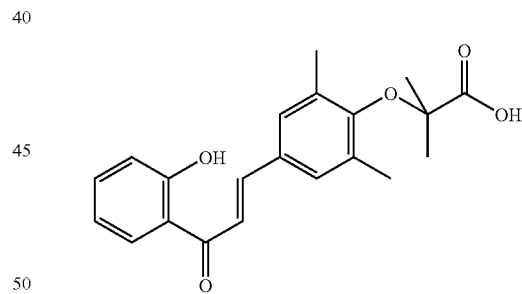

This compound was synthesized from 2'-hydroxyacetophenone and 3,5-dimethyl-4-ethyloxycarbonyldimethylmethyloxybenzaldehyde (starting material 6) according to general method 2 described earlier.

Purification was made by chromatography on silica gel (elution: cyclohexane/ethyl acetate 9:1) followed by preparative HPLC (reverse phase RP18, Licrospher 12 μm, elution: water-methanol-trifluoroacetic acid: 22:78:0.1).

$^1$H NMR DMSO-d$_6$ δppm: 1.57 (s, 6H), 2.31 (s, 6H), 6.96 (t, J=8.17 Hz, 1H), 7.04 (d, J=8.72 Hz, 1H), 7.35 (s, 2H), 7.49 (t, J=8.2 Hz, 1H), 7.58 (d, J=15.80 Hz,1 H), 7.84 (d, J=15.80 Hz, 1H), 7.94 (d, J=8.70 Hz, 1H), 12.87 (s, 1H).

MS (ES-MS): 353.1 (M−1).

Compound 12

1-[2-hydroxy-4-carboxydimethylmethyloxyphenyl]-3-4-methylthiophenyl]prop-2-en-1-one

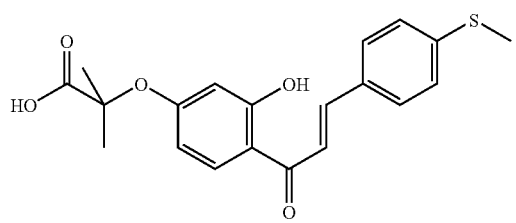

This compound was synthesized from 2'-hydroxy-4'-(ethoxycarbonyldimethylmethyloxy)acetophenone (starting material 1) and 4-methylthiobenzaldehyde according to general method 2 described earlier.

Purification was made by chromatography on silica gel (elution: cyclohexane/ethyl acetate 9:1) followed by preparative HPLC (reverse phase RP18, Licrospher 12 μm, elution: water-methanol-trifluoroacetic acid: 22:78:0.3).

$^1$H NMR DMSO-$d_6$ δppm: 1.60 (s, 6H), 2.54 (s, 3H), 6.25 (d, 1H), 6.43 (dd, J=2.47 Hz, 1H), 7.33 (d, J=8.56 Hz, 2H), 7.8 (d, 15.5 Hz, 1H), 7.86 (d, J=8.56 Hz, 2H), 7.98 (d, J=15.5 Hz, 1H), 8.29 (d, J=9.1 Hz, 1H), 13.34 (s, 1H).

MS (ES-MS): 373.1 (M−1).

Compound 13

1-[2,4-dihydroxyphenyl]-3-[4-carboxydimethylmethyloxyphenyl]prop-2-en-1-one

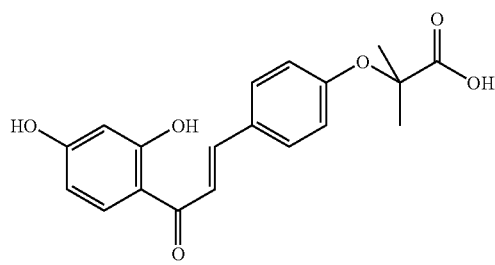

This compound was synthesized from 2',4'-dihydroxyacetophenone and 4-ethoxycarbonyldimethylmethyloxybenzaldehyde (starting material 4) according to general method 2 described earlier.

Purification was made by chromatography on silica gel (elution: cyclohexane/ethyl acetate 9:1) followed by preparative HPLC (reverse phase RP18, Licrospher 12 μm, elution: water—methanol—trifluoroacetic acid: 34:66:0.1).

$^1$H NMR DMSO-$d_6$ δppm: 1.57 (s, 6H), 6.29 (d, J=2.16 Hz, 1H), 6.41 (dd, J=9.18 Hz, J=2.16 Hz, 1H), 6.86 (d, J=8.64 Hz, 2H), 7.75 (d, J=15.67 Hz, 1H), 7.83-7.88 (m, 3H), 8.19 (d, J=9.18 Hz, 1H), 10.74 (s, 1H), 13.53 (s, 1H).

MS (maldi-Tof): 343.1 (M+1).

Compound 14

1-[4-hydroxyphenyl]-3-[4-carboxydimethylmethyloxyphenyl]prop-2-en-1-one

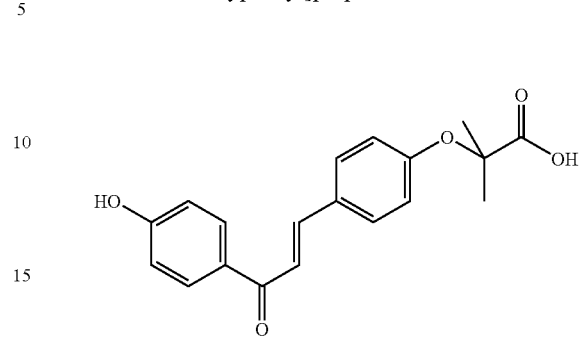

This compound was synthesized from 4'-hydroxyacetophenone and 4-ethoxycarbonyldimethylmethyloxybenzaldehyde (starting material 4) according to general method 2 described earlier.

Purification was made by chromatography on silica gel (elution: cyclohexane/ethyl acetate 9:1) followed by preparative HPLC (reverse phase RP18, Licrospher 12 μm, elution: water-methanol-trifluoroacetic acid: 34:66:0.1).

$^1$H NMR DMSO-$d_6$ δppm: 1.56 (s, 6H), 6.85 (d, J=8.63 Hz, 2H ), 6.90 (d, J=9.21 Hz, 2H), 7.63 (d, J=15.54 Hz, 1H), 7.78 (m, 3H), 8.05 (d, J=8.61 Hz, 2H), 10.40 (s, 1H), 13.22 (s, 1H).

MS (maldi-Tof): 327.1 (M+1).

Compound 15

1-[4-chlorophenyl]-3-[3,5-dimethyl-4-isopropyloxycarbonyldimethylmethyloxyphenyl]prop-2-en-1-one

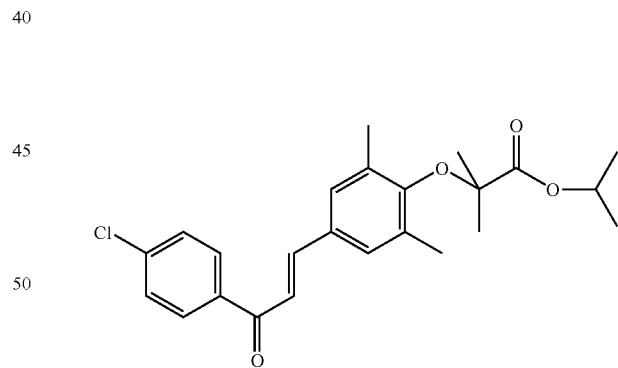

This compound was synthesized from 1-[4-chlorophenyl]-3-[3,5-dimethyl-4-hydroxyphenyl]prop-2-en-1-one (intermediate compound 1) and isopropyl bromoisobutyrate according to general method 4 described earlier.

Purification was made by chromatography on silica gel (elution: cyclohexane/ethyl acetate 9:1).

$^1$H NMR DMSO-$d_6$ δppm: 1.25 (d, J=6.06 Hz, 6H), 1.39 (s, 6H), 5.00 (sept, J=6.06 Hz, 1H), 7.57 (s, 2H), 7.62 (d, J=8.40 Hz, 2H), 7.64 (d, J=15.8 Hz, 1H), 7.81 (d, J=15.8 Hz, 1H), 8.16 (d, J=8.40 Hz, 2H).

MS (Maldi-Tof): 415.1 (M+1).

Compound 16

1-[4-chlorophenyl]-3-[3,5-dimethyl-4-tertbutyloxy-carbonyldimethylmethyloxyphenyl]prop-2-en-1-one

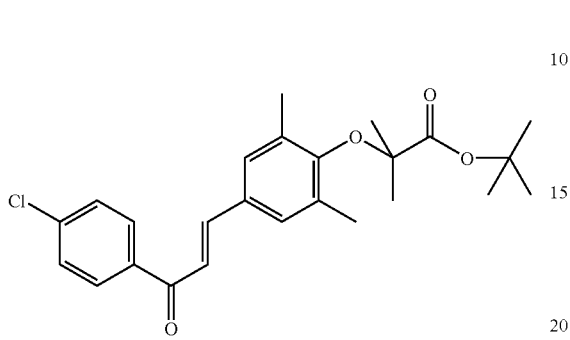

This compound was synthesized from 1-[4-chlorophenyl]-3-[3,5-dimethyl-4-hydroxyphenyl]prop-2-en-1-one (intermediate compound 1) and tertbutyl bromoisobutyrate according to general method 4 described earlier.

Purification was made by chromatography on silica gel (elution: cyclohexane/ethyl acetate 9:1).

Compound 17

1-[4-chlorophenyl]-3-[3,5-dimethyl-4-carboxydimethylmethyloxyphenyl]prop-2-en-1-one

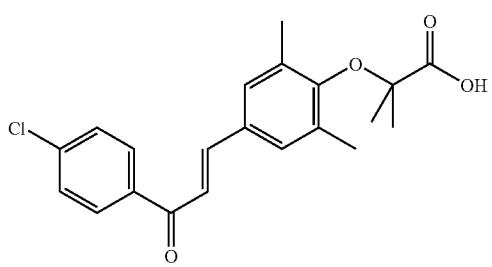

This compound was synthesized from 1-[4-chlorophenyl]-3-[3,5-dimethyl-4-tertbutyloxycarbonyldimethyl-methyloxyphenyl]prop-2-en-1-one (compound 16) according to general method 5 described earlier.

Purification was made by chromatography on silica gel (elution: dichloromethane/methanol 98:2).

$^1$H NMR DMSO-d$_6$ δppm: 1.39 (s, 6H), 2.22 (s, 6H), 7.58 (s, 2H), 7.67-7.62 (m, 3H), 7.82 (d, J=15.5 Hz, 1H), 8.17 (d, 1H), 12.96 (s, 1H).

MS (Maldi-Tof): 373.3 (M+1).

Compound 18

1-[2-hydroxy-4-carboxydimethylmethyloxyphenyl]-3-[4-chlorophenyl]prop-2-en-1-one

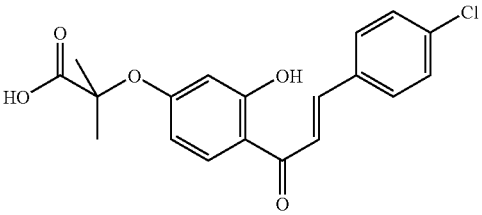

This compound was synthesized from 2'-hydroxy-4'-(ethoxycarbonyldimethylmethyloxy)acetophenone (starting material 1) and 4-chlorobenzaldehyde according to general method 2 described earlier.

Purification was made by chromatography on silica gel (elution: cyclohexane/ethyl acetate 9:1) followed by preparative HPLC (reverse phase RP18, Licrospher 12 μm, elution: water-methanol-trifluoroacetic acid: 22:78:0.1).

$^1$H NMR DMSO-d$_6$ δppm: 1.60 (s, 6H), 6.25 (d, J=2.47 Hz, 1H), 6.45 (dd, J=2.47 Hz, J=9.12 Hz, 1H), 6.55 (d, J=8.55 Hz, 2H), 7.82 (d, J=15.54 Hz, 1H), 7.97 (d, J=8.55 Hz, 2H), 8.03 (d, J=15.54 Hz, 1H), 8.29 (d, J=9.12 Hz, 1H), 13.20 (s, 1H), 13.39 (s, 1H).

MS (ES-MS): 359.0 (M−1).

Compound 19

1-[2-hydroxyphenyl]-3-[4-carboxydimethylmethylthiophenyl]prop-2-en-1-one

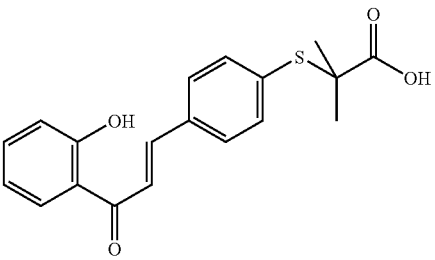

This compound was synthesized from 2'-hydroxyacetophenone and 4-ethyloxycarbonyldimethylmethylthiobenzaldehyde (starting material 8) according to general method 2 described earlier.

Purification was by made chromatography on silica gel (elution: dichloromethane/methanol 95:5) followed by preparative HPLC (reverse phase RP18, Licrospher 12 μm, elution: water-methanol-trifluoroacetic acid: 22:78:0.1).

$^1$H NMR DMSO-d$_6$ δppm: 1.44 (s, 6H), 6.99-7.05 (m, 1H), 7.52 (d, J=8.1 Hz, 2H), 7.58 (m, 1H), 7.83 (d, J=15.5 Hz, 1H), 7.92 (d, J=8.1 Hz, 1H), 8.09 (d, J=15.5 Hz, 1H), 8.26 (dd, J=1.62, J=8.6 Hz, 1H), 12.47 (s, 1H), 12.78 (s, 1H).

MS (Maldi-Tof): 242.9 (M+1).

Compound 20

1-[4-chloro-2-hydroxyphenyl]-3-[4-carboxydimethylmethylthiophenyl]prop-2-en-1-one

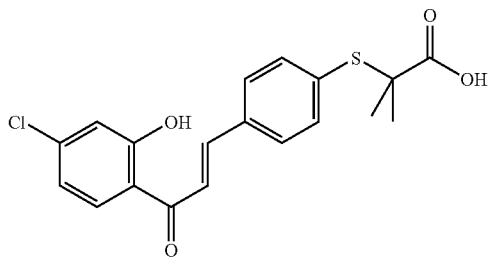

This compound was synthesized from 4'-chloro-2'-hydroxyacetophenone (starting material 3) and 4-ethyloxycarbonyldimethylmethylthiobenzaldehyde (starting material 8) according to general method 2 described earlier.

Purification was made by chromatography on silica gel (elution: dichloromethane/methanol 95:5) followed by preparative HPLC (reverse phase RP18, Licrospher 12 μm, elution: water-methanol-trifluoroacetic acid: 22:78:0.1).

$^1$H NMR DMSO-$d_6$ δppm: 1.43 (s, 6H), 7.05 (dd, J=1.7 Hz, J=8.46 Hz, 1H), 7.11 (d, J=2.25 Hz, 1H), 7.51 (d, J=7.92 Hz, 2H), 7.82 (d, J=15.8 Hz, 1H), 7.89 (d, J=7.9 Hz, 2H), 8.05 (d, J=15.2 Hz, 1H), 8.23 (d, J=8.46 Hz, 1H), 12.57 (s, 1H), 12.78 (s, 1H).

MS (Maldi-Tof): 377.0 (M−1).

Compound 21

1-[4-carboxydimethylmethyloxyphenyl]-3-[3,5-dimethyl-4-hydroxyphenyl]prop-2-en-1-one

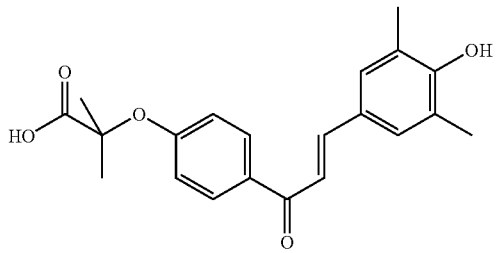

This compound was synthesized from 4'-ethyloxycarbonyldimethylmethyloxy acetophenone (starting material 9) and 3,5-dimethyl-4-hydroxybenzaldehyde according to general method 2 described earlier.

Purification was by made chromatography on silica gel (elution: dichloromethane/methanol 95:5) followed by preparative HPLC (reverse phase RP18, Licrospher 12 μm, elution: water-methanol-trifluoroacetic acid: 22:78:0.1).

$^1$H NMR DMSO-$d_6$ δppm: 1.60 (s, 6H), 2.21 (s, 6H), 6.91 (d, J=9.09 Hz, 2H), 7.48 (s, 2H), 7.57 (d, J=15.12 Hz, 1H), 7.70 (d, J=15.63 Hz, 1H), 8.09 (d, J=9.06 Hz, 2H), 8.9 (s, 1H), 13.29 (s, 1H).

MS (Maldi-Tof): 355.2 (M+1).

Compound 22

1-[4-methylthiophenyl]-3-[4-carboxydimethylmethyloxyphenyl]prop-2-en-1-one

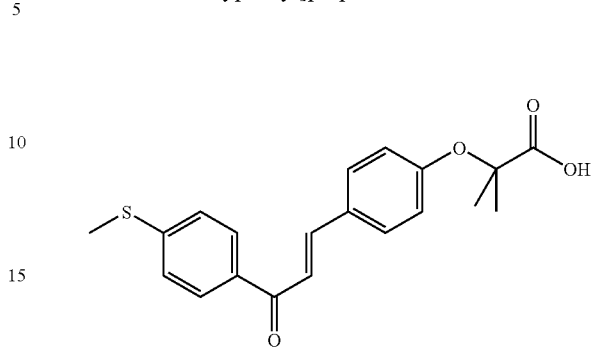

This compound was synthesized from 4'-methylthioacetophenone and 4-ethyloxycarbonyldimethylmethyloxybenzaldehyde (starting material 4) according to general method 2 described earlier.

Purification was by chromatography on silica gel (elution: dichloromethane/methanol 95:5) followed by preparative HPLC (reverse phase RP18, Licrospher 12 μm, elution: water-methanol-trifluoroacetic acid: 22:78:0.1).

$^1$H NMR DMSO-$d_6$ δppm: 1.57 (s, 6H), 2.57 (s, 3H), 6.86 (d, J=8.94 Hz, 2H), 7.41 (d, J=8.40 Hz, 2H), 7.69 (d, J=15.2 Hz, 1H), 7.84-7.78 (m, 3H), 8.09 (d, J=8.4 Hz, 2H), 13.21 (s, 1H).

MS (Maldi-Tof): 357.2 (M−1).

Compound 23

1-[4-carboxydimethylmethyloxyphenyl]-3-[4-chlorophenyl]prop-2-en-1-one

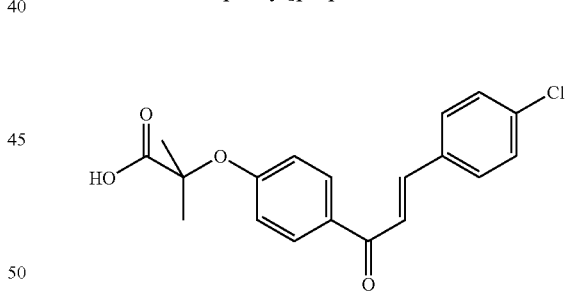

This compound was synthesized from 4'-ethyloxycarbonyl dimethylmethyloxyacetophenone (starting material 9) and 4-chlorobenzaldehyde according to general method 3 described earlier.

Purification was made by chromatography on silica gel (elution: dichloromethane/methanol 95:5) followed by preparative HPLC (reverse phase RP18, Licrospher 12 μm, elution: water-methanol-trifluoroacetic acid: 22:78:0.1).

$^1$H NMR DMSO-$d_6$ δppm: 1.72 (s, 6H), 6.97 (d, J=8.61 Hz, 2H), 7.39 (d, J=8.25 Hz, 2H), 7.50 (d, J=15.72 Hz, 1H), 7.57 (d, J=8.61 Hz, 2H), 7.77 (d, J=15.72 Hz, 1H), 7.99 (d, J=8.61 Hz, 2H), 13.30 (s, 1H).

MS (Maldi-Tof): 345.1 (M+1).

Compound 24

1-[4-carboxydimethylmethylthiophenyl]-3-[4-methylthiophenyl]prop-2-en-1-one

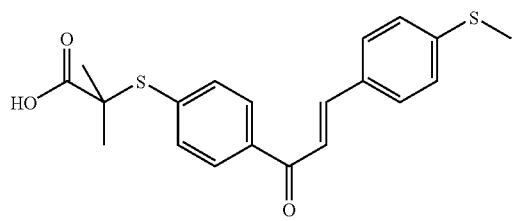

This compound was synthesized from 4'-ethyloxycarbonyl dimethylmethylthioacetophenone (starting material 12) and 4-methylthiobenzaldehyde according to general method 3 described earlier.

Purification was made by chromatography on silica gel (elution: dichloromethane/methanol 95:5) followed by preparative HPLC (reverse phase RP18, Licrospher 12 μm, elution: water-methanol-trifluoroacetic acid: 22:78:0.1).

$^1$H NMR DMSO-$d_6$ δppm: 1.46 (s, 6H), 2.54 (s, 3H), 7.33 (d, J=8.61 Hz, 2H), 7.59 (d, J=8.10 Hz, 2H), 7.73 (d, J=15.66 Hz, 1H), 7.85 (d, J=8.10 Hz, 2H), 7.92 (d, J=15.66 Hz, 1H), 8.13 (d, 8.10 Hz, 2H), 12.85 (s, 1H).

MS (Maldi-Tof): 373.1 (M+1).

Compound 25

1-[2-hydroxy-4-bromophenyl]-3-[3,5-dimethyl-4-carboxydimethylmethyloxyphenyl]prop-2-en-1-one

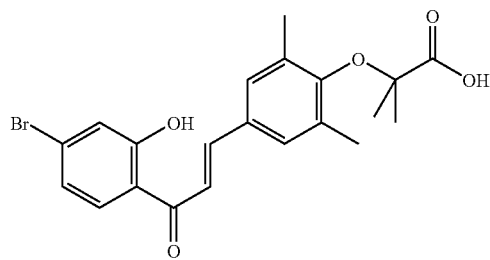

This compound was synthesized from 4'-bromo-2'-hydroxyacetophenone (starting material 11) and 3,5-dimethyl-4-ethyloxycarbonyldimethyloxybenzaldehyde (starting material 6) according to general method 2 described earlier.

Purification was made by chromatography on silica gel (elution: dichloromethane/methanol 95:5) followed by preparative HPLC (reverse phase RP18, Licrospher 12 μm, elution: water-methanol-trifluoroacetic acid: 22:78:0.1).

$^1$H NMR DMSO-$d_6$ δppm: 1.39 (s, 6H), 2.22 (s, 6H), 7.20 (dd, J=2.16, J=8.55 Hz, 1H), 7.25 (d, J=1.59 Hz, 1H), 7.60 (s, 2H), 7.73 (d, J=15.51 Hz, 1H), 7.86 (d, J=15.51 Hz, 1H), 8.16 (d, J=8.58 Hz, 1H), 12.70 (s, 1H), 13.30 (s, 1H).

MS (ES-MS): 432.9 (M−1).

Compound 26

1-[4-carboxydimethylmethyloxyphenyl]-3-[4-methylthiophenyl]prop-2-en-1-one

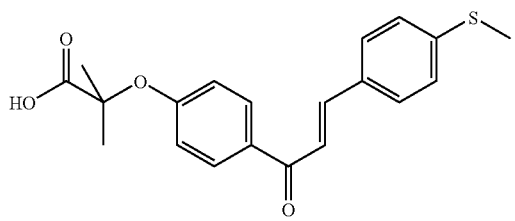

This compound was synthesized from 4'-ethyloxycarbonyldimethylmethyloxyacetophenone (starting material 9) and 4-methylthiobenzaldehyde according to general method 2 described earlier.

Purification was made by chromatography on silica gel (elution: dichloromethane/methanol 95:5) followed by preparative HPLC (reverse phase RP18, Licrospher 12 μm, elution: water-methanol-trifluoroacetic acid: 22:78:0.1).

$^1$H NMR DMSO-$d_6$ δppm: 1.60 (s, 6H), 2.53 (s, 3H), 6.93 (d, J=9.00 Hz, 2H), 7.32 (d, J=8.49 Hz, 2H), 7.68 (d, J=15.51 Hz, 1H), 7.82 (d, J=8.52 Hz, 2H), 7.89 (d, J=15.51 Hz, 1H), 8.13 (d, 9.00 Hz, 2H), 13.30 (s, 1H).

MS (Maldi-Tof): 355.0 (M+1).

Compound 27

1-[4-methylthiophenyl]-3-[3,5-dimethyl-4-tertbutyloxycarbonyldimethylmethyloxyphenyl]prop-2-en-1-one

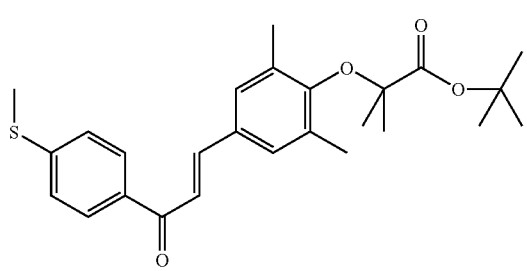

This compound was synthesized from 1-[4-methylthiophenyl]-3-[3,5-dimethyl-4-hydroxyphenyl]prop-2-en-1-one (intermediate compound 2) and tertbutyl bromoisobutyrate according to general method 4 described earlier.

Purification was made by chromatography on silica gel (elution: cyclohexane/ethyl acetate 8:2).

Compound 28

1-[4-methylthiophenyl]-3-[3,5-dimethyl-4-isopropyloxycarbonyldimethylmethyloxyphenyl]prop-2-en-1-one

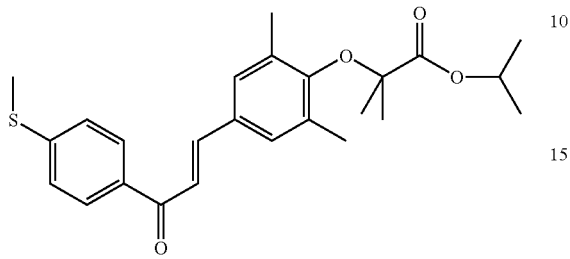

This compound was synthesized from 1-[4-methylthiophenyl]-3-[3,5-dimethyl-4-hydroxyphenyl]prop-2-en-1-one (intermediate compound 2) and isopropyl bromoisobutyrate according to general method 4 described earlier.

Purification was made by chromatography on silica gel (elution: cyclohexane/ethyl acetate 9:1).

$^1$H NMR DMSO-$d_6$ δppm: 1.25 (d, J=6.18 Hz, 6H), 1.39 (s, 6H), 2.18 (s, 6H), 2.57 (s, 3H), 4.99 (sept, J=6.18 Hz, 1H), 7.40 (d, J=8.28 Hz, 2H), 7.58 (s, 2H), 7.62 (d, J=15.5 Hz, 1H), 7.82 (d, J=15.5 Hz, 1H), 8.10 (d, J=8.28 Hz, 2H), 12.97 (s, 1H).

MS (Maldi-Tof): 427.1 (M+1).

Compound 29

1-[4-methylthiophenyl]-3-[3,5-dimethyl-4-carboxydimethylmethyloxyphenyl]prop-2-en-1-one

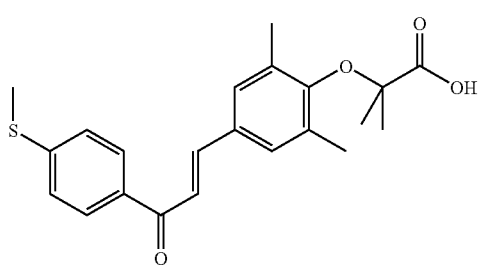

This compound was synthesized from 1-[4-methylthiophenyl]-3-[3,5-dimethyl-4-isopropyloxycarbonyldimethylmethyloxyphenyl]prop-2-en-1-one (compound 28) according to general method 5 described earlier.

Purification was made by chromatography on silica gel (elution: dichloromethane/methanol 98:2).

$^1$H NMR DMSO-$d_6$ δppm: 1.39 (s, 6H), 2.22 (s, 6H), 2.57 (s, 3H), 7.40 (d, J=8.55 Hz, 2H), 7.57 (s, 2H), 7.62 (d, J=15.5 Hz, 1H), 7.83 (d, J=15.5 Hz, 1H), 8.1 (d, J=8.55 Hz, 2H), 12.97 (s, 1H).

MS (ES-MS): 383.3 (M−1).

Compound 30

1-[2-methoxyphenyl]-3-[3,5-dimethyl-4-tertbutyloxycarbonyldimethylmethyloxyphenyl]prop-2-en-1-one

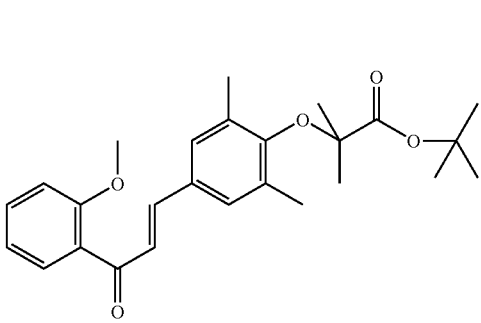

This compound was synthesized from 1-[2-methoxyphenyl]-3-[3,5-dimethyl-4-hydroxyphenyl]prop-2-en-1-one (intermediate compound 3) and tertbutyl bromoisobutyrate according to general method 4 described earlier.

Purification was made by chromatography on silica gel (elution: cyclohexane/ethyl acetate 9:1).

Compound 31

1-[2-methoxyphenyl]-3-[3,5-dimethyl-4-carboxydimethylmethyloxyphenyl]prop-2-en-1-one

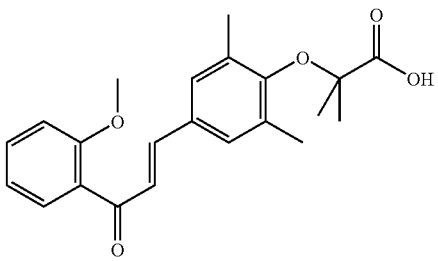

This compound was synthesized from 1-[2-methoxyphenyl]-3-[3,5-dimethyl-4-tertbutyloxycarbonyldimethylmethyloxyphenyl]prop-2-en-1-one (compound 30) according to general method 5 described earlier.

Purification was made by chromatography on silica gel (elution: dichloromethane/methanol 98:2).

$^1$H NMR DMSO-$d_6$ δppm: 1.38 (s, 6H), 2.19 (s, 6H), 3.93 (s, 3H), 7.05 (m, 1H), 7.20 (d, J=8.31 Hz, 1H), 7.25 (d, J=15.5 Hz, 1H), 7.37 (d, J=15.5 Hz, 1H), 7.39 (s, 2H), 7.46 (d, J=7.2 Hz, 1H), 7.53 (m, 1H), 12.93 (s, 1H).

MS (ES-MS): 367.1 (M−1).

Compound 32

1-[4-hexyloxyphenyl]-3-[3,5-dimethyl-4-tertbutyloxycarbonyldimethylmethyloxyphenyl]prop-2-en-1-one

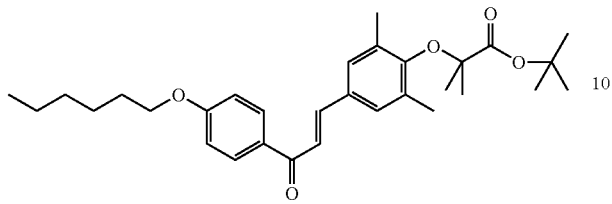

This compound was synthesized from 1-[4-hexyloxyphenyl]-3-[3,5-dimethyl-4-hydroxyphenyl]prop-2-en-1-one (intermediate compound 4) and tertbutyl bromoisobutyrate according to general method 4 described earlier.

Purification was made by chromatography on silica gel (elution: cyclohexane/ethyl acetate 95:5).

Compound 33

1-[4-hexyloxyphenyl]-3-[3,5-dimethyl-4-carboxydimethylmethyloxyphenyl]prop-2-en-1-one

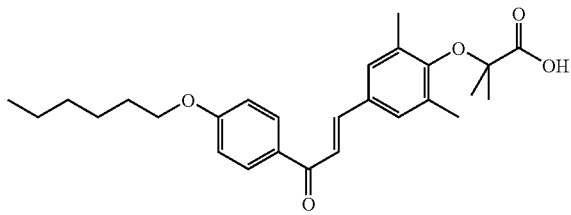

This compound was synthesized from 1-[4-hexyloxyphenyl]-3-[3,5-dimethyl-4-tertbutyloxycarbonyldimethylmethyloxyphenyl]prop-2-en-1-one (compound 32) according to general method 5 described earlier.

Purification was made by recrystallization in methanol.

$^1$H NMR DMSO-d$_6$ δppm: 0.88 (t, J=6.33 Hz, 3H), 1.30 (m, 4H), 1.39 (s, 6H), 1.44 (m, 2H), 1.73 (m, 2H), 2.22 (s, 6H), 4.06 (t, J=6.30 Hz, 2H), 7.06 (d, J=8.61 Hz, 2H), 7.56 (s, 2H), 7.58 (d, J=15.5 Hz, 1H), 7.82 (d, J=15.5 Hz, 1H), 8.13 (d, J=6.61 Hz, 2H).

MS (ES-MS): 437.2 (M−1).

Compound 34

2-(3,5-dimethyl-4-tertbutyloxycarbonyldimethylmethyloxyphenyl)-7-chloro-4H-1-benzopyran-4-one

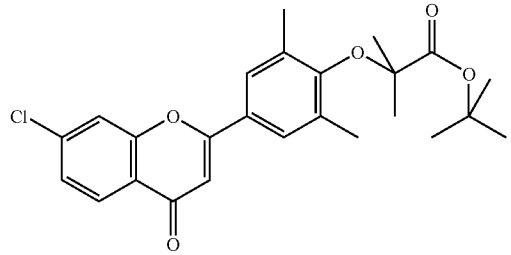

This compound was synthesized from 2-(3,5-dimethyl-4-hydroxyphenyl)-7-chloro-4H-1-benzopyran-4-one (intermediate compound 6) and tertbutyl bromoisobutyrate according to general method 4 described earlier.

Purification was made by precipitation in the solvent mixture dichloromethane/heptane.

Compound 35

2-(3,5-dimethyl-4-carboxydimethylmethyloxyphenyl)-7-chloro-4H-1-benzopyran-4-one

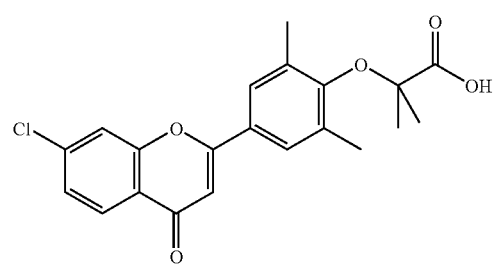

This compound was synthesized from 2-(3,5-dimethyl-4-tertbutyloxycarbonyldimethylmethyloxyphenyl)-7-chloro-4H-1-benzopyran-4-one (compound 34) according to general method 5 described earlier.

Purification was by preparative HPLC (reverse phase RP18, Licrospher 12 μm, elution: water-methanol-trifluoroacetic acid: 22:78:0.1).

$^1$H NMR DMSO-d$_6$ δppm: 1.24 (s, 6H), 2.28 (s, 6H), 7.02 (s, 1H), 7.56 (dd, J=8.71 Hz, J=1.75 Hz, 1H), 7.85 (s, 2H), 8.03 (d, J=1.75 Hz, 1H), 8.06 (d, J=8.71 Hz, 1H).

MS (Maldi-Tof): 387.1 (M+1).

Compound 36

1-[2-methyloxy-4-chlorophenyl]-3-[3,5-dimethyl-4-tertbutyloxycarbonyldimethylmethyloxyphenyl]prop-2-en-1-one

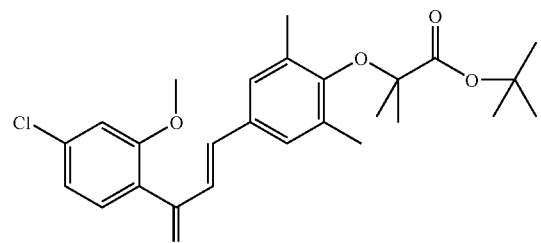

This compound was synthesized from 1-[2-methyloxy-4-chlorophenyl]-3-[3,5-dimethyl-4-hydroxyphenyl]prop-2-en-1-one (intermediate compound 7) and tert-butyl bromoisobutyrate according to general method 4 described earlier.

Purification was made by chromatography on silica gel (elution: cyclohexane/ethyl acetate 9:1).

Compound 37

1-[2-methyloxy-4-chlorophenyl]-3-[3,5-dimethyl-4-carboxydimethylmethyloxyphenyl]prop-2-en-1-one

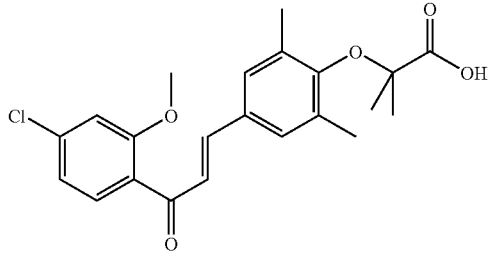

This compound was synthesized from 1-[2-methoxy-4-chlorophenyl]-3-[3,5-dimethyl-4-tertbutyloxycarbonyldimethylmethyloxyphenyl]prop-2-en-1-one (compound 36) according to general method 5 described earlier.

Purification was made by chromatography on silica gel (elution: dichloromethane/methanol 98:2).

$^1$H NMR DMSO-d$_6$ δppm: 1.38 (s, 6H), 2.19 (s, 6H), 3.89 (s, 3H), 7.12 (dd, J=7.98 Hz, J=1.71 Hz, 1H), 7.23 (d, J=15.56 Hz, 1H), 7.29 (s, J=1.71 Hz, 1H), 7.38 (d, J=15.7 Hz, 1H), 7.41 (s, 2H), 7.48 (d, J=7.98 Hz, 1H).

MS (ES-SM) :401.2 (M−1).

Compound 38

1-[4-heptylphenyl]-3-[3,5-dimethyl-4-tertbutyloxycarbonyldimethylmethyloxyphenyl]prop-2-en-1-one

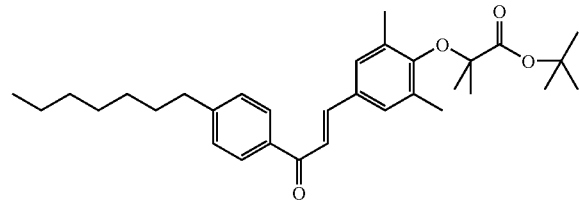

This compound was synthesized from 1-[4-heptylphenyl]-3-[3,5-dimethyl-4-hydroxyphenyl]prop-2-en-1-one (intermediate compound 9) and tertbutyl bromoisobutyrate according to general method 4 described earlier.

Purification was made by chromatography on silica gel (elution: cyclohexane/ethyl acetate 9:1).

Compound 39

1-[4-heptylphenyl]-3-[3,5-dimethyl-4-carboxydimethylmethyloxyphenyl]prop-2-en-1-one

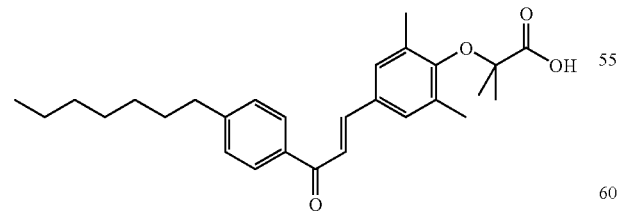

This compound was synthesized from 1-[4-heptylphenyl]-3-[3,5-dimethyl-4-tertbutyloxycarbonyldimethylmethyloxyphenyl]prop-2-en-1-one (compound 38) and tertbutyl bromoisobutyrate according to general method 4 described earlier.

Purification was made by chromatography on silica gel (elution: dichloromethane/methanol 98:2).

$^1$H NMR DMSO-d$_6$ δppm: 0.85 (m, 3H), 1.30-1.24 (m, 8H), 1.39 (s, 6H), 1.60 (m, 2H), 2.22 (s, 6H), 2.67 (t, 2H, J=7.4 Hz), 7.37 (d, J=8.04 Hz, 2H), 7.57 (s, 2H), 7.62 (d, J=15.66 Hz, 1H), 7.82 (d, J=15.69 Hz, 1H), 8.07 (d, J=8.07 Hz, 2H).

MS (ES-MS): 435.3 (M−1).

Compound 40

1-[4-bromophenyl]-3-[3,5-dimethyl-4-tertbutyloxycarbonyldimethylmethyloxyphenyl]prop-2-en-1-one

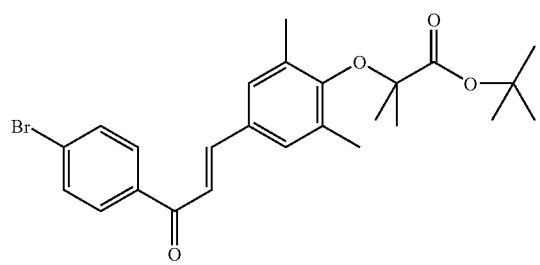

This compound was synthesized from 1-[4-bromophenyl]-3-[3,5-dimethyl-4-hydroxyphenyl]prop-2-en-1-one (intermediate compound 8) and tertbutyl bromoisobutyrate according to general method 4 described earlier.

Purification was made by chromatography on silica gel (elution: cyclohexane/ethyl acetate 9:1).

Compound 41

1-[4-bromophenyl]-3-[3,5-dimethyl-4-carboxydimethylmethyloxyphenyl]prop-2-en-1-one

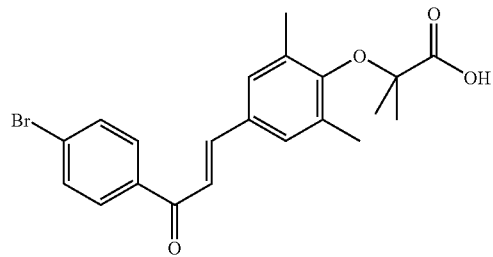

This compound was synthesized from 1-[4-bromophenyl]-3-[3,5-dimethyl-4-tertbutyloxycarbonyldimethylmethyloxyphenyl]prop-2-en-1-one (compound 40) according to general method 5 described earlier.

Purification was made by chromatography on silica gel (elution: dichloromethane/methanol 98:2).

$^1$H NMR DMSO-d$_6$ δppm: 1.39 (s, 6H), 2.22 (s, 6H), 7.58 (s, 2H), 7.65 (d, J=15.39 Hz, 1H), 7.84-7.77 (m, 3H), 8.09 (d, J=8.19 Hz, 1H), 13.01 (s, 1H).

MS (ES-MS): 417.2 (M−1).

Compound 42

1-[2-hydroxyphenyl]-3-[3,5-dimethyl-4-isopropyloxycarbonyldimethylmethyloxyphenyl]prop-2-en-1-one

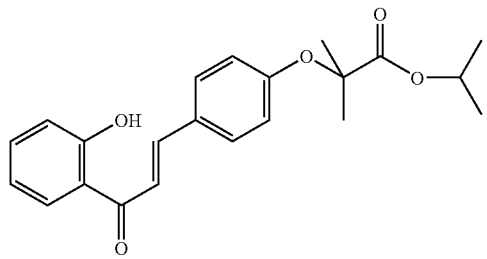

1-[2-hydroxyphenyl]-3-[4-carboxydimethylmethyloxyphenyl]prop-2-en-1-one (compound 4; 1 eq) was dissolved in dichloromethane. Dichloromethylmethyl ether (3 eq) was added and the mixture was kept under reflux for 8 hours. The solvent and excess reagent were eliminated by vacuum evaporation. The evaporation residue was taken up in isopropanol (50 eq) stirred for 12 hours at room temperature and the isopropanol was then eliminated by vacuum evaporation.

Purification was made by chromatography on silica gel (elution: toluene/ethyl acetate 7:3).

$^1$H NMR CDCl$_3$ δppm: 1.21 (d, J=6.09 Hz, 6H), 1.65 (s, 6 H), 5.10 (sept, J=6.10 Hz, 1H), 6.86 (d, J=8.65 Hz, 2H), 6.95 (m, 1H), 7.02 (dd, J=8.65 Hz, J=1.53 Hz, 1H), 7.48 (m, 1H), 7.54 (d, J=15.25 Hz, 1H), 7.57 (d, J=8.65 Hz, 2H), 7.87(d, J=15.25 Hz, 1H), 7.93 (d, J=8.40 Hz, 1 H), 12.94 (signal exchangeable D$_2$O, 1H).

MS (Maldi-Tof): 369.1 (M+1).

Compound 43

1-[4-trifluoromethylphenyl]-3-[3-methyl-4-tertiobutyloxycarbonylmethyloxyphenyl]prop-2-en-1-one

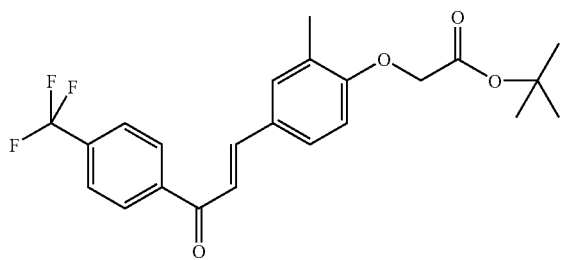

This compound was synthesized from 1-[4-trifluoromethylphenyl]-3-[3-methyl-4-hydroxyphenyl]prop-2-en-1-one (intermediate compound 10) and tertbutyl bromoacetate according to general method 4 described earlier.

Purification was made by chromatography on silica gel (elution: cyclohexane/ethyl acetate 9:1) and crystallization (cyclohexane).

Compound 44

1-[4-trifluoromethylphenyl]-3-[3-methyl-4-carboxymethyloxyphenyl]prop-2-en-1-one

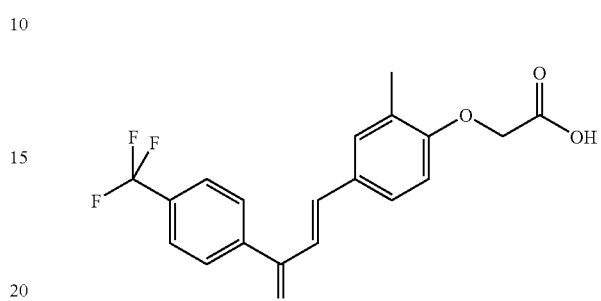

This compound was synthesized from 1-[4-trifluoromethylphenyl]-3-[3-methyl-4-tertiobutyloxycarbonylmethyloxyphenyl]prop-2-en-1-one (compound 43) according to general method 5 described earlier.

Purification was made by washing (water, dichloromethane).

$^1$H NMR DMSO-d$_6$ δppm: 2.24 (s, 3H), 4.81 (s, 2H), 6.92 (d, 1H, J=8.76 Hz), 7.68 (d, 1H, J=8.46 Hz), 7.72 (d, 1H, J=15.78 Hz), 7.81 (d, 1H, J=15.64 Hz), 7.81 (s, 1H), 7.93 (d, 2H, J=8.32 Hz), 8.31 (d, 2H, J=8.32 Hz).

MS (ES-MS): 365 (M+1).

Compound 45

1-[4-bromophenyl]-3-[3-tertiobutyl-4-tertiobutyloxycarbonyldimethylmethyloxyphenyl]prop-2-en-1-one

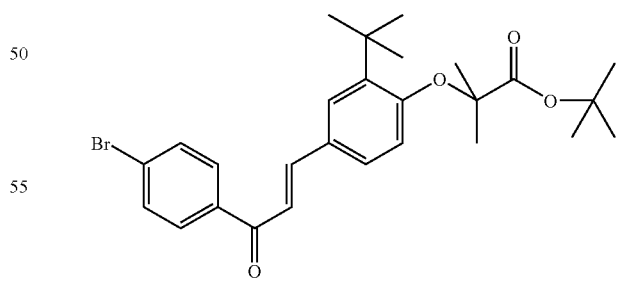

This compound was synthesized from 1-[4-bromophenyl]-3-[3-tertiobutyl-4-hydroxyphenyl]prop-2-en-1-one (intermediate compound 11) and tert-butyl bromoisobutyrate according to general method 4 described earlier.

Purification was made by chromatography on silica gel (elution: cyclohexane/ethyl acetate 9:1).

Compound 46

1-[4-bromophenyl]-3-[3-tertiobutyl-4-carboxydimethylmethyloxyphenyl]prop-2-en-1-one

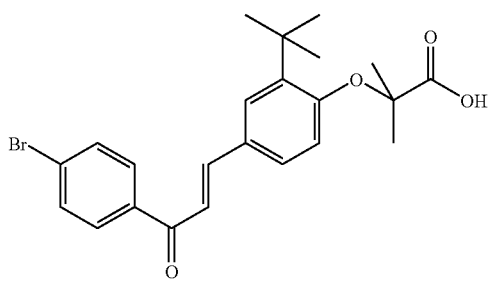

This compound was synthesized from 1-[4-bromophenyl]-3-[3-tertiobutyl-4-tertiobutyloxycarbonyldimethylmethyloxyphenyl]prop-2-en-1-one (compound 45) according to general method 5 described earlier.

Purification was made by washing (water, dichloromethane).

$^1$H NMR DMSO-$d_6$ δppm: 1.40 (s, 9H), 1.63 (s, 6H), 6.62 (d, 1H, J=8.46 Hz), 7.67-7.71 (m, 4H), 7.77 (d, 2H, J=8.49 Hz), 8.06 (d, 2H, J=8.49 Hz).

MS (ES-MS): 445.7 (M+1).

Compound 47

1-[2-trifluoromethyloxyphenyl]-3-[3,5-dimethyl-4-tertiobutyloxycarbonyldimethylmethyloxyphenyl]prop-2-en-1-one

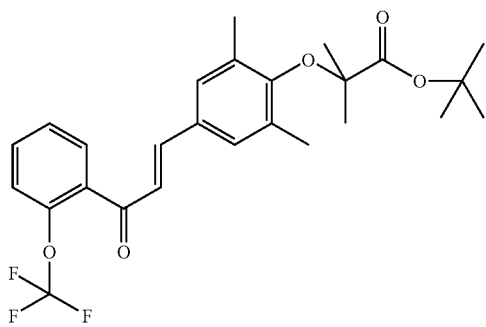

This compound was synthesized from 1-[2-trifluoromethyloxyphenyl]-3-[3,5-dimethyl-4-hydroxyphenyl]prop-2-en-1-one (intermediate compound 12) and tertbutyl bromoisobutyrate according to general method 4 described earlier.

Purification was made by chromatography on silica gel (elution: cyclohexane/ethyl acetate 9:1).

Compound 48

1-[2-trifluoromethyloxyphenyl]-3-[3,5-dimethyl-4-carboxydimethylmethyloxyphenyl]prop-2-en-1-one

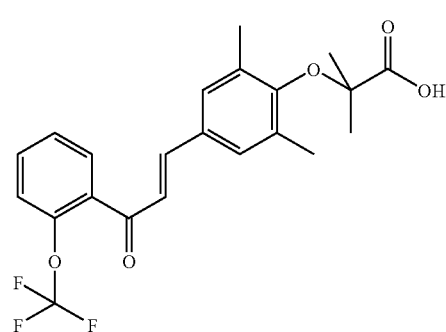

This compound was synthesized from 1-[2-trifluoromethyloxyphenyl]-3-[3,5-dimethyl-4-tertiobutyloxycarbonyldimethylmethyloxyphenyl]prop-2-en-1-one (compound 47) according to general method 5 described earlier.

Purification was made by washing (water).

$^1$H NMR CDCl$_3$ δppm: 1.55 (s, 6H), 2.28 (s, 6H), 7.12 (d, 1H, J=16.09 Hz), 7.26 (s, 2H), 7.40 (m, 2H), 7.48 (d, 1H, J=16.09 Hz), 7.55 (d, 1H, J=7.59 Hz), 7.65 (d, 1H, J=7.59).

MS (ES-MS): 423 (M+1).

Compound 49

1-[4-methylthiophenyl]-3-[3-trifluoromethyl-4-tertiobutyloxycarbonyldimethylmethyloxyphenyl]prop-2-en-1-one

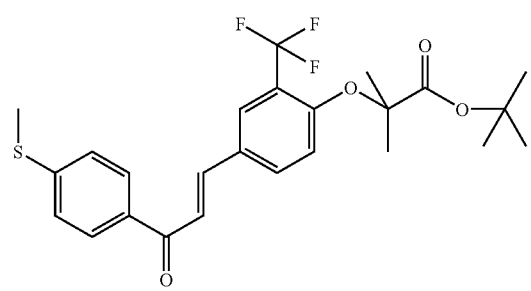

This compound was synthesized from 1-[4-methylthiophenyl]-3-[3-trifluoromethyl-4-hydroxyphenyl]prop-2-en-1-one (intermediate compound 13) and tertbutyl bromoisobutyrate according to general method 4 described earlier.

Purification was made by chromatography on silica gel (elution: cyclohexane/ethyl acetate 95:5).

Compound 50

1-[4-methylthiophenyl]-3-[3-trifluoromethyl-4-carboxydimethylmethyloxyphenyl]prop-2-en-1-one

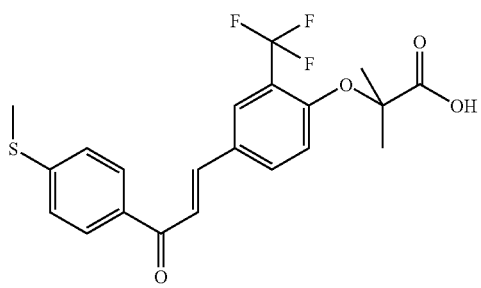

This compound was synthesized from 1-[4-methylthiophenyl]-3-[3-trifluoromethyl-4-tertiobutyloxycarbonyldimethylmethyloxyphenyl]prop-2-en-1-one (compound 49) according to general method 5 described earlier.

Purification was made by crystallization (acetonitrile).

$^1$H NMR DMSO-$d_6$ δppm: 1.59 (s, 6H), 2.55 (s, 3H), 6.95 (d, 1H, J=8.49 Hz), 7.40 (d, 2H, J=8.49 Hz), 7.72 (d, 1H, J=15.64 Hz), 7.92 (d, 1H, J=15.64 Hz), 8.06 (d, 1H, 8.49 Hz), 8.10 (d, 2H, J=8.49 Hz), 8.20 (s, 1H), 13.43 (s, 1H).

MS (Maldi-Tof): 425 (M+1).

Compound 51

1-[4-methylsulfonylphenyl]-3-[3,5-dimethyl-4-tertiobutyloxycarbonyldimethylmethyloxyphenyl]prop-2-en-1-one

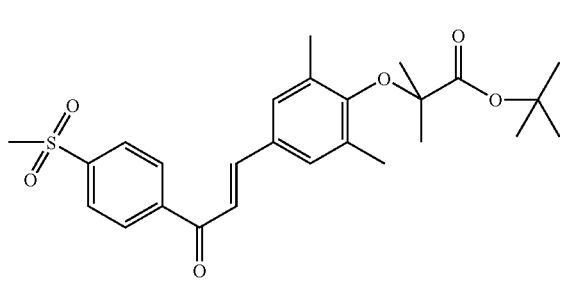

This compound was synthesized from 1-[4-methylsulfonylphenyl]-3-[3,5-dimethyl-4-hydroxyphenyl]prop-2-en-1-one (intermediate compound 14) and tertbutyl bromoisobutyrate according to general method 4 described earlier.

Purification was made by chromatography on silica gel (elution: cyclohexane/ethyl acetate 7:3).

Compound 52

1-[4-methylsulfonylphenyl]-3-[3,5-dimethyl-4-carboxydimethylmethyloxyphenyl]prop-2-en-1-one

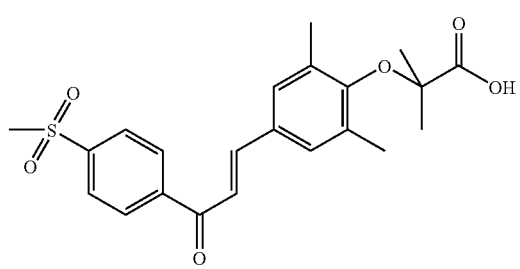

This compound was synthesized from 1-[4-methylsulfonylphenyl]-3-[3,5-dimethyl-4-tertiobutyloxycarbonyldimethylmethyloxyphenyl]prop-2-en-1-one (compound 51) according to general method 5 described earlier.

Purification was made by chromatography on silica gel (elution: dichloromethane/methanol 98/2) and crystallization (acetonitrile).

$^1$H NMR DMSO-$d_6$ δppm: 1.39 (s, 6H), 2.22 (s, 6H), 2.28 (s, 3H), 7.60 (s, 2H), 7.69 (d, 1H, J=15.50 Hz), 7.84 (d, 1H, J=15.50 Hz), 8.11 (d, 2H, J=8.38 Hz), 8.35 (d, 2H, J=8.38), 12.96 (s, 1H).

MS (ES-MS): 417.2 (M+1).

Compound 53

1-[4-trifluoromethylthiophenyl]-3-[3,5-dimethyl-4-tertiobutyloxycarbonyldimethylmethyloxyphenyl]prop-2-en-1-one

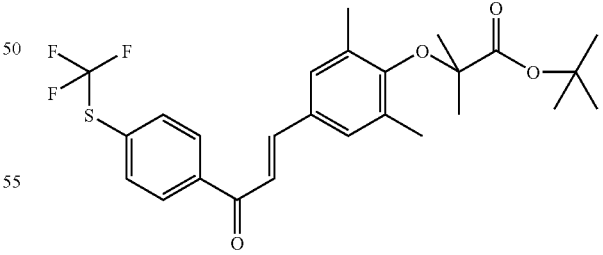

This compound was synthesized from 1-[4-trifluoromethylthiophenyl]-3-[3,5-dimethyl-4-hydroxyphenyl]prop-2-en-1-one (intermediate compound 15) and tert-butyl bromoisobutyrate according to general method 4 described earlier.

Purification was made by chromatography on silica gel (elution: cyclohexane/ethyl acetate 7:3).

Compound 54

1-[4-trifluoromethylthiophenyl]-3-[3,5-dimethyl-4-carboxydimethylmethyloxyphenyl]prop-2-en-1-one

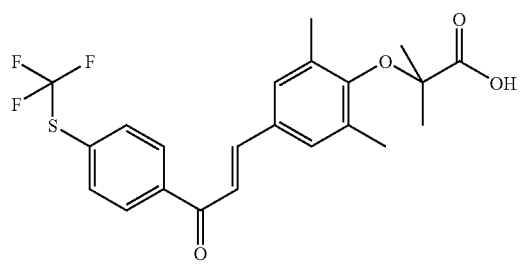

This compound was synthesized from 1-[4-trifluoromethylthiophenyl]-3-[3,5-dimethyl-4-tertiobutyloxycarbonyldimethylmethyloxyphenyl]prop-2-en-1-one (compound 53) according to general method 5 described earlier.

Purification was made by chromatography on silica gel (elution: dichloromethane/methanol 98:2).

$^1$H NMR DMSO-$d_6$ δppm: 1.39 (s, 6H), 2.22 (s, 6H), 7.58 (s, 2H), 7.66 (d, 1H, J=15.81 Hz), 7.83 (d, 1H, J=15.81 Hz), 7.89 (d, 2H, J=7.62 Hz), 8.24 (d, 2H, J=7.62 Hz), 12.97 (s, 1H).

MS (ES-MS): 439.1 (M+1).

Compound 55

1-[4-isopropylphenyl]-3-[3,5-dimethyl-4-tertiobutyloxycarbonyldimethylmethyloxyphenyl]prop-2-en-1-one

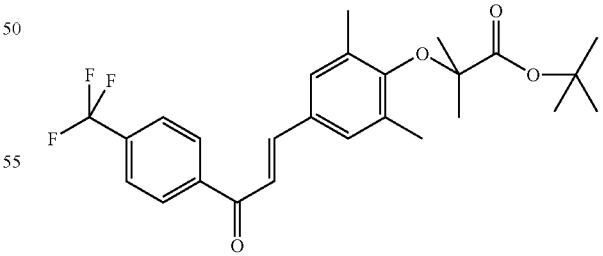

This compound was synthesized from 1-[4-isopropylphenyl]-3-[3,5-dimethyl-4-hydroxyphenyl]prop-2-en-1-one (intermediate compound 16) and tertbutyl bromoisobutyrate according to general method 4 described earlier.

Purification was made by chromatography on silica gel (elution: cyclohexane/ethyl acetate 7:3).

Compound 56

1-[4-isopropylphenyl]-3-[3,5-dimethyl-4-carboxydimethylmethyloxyphenyl]prop-2-en-1-one

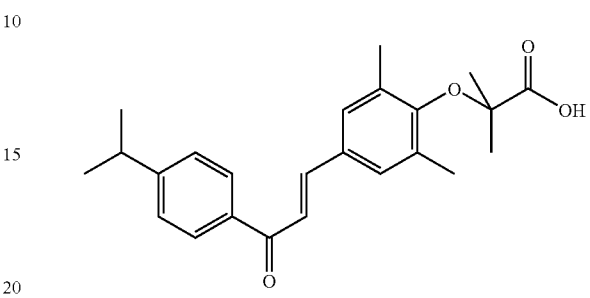

This compound was synthesized from 1-[4-isopropylphenyl]-3-[3,5-dimethyl-4-tertiobutyloxycarbonyldimethylmethyloxyphenyl]prop-2-en-1-one (compound 55) according to general method 5 described earlier.

Purification was made by chromatography on silica gel (elution: dichloromethane/methanol 98:2).

$^1$H NMR DMSO-$d_6$ δppm: 1.30 (d, 6H, J=7.08 Hz), 1.57 (s, 6H), 2.30 (s, 6H), 2.99 (m, 1H), 7.32 (s, 2H), 7.37 (d, 2H, J=8.16 Hz), 7.45 (d, 1H, J=15.51 Hz), 7.73 (d, 1H, J=15.51 Hz), 7.98 (d, 2H, J=8.16 Hz).

MS (ES-MS): 381.2 (M+1).

Compound 57

1-[4-trifluoromethylphenyl]-3-[3,5-dimethyl-4-tertiobutyloxycarbonyldimethylmethyloxyphenyl]prop-2-en-1-one This compound was synthesized from 1-[4-trifluoromethylphenyl]-3-[3,5-dimethyl-4-hydroxyphenyl]prop-2-en-1-one (intermediate compound 17) and tertbutyl bromoisobutyrate according to general method 4 described earlier.

Purification was made by chromatography on silica gel (elution: cyclohexane/ethyl acetate 95:5).

Compound 58

1-[4-trifluoromethylphenyl]-3-[3,5-dimethyl-4-carboxydimethylmethyloxyphenyl]prop-2-en-1-one

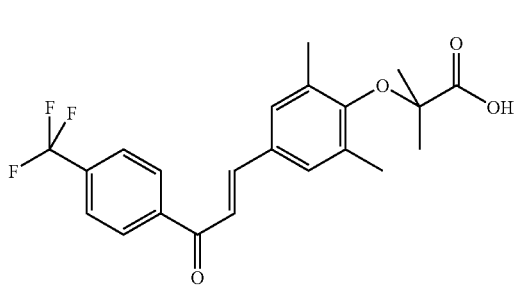

This compound was synthesized from 1-[4-trifluoromethylphenyl]-3-[3,5-dimethyl-4-tertiobutyloxycarbonyldimethylmethyloxyphenyl]prop-2-en-1-one (compound 57) according to general method 5 described earlier.

Purification was made by chromatography on silica gel (elution: dichloromethane/methanol 98:2).

$^1$H NMR CDCl$_3$ δppm: 1.59 (s, 6H), 2.31 (s, 6H), 7.34 (s, 2H), 7.41 (d, 1H J=15.25 Hz), 7.74 (d, 1H, J=15.25 Hz), 7.78 (d, 2H, J=8.44 Hz), 8.11 (d, 2H, J=8.44 Hz).

MS (ES-MS): 407.3 (M+1).

Compound 59

1-[2-methylthiophenyl]-3-[3,5-dimethyl-4-tertiobutyloxycarbonyldimethylmethyloxyphenyl]prop-2-en-1-one

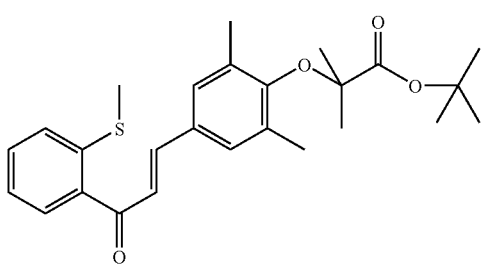

This compound was synthesized from 1-[2-methylthiophenyl]-3-[3,5-dimethyl-4-hydroxyphenyl]prop-2-en-1-one (intermediate compound 18) and tertbutyl bromoisobutyrate according to general method 4 described earlier.

Purification was made by chromatography on silica gel (elution: cyclohexane/ethylacetate 8:2).

Compound 60

1-[2-methylthiophenyl]-3-[3,5-dimethyl-4-carboxydimethylmethyloxyphenyl]prop-2-en-1-one

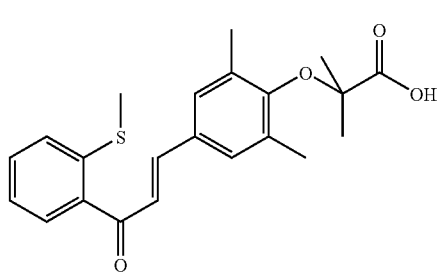

This compound was synthesized from 1-[2-methylthiophenyl]-3-[3,5-dimethyl-4-tertiobutyloxycarbonyldimethylmethyloxyphenyl]prop-2-en-1-one (compound 59) according to general method 5 described earlier.

Purification was made by chromatography on silica gel (elution: dichloromethane/methanol 98:2).

$^1$H NMR DMSO-d$_6$ δppm: 1.38 (s, 6H), 2.20 (s, 6H), 3.34 (s, 3H), 7.30 (d, 1H, J=7.68 Hz), 7.44-7.59 (m, 6H), 7.91 (d, 1H, J=7.68 Hz).

MS (Maldi-Tof): 383.0 (M−1).

Compound 61

1-[4-trifluoromethyloxyphenyl]-3-[3,5-dimethyl-4-tertiobutyloxycarbonyldimethylmethyloxyphenyl]prop-2-en-1-one

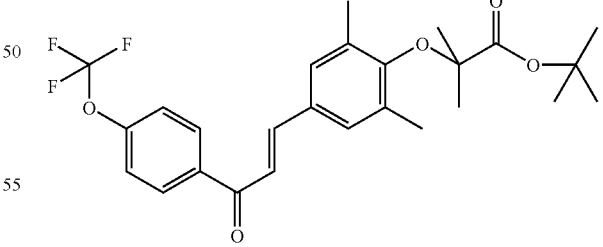

This compound was synthesized from 1-[4-trifluoromethyloxyphenyl]-3-[3,5-dimethyl-4-hydroxyphenyl]prop-2-en-1-one (intermediate compound 19) and tertbutyl bromoisobutyrate according to general method 4 described earlier.

Purification was made by chromatography on silica gel (elution: cyclohexane/ethyl acetate 9:1).

Compound 62

1-[4-trifluoromethyloxyphenyl]-3-[3,5-dimethyl-4-carboxydimethylmethyloxyphenyl]prop-2-en-1-one

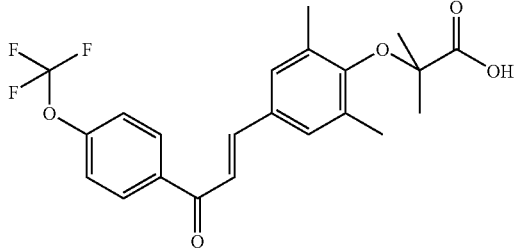

This compound was synthesized from 1-[4-trifluoromethyloxyphenyl]-3-[3,5-dimethyl-4-tertiobutyloxycarbonyldimethylmethyloxyphenyl]prop-2-en-1-one (compound 61) according to general method 5 described earlier.

Purification was made by chromatography on silica gel (elution: dichloromethane/methanol 98:2).

$^1$H NMR DMSO-$d_6$ δppm: 1.39 (s, 6H), 2.22 (s, 6H), 7.55 (d, 2H, J=8.45 Hz), 7.59 (s, 2H), 7.66 (d, 1H, J=15.36 Hz), 7.83 (d, 1H, J=15.39 Hz), 8.28 (d, 2H, J=8.45 Hz), 12.95 (s, 1H).

MS (ES-MS): 423.2 (M+1).

Compound 63

1-[4-iodophenyl]-3-[3,5-dimethyl-4-tertiobutyloxycarbonyldimethylmethyloxyphenyl]prop-2-en-1-one

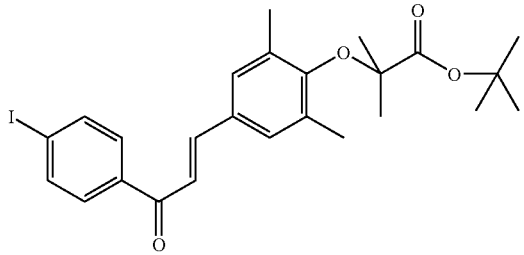

This compound was synthesized from 1-[4-iodophenyl]-3-[3,5-dimethyl-4-hydroxyphenyl]prop-2-en-1-one (intermediate compound 20) and tert-butyl bromoisobutyrate according to general method 4 described earlier.

Purification was made by chromatography on silica gel (elution: cyclohexane/ethyl acetate 9:1).

Compound 64

1-[4-iodophenyl]-3-[3,5-dimethyl-4-carboxydimethylmethyloxyphenyl]prop-2-en-1-one

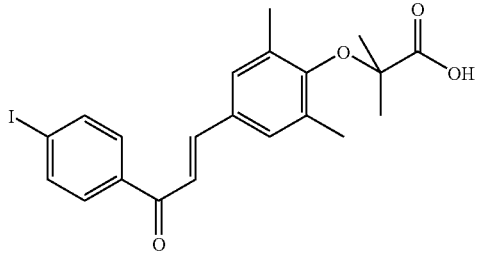

This compound was synthesized from 1-[4-iodophenyl]-3-[3,5-dimethyl-4-tertiobutyloxycarbonyldimethylmethyloxyphenyl]prop-2-en-1-one (compound 63) according to general method 5 described earlier.

Purification was made by chromatography on silica gel (elution: dichloromethane/methanol 98:2).

$^1$H NMR DMSO-$d_6$ δppm: 1.39 (s, 6H), 2.22 (s, 6H), 7.57 (s, 2H), 7.64 (d, 1H, J=15.51 Hz), 7.79 (d, 1H, J=15.51 Hz), 7.91 (d, 2H, J=8.58 Hz), 7.96 (d, 2H, J=8.58 Hz), 12.95 (s, 1H).

MS (ES-MS): 465.1 (M+1).

Compound 65

1-[4-fluorophenyl]-3-[3,5-dimethyl-4-tertiobutyloxycarbonyldimethylmethyloxyphenyl]prop-2-en-1-one

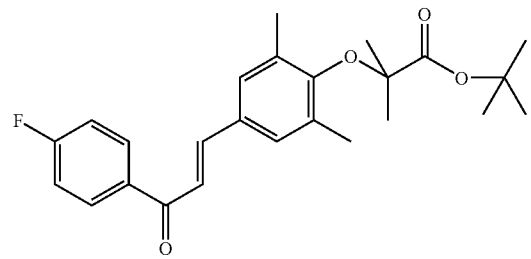

This compound was synthesized from 1-[4-fluorophenyl]-3-[3,5-dimethyl-4-hydroxyphenyl]prop-2-en-1-one (intermediate compound 21) and tertbutyl bromoisobutyrate according to general method 4 described earlier.

Purification was made by chromatography on silica gel (elution: cyclohexane/ethyl acetate 9:1).

Compound 66

1-[4-fluorophenyl]-3-[3,5-dimethyl-4-carboxydimethylmethyloxyphenyl]prop-2-en-1-one

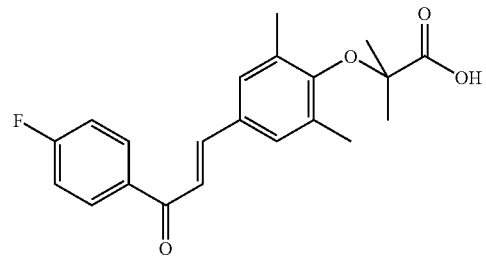

This compound was synthesized from 1-[4-fluorophenyl]-3-[3,5-dimethyl-4-tertiobutyloxycarbonyldimethylmethyloxyphenyl]prop-2-en-1-one (compound 65) according to general method 5 described earlier.

Purification was made by chromatography on silica gel (elution: dichloromethane/methanol 98:2).

$^1$H NMR DMSO-$d_6$ δppm: 1.39 (s, 6H), 2.22 (s, 6H), 7.38 (d, 2H, J=8.55 Hz), 7.42 (d, 1H, J=8.58 Hz), 7.59 (s, 2H), 7.64 (d, 1H, J=15.51 Hz), 7.85 (d, 1H, J=15.54 Hz), 8.24 (dd, 2H, J=5.34 Hz, J=8.55 Hz).

MS (ES-MS): 437.2 (M−1).

Compound 67

1-[4-nonyloxyphenyl]-3-[3,5-dimethyl-4-tertiobutyloxycarbonyldimethylmethyloxyphenyl]prop-2-en-1-one

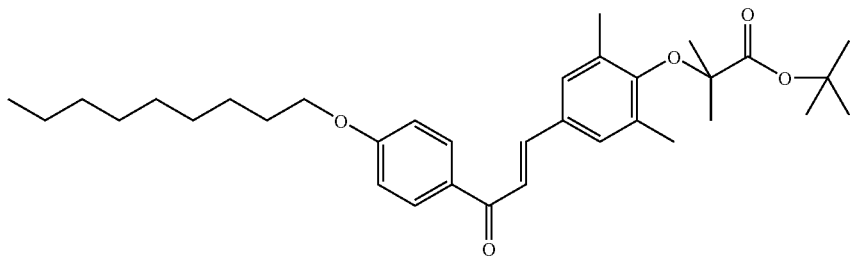

This compound was synthesized from 1-[4-nonyloxyphenyl]-3-[3,5-dimethyl-4-hydroxyphenyl]prop-2-en-1-one (intermediate compound 22) and tertbutyl bromoisobutyrate according to general method 4 described earlier.

Purification was made by chromatography on silica gel (elution: cyclohexane/ethyl acetate 85:15).

Compound 68

1-[4-nonyloxyphenyl]-3-[3,5-dimethyl-4-carboxydimethylmethyloxyphenyl]prop-2-en-1-one

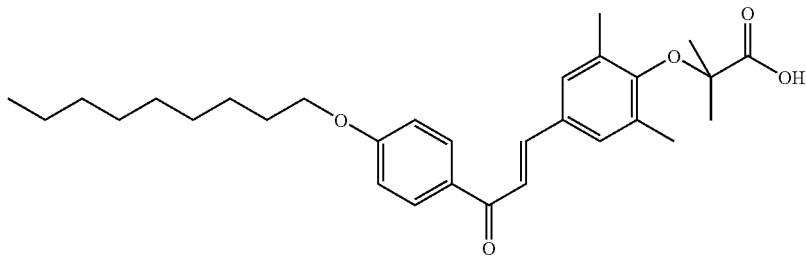

This compound was synthesized from 1-[4-nonyloxyphenyl]-3-[3,5-dimethyl-4-tertiobutyloxycarbonyldimethylmethyloxyphenyl]prop-2-en-1-one (compound 67) according to general method 5 described earlier.

Purification was made by crystallization (heptane/dichloromethane).

$^1$H NMR DMSO-$d_6$ δppm: 0.86 (m, 3H), 1.26 (m, 12H), 1.39 (s, 6H), 1.72 (m, 2H), 2.22 (s, 6H), 4.07 (t, 2H, J=6.60 Hz), 7.07 (d, 2H, J=8.79 Hz), 7.56 (s, 2H), 7.59 (d, 1H, J=15.39 Hz), 7.83 (d, 1H, J=15.39 Hz), 8.14 (d, 2H, J=8.79 Hz), 12.94 (s, 1H).

MS (ES-MS): 479.2 (M−1).

Compound 69

1-[4-propyloxyphenyl]-3-[3,5-dimethyl-4-tertiobutyloxycarbonyldimethylmethyloxyphenyl]prop-2-en-1-one

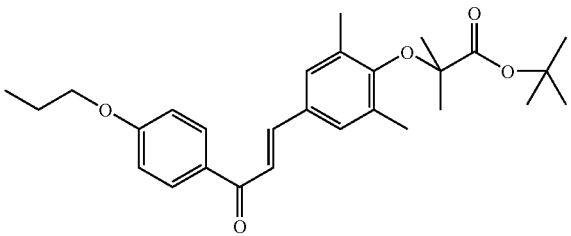

This compound was synthesized from 1-[4-propyloxyphenyl]-3-[3,5-dimethyl-4-hydroxyphenyl]prop-2-en-1-one (intermediate compound 23) and tertbutyl bromoisobutyrate according to general method 4 described earlier.

Purification was made by chromatography on silica gel (elution: cyclohexane/ethyl acetate 90:10).

Compound 70

1-[4-propyloxyphenyl]-3-[3,5-dimethyl-4-carboxy-dimethylmethyloxyphenyl]prop-2-en-1-one

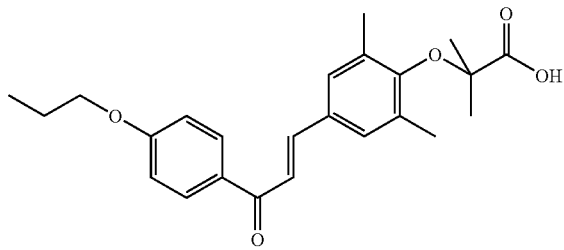

This compound was synthesized from 1-[4-propyloxyphenyl]-3-[3,5-dimethyl-4-tertiobutyloxycarbonyldimethylmethyloxyphenyl]prop-2-en-1-one (compound 69) according to general method 5 described earlier.

Purification was made by crystallization (heptane/dichloromethane).

$^1$H NMR CDCl$_3$ δppm: 1.07 (t, 3H, J=7.53 Hz), 1.56 (s, 6H), 1.85 (m, 2H), 2.30 (s, 6H), 4.01 (t, 2H, J=6.42 Hz), 6.98 (d, 2H, J=8.67 Hz), 7.31 (s, 2H), 7.46 (d, 1H, J=15.81 Hz), 7.72 (d, 1H, J=15.81 Hz), 8.04 (d, 2H, J=8.67 Hz).

MS (ES-MS): 396 (M+1).

Compound 71

1-[4-methylthiophenyl]-3-[3,5-dimethyl-4-tertiobutyloxycarbonylmethyloxyphenyl]prop-2-en-1-one

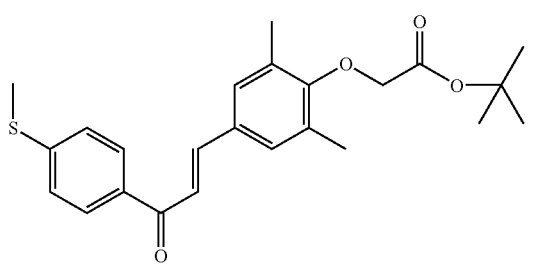

This compound was synthesized from 1-[4-methylthiophenyl]-3-[3,5-dimethyl-4-hydroyphenyl]prop-2-en-1-one (intermediate compound 2) and tertbutyl bromoacetate according to general method 4 described earlier.

Purification was made by chromatography on silica gel (elution: cyclohexane/ethyl acetate 95:5).

Compound 72

1-[4-methylthiophenyl]-3-[3,5-dimethyl-4-carboxymethyloxyphenyl]prop-2-en-1-one

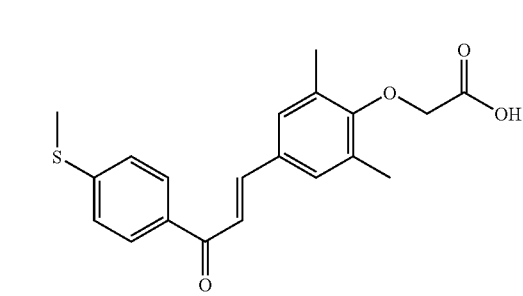

This compound was synthesized from 1-[4-methylthiophenyl]-3-[3,5-dimethyl-4-tertiobutyloxycarbonylmethyloxyphenyl]prop-2-en-1-one (compound 71) according to general method 5 described earlier.

Purification was made by crystallization (heptane/dichloromethane).

$^1$H NMR CDCl$_3$ δppm: 2.36 (s, 6H), 2.55 (s, 3H), 4.52 (s, 2H), 7.32 (d, 2H, J=8.19 Hz), 7.43 (s, 2H), 7.45 (d, 1H, J=15.24 Hz), 7.74 (d, 1H, J=15.24 Hz), 7.97 (d, 2H, J=8.19 Hz).

MS (ES-MS): 355 (M–1).

Compound 73

1-[4-methylthiophenyl]-3-[3,5-diisopropyl-4-tertiobutyloxycarbonylmethyloxyphenyl]prop-2-en-1-one

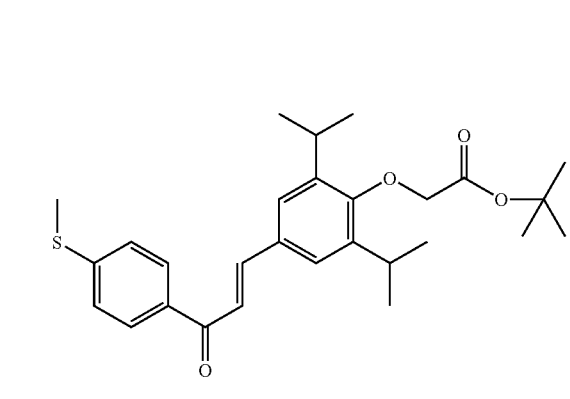

This compound was synthesized from 1-[4-methylthiophenyl]-3-[3,5-diisopropyl-4-hydroxyphenyl]prop-2-en-1-one (intermediate compound 24) and tertbutyl bromoacetate according to general method 4 described earlier.

Purification was made by chromatography on silica gel (elution: cyclohexane/ethyl acetate 95:5).

Compound 74

1-[4-methylthiophenyl]-3-[3,5-diisopropyl-4-carboxymethyloxyphenyl]prop-2-en-1-one

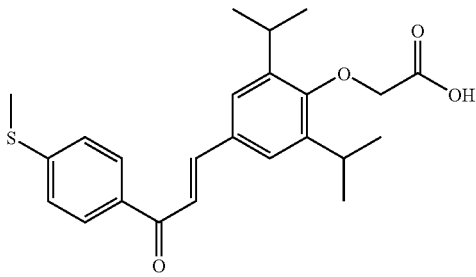

This compound was synthesized from 1-[4-methylthiophenyl]-3-[3,5-diisopropyl-4-tertiobutyloxycarbonylmethyloxyphenyl]prop-2-en-1-one (compound 73) according to general method 5 described earlier.

Purification was made by crystallization (heptane/dichloromethane).

$^1$H NMR DMSO-$d_6$ δppm: 1.30 (d, 12H, J=6.90 Hz), 2.56 (s, 3H), 3.32 (m, 2H), 4.50 (s, 2H), 7.30 (d, 2H, J=8.28 Hz), 7.41 (s, 2H), 7.45 (d, 1H, J=14.46 Hz), 7.78 (d, 1H, J=14.46 Hz), 7.98 (d, 2H, J=8.28 Hz).

MS (ES-MS): 411.1 (M−1).

Compound 75

1-[4-octadecyloxyphenyl]-3-[3,5-dimethyl-4-tertiobutyloxycarbonyldimethylmethyloxyphenyl]prop-2-en-1-one

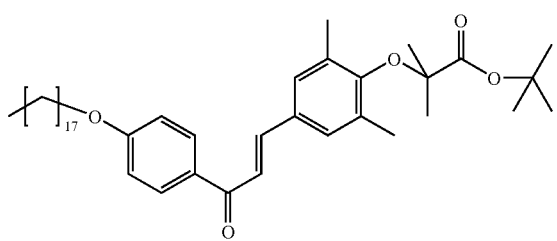

This compound was synthesized from 1-[4-octadecyloxyphenyl]-3-[3,5-dimethyl-4-hydroxyphenyl]prop-2-en-1-one (intermediate compound 25) and tertbutyl bromoisobutyrate according to general method 4 described earlier.

Purification was made by chromatography on silica gel (elution: cyclohexane/ethyl acetate 9:1).

Compound 76

1-[4-octadecyloxyphenyl]-3-[3,5-dimethyl-4-carboxydimethylmethyloxyphenyl]prop-2-en-1-one

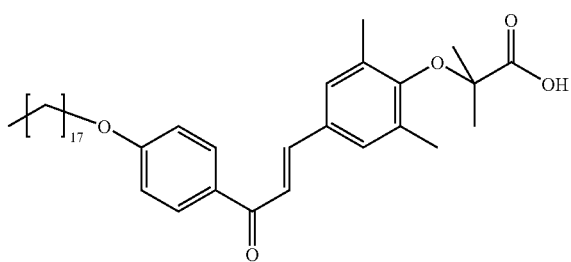

This compound was synthesized from 1-[4-octadecyloxyphenyl]-3-[3,5-dimethyl-4-tertiobutyloxycarbonyldimethylmethyloxyphenyl]prop-2-en-1-one (compound 75) according to general method 5 described earlier.

Purification was made by chromatography on silica gel (elution: dichloromethane/methanol 98/2) and crystallization (heptane/dichloromethane).

$^1$H NMR DMSO-$d_6$ δppm: 0.88 (m, 3H), 1.26 (m, 30H), 1.55 (s, 6H), 1.81 (m; 2H), 2.29 (s, 6H), 4.03 (m, 2H), 6.97 (d, 2H, J=9.01 Hz), 7.30 (s, 2H), 7.47 (d, 1H, J=15.60 Hz), 7.72 (d, 1H, J=15.60 Hz), 8.04 (d, 2H, J=9.01 Hz).

MS (ES-MS): 606.9 (M+1).

Compound 77

1-[4-dodecyloxyphenyl]-3-[3,5-dimethyl-4-tertiobutyloxycarbonyldimethylmethyloxyphenyl]prop-2-en-1-one

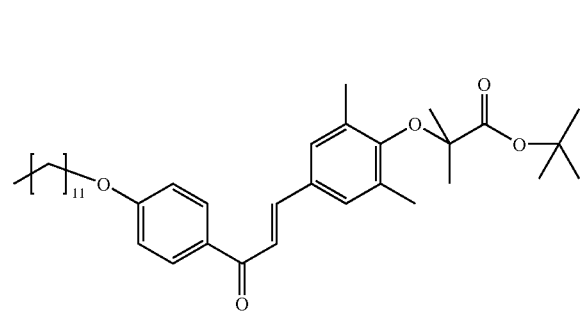

This compound was synthesized from 1-[4-dodecyloxyphenyl]-3-[3,5-dimethyl-4-hydroxyphenyl]prop-2-en-1-one (intermediate compound 26) and tertbutyl bromoisobutyrate according to general method 4 described earlier.

Purification was made by chromatography on silica gel (elution: cyclohexane/ethyl acetate 9:1).

Compound 78

1-[4-dodecyloxyphenyl]-3-[3,5-dimethyl-4-carboxydimethylmethyloxyphenyl]prop-2-en-1-one

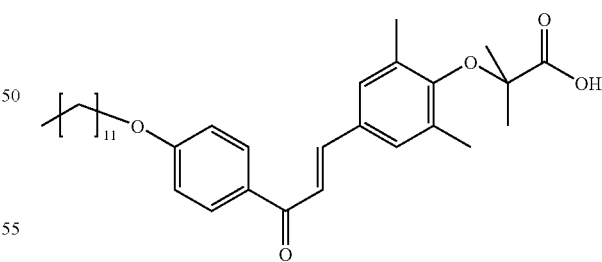

This compound was synthesized from 1-[4-dodecyloxyphenyl]-3-[3,5-dimethyl-4-tertiobutyloxycarbonyldimethylmethyloxyphenyl]prop-2-en-1-one (compound 77) according to general method 5 described earlier.

Purification was made by chromatography on silica gel (elution: dichloromethane/methanol 98/2) and crystallization (heptane/dichloromethane).

$^1$H NMR DMSO-$d_6$ δppm: 0.84 (m, 3H), 1.23 (m, 18H), 1.39 (s, 6H), 1.73 (m, 2H), 2.22 (s, 6H), 4.06 (m, 2H), 7.05 (d, 2H, J=8.79 Hz), 7.56 (s, 2H), 7.59 (d, 1H, J=15.35 Hz), 7.83 (d, 1H, J=15.35 Hz), 8.14 (d, 2H, J=8.79 Hz), 12.94 (s, 1H).
MS (ES-MS): 522.7 (M+1).

Compound 79

1-[4-methyloxyphenyl]-3-[3,5-dimethyl-4-tertiobutyloxycarbonyldimethylmethyloxyphenyl]prop-2-en-1-one

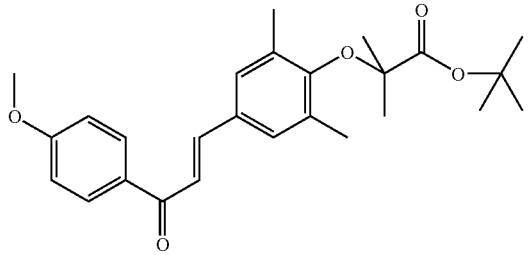

This compound was synthesized from 1-[4-methoxyphenyl]-3-[3,5-dimethyl-4-hydroxyphenyl]prop-2-en-1-one (intermediate compound 27) and tertbutyl bromoisobutyrate according to general method 4 described earlier.

Purification was made by chromatography on silica gel (elution: cyclohexane/ethyl acetate 9:1).

Compound 80

1-[4-methyloxyphenyl]-3-[3,5-dimethyl-4-carboxydimethylmethyloxyphenyl]prop-2-en-1-one

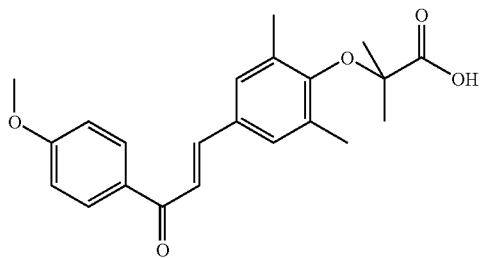

This compound was synthesized from 1-[4-methyloxyphenyl]-3-[3,5-dimethyl-4-tertiobutyloxycarbonyldimethylmethyloxyphenyl]prop-2-en-1-one (compound 79) according to general method 5 described earlier.

Purification was made by chromatography on silica gel (elution: dichloromethane/methanol 98:2).

$^1$H NMR DMSO-$d_6$ δppm: 1.39 (s, 6H), 2.22 (s, 6H), 3.87 (s, 3H), 7.09 (d, 2H, J=8.52 Hz), 7.56-7.62 (m, 3H), 7.83 (d, 1H, J=15.96 Hz), 8.17 (d, 2H, J=8.52 Hz), 12.95 (s, 1H).
MS (ES-MS): 367.2(M−1).

Compound 81

1-[2-hexyloxyphenyl]-3-[3,5-dimethyl-4-tertiobutyloxycarbonyldimethylmethyloxyphenyl]prop-2-en-1-one

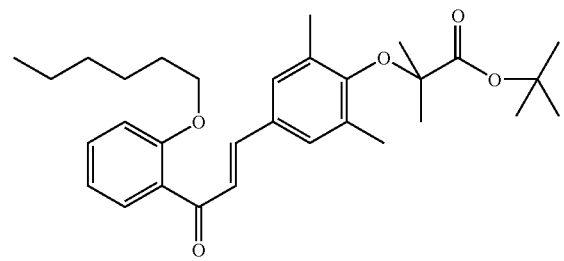

This compound was synthesized from 1-[2-hexyloxyphenyl]-3-[3,5-dimethyl-4-hydroxyphenyl]prop-2-en-1-one (intermediate compound 28) and tertbutyl bromoisobutyrate according to general method 4 described earlier.

Purification was made by chromatography on silica gel (elution: cyclohexane/ethyl acetate 95:5).

Compound 82

1-[2-hexyloxyphenyl]-3-[3,5-dimethyl-4-carboxydimethylmethyloxyphenyl]prop-2-en-1-one

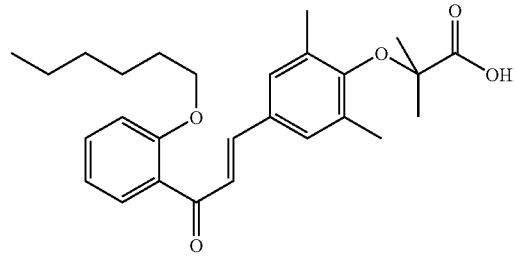

This compound was synthesized from 1-[2-hexyloxyphenyl]-3-[3,5-dimethyl-4-tertiobutyloxycarbonyldimethylmethyloxyphenyl]prop-2-en-1-one (compound 81) according to general method 5 described earlier.

Purification was made by chromatography on silica gel (elution: dichloromethane/methanol 98/2) and crystallization (heptane/dichloromethane).

$^1$H NMR DMSO-$d_6$ δppm: 0.80 (t, 3H, J=7.14 Hz), 1.23 (m, 4H), 1.40 (m, 2H), 1.55 (s, 6H), 1.78 (m, 2H), 2.27 (s, 6H), 4.06 (t, 2H, J=6.45 Hz), 6.98 (d, 1H, J=8.68 Hz), 7.02 (dd, 1H, J=7.48 Hz), 7.26 (s, 2H), 7.38 (d, 1H, J=15.84 Hz), 7.48 (dd, 1H, J=8.68 Hz. J=1.71 Hz), 7.60 (d, 1H, J=15.84 Hz), 7.65 (dd, 1H, J=7.48, J=1.71 Hz).
MS (ES-MS): 439.3 (M+1).

Compound 83

1-[4-hexylthiophenyl]-3-[3,5-dimethyl-4-tertiobutyloxycarbonyldimethylmethyloxyphenyl]prop-2-en-1-one

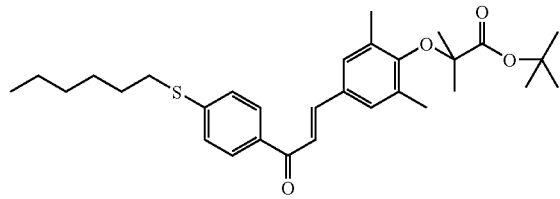

This compound was synthesized from 1-[4-hexylthiophenyl]-3-[3,5-dimethyl-4-hydroxyphenyl]prop-2-en-1-one (intermediate compound 29) and tertbutyl bromoisobutyrate according to general method 4 described earlier.

Purification was made by chromatography on silica gel (elution: cyclohexane/ethyl acetate 9:1).

Compound 84

1-[4-hexylthiophenyl]-3-[3,5-dimethyl-4-carboxydimethylmethyloxyphenyl]prop-2-en-1-one

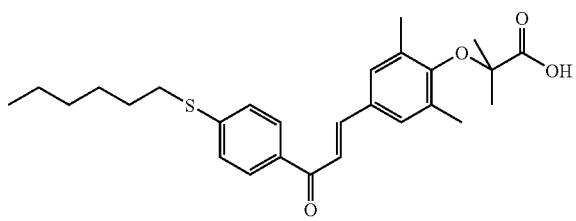

This compound was synthesized from 1-[4-hexylthiophenyl]-3-[3,5-dimethyl-4-tertiobutyloxycarbonyldimethylmethyloxyphenyl]prop-2-en-1-one (compound 77) according to general method 5 described earlier.

Purification was made by chromatography on silica gel (elution: dichloromethane/methanol 98:2).

$^1$H NMR DMSO-$d_6$ δppm: 0.84 (m, 3H), 1.23 (m, 6H), 1.39 (s, 6H), 1.72 (m, 2H), 2.22 (s, 6H), 4.06 (t, 2H, J=6.50 Hz), 7.05 (d, 2H, J=8.79 Hz), 7.56 (s, 2H), 7.59 (d, 1H, J=15.93 Hz), 7.83 (d, 1H, J=15.93 Hz), 8.14 (d, 2H, J=8.79 Hz), 12.96 (s, 1H).

Compound 85

1-[4-tertiobutyloxycarbonyldimethylmethyloxyphenyl]-3-[3,5-ditertiobutyl-4-hydroxyphenyl]prop-2-en-1-one

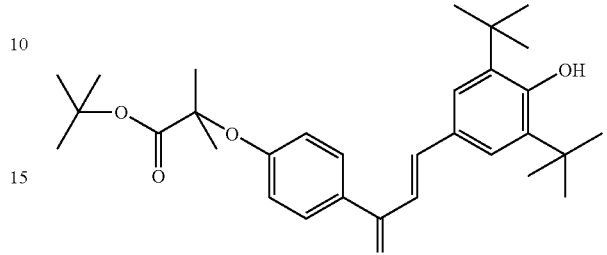

This compound was synthesized from 1-[4-hydroxyphenyl]-3-[3,5-ditertiobutyl-4-hydroxyphenyl]prop-2-en-1-one (intermediate compound 30) and tert-butyl bromoisobutyrate according to general method 4 described earlier.

Purification was made by chromatography on silica gel (elution: cyclohexane/ethyl acetate 9:1).

Compound 86

1-[4-carboxydimethylmethyloxyphenyl]-3-[3,5-ditertiobutyl-4-hydroxyphenyl]prop-2-en-1-one

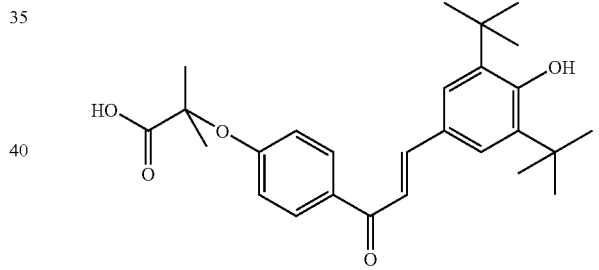

This compound was synthesized from 1-[4-tertiobutyloxycarbonyldimethylmethyloxyphenyl]-3-[3,5-ditertiobutyl-4-hydroxyphenyl]prop-2-en-1-one (compound 85) according to general method 5 described earlier.

Purification was made by chromatography on silica gel (elution: dichloromethane/methanol 98:2).

$^1$H NMR DMSO-$d_6$ δppm: 1.43 (s, 18H), 1.68 (s, 6H), 6.91 (d, 2H, J=8.47 Hz), 7.54 (s, 2H), 7.53-7.67 (m, 2H), 8.11 (d, 2H, J=8.47 Hz), 13.26 (s, 1H).

MS (ES-MS): 437.2 (M−1).

Example 2

Evaluation of the Antioxidant Properties of the Inventive Compounds ZM

1. Protection against LDL Oxidation by Copper:

The inventive compounds which were tested are the compounds whose preparation is described in the above examples.

LDL oxidation is an important alteration and plays a predominant role in the establishment and development of atherosclerosis (Jurgens G et al., 1987). The following protocol allows to demonstrate the antioxidant properties of compounds. Unless otherwise indicated, the reagents were from Sigma (St Quentin, France). LDL were prepared according to the method described by (Havel R J et al., 1955). The solutions of test compounds were prepared at $10^{-2}$ M concentration in bicarbonate buffer (pH 9) and diluted in PBS to obtain final concentrations ranging from 0.1 to 100 µM for a total ethanol concentration of % (V/V). Prior to oxidation, EDTA was removed from the LDL preparation by dialysis. Oxidation then took place at 30° C. by addition of 100 µl of 16.6 µM CuSO$_4$ solution to 160 µL of LDL (125 µg protein/ml) and 20 µl of a test compound solution. The formation of dienes, the species under observation, was followed by measuring optical density at 234 nm in the samples treated with the compounds but in the presence or absence of copper. Optical density at 234 nm was measured every 10 minutes for 8 hours in a thermostated spectrophotometer (Tecan Ultra 380). The compounds were considered to have antioxidant activity when they induced a longer lag phase and reduced the rate of oxidation and the amount of dienes formed in comparison with the control sample. The inventors demonstrate that the inventive compounds have at least one of the above-described antioxidant properties indicating that the inventive compounds have intrinsic antioxidant activity.

Typical results are given in FIGS. 1-1 to 1-14 illustrating the antioxidant properties of inventive compounds 2, 3, 4, 5, 6, 7, 9, 10, 12, 14, 17, 18, 19, 21, 22, 25, 29, 31, 33, 35, 37, 38 and 41.

2. Evaluation of Protection Conferred by the Inventive Compounds against Lipid Peroxidation:

The inventive compounds tested are the compounds whose preparation is described in the above examples. LDL oxidation was determined by the TBARS method. According to the same principle described earlier, LDL were oxidized with CuSO$_4$ and lipid peroxidation was determined as follows: TBARS were measured by a spectrophotometric method, lipid hydroperoxidation was measured using lipid-dependent peroxidation of iodide to iodine. The results are expressed as nmol of malondialdehyde (MDA) or as nmol of hydroperoxide/mg of protein.

The previous results obtained by measuring inhibition of conjugated diene formation were confirmed by the experiments measuring LDL lipid peroxidation. The inventive compounds also effectively protected LDL against lipid peroxidation induced by copper (oxidizing agent).

Example 3

Measurement of the Antioxidant Properties of the Inventive Compounds on Cell Cultures The antioxidant properties of the compounds were also evaluated by means of a fluorescent tag the oxidation of which is followed by appearance of a fluorescence signal. The reduction in the intensity of the emitted fluorescence signal was determined in cells treated with the compounds in the following manner.

Prior to stress the cells with an oxidative agent such as AAPH (CAS number 2997-92-4), cells are incubated with compounds of interest at 25 µM for 24 h. Then the culture medium is discarded and cells are rinsed two times with PBS. Cells are then incubated 30 min at 37° C. with a cell-permeant indicator for reactive oxygen species that is nonfluorescent until the acetate groups are removed by intracellular esterases and oxidation occurs within the cell 5-(and-6)-carboxy-2',7'-dichlorodihydrofluorescein diacetate (carboxy-H$_2$DCFDA). The probes are prepared in PBS and incubated at the final concentration of 25 µM. After the incubation with the probe, cells are rinsed and incubated another 30 min with the oxidative solution containing AAPH at 750 µM in culture medium without phenol red and serum.

The fluorescence is then measured with a fluorimeter with the following wavelength, Em=488 and Ex=535.

The results are compared to the untreated cells: if a compound possesses oxidative protection properties, the fluorescence drops in the treated conditions. Two different cell types have been tested with the inventive compounds. Human normal primary fibroblasts and HaCat cells which are a human keratinocyte cell line. Typical results are given in FIGS. 7.1 and 7.2 illustrating the antioxidant properties of inventive compounds 29, 33, 41, 70, 62, 58, 54.

In both cell types, Trolox (TLx) did protect the cells from free radicals. Fluorescence intensity was lower in the cells incubated with the inventive compounds than in untreated cells. A 60% and 46% oxidation-reduction is observed in fibroblasts and keratinocytes respectively. Treated cells with inventive compounds are also protected from free radicals and then possess antioxidant properties. Indeed, for example incubation with compound 70 reduced the induced MPH oxidation to 53% and 47% in fibroblasts and keratinocytes respectively.

These findings indicate that the inventive compounds promote inhibition of the production of oxidative species in cells subjected to oxidative stress. The previously described antioxidant properties are also effective at inducing antiradical protection in cultured cells.

Example 4

Evaluation of PPAR Activation in vitro by the Inventive Compounds

The inventive compounds having a carboxylic acid function, which were tested, are the compounds whose preparation is described in the above examples. Nuclear receptors of the PPAR subfamily which are activated by two major pharmaceutical classes—fibrates and glitazones, widely used in the clinic for the treatment of dyslipidemias and diabetes—play an important role in lipid and glucose homeostasis. The following experimental data show that the inventive compounds activate PPARα, PPARγ and PPARδ in vitro.

PPAR activation was tested in vitro in RK13 or COS-7 fibroblast cell lines by measuring the transcriptional activity of chimeras composed of the DNA binding domain of the yeast Gal4 transcription factor and the ligand binding domain of the different PPARs. These latter results were then confirmed in cell lines according to the following protocols.

Culture protocols: RK13 were from ECACC (Porton Down, UK) and were grown in DMEM medium supplemented with 10% (V/V) fetal calf serum, 100 U/ml penicillin (Gibco, Paisley, UK) and 2 mM L-glutamine (Gibco, Paisley, UK). COS-7 cells were from ATCC and were grown in DMEM medium supplemented with 10% (V/V) fetal calf serum, 1% penicillin/streptomycine (Biochrom, AG), 1% of amino acids (Gibco) and 1% sodium pyruvate (Gibco).

The culture medium was changed every two days. Cells were kept at 37° C. in a humidified 95% air/5% CO$_2$ atmosphere.

Description of plasmids used for transfection: The plasmids Gal4(RE)_TkpGL3, pGal4-hPPARα, pGal4-hPPARγ, pGal4-hPPARδ and pGal4-φ have been described in the literature (Raspe E et al., 1999). The pGal4-hPPARα, pGal4-hPPARγ and pGal4-hPPARδ constructs were obtained by cloning into the pGal4-φ vector PCR-amplified DNA fragments corresponding to the DEF domains of the human PPARs nuclear receptors.

Transfection of RK13: RK13 cells were seeded in 24-well culture dishes at $5\times10^4$ cells/well and transfected for 2 hours with the reporter plasmid Gal4(RE)_TkpGL3 (50 ng/well), the expression vectors pGal4-φ, pGal4-hPPARα, pGal4-hPPARγ and pGal-hPPARδ (100 ng/well) and the transfection efficiency control vector pRL-CMV (1 ng/well) according to the previously described protocol (Raspe E, Madsen L, Lefebvre A M, Leitersdorf I, Gelman L, Peinado-Onsurbe J, Dallongeville J, Fruchart J C, Berge R and Staels B, 1999), then incubated for 36 hours with the test compounds. RK13 cells were incubated with the different compounds at concentrations of 10, 30 and 100 μM or 1, 10 and 100 μM for 24 hours. At the end of the experiment, the cells were lysed (Gibco, Paisley, UK) and luciferase activity was determined with a Dual-Luciferase™ Reporter Assay System kit (Promega, Madison, Wis., USA) according to the supplier's instructions. The protein content of the cell extracts was then measured with the Bio-Rad Protein Assay (Bio-Rad, Munich, Germany) as directed by the supplier.

Transfection of COS7: Cells in suspension are transfected, in the presence of 10% (V/V) fetal calf serum, with 150 ng of DNA per well with a pGal4-PPAR/Gal4(RE)_TkpGL3 ratio of 1/10. Cells are then seeded in 96 well plates ($4\times10^4$ cells/well) and incubated for 24 hours at 37° C. Activation with compounds is performed on 24 hours at 37° C. in culture medium without serum. At the end of the activation period, cells are lysed and luciferase activity is determined, using the Steady Glow Luciferase Kit (Promega), according to the supplier's instructions.

The inventors demonstrate an increase in luciferase activity in cells treated with the inventive compounds and transfected with the pGal4-hPPAR and pGal(RE)_TkpGal3 plasmids. Said induction of luciferase activity indicates that the inventive compounds are activators of PPAR. The results are given in FIGS. 2-1 to 2-19 which illustrate the PPAR activator properties of inventive compounds.

Example 5

Evaluation of the Anti-Inflammatory Properties of the Inventive Compounds

An inflammatory response is observed in many neurological disorders, including multiple sclerosis, Alzheimer's and Parkinson's diseases, cerebral ischemia and head trauma. Inflammation is also an important factor in neurodegeneration. In stroke, one of the first reaction of glial cells is to release cytokines and free radicals. This release of cytokines and free radicals results in an inflammatory response in the brain which can lead to neuronal death (Rothwell N.J., 1997).

TNF-α (tumor necrosis factor alpha) and IL-6 (interleukin-6) are two important markers of the inflammatory response to stress. The anti-inflammatory property of the compound 29 was evaluated as follows:

Human THP-1 monocytes were differentiated in macrophages by a 72 h incubation with 30 ng/ml of PMA (Phorbol Myristate Acetate). Differentiated macrophages were then treated with the inventive compound 29 at different concentrations during 24 h in culture medium without serum. Stimulation with LPS 1 μg/ml was finally performed during 6 hours (LPS bacterial endotoxin (*Escherichia coli* 0111 :B4) (Sigma, France) was reconstituted in distilled water).

TNF-α and IL-6 secretion were quantified in the culture medium of LPS-stimulated cells with TNF-α and IL6 ELISA kits (Immunotech, France).

The treatment of LPS-stimulated macrophages with the compound 29 induced the decrease of TNF-α and IL6 secretion. These results show that the inventive compounds have anti-inflammatory properties. The results are given in FIGS. 8-1 and 8-2.

Example 6

Evaluation of the Neuroprotective Effects of the Inventive Compounds in a Cerebral Ischemia-Reperfusion Model Prophylactic Model:
1. Treatments of Animals
1.1 Animals and Administration of the Compounds C57 black/6 mice (wild-type) were used for this experiment. Animals were maintained on a 12 hour light-dark cycle at a temperature of 20° C.±3° C. Water and food were available ad libitum. Food intake and weight gain were recorded all along the experiment. The inventive compounds (200 mg/kg/day) or the vehicle (0.5% carboxycellulose (CMC)) were administered to the animals by gavage, for 14 days before ischemia induction in the middle cerebral artery.

1.2 Ischemia Induction-Reperfusion by Intraluminal Occlusion of the Middle Cerebral Artery Animals were anesthetized by intraperitoneal injection of 300 mg/kg chloral hydrate. A rectal probe was inserted and body temperature was maintained at 37° C.±0.5° C. Blood pressure was monitored throughout the experiment. Under a surgical microscope, the right carotid artery was exposed by a median incision in the neck. The pterygopalatine artery was ligated at its origin and an arteriotomy was fashioned in the external carotid artery so as to insert a nylon monofilament, which was gently advanced to the common carotid artery and then into the internal carotid artery so as to occlude the origin of the middle cerebral artery. The filament was withdrawn one hour later to allow reperfusion.

2. Measurement of Brain Infarct Volume

Twenty-four hours after reperfusion, animals previously treated or not with the compounds were euthanized by pentobarbital overdose. Brains were rapidly frozen and sliced. Sections were stained with cresyl violet. Unstained zones of the brain sections were considered to be damaged by the infarct. Areas were measured and the volume of the infarct and the two hemispheres was calculated by the following formula: (corrected infarct volume=infarct volume−(volume of right hemisphere−volume of left hemisphere)) to compensate for cerebral oedema. Analysis of the brain sections from treated animals revealed a marked decrease in infarct volume as compared with untreated animals. When the inventive compounds were administered to the animals before the ischemia (prophylactic effect), they were capable of inducing neuroprotection.

An example of the results is given in FIG. 3-1 which illustrates the prophylactic neuroprotective properties of inventive compounds 15 and 42.

Curative or Acute Phase Treatment Model

1. Ischemia Induction/Reperfusion by Intraluminal Occlusion of the Middle Cerebral Artery Animals such as those described previously were used for this experiment. Animals were anesthetized by intraperitoneal injection of 300 mg/kg chloral hydrate. A rectal probe was inserted and body temperature was maintained at 37° C.±0.5° C. Blood pressure was monitored throughout the experiment. Under a surgical microscope, the right carotid artery was exposed by a median incision in the neck. The pterygopalatine artery was ligated at its origin and an arteriotomy was fashioned in the external carotid artery so as to insert a nylon monofilament, which was gently advanced to the common carotid artery and then into the internal carotid artery so as to occlude the origin of the middle cerebral artery. The filament was withdrawn one hour later to allow reperfusion.

2. Treatment of Animals

Animals first subjected to ischemia-reperfusion were treated with the inventive compounds by the oral or systemic route one or more times after reperfusion.

3. Measurement of Brain Infarct Volume

Seventy-two hours after reperfusion, animals previously treated or not with the compounds were euthanized by pentobarbital overdose. Brains were rapidly frozen and sliced. Sections were stained with cresyl violet. Unstained zones of the brain sections were considered to be damaged by the infarct. Areas were measured and the volume of the infarct and the two hemispheres was calculated by the following formula: (corrected infarct volume=infarct volume−(volume of right hemisphere−volume of left hemisphere)) to compensate for cerebral oedema. In the case of curative treatment (treatment of the acute phase), animals treated with the inventive compounds had fewer brain lesions than untreated animals. In fact, the infarct volume was smaller when the inventive compounds were administered one or more times after ischemia-reperfusion.

An example of the results is given in FIG. 3-2 which illustrates the acute neuroprotective properties of inventive compounds 15 and 42.

The use of the inventive compounds in different experimental models shows that said novel compounds have intrinsic antioxidant activity, are capable of delaying and reducing the effects of an oxidative stress. In addition, the inventive compounds also exhibit anti-inflammatory activity and are capable of activating the PPAR nuclear receptors. Finally, use of the inventive compounds, containing an ester function or a carboxylic acid function, in an animal ischemia-reperfusion model revealed the beneficial neuroprotective effect of both preventive and curative treatment.

Example 7

Evaluation of the Effects on Lipid Metabolism in vivo

The inventive compounds tested are the compounds whose preparation is described in the above examples. Fibrates, widely used in the clinic for the treatment of dyslipidemias underlying the development of atherosclerosis, one of the leading causes of morbidity and mortality in the industrialized world, are potent activators of the PPARα nuclear receptor, which regulates the expression of genes involved in lipid transport (apolipoproteins such as Apo AI, Apo AII and Apo CIII, membrane transporters such as FAT) and catabolism (ACO, CPT-I and CPT-II). In humans and rodents, treatment with PPARα activators therefore leads to a decrease in circulating levels of cholesterol and triglycerides.

The following protocols were designed to demonstrate a decrease in circulating triglycerides and cholesterol levels as well as the interest of the inventive compounds in a context of preventing and/or treating cardiovascular diseases.

Treatment of animals: hApoE2 knock-in transgenic mice were kept on a 12-hour light/dark cycle at a constant temperature of 20±3° C. After a 1 week acclimation, mice were separated in groups of 6 animals selected such that the distribution of their body weight and plasmatic lipid levels determined before the experiment were uniform. The test compounds were suspended in carboxymethylcellulose and administered by intragastric gavage at the indicated doses, once a day for 7 or 8 days. Animals had access to food and water ad libitum. At the end of the experiment the animals were weighed and sacrificed under anesthesia. Blood was collected on EDTA. Plasma was prepared by centrifugation at 3000 rpm for 20 minutes. Organs were harvested, frozen in liquid nitrogen and stored at −80° C. for subsequent analysis.

Measurement of serum lipids: Serum lipid concentrations (total cholesterol and triglycerides) were determined by a colorimetric assay (Boehringer, Mannheim, Germany) according to the supplier's instructions.

The results are exemplified in FIGS. 4-1 to 4-22 which illustrate the activity of inventive compounds 7, 17, 29, 33, 41, 82, 70, 62, 58, 54 and 50 on triglyceride and cholesterol metabolism.

Example 8

Evaluation of the Antidiabetic Effect

Genetically modified C57BLKS-m Lepr$^{db}$ mice were used to asses antidiabetic effect of the inventive compounds. Mice were randomized according to their plasma lipid, glucose and insulin contents. Treatments were administered once daily by gavage (10 ml/kg) for the duration of the treatment. For oral administrations, the drugs were suspended in CMC 1% or CMC 1%+Tween 80 0.1%. The plasma glucose was measured using a kit reagent from Biomerieux (France). The plasma insulin was measured using a solid phase two-site enzyme immunoassay from Crystal Chem Inc. (USA). The results are exemplified in FIGS. 5-1 to 5-4 which illustrate the activity of inventive compounds 29 and 62 on glucose and insulin.

Example 9

In vivo Evaluation of the PPARδ Properties

The P//PARα knock-out mouse model was used to characterize in vivo PPARδ activation. Animals were treated for 3 days at the dose of 150 mg/kg/day. Total RNA was isolated from heart and skeletal muscle (quadriceps). Messenger RNAs were quantified by quantitative RT-PCR: total RNA was extracted from fragments of skeletal muscle or heart, using the RNeasy® Fibrous Tissue kit (Qiagen), according to the manufacturer's instructions. Reverse transcription was performed on 1 µg of total RNA (quantified using the Ribogreen RNA quantification kit (Molecular Probes)) by action of 1 µl of MMLV-RT enzyme (Sigma) during 1 hour at 37° C. in a total volume of 20 µl. The reaction conditions were 1× buffer (Sigma), 1.5 mM DTT, 0.18 mM dNTPs (Promega), 200 ng pdN6 (Amersham), 30 U RNase inhibitor (Sigma). Quantitative PCR was then carried out using the MyiQ Single-Color Real-Time PCR Detection System (Biorad). Briefly PCR reactions were performed in 96 well plates on 5 µl of diluted reverse transcription mix using the iQ SYBR Green Supermix kit. The reaction conditions were: 25 µl of volume reaction, 3 mM of MgCl2, and 0.5 µl of each reverse and forward primer solutions (10 pMol), Tm of 55° C. The primers pairs are specific for each target genes. For PDK4:

forward primer: 5'-TACTCCACTGCTCCMCACCTG-3' (SEQ ID NO:1) and reverse primer: 5'-GTTCTTCGGTTC-CCTGCTTG-3' (SEQ ID NO:2); for UCP2: forward primer: 5'-GTCGGAGATACCAGAGCACTGTCG-3' (SEQ ID NO:3) and reverse primer: 5'-CACATCAACAGGGGAG-GCGA-3' (SEQ ID NO:4); for UCP3: forward primer: 5'-GCACCGCCAGATGAGTTTTG-3' (SEQ ID NO:5) and reverse primer: 5'-GACGCTGGAGTGGTCCGCTC-3' (SEQ ID NO:6).

The quantity of fluorescence emitted is directly proportional to the quantity of complementary DNA present at the start of the reaction and amplified during the PCR. The relative levels of expression were determined using the standard curve for each transcript. The results were then normalized in regard to the signals obtained with the 18 S control (forward primer: 5'-CGGACACGGACAGGATTGACAG-3' (SEQ ID NO:7) and reverse primer 5'-AATCTCGGGTGGCT-GAACGC-3' (SEQ ID NO:8)). The induction factor, i.e. the ratio between the relative signal induced by the compound according to the invention and the average of the values relating to the control group, was then calculated for each sample. The higher this factor, the more the compound promotes target gene expression. The final result is depicted as the average of the induction values in each experimental group.

Results are shown in FIGS. 6-1 to 6-3: induction, after treatment, of UCP2 expression in the skeletal muscle and UCP3 and PDK4 expression in the heart demonstrates in vivo the activation of PPARδ isoform by compound 41.

Example 10

Pharmaceutical Compositions

The following examples present pharmaceutical compositions comprising compounds of the invention in association with other active ingredients. The same could apply to pharmaceutical comprising at least one compound of formula (I), without any other active ingredient. They are prepared by any well known method.

Example A

| Ingredient | Quantity (mg) |
| --- | --- |
| Simvastatin | 10 |
| 1-[4-methylthiophenyl]-3-[3,5-dimethyl-4-carboxydimethylmethyloxyphenyl]prop-2-en-1-one | 10 |
| Tripalmitin | 150 |
| Medium Chain Mono & Diglycerides Caprylic/Capric Glycerides | 100 |
| D-alpha-tocopheryl polyethylene glycol 1000 succinate | 750 |
| Propylene Glycol Monolaurate | 15.25 |

Example B

| Ingredient | Quantity (mg) |
| --- | --- |
| Ezetimibe | 1 |
| 1-[4-trifluoromethyloxyphenyl]-3-[3,5-dimethyl-4-carboxydimethylmethyloxyphenyl]prop-2-en-1-one | 15 |
| Caprylic/Capric Trygliceride | 150 |

-continued

| Ingredient | Quantity (mg) |
| --- | --- |
| D-alpha-tocopheryl polyethylene glycol 1000 succinate | 450 |
| Polyethylene glycol 660-12 hydroxystearate | 150 |

Example C

| Ingredient | Quantity (mg) |
| --- | --- |
| Rosiglitazone, maleate | 3 |
| 1-[4-trifluoromethylphenyl]-3-[3,5-dimethyl-4-carboxydimethylmethyloxyphenyl]prop-2-en-1-one | 40 |
| Caprylic/Capric Trygliceride | 150 |
| D-alpha-tocopheryl polyethylene glycol 1000 succinate | 450 |
| Polyethylene glycol 660-12 hydroxystearate | 150 |

Example D

| Ingredient | Quantity (mg) |
| --- | --- |
| Simvastatine | 10 |
| 1-[4-methylthiophenyl]-3-[3,5-dimethyl-4-carboxydimethylmethyloxyphenyl]prop-2-en-1-one | 0.5 |
| Caprylic/Capric Trygliceride | 150 |
| D-alpha-tocopheryl polyethylene glycol 1000 succinate | 450 |
| Polyethylene glycol 660-12 hydroxystearate | 150 |

Example E

| Ingredient | Quantity (mg) |
| --- | --- |
| Irbesartan | 50 |
| 1-[4-bromophenyl]-3-[3,5-dimethyl-4-carboxydimethylmethyloxyphenyl]prop-2-en-1-one | 0.3 |
| Caprylic/Capric Trygliceride | 150 |
| D-alpha-tocopheryl polyethylene glycol 1000 succinate | 450 |
| Polyethylene glycol 660-12 hydroxystearate | 150 |

Example F

| Ingredient | Quantity (mg) |
| --- | --- |
| Fenofibrate | 50 |
| 1-[4-trifluoromethylthiophenyl]-3-[3,5-dimethyl-4-carboxydimethylmethyloxyphenyl]prop-2-en-1-one | 10 |
| Caprylic/Capric Trygliceride | 150 |
| D-alpha-tocopheryl polyethylene glycol 1000 succinate | 450 |
| Polyethylene glycol 660-12 hydroxystearate | 150 |

BIBLIOGRAPHY

Braissant O and Wahli W, *Differential expression of peroxisome proliferator-activated receptor-alpha, -beta, and -gamma during rat embryonic development*, Endocrinology, 1998, 139 (6), 2748-54

Desvergne B and Wahli W, *Peroxisome proliferator-activated receptors: nuclear control of metabolism*, Endocr Rev, 1999, 20 (5), 649-88

Gilgun-Sherki Y, et al., *Oxidative stress induced-neurodegenerative diseases: the need for antioxidants that penetrate the blood brain barrier*, Neuropharmacology, 2001, 40 (8), 959-75

Guerre-Millo M, et al., *Peroxisome proliferator-activated receptor alpha activators improve insulin sensitivity and reduce adiposity*, J Biol Chem, 2000, 275 (22), 16638-42

Havel R J, et al., *The distribution and chemical composition of ultracentrifugally separated lipoproteins in human serum*, J Clin Invest, 1955, 34 (9), 1345-53

Hourton D, et al., *Oxidized low-density lipoprotein and peroxisome-proliferator-activated receptor alpha down-regulate platelet-activating-factor receptor expression in human macrophages*, Biochem J, 2001, 354 (Pt 1), 225-32

Jurgens G, et al., *Modification of human serum low density lipoprotein by oxidation—characterization and pathophysiological implications*, Chem Phys Lipids, 1987, 45 (24), 315-36

Kliewer S A, et al., *Fatty acids and eicosanoids regulate gene expression through direct interactions with peroxisome proliferator-activated receptors alpha and gamma*, Proc Natl Acad Sci USA, 1997, 94 (9), 4318-23

Komuves L G, et al., *Stimulation of PPARalpha promotes epidermal keratinocyte differentiation in vivo*, J Invest Dermatol, 2000, 115 (3), 353-60

Mates J M, et al., *Antioxidant enzymes and human diseases*, Clin Biochem, 1999, 32 (8), 595-603

Ram V J, *Therapeutic role of peroxisome proliferator-activated receptors in obesity, diabetes and inflammation*, Prog Drug Res, 2003, 60 93-132

Raspe E, et al., *Modulation of rat liver apolipoprotein gene expression and serum lipid levels by tetradecylthioacetic acid (TTA) via PPARalpha activation*, J Lipid Res, 1999, 40 (11), 2099-110

Rothwell N J, *Cytokines and acute neurodegeneration*, Mol Psychiatry, 1997, 2 (2), 120-1

Spiegelman B M, *PPAR-gamma: adipogenic regulator and thiazolidinedione receptor*, Diabetes, 1998, 47 (4), 507-14

Staels B and Auwerx J, *Regulation of apo A-I gene expression by fibrates*, Atherosclerosis, 1998, 137 Suppl S19-23

The invention claimed is:

1. A pharmaceutical composition comprising, in a pharmaceutically acceptable support, at least one compound represented by formula (I) in association with another therapeutically active ingredient, wherein said compound is a substituted 1,3-diphenylprop-2-en-1-one derivative represented by formula (I) below:

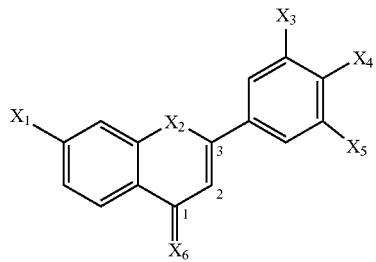

(I)

in which:

X1 represents a halogen or a —R1 group or a group corresponding to the following formula: -G1-R1, X2 represents a hydrogen atom or a thionitroso group or a hydroxy group or an alkylcarbonyloxy or an unsubstituted alkyloxy group or a thiol group or an alkylthio group or an alkylcarbonylthio group, X2 can also represent an oxygen or sulfur atom bound to carbon 3 of the propene chain, so as to form a derivative of the type 2-phenyl-4H-1-benzopyran-4-one or of the type 2-phenyl-4H-1-benzothiopyran-4-one, X3 represents a —R3 group or a group corresponding to the following formula: -G3-R3, X4 represents a halogen or a thionitroso group or a —R4 group or a group corresponding to the following formula: -G4-R4, X5 represents a —R5 group or a group corresponding to the following formula: -G5-R5, X6 is an oxygen atom or a nitrogen atom, in the case where X6 is a nitrogen atom, it carries a hydrogen atom or a hydroxy group or an alkyloxy group, R1, R3, R4, R5, which are the same or different, represent a hydrogen atom or an alkyl group substituted or not by a substituent selected from group 1 or group 2 defined hereinbelow, G1, G3, G4, G5, which are the same or different, represent an oxygen or sulfur atom, with at least one of the groups X1, X3, X4 or X5 corresponding to the formula -G-R, and with at least one of the groups R1, R3, R4 or R5 present in the form of an alkyl group containing at least one substituent of group 1 or 2, said alkyl group being bound directly to the ring or being associated with a group G according to the formula -G-R, the substituents of group 1 are selected in the group consisting of carboxy groups corresponding to the formula: —$COOR_6$ and carbamoyl groups corresponding to the formula: —$CONR_6R_7$, the substituents of group 2 are selected in the group consisting of sulfonic acid (—$SO_3H$) and sulfonamide groups corresponding to the formula: —$SO_2NR_6R_7$, with $R_6$ and $R_7$, which are the same or different, representing a hydrogen atom or an alkyl group possibly substituted by at least one group of the type 1 or 2, the optical and geometric isomers, racemates, tautomers, salts, and mixtures thereof.

2. The composition according to claim 1, wherein compounds are of formula (I) with the exception of compounds represented by formula (I) in which:

X1, X2, X3 and X5 each represent a hydrogen atom, X6 represents an oxygen atom and X4 represents a group corresponding to the formula —O—$CR_8R_9$—$COOR_{10}$, where $R_8$ and R9, which are the same or different, represent a C1 to C2 alkyl group, and $R_{10}$ represents a hydrogen atom or a C1 to C7 alkyl group, and X2, X3 and X5 each represent a hydrogen atom, X1 represents a halogen atom or a —R1 or -G1-R1 group, where R1 represents an unsubstituted C1-C2 alkyl group and G1 represents an oxygen atom, X6 represents an oxygen atom and X4 represents a group corresponding to the formula —O—$CR_{11}R_{12}$—$COOR_{10}$, where $R_{11}$ and $R_{12}$, which are the same or different, represent a hydrogen atom or a C1 to C2 alkyl group, and $R_{10}$ represents a hydrogen atom or a C1 to C7 alkyl group, and X2 represents a hydrogen atom and X1 represents -G1-R1 where G1 represents an oxygen atom and R1 represents —$CH_2COOH$.

3. The pharmaceutical composition according to claim 1, wherein the other therapeutically active ingredient is selected in the group consisting of antidiabetics, insulin, lipid-lowering and/or cholesterol-lowering molecules, anti-hypertension agents and hypotension agents, anti-platelet agents, anti-obesity agents, anti-inflammatories, anti-oxidant agents, agents used in the treatment of cardiac insufficiency, agents used for the treatment of coronary insufficiency, anti-neoplastic agents, anti-asthmatics, corticoids, vasodilatators and/or anti-ischemic agents.

4. The pharmaceutical composition according to claim 3, wherein the other therapeutically active ingredient is selected in the group consisting of:

The PPARγ agonist rosiglitazone
The angiotensin II receptor antagonist irbesartan
The cholesterol absorption inhibitor ezetimibe
The HmGCoA inhibitor "simvastatin"
Fenofibrate.

5. The composition according to claim 1 wherein compound of formula (I) is selected in the group consisting of:

1-[2-hydroxy-4-chlorophenyl]-3-[4-carboxydimethylmethyloxyphenyl]prop-2-en-1-one,
1-[2-hydroxy-4-chlorophenyl]-3-[4-isopropyloxycarbonyl dimethylmethyloxyphenyl]prop-2-en-1-one,
1-[2-hydroxyphenyl]-3-[4-carboxydimethylmethyloxyphenyl]prop-2-en-1-one,
1-[2-hydroxyphenyl]-3-[4-isopropyloxycarbonyldimethylmethyloxyphenyl]prop-2-en-1-one,
1-[2-methylcarbonyloxyphenyl]-3-[4-carboxydimethylmethyloxyphenyl]prop-2-en-1-one,
1-[2-methylcarbonyloxyphenyl]-3-[4-isopropyloxycarbonyldimethyl methyloxyphenyl]prop-2-en-1-one,
1-[2-hydroxyphenyl]-3-[4-carboxydimethylmethyloxyphenyl]-1-hydroxyiminoprop-2-ene,
1-[2-hydroxyphenyl]-3-[4-isopropyloxycarbonyldimethylmethyloxyphenyl]-1-hydroxyiminoprop-2-ene,
1-[2-hydroxy-4-carboxydimethylmethyloxyphenyl]-3-[3,5-ditertbutyl-4-hydroxyphenyl]prop-2-en-1-one,
1-[2-hydroxy-4-isopropyloxycarbonyldimethyl-methyloxyphenyl]-3-[3,5-ditertbutyl-4-hydroxyphenyl]prop-2-en-1-one,
1-[2-hydroxy-4-ethoxycarbonyldimethylmethyloxyphenyl]-3-[3,5-ditertbutyl-4-hydroxyphenyl]prop-2-en-1-one,
1-[2-hydroxyphenyl]-3-[3-carboxydimethylmethyloxy-4-hydroxy-5-tertbutylphenyl]prop-2-en-1-one,
1-[2-hydroxyphenyl]-3-[3-isopropyloxycarbonyldimethylmethyloxy-4-hydroxy-5-tertbutylphenyl]prop-2-en-1-one,
1-[2-hydroxy-4-chlorophenyl]-3-[3-carboxydimethylmethyloxy-4-hydroxy-5-tertbutylphenyl]prop-2-en-1-one,
1-[2-hydroxy-4-chlorophenyl]-3-[3-isopropyloxycarbonyldimethylmethyloxy-4-hydroxy-5-tertbutylphenyl]prop-2-en-1-one,
1-[2-hydroxyphenyl]-3-[3-carboxydimethylmethyl-4-hydroxy-5-tertbutylphenyl]prop-2-en-1-one,
1-[2-hydroxyphenyl]-3-[3-isopropyloxycarbonyldimethylmethyl-4-hydroxy-5-tertbutylphenyl]prop-2-en-1-one,
1-[2-hydroxy-4-chlorophenyl]-3-[3-carboxydimethylmethyl-4-hydroxy-5-tertbutylphenyl]prop-2-en-1-one,
1-[2-hydroxy-4-chlorophenyl]-3-[3-isopropyloxycarbonyldimethylmethyl-4-hydroxy-5-tertbutylphenyl]prop-2-en-1-one,
1-[2-hydroxy-4-chlorophenyl]-3-[3,5-dimethoxy-4-carboxydimethylmethyl oxyphenyl]prop-2-en-1-one,
1-[2-hydroxy-4-chlorophenyl]-3-[3,5-dimethoxy-4-isopropyloxycarbonyldimethylmethyloxyphenyl]prop-2-en-1-one,
1-[2-hydroxyphenyl]-3-[3,5-dimethoxy-4-carboxydimethylmethyloxyphenyl]prop-2-en-1-one,
1-[2-hydroxyphenyl]-3-[3,5-dimethoxy-4-isopropyloxycarbonyldimethylmethyloxyphenyl]prop-2-en-1-one,
1-[2-hydroxy-4-carboxydimethylmethyloxyphenyl]-3-[3,5-dimethoxy-4-hydroxyphenyl]prop-2-en-1-one,
1-[2-hydroxy-4-isopropyloxycarbonyldimethyl-methyloxyphenyl]-3-[3,5-dimethoxy-4-hydroxyphenyl]prop-2-en-1-one,
1-[2-hydroxy-4-chlorophenyl]-3-[3,4-dihydroxy-5-carboxydimethylmethyloxyphenyl]prop-2-en-1-one,
1-[2-hydroxy-4-chlorophenyl]-3-[3,4-dihydroxy-5-isopropyloxycarbonyldimethylmethyloxyphenyl]-2-propen-1-one,
1-[2-hydroxy-4-carboxydimethylmethyloxyphenyl]-3-[3,5-dimethyl-4-hydroxyphenyl]prop-2-en-1-one, 1-[2-hydroxy-4-isopropyloxycarbonyldimethyl-methyloxyphenyl]-3-[3,5-dimethyl-4-hydroxyphenyl]prop-2-en-1-one,
1-[2-hydroxy-4-chlorophenyl]-3-[3,5-dimethyl-4-carboxydimethylmethyl oxyphenyl]prop-2-en-1-one,
1-[2-hydroxy-4-chlorophenyl]-3-[3,5-dimethyl-4-isopropyloxycarbonyldimethylmethyloxyphenyl]prop-2-en-1-one,
1-[2-hydroxyphenyl]-3-[3,5-dimethyl-4-carboxydimethylmethyloxyphenyl]prop-2-en-1-one,
1-[2-hydroxyphenyl]-3-[3,5-dimethyl-4-isopropyloxycarbonyl dimethylmethyloxyphenyl]prop-2-en-1-one,
1-[2-hydroxyphenyl]-3-[3-carboxydimethylmethyloxyphenyl]prop-2-en-1-one,
1-[2-hydroxyphenyl]-3-[3-isopropyloxycarbonyldimethylmethyloxyphenyl]prop-2-en-1-one,
1-[2-hydroxyphenyl]-3-[4-carboxydimethylmethylthiophenyl]prop-2-en-1-one,
1-[2-hydroxyphenyl]-3-[4-isopropyloxycarbonyldimethylmethylthiophenyl]prop-2-en-1-one,
1-[2-mercapto-4-methyloxyphenyl]-3-[4-carboxydimethylmethyloxyphenyl]prop-2-en-1-one,
1-[2-mercapto-4-methyloxyphenyl]-3-[4-isopropyloxycarbonyldimethylmethyloxyphenyl]prop-2-en-1-one,
1-[4-heptylphenyl]-3-[3-methyl-4-carboxydimethymethyloxyphenyl]prop-2-en-1-one,
1-[4-heptylphenyl]-3-[3-methyl-4-isopropyloxycarbonyldimethylmethyloxyphenyl]prop-2-en-1-one,
1-[2-hydroxy-4-carboxydimethylmethyloxyphenyl]-3-[3-hydroxyphenyl]prop-2-en-1-one,
1-[2-hydroxy-4-carboxydimethylmethyloxyphenyl]-3-[4-methylthiophenyl]prop-2-en-1-one,
1-[2,4-dihydroxyphenyl]-3-[4-carboxydimethylmethyloxyphenyl]prop-2-en-1-one,
1-[4-hydroxyphenyl]-3-[4-carboxydimethylmethyloxyphenyl]prop-2-en-1-one,
1-[4-chlorophenyl]-3-[3,5-dimethyl-4-tertbutyloxycarbonyldimethylmethyloxyphenyl]prop-2-en-1-one,
1-[4-chlorophenyl]-3-[3,5-dimethyl-4-isopropyloxycarbonyldimethylmethyloxyphenyl]prop-2-en-1-one,
1-[4-chlorophenyl]-3-[3,5-dimethyl-4-carboxydimethylmethyloxyphenyl]prop-2-en-1-one,
1-[2-hydroxy-4-carboxydimethylmethyloxyphenyl]-3-[4-chlorophenyl]prop-2-en-1-one,
1-[4-chloro-2-hydroxyphenyl]-3-[4-carboxydimethylmethylthiophenyl]prop-2-en-1-one,
1-[4-carboxydimethylmethyloxyphenyl]-3-[3,5-dimethyl-4-hydroxyphenyl]prop-2-en-1-one,
1-[4-methylthiophenyl]-3-[4-carboxydimethylmethyloxyphenyl]prop-2-en-1-one,
1-[4-carboxydimethylmethyloxyphenyl]-3-[4-chlorophenyl]prop-2-en-1-one,
1-[4-carboxydimethylmethylthiophenyl]-3-[4-methylthiophenyl]prop-2-en-1-one,
1-[2-hydroxy-4-bromophenyl]-3-[3,5-dimethyl-4-carboxydimethylmethyloxyphenyl]prop-2-en-1-one,
1-[4-carboxydimethylmethyloxyphenyl]-3-[4-methylthiophenyl]prop-2-en-1-one,
1-[4-methylthiophenyl]-3-[3,5-dimethyl-4-tertbutyloxycarbonyldimethylmethyloxyphenyl]prop-2-en-1-one,
1-[4-methylthiophenyl]-3-[3,5-dimethyl-4-isopropyloxycarbonyldimethylmethyloxyphenyl]prop-2-en-1-one,
1-[4-methylthiophenyl]-3-[3,5-dimethyl-4-carboxydimethylmethyloxyphenyl]prop-2-en-1-one,
1-[2-methoxyphenyl]-3-[3,5-dimethyl-4-tertbutyloxycarbonyldimethylmethyloxyphenyl]prop-2-en-1-one,
1-[2-methoxyphenyl]-3-[3,5-dimethyl-4-carboxydimethylmethyloxyphenyl]prop-2-en-1-one,
1-[4-hexyloxyphenyl]-3-[3,5-dimethyl-4-tertbutyloxycarbonyldimethylmethyloxyphenyl]prop-2-en-1-one,
1-[4-hexyloxyphenyl]-3-[3,5-dimethyl-4-carboxydimethylmethyloxyphenyl]prop-2-en-1-one,
2-(3,5-dimethyl-4-tertbutyloxycarbonyldimethyl-methyloxyphenyl)-7-chloro-4H-1-benzopyran-4-one,
2-(3,5-dimethyl-4-carboxydimethylmethyloxyphenyl)-7-chloro4H-1-benzopyran-4-one,
1-[2-methyloxy-4-chlorophenyl]-3-[3,5-dimethyl-4-tertbutyloxycarbonyldimethylmethyloxyphenyl]prop-2-en-1-one,
1-[2-methyloxy-4-chlorophenyl]-3-[3,5-dimethyl-4-carboxydimethylmethyloxyphenyl]prop-2-en-1-one,
1-[4-heptylphenyl]-3-[3,5-dimethyl-4-tertbutyloxycarbonyldimethylmethyloxyphenyl]prop-2-en-1-one,
1-[4-heptylphenyl]-3-[3,5-dimethyl-4-carboxydimethylmethyloxyphenyl]prop-2-en-1-one,
1-[4-bromophenyl]-3-[3,5-dimethyl-4-tertbutyloxycarbonyldimethylmethyloxyphenyl]prop-2-en-1-one,
1-[4-bromophenyl]-3-[3,5-dimethyl-4-carboxy dimethylmethyloxyphenyl]prop-2-en-1-one,
1-[4-trifluoromethylphenyl]-3-[3-methyl-4-tertiobutyloxycarbonylmethyloxyphenyl]prop-2-en-1-one,
1-[4-trifluoromethylphenyl]-3-[3-methyl-4-carboxymethyloxyphenyl]prop-2-en-1-one,
1-[4-bromophenyl]-3-[3-tertiobutyl-4-tertiobutyloxydimethymethyloxyphenyl]prop-2-en-1-one,
1-[4-bromophenyl]-3-[3-tertiobutyl-4-carboxydimethylmethyloxyphenyl]prop-2-en-1-one,
1-[4-bromophenyl]-3-[3-trifluoromethyl-4-carboxydimethylmethyloxypheny]prop-2-en-1-one,
1-[4-bromophenyl]-3-[3-cyclohexyl-4-tertiobutyloxycarbonyldimethylmethyloxyphenyl]prop-2-en-1-one,
1-[4-bromophenyl]-3-[3-cyclohexyl-4-carboxydimethylmethyoxyphenyl]prop-2-en-1-one,
1-[4-methylthiophenyl]-3-[3-trifluoromethyl-4-tertiobutyloxycarbonyldimethylmethyloxyphenyl]prop-2-en-1-one,
1-[4-methylthiophenyl]-3-[3-trifluoromethyl-4-carboxydimethylmethyloxyphenyl]prop-2-en-1-one,
1-[4-methylsulfonylphenyl]-3-[3,5-dimethyl-4-tertiobutyloxycarbonyldimethylmethyloxyphenyl]prop-2-en-1-one,
1-[4-methylsulfonylphenyl]-3-[3,5-dimethyl-4-carboxydimethylmethyloxyphenyl]prop-2-en-1-one,
1-[4-trifluoromethylthiophenyl]-3-[3,5-dimethyl-4-tertiobutyloxycarbonyldimethylmethyloxyphenyl]prop-2-en-1-one,
1-[4-trifluoromethylthiophenyl]-3-[3,5-dimethyl-4-carboxydimethylmethyloxyphenyl]prop-2-en-1-one,
1-[4-isopropylphenyl]-3-[3,5-dimethyl-4-tertiobutyloxycarbonyldimethylmethyloxyphenyl]prop-2-en-1-one,
1-[4-isopropylphenyl]-3-[3,5-dimethyl-4-carboxydimethylmethyloxyphenyl]prop-2-en-1-one,
1-[4-trifluoromethylphenyl]-3-[3,5-dimethyl-4-tertiobutyloxycarbonyldimethylmethyloxyphenyl]prop-2-en-1-one,
1-[4-trifluoromethylphenyl]-3-[3,5-dimethyl-4-carboxydimethylmethyloxyphenyl]prop-2-en-1-one,
1-[4-hydroxyphenyl]-3-[3,5-dimethyl-4-carboxydimethylmethyloxyphenyl]prop-2-en-1-one,
1-[2-methylthiophenyl]-3-[3,5-dimethyl-4-tertiobutyloxycarbonyldimethylmethyloxyphenyl]prop-2-en-1-one, 1-[2-methylthiophenyl]-3-[3,5-dimethyl-4-carboxydimethylmethyloxyphenyl]prop-2-en-1-one,
1-[4-trifluoromethyloxyphenyl]-3-[3,5-dimethyl-4-tertiobutyloxycarbonyldimethylmethyloxyphenyl]prop-2-en-1-one,
1-[4-trifluoromethyloxyphenyl]-3-[3,5-dimethyl-4-carboxydimethylmethyloxyphenyl]prop-2-en-1-one,
1-[4-iodophenyl]-3-[3,5-dimethyl-4-tertiobutyloxycarbonyldimethylmethyloxyphenyl]prop-2-en-1-one,
1-[4-iodophenyl]-3-[3,5-dimethyl-4-carboxydimethylmethyloxyphenyl]prop-2-en-1-one,
1-[4-fluorophenyl]-3-[3,5-dimethyl-4-tertiobutyloxycarbonyldimethylmethyloxyphenyl]prop-2-en-1-one,
1-[4-fluorophenyl]-3-[3,5-dimethyl-4-carboxydimethylmethyloxyphenyl]prop-2-en-1-one,
1-[4-nonyloxyphenyl]-3-[3,5-dimethyl-4-tertiobutyloxycarbonyldimethylmethyloxyphenyl]prop-2-en-1-one,
1-[4-nonyloxyphenyl]-3-[3,5-dimethyl-4-carboxydimethylmethyloxyphenyl]prop-2-en-1-one,
1-[4-propyloxyphenyl]-3-[3,5-dimethyl-4-tertiobutyloxycarbonyldimethylmethyloxyphenyl]prop-2-en-1-one,
1-[4-propyloxyphenyl]-3-[3,5-dimethyl-4-carboxydimethylmethyloxyphenyl]prop-2-en-1-one,
1-[4-methylthiophenyl]-3-[3,5-dimethyl-4-tertiobutyloxycarbonylmethyloxyphenyl]prop-2-en-1-one,
1-[4-methylthiophenyl]-3-[3,5-dimethyl-4-carboxymethyloxyphenyl]prop-2-en-1-one,
1-[4-methylthiophenyl]-3-[3,5-diisopropyl-4-tertiobutyloxycarbonylmethyloxyphenyl]prop-2-en-1-one,
1-[4-methylthiophenyl]-3-[3,5-diisopropyl-4-carboxymethyloxyphenyl]prop-2-en-1-one,
1-[4-(2-bromoethyloxy)phenyl]-3-[3,5-dimethyl-4-carboxydimethylmethyloxyphenyl]prop-2-en-1-one,
1-[4-octadecyloxyphenyl]-3-[3,5-dimethyl-4-tertiobutyloxycarbonyldimethylmethyloxyphenyl]prop-2-en-1-one,
1-[4-octadecyloxyphenyl]-3-[3,5-dimethyl-4-carboxydimethylmethyloxyphenyl]prop-2-en-1-one,
1-[4-dodecyloxyphenyl]-3-[3,5-dimethyl-4-tertiobutyloxycarbonyldimethylmethyloxyphenyl]prop-2-en-1-one,
1-[4-dodecyloxyphenyl]-3-[3,5-dimethyl-4-carboxydimethylmethyloxyphenyl]prop-2-en-1-one,
1-[4-methyloxyphenyl]-3-[3,5-dimethyl-4-tertiobutyloxycarbonyldimethylmethyloxyphenyl]prop-2-en-1-one,
1-[4-methyloxyphenyl]-3-[3,5-dimethyl-4-carboxydimethylmethyloxyphenyl]prop-2-en-1-one,
1-[2-hexyloxyphenyl]-3-[3,5-dimethyl-4-tertiobutyloxycarbonyldimethylmethyloxyphenyl]prop-2-en-1-one,
1-[2-hexyloxyphenyl]-3-[3,5-dimethyl-4-carboxydimethylmethyloxyphenyl]prop-2-en-1-one,
1-[4-hexylthiophenyl]-3-[3,5-dimethyl-4-tertiobutyloxycarbonyldimethylmethyloxyphenyl]prop-2-en-1-one,
1-[4-hexylthiophenyl]-3-[3,5-dimethyl-4-carboxydimethylmethyloxyphenyl]prop-2-en-1-one,
1-[4-tertiobutyloxycarbonyldimethylmethyloxyphenyl]-3-[3,5-ditertiobutyl-4-hydroxyphenyl]prop-2-en-1-one,
1-[4-carboxydimethylmethyloxyphenyl]-3-[3,5-ditertiobutyl-4-hydroxyphenyl]prop-2-en-1-one.

6. The composition according to claim 1 wherein compound of formula (I) is selected in the group consisting of:
1-[4-methylthiophenyl]-3-[3,5-dimethyl-4-carboxydimethylmethyloxyphenyl]prop-2-en-1-one,
1-[4-bromophenyl]-3-[3,5-dimethyl-4-carboxydimethylmethyloxyphenyl]prop-2-en-1-one,
1-[4-trifluoromethyloxyphenyl]-3-[3,5-dimethyl-4-carboxydimethylmethyloxyphenyl]prop-2-en-1-one,
1-[4-trifluoromethylphenyl]-3-[3,5-dimethyl-4-carboxydimethylmethyloxyphenyl]prop-2-en-1-one,
1-[4-hexyloxyphenyl]-3-[3,5-dimethyl-4-carboxydimethylmethyloxyphenyl]prop-2-en-1-one,
1-[4-trifluoromethylthiophenyl]-3-[3,5-dimethyl-4-carboxydimethylmethyloxyphenyl]prop-2-en-1-one,
1-[4-propyloxyphenyl]-3-[3,5-dimethyl-4-carboxydimethylmethyloxyphenyl]prop-2-en-1-one.

7. The composition according to claim 1, for the treatment of restenosis, atherosclerosis, type 2 diabetes, obesity, or hypertension.

8. The composition according to claim 1, for the treatment of type 2 diabetes and obesity.

9. A compound selected in the group consisting of:
1-[4-trifluoromethylphenyl]-3-[3-methyl-4-tertiobutyloxycarbonylmethyloxyphenyl]prop-2-en-1-one,
1-[4-trifluoromethylphenyl]-3-[3-methyl-4-carboxymethyloxyphenyl]prop-2-en-1-one,
1-[4-bromophenyl]-3-[3-tertiobutyl-4-tertiobutyloxycarbonyldimethylmethyloxyphenyl]prop-2-en-1-one,
1-[4-bromophenyl]-3-[3-tertiobutyl-4-carboxydimethylmethyloxyphenyl]prop-2-en-1-one,
1-[4-bromophenyl]-3-[3-trifluoromethyl-4-carboxydimethylmethyloxypheny]prop-2-en-1-one,
1-[4-bromophenyl]-3-[3-cyclohexyl-4-tertiobutyloxycarbonyldimethylmethyloxyphenyl]prop-2-en-1-one,
1-[4-bromophenyl]-3-[3-cyclohexyl-4-carboxydimethylmethyloxyphenyl]prop-2-en-1-one,
1-[4-methylthiophenyl]-3-[3-trifluoromethyl-4-tertiobutyloxycarbonyldimethylmethyloxyphenyl]prop-2-en-1-one,
1-[4-methylthiophenyl]-3-[3-trifluoromethyl-4-carboxydimethylmethyloxyphenyl]prop-2-en-1-one,
1-[4-methylsulfonylphenyl]-3-[3,5-dimethyl-4-tertiobutyloxycarbonyldimethylmethyloxyphenyl]prop-2-en-1-one,
1-[4-methylsulfonylphenyl]-3-[3,5-dimethyl-4-carboxydimethylmethyloxyphenyl]prop-2-en-1-one,
1-[4-trifluoromethylthiophenyl]-3-[3,5-dimethyl-4-tertiobutyloxycarbonyldimethylmethyloxyphenyl]prop-2-en-1-one,
1-[4-trifluoromethylthiophenyl]-3-[3,5-dimethyl-4-carboxydimethylmethyloxyphenyl]prop-2-en-1-one,
1-[4-isopropylphenyl]-3-[3,5-dimethyl-4-tertiobutyloxycarbonyldimethylmethyloxyphenyl]prop-2-en-1-one,
1-[4-isopropylphenyl]-3-[3,5-dimethyl-4-carboxydimethylmethyloxyphenyl]prop-2-en-1-one,
1-[4-trifluoromethylphenyl]-3-[3,5-dimethyl-4-tertiobutyloxycarbonyldimethylmethyloxyphenyl]prop-2-en-1-one,
1-[4-trifluoromethylphenyl]-3-[3,5-dimethyl-4-carboxydimethylmethyloxyphenyl]prop-2-en-1-one,
1-[4-hydroxyphenyl]-3-[3,5-dimethyl-4-carboxydimethylmethyloxyphenyl]prop-2-en-1-one,
1-[2-methylthiophenyl]-3-[3,5-dimethyl-4-tertiobutyloxycarbonyldimethylmethyloxyphenyl]prop-2-en-1-one,
1-[2-methylthiophenyl]-3-[3,5-dimethyl-4-carboxydimethylmethyloxypheny]prop-2-en-1-one,
1-[4-trifluoromethyloxyphenyl]-3-[3,5-dimethyl-4-tertiobutyloxycarbonyldimethylmethyloxyphenyl]prop-2-en-1-one,
1-[4-trifluoromethyloxyphenyl]-3-[3,5-dimethyl-4-carboxydimethylmethyloxyphenyl]prop-2-en-1-one, 1-[4-iodophenyl]-3-[3,5-dimethyl-4-tertiobutyloxycarbonyldimethylmethyloxyphenyl]prop-2-en-1-one,
1-[4-iodophenyl]-3-[3,5-dimethyl-4-carboxydimethylmethyloxyphenyl]prop-2-en-1-one,
1-[4-fluorophenyl]-3-[3,5-dimethyl-4-tertiobutyloxycarbonyldimethylmethyloxyphenyl]prop-2-en-1-one,
1-[4-fluorophenyl]-3-[3,5-dimethyl-4-carboxydimethylmethyloxyphenyl]prop-2-en-1-one,
1-[4-nonyloxyphenyl]-3-[3,5-dimethyl-4-tertiobutyloxycarbonyldimethylmethyloxyphenyl]prop-2-en-1-one,
1-[4-nonyloxyphenyl]-3-[3,5-dimethyl-4-carboxydimethylmethyloxyphenyl]prop-2-en-1-one,
1-[4-propyloxyphenyl]-3-[3,5-dimethyl-4-tertiobutyloxycarbonyldimethylmethyloxyphenyl]prop-2-en-1-one,
1-[4-propyloxyphenyl]-3-[3,5-dimethyl-4-carboxydimethylmethyloxyphenyl]prop-2-en-1-one,
1-[4-methylthiophenyl]-3-[3,5-dimethyl-4-tertiobutyloxycarbonylmethyloxyphenyl]prop-2-en-1-one,
1-[4-methylthiophenyl]-3-[3,5-dimethyl-4-carboxymethyloxyphenyl]prop-2-en-1-one,
1-[4-methylthiophenyl]-3-[3,5-diisopropyl-4-tertiobutyloxycarbonylmethyloxyphenyl]prop-2-en-1-one,
1-[4-methylthiophenyl]-3-[3,5-diisopropyl-4-carboxymethyloxyphenyl]prop-2-en-1-one,
1-[4-(2-bromoethyloxy)phenyl]-3-[3,5-dimethyl-4-carboxydimethylmethyloxyphenyl]prop-2-en-1-one,
1-[4-octadecyloxyphenyl]-3-[3,5-dimethyl-4-tertiobutyloxycarbonyldimethylmethyloxyphenyl]prop-2-en-1-one,
1-[4-octadecyloxyphenyl]-3-[3,5-dimethyl-4-carboxydimethylmethyloxyphenyl]prop-2-en-1-one,
1-[4-dodecyloxyphenyl]-3-[3,5-dimethyl-4-tertiobutyloxycarbonyldimethylmethyloxyphenyl]prop-2-en-1-one,
1-[4-dodecyloxyphenyl]-3-[3,5-dimethyl-4-carboxydimethylmethyloxyphenyl]prop-2-en-1-one,
1-[4-methyloxyphenyl]-3-[3,5-dimethyl-4-tertiobutyloxycarbonyldimethylmethyloxyphenyl]prop-2-en-1-one,
1-[4-methyloxyphenyl]-3-[3,5-dimethyl-4-carboxydimethylmethyloxyphenyl]prop-2-en-1-one,
1-[2-hexyloxyphenyl]-3-[3,5-dimethyl-4-tertiobutyloxycarbonyldimethylmethyloxyphenyl]prop-2-en-1-one,
1-[2-hexyloxyphenyl]-3-[3,5-dimethyl-4-carboxydimethylmethyloxyphenyl]prop-2-en-1-one,
1-[4-hexylthiophenyl]-3-[3,5-dimethyl-4-tertiobutyloxycarbonyldimethylmethyloxyphenyl]prop-2-en-1-one,
1-[4-hexylthiophenyl]-3-[3,5-dimethyl-4-carboxydimethylmethyloxypheny]prop-2-en-1-one,
1-[4-tertiobutyloxycarbonyldimethylmethyloxyphenyl]-3-[3,5-ditertiobutyl-4-hydroxyphenyl]prop-2-en-1-one,
1-[4-carboxydimethylmethyloxyphenyl]-3-[3,5-ditertiobutyl-4-hydroxyphenyl]prop-2-en-1-one.

* * * * *

UNITED STATES PATENT AND TRADEMARK OFFICE
CERTIFICATE OF CORRECTION

| | | |
|---|---|---|
| PATENT NO. | : 7,566,737 B2 | Page 1 of 1 |
| APPLICATION NO. | : 11/493040 | |
| DATED | : July 28, 2009 | |
| INVENTOR(S) | : Delhomel et al. | |

It is certified that error appears in the above-identified patent and that said Letters Patent is hereby corrected as shown below:

In claim 1, column 123, lines 55-65, please replace formula (I) with the following formula (I):

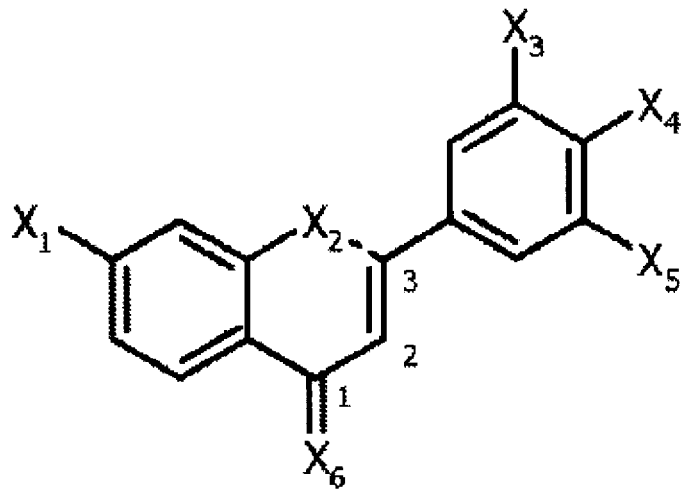

Signed and Sealed this
Twenty-seventh Day of November, 2012

David J. Kappos
*Director of the United States Patent and Trademark Office*